US008168205B2

(12) United States Patent
Kunsch et al.

(10) Patent No.: US 8,168,205 B2
(45) Date of Patent: May 1, 2012

(54) STREPTOCOCCUS PNEUMONIAE POLYPEPTIDES

(75) Inventors: Charles A. Kunsch, Norcross, GA (US); Gil H. Choi, Rockville, MD (US); Patrick J. Dillon, Carlsbad, CA (US); Craig A. Rosen, Laytonsville, MD (US); Steven C. Barash, Rockville, MD (US); Michael R. Fannon, Silver Spring, MD (US); Brian A. Dougherty, Killingworth, CT (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 12/635,794

(22) Filed: Dec. 11, 2009

(65) Prior Publication Data

US 2010/0221287 A1 Sep. 2, 2010

Related U.S. Application Data

(60) Continuation of application No. 11/563,552, filed on Nov. 27, 2006, now abandoned, which is a division of application No. 10/158,844, filed on Jun. 3, 2002, now Pat. No. 7,141,418, which is a division of application No. 08/961,527, filed on Oct. 30, 1997, now Pat. No. 6,420,135.

(60) Provisional application No. 60/029,960, filed on Oct. 31, 1996.

(51) Int. Cl.
C07K 1/00 (2006.01)
C07K 14/00 (2006.01)
C07K 17/00 (2006.01)
A61K 39/00 (2006.01)
A61K 39/02 (2006.01)
A61K 39/09 (2006.01)
A61K 39/38 (2006.01)

(52) U.S. Cl. ............... 424/244.1; 424/184.1; 424/234.1; 530/350

(58) Field of Classification Search .................. None
See application file for complete search history.

(56) References Cited

U.S. PATENT DOCUMENTS

| 5,302,527 | A | 4/1994 | Birkett et al. |
| 6,251,581 | B1 | 6/2001 | Ullman et al. |
| 6,251,588 | B1 | 6/2001 | Shannon et al. |
| 6,573,082 | B1 | 6/2003 | Choi et al. |
| 6,699,703 | B1 | 3/2004 | Doucette-Stamm et al. |

FOREIGN PATENT DOCUMENTS

| EP | 0 622 081 A2 | 11/1994 |
| EP | 0 687 688 A1 | 12/1995 |
| JP | 8-116973 | 5/1996 |
| WO | WO-93/10238 | 5/1993 |
| WO | WO-95/06732 | 3/1995 |
| WO | WO-95/14712 | 6/1995 |
| WO | WO-95/31548 | 11/1995 |
| WO | WO-96/05859 | 2/1996 |
| WO | WO-96/08582 | 3/1996 |
| WO | WO-96/16082 | 5/1996 |
| WO | WO-96/33276 | 10/1996 |
| WO | WO-97/43303 | 11/1997 |
| WO | WO-98/18930 | 5/1998 |
| WO | WO-98/26072 | 6/1998 |
| WO | WO-99/15675 | 4/1999 |

OTHER PUBLICATIONS

Passarge, Eberhard. Color Atlas of Genetics. 1995 Thieme Medical Publishers, In. New York, p. 48-49.*
Abbas et al. Cellular and Molecular Immunology 4th edition, 2000 Chapter 15 p. 360-362.*
Ellis, R.W. (Chapter 29 of "Vaccines" [Plotkin, S.A. et al. (eds) published by W. B. Saunders company (Philadelphia) in 1988, p. 571.*
(McDaniel et al. Infection and Immunity, Jan. 1991, p. 222-228.*
Poolman et al. Expert Rev. Vaccines 3(5), 597-604 (2004).*
Adamou et al., "Identification and characterization of a novel family of Pneumococcal proteins that are protective against sepsis," *Infection and Immunity*, 69(2):949-958 (2001).
Altschul, et al., "Basic local alignment search tool," *J. Mol. Biol.*, 215:403-410 (1990).
Gagnon, et al., "Cloning, sequencing and expression in *Escherichia coli* of the ptsI gene encoding enzyme I of the phosphoenolpyruvate: sugar phosphotransferase transport system from *Streptoccus salivarius*," *Gene*, 121:71-78 (1992).
Gasc, et al., *J. Bacteriology*, 173:7361-7367 (1991).
Hillier, et al., GenBank Accession No. H38607 (1995).
Hillier, et al., GenBank Accession No. R54118 (1995).
Hillier, et al., GenBank Accession No. R15155 (1995).
Hillier, et al., GenBank Accession No. R01821 (1995).
Hillier, et al., GenBank Accession No. H04394 (1995).
Hillier, et al., GenBank Accession No. R66534 (1995).
Hillier, et al., GenBank Accession No. H65672 (1995).
Hillier, et al., GenBank Accession No. H01173 (1995).
Kaneko, et al (DNA Research 2 pp. 153-166), 1995.
Martin, et al., "Relatedness of penicillin-binding protein 1a genes from different clones of penicillin-resistant *Streptococcus pneumoniae* isolated in South Africa and Spain," *The EMBO Journal*, 11(11):3831-3836 (1992).
Merriam Webster's Collegiate Dictionary, 10th edition, p. 545 (1997).

(Continued)

*Primary Examiner* — Oluwatosin Ogunbiyi
(74) *Attorney, Agent, or Firm* — Human Genome Sciences, Inc.

(57) ABSTRACT

The present invention provides polynucleotide sequences of the genome of *Streptococcus pneumoniae*, polypeptide sequences encoded by the polynucleotide sequences, corresponding polynucleotides and polypeptides, vectors and hosts comprising the polynucleotides, and assays and other uses thereof. The present invention further provides polynucleotide and polypeptide sequence information stored on computer readable media, and computer-based systems and methods which facilitate its use.

6 Claims, 2 Drawing Sheets

OTHER PUBLICATIONS

Pearce, et al., "Genetic identification of exported proteins in *Streptococcus pneumoniae*," Molecular Microbiology, 9(5):1037-1050 (1993).

Pearson, et al., "Improved tools for biological sequence comparison," *Proc. Natl. Acad. Sci.*, 85:2444-2448 (1988).

Rudinger, Peptide Hormones "*Characteristics of the amino acids as components of a peptide hormone sequence*," J.A. Parsons (Ed.) University Park Press, Baltimore, pp. 5-7 (1996).

Tan, et al., GenBank Accession No. M87840 (1995).

Zhang, et al., *J. Clin. Microbiol.*, 33(3):596-601, 1995.

* cited by examiner

STREPTOCOCCUS PNEUMONIAE POLYPEPTIDES

CROSS REFERENCE TO RELATED APPLICATIONS

This application is a continuation of U.S. application Ser. No. 11/563,552, filed Nov. 27, 2006 (now abandoned), which is a divisional of U.S. application Ser. No. 10/158,844, filed Jun. 3, 2002 (now U.S. Pat. No. 7,141,418, issued Nov. 28, 2006), which is a divisional of U.S. application Ser. No. 08/961,527, filed Oct. 30, 1997 (now U.S. Pat. No. 6,420,135, issued Jul. 16, 2002), which is a non-provisional of and claims benefit under 35 U.S.C. §119(e) of U.S. Provisional Application No. 60/029,960, filed Oct. 31, 1996, each of which is incorporated by reference herein in its entirety.

STATEMENT UNDER 37 C.F.R. §1.77(b)(5)

This application refers to a "Sequence Listing" listed below, which is provided as a text document. The document is entitled "PB340P1D2C1_SeqList.txt" (2,796,867 bytes, created Dec. 10, 2009), and is hereby incorporated by reference in its entirety herein.

FIELD OF THE INVENTION

The present invention relates to the field of molecular biology. In particular, it relates to, among other things, nucleotide sequences of *Streptococcus pneumoniae*, contigs, ORFs, fragments, probes, primers and related polynucleotides thereof, peptides and polypeptides encoded by the sequences, and uses of the polynucleotides and sequences thereof, such as in fermentation, polypeptide production, assays and pharmaceutical development, among others.

BACKGROUND OF THE INVENTION

*Streptococcus pneumoniae* has been one of the most extensively studied microorganisms since its first isolation in 1881. It was the object of many investigations that led to important scientific discoveries. In 1928, Griffith observed that when heat-killed encapsulated pneumococci and live strains constitutively lacking any capsule were concomitantly injected into mice, the nonencapsulated could be converted into encapsulated pneumococci with the same capsular type as the heat-killed strain. Years later, the nature of this "transforming principle," or carrier of genetic information, was shown to be DNA. (Avery, O. T., et al., *J. Exp. Med.*, 79:137-157 (1944)).

In spite of the vast number of publications on *S. pneumoniae* many questions about its virulence are still unanswered, and this pathogen remains a major causative agent of serious human disease, especially community-acquired pneumonia. (Johnston, R. B., et al., *Rev. Infect. Dis.* 13(Suppl. 6):S509-517 (1991)). In addition, in developing countries, the pneumococcus is responsible for the death of a large number of children under the age of 5 years from pneumococcal pneumonia. The incidence of pneumococcal disease is highest in infants under 2 years of age and in people over 60 years of age. Pneumococci are the second most frequent cause (after *Haemophilus influenzae* type b) of bacterial meningitis and otitis media in children. With the recent introduction of conjugate vaccines for *H. influenzae* type b, pneumococcal meningitis is likely to become increasingly prominent. *S. pneumoniae* is the most important etiologic agent of community-acquired pneumonia in adults and is the second most common cause of bacterial meningitis behind *Neisseria meningitidis*.

The antibiotic generally prescribed to treat *S. pneumoniae* is benzylpenicillin, although resistance to this and to other antibiotics is found occasionally. Pneumococcal resistance to penicillin results from mutations in its penicillin-binding proteins. In uncomplicated pneumococcal pneumonia caused by a sensitive strain, treatment with penicillin is usually successful unless started too late. Erythromycin or clindamycin can be used to treat pneumonia in patients hypersensitive to penicillin, but resistant strains to these drugs exist. Broad spectrum antibiotics (e.g., the tetracyclines) may also be effective, although tetracycline-resistant strains are not rare. In spite of the availability of antibiotics, the mortality of pneumococcal bacteremia in the last four decades has remained stable between 25 and 29%. (Gillespie, S. H., et al., *J. Med. Microbiol.* 28:237-248 (1989).

*S. pneumoniae* is carried in the upper respiratory tract by many healthy individuals. It has been suggested that attachment of pneumococci is mediated by a disaccharide receptor on fibronectin, present on human pharyngeal epithelial cells. (Anderson, B. J., et al, *J. Immunol.* 142:2464-2468 (1989). The mechanisms by which pneumococci translocate from the nasopharynx to the lung, thereby causing pneumonia, or migrate to the blood, giving rise to bacteremia or septicemia, are poorly understood. (Johnston, R. B., et al., *Rev. Infect. Dis.* 13(Suppl. 6):S509-517 (1991).

Various proteins have been suggested to be involved in the pathogenicity of *S. pneumoniae*, however, only a few of them have actually been confirmed as virulence factors. Pneumococci produce an IgA1 protease that might interfere with host defense at mucosal surfaces. (Kornfield, S. J., et al., *Rev. Inf. Dis.* 3:521-534 (1981). *S. pneumoniae* also produces neuraminidase, an enzyme that may facilitate attachment to epithelial cells by cleaving sialic acid from the host glycolipids and gangliosides. Partially purified neuraminidase was observed to induce meningitis-like symptoms in mice; however, the reliability of this finding has been questioned because the neuraminidase preparations used were probably contaminated with cell wall products. Other pneumococcal proteins besides neuraminidase are involved in the adhesion of pneumococci to epithelial and endothelial cells. These pneumococcal proteins have as yet not been identified. Recently, Cundell et al., reported that peptide permeases can modulate pneumococcal adherence to epithelial and endothelial cells. It was, however, unclear whether these permeases function directly as adhesions or whether they enhance adherence by modulating the expression of pneumococcal adhesions. (DeVelasco, E. A., et al., *Micro. Rev.* 59:591-603 (1995). A better understanding of the virulence factors determining its pathogenicity will need to be developed to cope with the devastating effects of pneumococcal disease in humans.

Ironically, despite the prominent role of *S. pneumoniae* in the discovery of DNA, little is known about the molecular genetics of the organism. The *S. pneumoniae* genome consists of one circular, covalently closed, double-stranded DNA and a collection of so-called variable accessory elements, such as prophages, plasmids, transposons and the like. Most physical characteristics and almost all of the genes of *S. pneumoniae* are unknown. Among the few that have been identified, most have not been physically mapped or characterized in detail. Only a few genes of this organism have been sequenced. (See, for instance current versions of GENBANK and other nucleic acid databases, and references that relate to the genome of *S. pneumoniae* such as those set out elsewhere herein.)

It is clear that the etiology of diseases mediated or exacerbated by *S. pneumoniae*, infection involves the programmed expression of *S. pneumoniae* genes, and that characterizing the genes and their patterns of expression would add dramatically to our understanding of the organism and its host interactions. Knowledge of *S. pneumoniae* genes and genomic organization would improve our understanding of disease etiology and lead to improved and new ways of preventing, ameliorating, arresting and reversing diseases. Moreover, characterized genes and genomic fragments of *S. pneumoniae* would provide reagents for, among other things, detecting, characterizing and controlling *S. pneumoniae* infections. There is a need to characterize the genome of *S. pneumoniae* and for polynucleotides of this organism.

SUMMARY OF THE INVENTION

The present invention is based on the sequencing of fragments of the *Streptococcus pneumoniae* genome. The primary nucleotide sequences which were generated are provided in SEQ ID NOS:1-391.

The present invention provides the nucleotide sequence of several hundred contigs of the *Streptococcus pneumoniae* genome, which are listed in tables below and set out in the Sequence Listing submitted herewith, and representative fragments thereof, in a form which can be readily used, analyzed, and interpreted by a skilled artisan. In one embodiment, the present invention is provided as contiguous strings of primary sequence information corresponding to the nucleotide sequences depicted in SEQ ID NOS:1-391.

The present invention further provides nucleotide sequences which are at least 95% identical to the nucleotide sequences of SEQ ID NOS:1-391.

The nucleotide sequence of SEQ ID NOS:1-391, a representative fragment thereof, or a nucleotide sequence which is at least 95% identical to the nucleotide sequence of SEQ ID NOS:1-391 may be provided in a variety of mediums to facilitate its use. In one application of this embodiment, the sequences of the present invention are recorded on computer readable media. Such media includes, but is not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

The present invention further provides systems, particularly computer-based systems which contain the sequence information herein described stored in a data storage means. Such systems are designed to identify commercially important fragments of the *Streptococcus pneumoniae* genome.

Another embodiment of the present invention is directed to fragments of the *Streptococcus pneumoniae* genome having particular structural or functional attributes. Such fragments of the *Streptococcus pneumoniae* genome of the present invention include, but are not limited to, fragments which encode peptides, hereinafter referred to as open reading frames or ORFs, fragments which modulate the expression of an operably linked ORF, hereinafter referred to as expression modulating fragments or EMFs, and fragments which can be used to diagnose the presence of *Streptococcus pneumoniae* in a sample, hereinafter referred to as diagnostic fragments or DFs.

Each of the ORFs in fragments of the *Streptococcus pneumoniae* genome disclosed in Tables 1-3, and the EMFs found 5' to the ORFs, can be used in numerous ways as polynucleotide reagents. For instance, the sequences can be used as diagnostic probes or amplification primers for detecting or determining the presence of a specific microbe in a sample, to selectively control gene expression in a host and in the production of polypeptides, such as polypeptides encoded by ORFs of the present invention, particular those polypeptides that have a pharmacological activity.

The present invention further includes recombinant constructs comprising one or more fragments of the *Streptococcus pneumoniae* genome of the present invention. The recombinant constructs of the present invention comprise vectors, such as a plasmid or viral vector, into which a fragment of the *Streptococcus pneumoniae* has been inserted.

The present invention further provides host cells containing any of the isolated fragments of the *Streptococcus pneumoniae* genome of the present invention. The host cells can be a higher eukaryotic host cell, such as a mammalian cell, a lower eukaryotic cell, such as a yeast cell, or a procaryotic cell such as a bacterial cell.

The present invention is further directed to isolated polypeptides and proteins encoded by ORFs of the present invention. A variety of methods, well known to those of skill in the art, routinely may be utilized to obtain any of the polypeptides and proteins of the present invention. For instance, polypeptides and proteins of the present invention having relatively short, simple amino acid sequences readily can be synthesized using commercially available automated peptide synthesizers. Polypeptides and proteins of the present invention also may be purified from bacterial cells which naturally produce the protein. Yet another alternative is to purify polypeptide and proteins of the present invention from cells which have been altered to express them.

The invention further provides methods of obtaining homologs of the fragments of the *Streptococcus pneumoniae* genome of the present invention and homologs of the proteins encoded by the ORFs of the present invention. Specifically, by using the nucleotide and amino acid sequences disclosed herein as a probe or as primers, and techniques such as PCR cloning and colony/plaque hybridization, one skilled in the art can obtain homologs.

The invention further provides antibodies which selectively bind polypeptides and proteins of the present invention. Such antibodies include both monoclonal and polyclonal antibodies.

The invention further provides hybridomas which produce the above-described antibodies. A hybridoma is an immortalized cell line which is capable of secreting a specific monoclonal antibody.

The present invention further provides methods of identifying test samples derived from cells which express one of the ORFs of the present invention, or a homolog thereof. Such methods comprise incubating a test sample with one or more of the antibodies of the present invention, or one or more of the DFs of the present invention, under conditions which allow a skilled artisan to determine if the sample contains the ORF or product produced therefrom.

In another embodiment of the present invention, kits are provided which contain the necessary reagents to carry out the above-described assays.

Specifically, the invention provides a compartmentalized kit to receive, in close confinement, one or more containers which comprises: (a) a first container comprising one of the antibodies, or one of the DFs of the present invention; and (b) one or more other containers comprising one or more of the following: wash reagents, reagents capable of detecting presence of bound antibodies or hybridized DFs.

Using the isolated proteins of the present invention, the present invention further provides methods of obtaining and identifying agents capable of binding to a polypeptide or protein encoded by one of the ORFs of the present invention. Specifically, such agents include, as further described below, antibodies, peptides, carbohydrates, pharmaceutical agents and the like. Such methods comprise steps of: (a) contacting an agent with an isolated protein encoded by one of the ORFs of the present invention; and (b) determining whether the agent binds to said protein.

The present genomic sequences of *Streptococcus pneumoniae* will be of great value to all laboratories working with this organism and for a variety of commercial purposes. Many fragments of the *Streptococcus pneumoniae* genome will be immediately identified by similarity searches against GenBank or protein databases and will be of immediate value to *Streptococcus pneumoniae* researchers and for immediate commercial value for the production of proteins or to control gene expression.

The methodology and technology for elucidating extensive genomic sequences of bacterial and other genomes has and will greatly enhance the ability to analyze and understand chromosomal organization. In particular, sequenced contigs and genomes will provide the models for developing tools for the analysis of chromosome structure and function, including the ability to identify genes within large segments of genomic DNA, the structure, position, and spacing of regulatory elements, the identification of genes with potential industrial applications, and the ability to do comparative genomic and molecular phylogeny.

DETAILED DESCRIPTION OF ILLUSTRATIVE EMBODIMENTS

Figure 1:
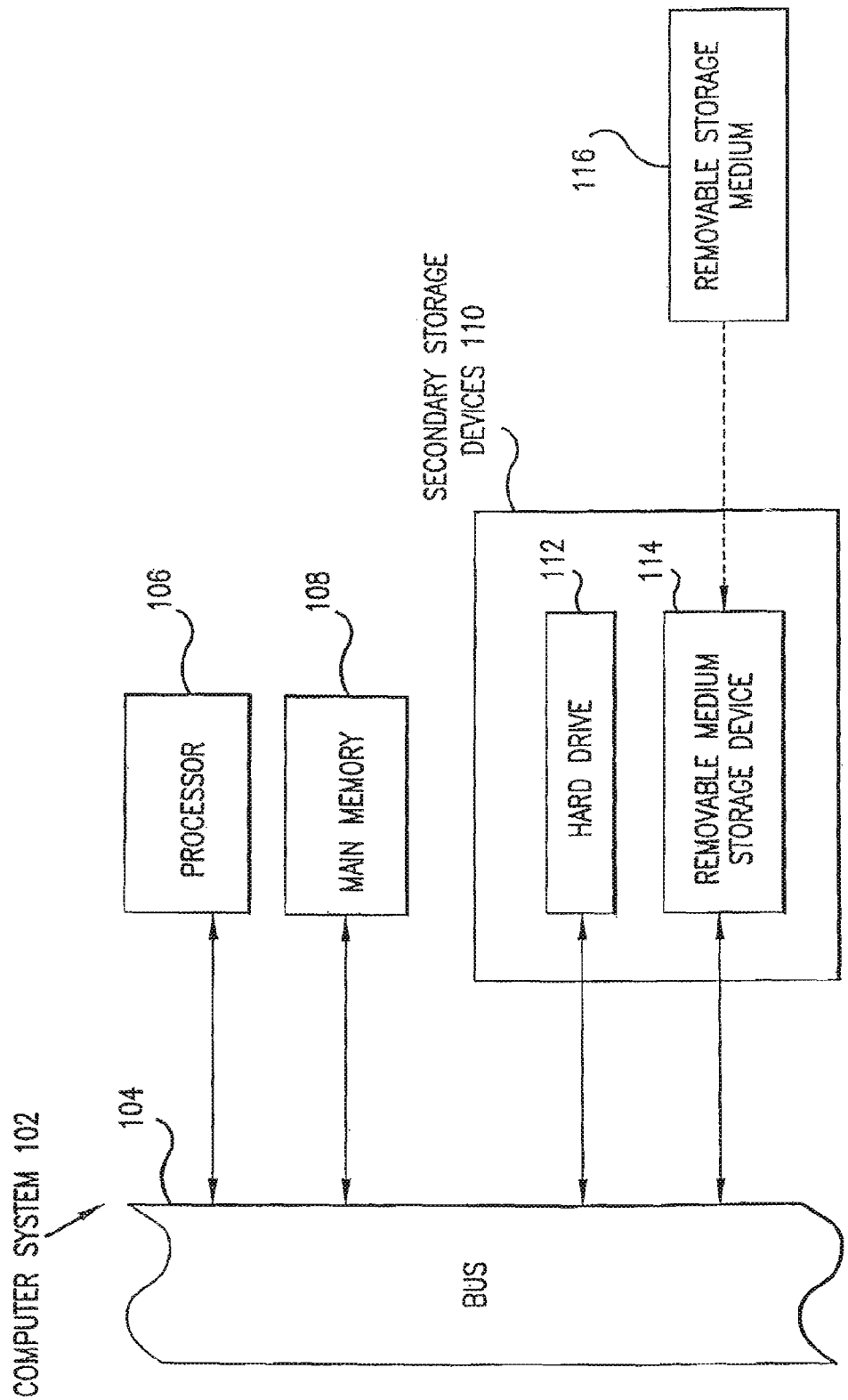
FIG. 1 is a block diagram of a computer system (102) that can be used to implement computer-based systems of present invention.
Figure 2:
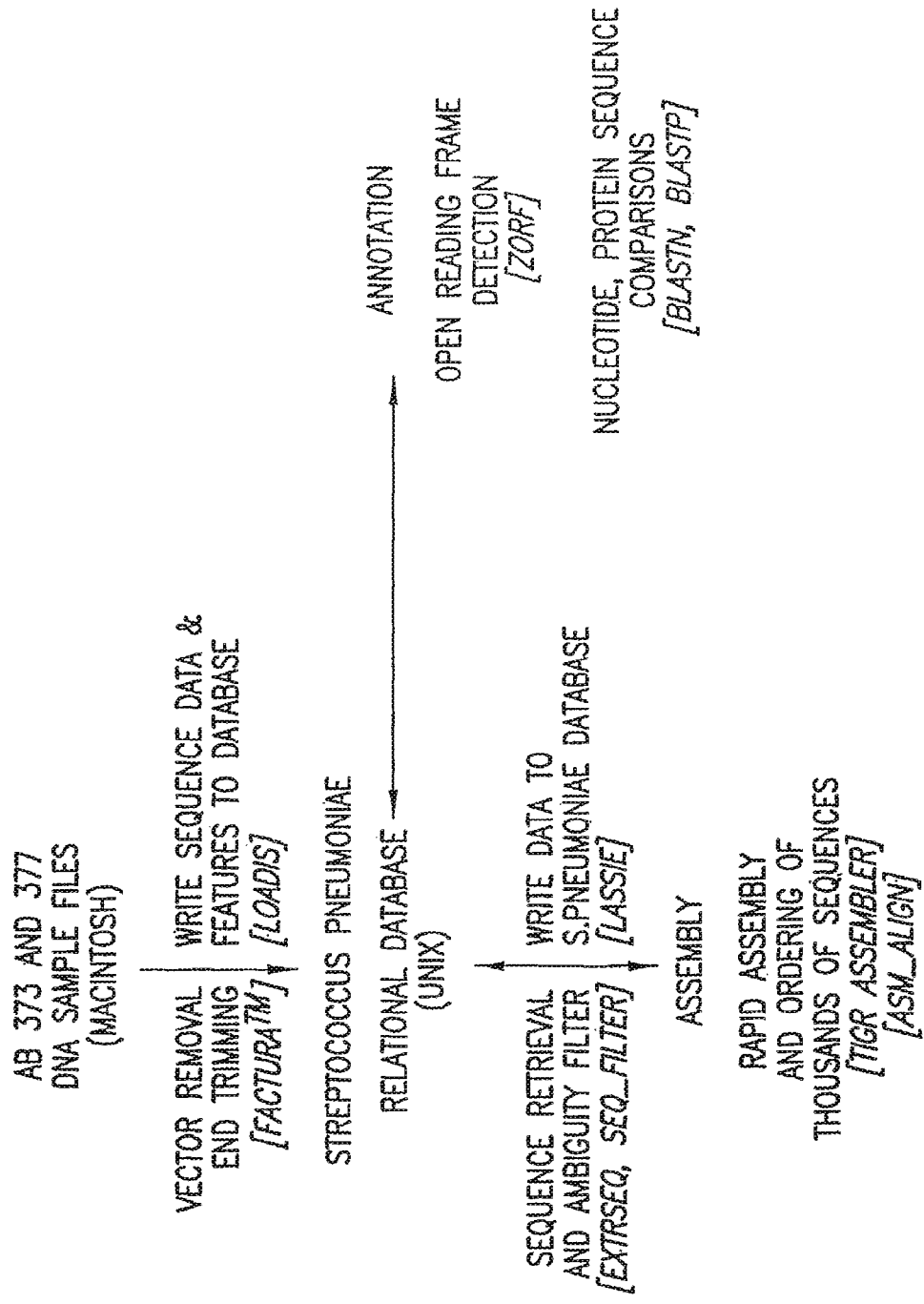
FIG. 2 is a schematic diagram depicting the data flow and computer programs used to collect, assemble, edit and annotate the contigs of the *Streptococcus pneumoniae* genome of the present invention. Both Macintosh and Unix platforms are used to handle the AB 373 and 377 sequence data files, largely as described in Kerlavage et al., *Proceedings of the Twenty-Sixth Annual Hawaii International Conference on System Sciences*, 585, IEEE Computer Society Press, Washington D.C. (1993). Factura (AB) is a Macintosh program designed for automatic vector sequence removal and end-trimming of sequence files. The program Loadis runs on a Macintosh platform and parses the feature data extracted from the sequence files by Factura to the Unix based *Streptococcus pneumoniae* relational database. Assembly of contigs (and whole genome sequences) is accomplished by retrieving a specific set of sequence files and their associated features using Extrseq, a Unix utility for retrieving sequences from an SQL database. The resulting sequence file is processed by seq_filter to trim portions of the sequences with more than 2% ambiguous nucleotides. The sequence files were assembled using TIGR Assembler, an assembly engine designed at The Institute for Genomic Research (TIGR) for rapid and accurate assembly of thousands of sequence fragments. The collection of contigs generated by the assembly step is loaded into the database with the lassie program. Identification of open reading frames (ORFs) is accomplished by processing contigs with zorf or GenMark. The ORFs are searched against *S. pneumoniae* sequences from GenBank and against all protein sequences using the BLASTN and BLASTP programs, described in Altschul et al., *J. Mol. Biol.* 215: 403-410 (1990)). Results of the ORF determination and similarity searching steps were loaded into the database. As described below, some results of the determination and the searches are set out in Tables 1-3.

The present invention is based on the sequencing of fragments of the *Streptococcus pneumoniae* genome and analysis of the sequences. The primary nucleotide sequences generated by sequencing the fragments are provided in SEQ ID NOS:1-391. (As used herein, the "primary sequence" refers to the nucleotide sequence represented by the IUPAC nomenclature system.)

In addition to the aforementioned *Streptococcus pneumoniae* polynucleotide and polynucleotide sequences, the present invention provides the nucleotide sequences of SEQ ID NOS: 1-391, or representative fragments thereof, in a form which can be readily used, analyzed, and interpreted by a skilled artisan.

As used herein, a "representative fragment of the nucleotide sequence depicted in SEQ ID NOS:1-391" refers to any portion of the SEQ ID NOS:1-391 which is not presently represented within a publicly available database. Preferred representative fragments of the present invention are *Streptococcus pneumoniae* open reading frames (ORFs), expression modulating fragment (EMFs) and fragments which can be used to diagnose the presence of *Streptococcus pneumoniae* in sample (DFs). A non-limiting identification of preferred representative fragments is provided in Tables 1-3. As discussed in detail below, the information provided in SEQ ID NOS:1-391 and in Tables 1-3 together with routine cloning, synthesis, sequencing and assay methods will enable those skilled in the art to clone and sequence all "representative fragments" of interest, including open reading frames encoding a large variety of *Streptococcus pneumoniae* proteins.

While the presently disclosed sequences of SEQ ID NOS: 1-391 are highly accurate, sequencing techniques are not perfect and, in relatively rare instances, further investigation of a fragment or sequence of the invention may reveal a nucleotide sequence error present in a nucleotide sequence disclosed in SEQ ID NOS:1-391. However, once the present invention is made available (i.e., once the information in SEQ ID NOS:1-391 and Tables 1-3 has been made available), resolving a rare sequencing error in SEQ ID NOS:1-391 will be well within the skill of the art. The present disclosure makes available sufficient sequence information to allow any of the described contigs or portions thereof to be obtained readily by straightforward application of routine techniques. Further sequencing of such polynucleotide may proceed in like manner using manual and automated sequencing methods which are employed ubiquitous in the art. Nucleotide sequence editing software is publicly available. For example, Applied Biosystem's (AB) AutoAssembler can be used as an aid during visual inspection of nucleotide sequences. By employing such routine techniques potential errors readily may be identified and the correct sequence then may be ascertained by targeting further sequencing effort, also of a routine nature, to the region containing the potential error.

Even if all of the very rare sequencing errors in SEQ ID NOS:1-391 were corrected, the resulting nucleotide sequences would still be at least 95% identical, nearly all would be at least 99% identical, and the great majority would be at least 99.9% identical to the nucleotide sequences of SEQ ID NOS:1-391.

As discussed elsewhere herein, polynucleotides of the present invention readily may be obtained by routine application of well known and standard procedures for cloning and sequencing DNA. Detailed methods for obtaining libraries and for sequencing are provided below, for instance. A wide variety of *Streptococcus pneumoniae* strains that can be used to prepare *S. pneumoniae* genomic DNA for cloning and for obtaining polynucleotides of the present invention are available to the public from recognized depository institutions, such as the American Type Culture Collection (ATCC™). While the present invention is enabled by the sequences and other information herein disclosed, the *S. pneumoniae* strain that provided the DNA of the present Sequence Listing, Strain 7/87 14.8.91, has been deposited in the ATCC™, as a convenience to those of skill in the art. As a further convenience, a library of *S. pneumoniae* genomic DNA, derived from the same strain, also has been deposited in the ATCC™. The *S. pneumoniae* strain was deposited on Oct. 10, 1996, and was given Deposit No. 55840, and the cDNA library was deposited on Oct. 11, 1996 and was given Deposit No. 97755. The genomic fragments in the library are 15 to 20 kb fragments generated by partial Sau3A1 digestion and they are inserted into the BamHI site in the well-known lambda-derived vector lambda DASH II (Stratagene, La Jolla, Calif.). The provision of the deposits is not a waiver of any rights of the inventors or their assignees in the present subject matter.

The nucleotide sequences of the genomes from different strains of *Streptococcus pneumoniae* differ somewhat. However, the nucleotide sequences of the genomes of all *Streptococcus pneumoniae* strains will be at least 95% identical, in corresponding part, to the nucleotide sequences provided in SEQ ID NOS:1-391. Nearly all will be at least 99% identical and the great majority will be 99.9% identical.

Thus, the present invention further provides nucleotide sequences which are at least 95%, preferably 99% and most preferably 99.9% identical to the nucleotide sequences of SEQ ID NOS:1-391, in a form which can be readily used, analyzed and interpreted by the skilled artisan.

Methods for determining whether a nucleotide sequence is at least 95%, at least 99% or at least 99.9% identical to the nucleotide sequences of SEQ ID NOS:1-391 are routine and readily available to the skilled artisan. For example, the well known fasta algorithm described in Pearson and Lipman, *Proc. Natl. Acad. Sci. USA* 85: 2444 (1988) can be used to generate the percent identity of nucleotide sequences. The BLASTN program also can be used to generate an identity score of polynucleotides compared to one another.

Computer Related Embodiments

The nucleotide sequences provided in SEQ ID NOS:1-391, a representative fragment thereof, or a nucleotide sequence at least 95%, preferably at least 99% and most preferably at least 99.9% identical to a polynucleotide sequence of SEQ ID NOS:1-391 may be "provided" in a variety of mediums to facilitate use thereof. As used herein, provided refers to a manufacture, other than an isolated nucleic acid molecule, which contains a nucleotide sequence of the present invention; i.e., a nucleotide sequence provided in SEQ ID NOS:1-391, a representative fragment thereof, or a nucleotide sequence at least 95%, preferably at least 99% and most preferably at least 99.9% identical to a polynucleotide of SEQ ID NOS:1-391. Such a manufacture provides a large portion of the *Streptococcus pneumoniae* genome and parts thereof (e.g., a *Streptococcus pneumoniae* open reading frame (ORF)) in a form which allows a skilled artisan to examine the manufacture using means not directly applicable to examining the *Streptococcus pneumoniae* genome or a subset thereof as it exists in nature or in purified form.

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories, such as magnetic/optical storage media. A skilled artisan can readily appreciate how any of the presently known computer readable mediums can be used to create a manufacture comprising computer readable medium having recorded thereon a nucleotide sequence of the present invention. Likewise, it will be clear to those of skill how additional computer readable media that may be developed also can be used to create analogous manufactures having recorded thereon a nucleotide sequence of the present invention.

As used herein, "recorded" refers to a process for storing information on computer readable medium. A skilled artisan can readily adopt any of the presently know methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. A skilled artisan can readily adapt any number of data-processor structuring formats (e.g., text file or database) in order to obtain computer readable medium having recorded thereon the nucleotide sequence information of the present invention.

Computer software is publicly available which allows a skilled artisan to access sequence information provided in a computer readable medium. Thus, by providing in computer readable form the nucleotide sequences of SEQ ID NOS:1-391, a representative fragment thereof, or a nucleotide sequence at least 95%, preferably at least 99% and most preferably at least 99.9% identical to a sequence of SEQ ID NOS:1-391 the present invention enables the skilled artisan routinely to access the provided sequence information for a wide variety of purposes.

The examples which follow demonstrate how software which implements the BLAST (Altschul et al., *J. Mol. Biol.* 215:403-410 (1990)) and BLAZE (Brutlag et al., *Comp. Chem.* 17:203-207 (1993)) search algorithms on a Sybase system was used to identify open reading frames (ORFs) within the *Streptococcus pneumoniae* genome which contain homology to ORFs or proteins from both *Streptococcus pneumoniae* and from other organisms. Among the ORFs discussed herein are protein encoding fragments of the *Streptococcus pneumoniae* genome useful in producing commercially important proteins, such as enzymes used in fermentation reactions and in the production of commercially useful metabolites.

The present invention further provides systems, particularly computer-based systems, which contain the sequence information described herein. Such systems are designed to identify, among other things, commercially important fragments of the *Streptococcus pneumoniae* genome.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention.

As stated above, the computer-based systems of the present invention comprise a data storage means having stored therein a nucleotide sequence of the present invention and the necessary hardware means and software means for supporting and implementing a search means.

As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of the present genomic sequences which match a particular target sequence or target motif. A variety of known algorithms are disclosed publicly and a variety of commercially available software for conducting search means are and can be used in the computer-based systems of the present invention. Examples of such software includes, but is not limited to, MacPattem (EMBL), BLASTN and BLASTX (NCBIA). A skilled artisan can readily recognize that any one of the available algorithms or implementing software packages for conducting homology searches can be adapted for use in the present computer-based systems.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzymic active sites and signal sequences. Nucleic acid target motifs include, but are not limited to, promoter sequences, hairpin structures and inducible expression elements (protein binding sequences).

A variety of structural formats for the input and output means can be used to input and output the information in the computer-based systems of the present invention. A preferred format for an output means ranks fragments of the *Streptococcus pneumoniae* genomic sequences possessing varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments of the *Streptococcus pneumoniae* genome. In the present examples, implementing software which implement the BLAST and BLAZE algorithms, described in Altschul et al., *J. Mol. Biol.* 215: 403-410 (1990), is used to identify open reading frames within the *Streptococcus pneumoniae* genome. A skilled artisan can readily recognize that any one of the publicly available homology search programs can be used as the search means for the computer-based systems of the present invention. Of course, suitable proprietary systems that may be known to those of skill also may be employed in this regard.

FIG. 1 provides a block diagram of a computer system illustrative of embodiments of this aspect of present invention. The computer system 102 includes a processor 106 connected to a bus 104. Also connected to the bus 104 are a main memory 108 (preferably implemented as random access memory, RAM) and a variety of secondary storage devices 110, such as a hard drive 112 and a removable medium storage device 114. The removable medium storage device 114 may represent, for example, a floppy disk drive, a CD-ROM drive, a magnetic tape drive, etc. A removable storage medium 116 (such as a floppy disk, a compact disk, a magnetic tape, etc.) containing control logic and/or data recorded therein may be inserted into the removable medium storage device 114. The computer system 102 includes appropriate software for reading the control logic and/or the data from the removable medium storage device 114, once it is inserted into the removable medium storage device 114.

A nucleotide sequence of the present invention may be stored in a well known manner in the main memory 108, any of the secondary storage devices 110, and/or a removable storage medium 116. During execution, software for accessing and processing the genomic sequence (such as search tools, comparing tools, etc.) reside in main memory 108, in accordance with the requirements and operating parameters of the operating system, the hardware system and the software program or programs.

Biochemical Embodiments

Other embodiments of the present invention are directed to isolated fragments of the *Streptococcus pneumoniae* genome. The fragments of the *Streptococcus pneumoniae* genome of the present invention include, but are not limited to fragments which encode peptides and polypeptides, hereinafter open reading frames (ORFs), fragments which modulate the expression of an operably linked ORF, hereinafter expression modulating fragments (EMFs) and fragments which can be used to diagnose the presence of *Streptococcus pneumoniae* in a sample, hereinafter diagnostic fragments (DFs).

As used herein, an "isolated nucleic acid molecule" or an "isolated fragment of the *Streptococcus pneumoniae* genome" refers to a nucleic acid molecule possessing a specific nucleotide sequence which has been subjected to purification means to reduce, from the composition, the number of compounds which are normally associated with the composition. Particularly, the term refers to the nucleic acid molecules having the sequences set out in SEQ ID NOS:1-391, to representative fragments thereof as described above, to polynucleotides at least 95%, preferably at least 99% and especially preferably at least 99.9% identical in sequence thereto, also as set out above.

A variety of purification means can be used to generate the isolated fragments of the present invention. These include, but are not limited to methods which separate constituents of a solution based on charge, solubility, or size.

In one embodiment, *Streptococcus pneumoniae* DNA can be enzymatically sheared to produce fragments of 15-20 kb in length. These fragments can then be used to generate a *Streptococcus pneumoniae* library by inserting them into lambda clones as described in the Examples below. Primers flanking, for example, an ORF, such as those enumerated in Tables 1-3 can then be generated using nucleotide sequence information provided in SEQ ID NOS:1-391. Well known and routine techniques of PCR cloning then can be used to isolate the ORF from the lambda DNA library or *Streptococcus pneumoniae* genomic DNA. Thus, given the availability of SEQ ID NOS:1-391, the information in Tables 1, 2 and 3, and the information that may be obtained readily by analysis of the sequences of SEQ ID NOS:1-391 using methods set out above, those of skill will be enabled by the present disclosure to isolate any ORF-containing or other nucleic acid fragment of the present invention.

The isolated nucleic acid molecules of the present invention include, but are not limited to single stranded and double stranded DNA, and single stranded RNA.

As used herein, an "open reading frame," ORF, means a series of triplets coding for amino acids without any termination codons and is a sequence translatable into protein.

Tables 1, 2, and 3 list ORFs in the *Streptococcus pneumoniae* genomic contigs of the present invention that were identified as putative coding regions by the GeneMark software using organism-specific second-order Markov probability transition matrices. It will be appreciated that other criteria can be used, in accordance with well known analytical methods, such as those discussed herein, to generate more inclusive, more restrictive, or more selective lists.

Table 1 sets out ORFs in the *Streptococcus pneumoniae* contigs of the present invention that over a continuous region of at least 50 bases are 95% or more identical (by BLAST analysis) to a nucleotide sequence available through Gen-Bank in October, 1997.

Table 2 sets out ORFs in the *Streptococcus pneumoniae* contigs of the present invention that are not in Table 1 and match, with a BLASTP probability score of 0.01 or less, a polypeptide sequence available through GenBank in October, 1997.

Table 3 sets out ORFs in the *Streptococcus pneumoniae* contigs of the present invention that do not match significantly, by BLASTP analysis, a polypeptide sequence available through GenBank in October, 1997.

In each table, the first and second columns identify the ORF by, respectively, contig number and ORF number within the contig; the third column indicates the first nucleotide of the ORF (actually the first nucleotide of the stop codon immediately preceding the ORF), counting from the 5' end of the contig strand; and the fourth column, "stop (nt)" indicates the last nucleotide of the stop codon defining the 3'end of the ORF.

In Tables 1 and 2, column five, lists the Reference for the closest matching sequence available through GenBank. These reference numbers are the databases entry numbers commonly used by those of skill in the art, who will be familiar with their denominators. Descriptions of the nomenclature are available from the National Center for Biotechnology Information. Column six in Tables 1 and 2 provides the gene name of the matching sequence; column seven provides the BLAST identity score and column eight the BLAST similarity score from the comparison of the ORF and the homologous gene; and column nine indicates the length in nucleotides of the highest scoring segment pair identified by the BLAST identity analysis.

Each ORF described in the tables is defined by "start (nt)" (5') and "stop (nt)" (3') nucleotide numbers. These position numbers refer to the boundaries of each ORF and provide orientation with respect to whether the forward or reverse strand is the coding strand and which reading frame the coding sequence is contained. The "start" position is the first nucleotide of the triplet encoding a stop codon just 5' to the ORF and the "stop" position is the last nucleotide of the triplet encoding the next in-frame stop codon (i.e., the stop codon at the 3' end of the ORF). Those of ordinary skill in the art appreciate that preferred fragments within each ORF described in the table include fragments of each ORF which include the entire sequence from the delineated "start" and "stop" positions excepting the first and last three nucleotides since these encode stop codons. Thus, polynucleotides set out as ORFs in the tables but lacking the three (3) 5' nucleotides and the three (3) 3' nucleotides are encompassed by the present invention. Those of skill also appreciate that particularly preferred are fragments within each ORF that are polynucleotide fragments comprising polypeptide coding sequence. As defined herein, "coding sequence" includes the fragment within an ORF beginning at the first in-frame ATG (triplet encoding methionine) and ending with the last nucleotide prior to the triplet encoding the 3' stop codon. Preferred are fragments comprising the entire coding sequence and fragments comprising the entire coding sequence, excepting the coding sequence for the N-terminal methionine. Those of skill appreciate that the N-terminal methionine is often removed during post-translational processing and that polynucleotides lacking the ATG can be used to facilitate production of N-terminal fusion proteins which may be beneficial in the production or use of genetically engineered proteins. Of course, due to the degeneracy of the genetic code many polynucleotides can encode a given polypeptide. Thus, the invention further includes polynucleotides comprising a nucleotide sequence encoding a polypeptide sequence itself encoded by the coding sequence within an ORF described in Tables 1-3 herein. Further, polynucleotides at least 95%, preferably at least 99% and especially preferably at least 99.9% identical in sequence to the foregoing polynucleotides, are contemplated by the present invention.

Polypeptides encoded by polynucleotides described above and elsewhere herein are also provided by the present invention as are polypeptide comprising a an amino acid sequence at least about 95%, preferably at least 97% and even more preferably 99% identical to the amino acid sequence of a polypeptide encoded by an ORF shown in Tables 1-3. These polypeptides may or may not comprise an N-terminal methionine.

The concepts of percent identity and percent similarity of two polypeptide sequences is well understood in the art. For example, two polypeptides 10 amino acids in length which differ at three amino acid positions (e.g., at positions 1, 3 and 5) are said to have a percent identity of 70%. However, the same two polypeptides would be deemed to have a percent similarity of 80% if, for example at position 5, the amino acids moieties, although not identical, were "similar" (i.e., possessed similar biochemical characteristics). Many programs for analysis of nucleotide or amino acid sequence similarity, such as fasta and BLAST specifically list percent identity of a matching region as an output parameter. Thus, for instance, Tables 1 and 2 herein enumerate the percent identity of the highest scoring segment pair in each ORF and its listed relative. Further details concerning the algorithms and criteria used for homology searches are provided below and are described in the pertinent literature highlighted by the citations provided below.

It will be appreciated that other criteria can be used to generate more inclusive and more exclusive listings of the types set out in the tables. As those of skill will appreciate, narrow and broad searches both are useful. Thus, a skilled artisan can readily identify ORFs in contigs of the *Streptococcus pneumoniae* genome other than those listed in Tables 1-3, such as ORFs which are overlapping or encoded by the opposite strand of an identified ORF in addition to those ascertainable using the computer-based systems of the present invention.

As used herein, an "expression modulating fragment," EMF, means a series of nucleotide molecules which modulates the expression of an operably linked ORF or EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event.

EMF sequences can be identified within the contigs of the *Streptococcus pneumoniae* genome by their proximity to the ORFs provided in Tables 1-3. An intergenic segment, or a fragment of the intergenic segment, from about 10 to 200 nucleotides in length, taken from any one of the ORFs of Tables 1-3 will modulate the expression of an operably linked ORF in a fashion similar to that found with the naturally linked ORF sequence. As used herein, an "intergenic segment" refers to fragments of the *Streptococcus pneumoniae* genome which are between two ORF(s) herein described. EMFs also can be identified using known EMFs as a target sequence or target motif in the computer-based systems of the present invention. Further, the two methods can be combined and used together.

The presence and activity of an EMF can be confirmed using an EMF trap vector. An EMF trap vector contains a cloning site linked to a marker sequence. A marker sequence encodes an identifiable phenotype, such as antibiotic resistance or a complementing nutrition auxotrophic factor, which can be identified or assayed when the EMF trap vector is placed within an appropriate host under appropriate conditions. As described above, a EMF will modulate the expression of an operably linked marker sequence. A more detailed discussion of various marker sequences is provided below. A sequence which is suspected as being an EMF is cloned in all three reading frames in one or more restriction sites upstream from the marker sequence in the EMF trap vector. The vector is then transformed into an appropriate host using known procedures and the phenotype of the transformed host in examined under appropriate conditions. As described above, an EMF will modulate the expression of an operably linked marker sequence.

As used herein, a "diagnostic fragment," DF, means a series of nucleotide molecules which selectively hybridize to *Streptococcus pneumoniae* sequences. DFs can be readily identified by identifying unique sequences within contigs of the *Streptococcus pneumoniae* genome, such as by using well-known computer analysis software, and by generating and testing probes or amplification primers consisting of the DF sequence in an appropriate diagnostic format which determines amplification or hybridization selectivity.

The sequences falling within the scope of the present invention are not limited to the specific sequences herein described, but also include allelic and species variations thereof. Allelic and species variations can be routinely determined by comparing the sequences provided in SEQ ID NOS: 1-391, a representative fragment thereof, or a nucleotide sequence at least 95%, preferably at least 99% and most at least preferably 99.9% identical to SEQ ID NOS:1-391, with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated. Any specific sequence disclosed herein can be readily screened for errors by resequencing a particular fragment, such as an ORF, in both directions (i.e., sequence both strands). Alternatively, error screening can be performed by sequencing corresponding polynucleotides of *Streptococcus pneumoniae* origin isolated by using part or all of the fragments in question as a probe or primer.

Preferred DFs of the present invention comprise at least about 17, preferably at least about 20, and more preferably at least about 50 contiguous nucleotides within an ORF set out in Tables 1-3. Most highly preferred DFs specifically hybridize to a polynucleotide containing the sequence of the ORF from which they are derived. Specific hybridization occurs even under stringent conditions defined elsewhere herein.

Each of the ORFs of the *Streptococcus pneumoniae* genome disclosed in Tables 1, 2 and 3, and the EMFs found 5' to the ORFs, can be used as polynucleotide reagents in numerous ways. For example, the sequences can be used as diagnostic probes or diagnostic amplification primers to detect the presence of a specific microbe in a sample, particularly *Streptococcus pneumoniae*. Especially preferred in this regard are ORFs such as those of Table 3, which do not match previously characterized sequences from other organisms and thus are most likely to be highly selective for *Streptococcus pneumoniae*. Also particularly preferred are ORFs that can be used to distinguish between strains of *Streptococcus pneumoniae*, particularly those that distinguish medically important strain, such as drug-resistant strains.

In addition, the fragments of the present invention, as broadly described, can be used to control gene expression through triple helix formation or antisense DNA or RNA, both of which methods are based on the binding of a polynucleotide sequence to DNA or RNA. Triple helix-formation optimally results in a shut-off of RNA transcription from DNA, while antisense RNA hybridization blocks translation of an mRNA molecule into polypeptide. Information from the sequences of the present invention can be used to design antisense and triple helix-forming oligonucleotides. Polynucleotides suitable for use in these methods are usually 20 to 40 bases in length and are designed to be complementary to a region of the gene involved in transcription, for triple-helix formation, or to the mRNA itself, for antisense inhibition. Both techniques have been demonstrated to be effective in model systems, and the requisite techniques are well known and involve routine procedures. Triple helix techniques are discussed in, for example, Lee et al., *Nucl. Acids Res.* 6:3073 (1979); Cooney et al., *Science* 241:456 (1988); and Dervan et al., *Science* 251:1360 (1991). Antisense techniques in general are discussed in, for instance, Okano, *J. Neurochem.* 56:560 (1991) and *Oligodeoxynucleotides as Antisense Inhibitors of Gene Expression*, CRC Press, Boca Raton, Fla. (1988)).

The present invention further provides recombinant constructs comprising one or more fragments of the *Streptococcus pneumoniae* genomic fragments and contigs of the present invention. Certain preferred recombinant constructs of the present invention comprise a vector, such as a plasmid or viral vector, into which a fragment of the *Streptococcus pneumoniae* genome has been inserted, in a forward or reverse orientation. In the case of a vector comprising one of the ORFs of the present invention, the vector may further comprise regulatory sequences, including for example, a promoter, operably linked to the ORF. For vectors comprising the EMFs of the present invention, the vector may further comprise a marker sequence or heterologous ORF operably linked to the EMF.

Large numbers of suitable vectors and promoters are known to those of skill in the art and are commercially available for generating the recombinant constructs of the present invention. The following vectors are provided by way of example. Useful bacterial vectors include phagescript, PsiX174, pBluescript SK, pBS KS, pNH8a, pNH16a, pNH18a, pNH46a (available from Stratagene); pTrc99A, pKK223-3, pKK 233-3, pDR540, pRIT5 (available from Pharmacia). Useful eukaryotic vectors include pWLneo, pSV2cat, pOG44, pXT1, pSG (available from Stratagene) pSVK3, pBPV, pMSG, pSVL (available from Pharmacia).

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda PR, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

The present invention further provides host cells containing any one of the isolated fragments of the *Streptococcus pneumoniae* genomic fragments and contigs of the present invention, wherein the fragment has been introduced into the host cell using known methods. The host cell can be a higher eukaryotic host cell, such as a mammalian cell, a lower eukaryotic host cell, such as a yeast cell, or a procaryotic cell, such as a bacterial cell.

A polynucleotide of the present invention, such as a recombinant construct comprising an ORF of the present invention, may be introduced into the host by a variety of well established techniques that are standard in the art, such as calcium phosphate transfection, DEAE, dextran mediated transfection and electroporation, which are described in, for instance, Davis, L. et al., BASIC METHODS IN MOLECULAR BIOLOGY (1986).

A host cell containing one of the fragments of the *Streptococcus pneumoniae* genomic fragments and contigs of the present invention, can be used in conventional manners to produce the gene product encoded by the isolated fragment (in the case of an ORF) or can be used to produce a heterologous protein under the control of the EMF.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the Genetic Code, encode an identical polypeptide sequence.

Preferred nucleic acid fragments of the present invention are the ORFs and subfragments thereof depicted in Tables 2 and 3 which encode proteins.

A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Such short fragments as may be obtained most readily by synthesis are useful, for example, in generating antibodies against the native polypeptide, as discussed further below.

In an alternative method, the polypeptide or protein is purified from bacterial cells which naturally produce the polypeptide or protein. One skilled in the art can readily employ well-known methods for isolating polypeptides and proteins to isolate and purify polypeptides or proteins of the present invention produced naturally by a bacterial strain, or by other methods. Methods for isolation and purification that can be employed in this regard include, but are not limited to, immunochromatography, HPLC, size-exclusion chromatography, ion-exchange chromatography, and immuno-affinity chromatography.

The polypeptides and proteins of the present invention also can be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. Those skilled in the art can readily adapt procedures for introducing and expressing either recombinant or synthetic sequences into eukaryotic or prokaryotic cells in order to generate a cell which produces one of the polypeptides or proteins of the present invention.

Any host/vector system can be used to express one or more of the ORFs of the present invention. These include, but are not limited to, eukaryotic hosts such as HeLa cells, CV-1 cell, COS cells, and Sf9 cells, as well as prokaryotic host such as *E. coli* and *B. subtilis*. The most preferred cells are those which do not normally express the particular polypeptide or protein or which expresses the polypeptide or protein at low natural level.

"Recombinant," as used herein, means that a polypeptide or protein is derived from recombinant (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. coli*, will be free of glycosylation modifications; polypeptides or proteins expressed in yeast will have a glycosylation pattern different from that expressed in mammalian cells.

"Nucleotide sequence" refers to a heteropolymer of deoxyribonucleotides. Generally, DNA segments encoding the polypeptides and proteins provided by this invention are assembled from fragments of the *Streptococcus pneumoniae* genome and short oligonucleotide linkers, or from a series of oligonucleotides, to provide a synthetic gene which is capable of being expressed in a recombinant transcriptional unit comprising regulatory elements derived from a microbial or viral operon.

Recombinant expression vehicle or vector" refers to a plasmid or phage or virus or vector, for expressing a polypeptide from a DNA (RNA) sequence. The expression vehicle can comprise a transcriptional unit comprising an assembly of (1) a genetic regulatory elements necessary for gene expression in the host, including elements required to initiate and maintain transcription at a level sufficient for suitable expression of the desired polypeptide, including, for example, promoters and, where necessary, an enhancer and a polyadenylation signal; (2) a structural or coding sequence which is transcribed into mRNA and translated into protein, and (3) appropriate signals to initiate translation at the beginning of the desired coding region and terminate translation at its end. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

"Recombinant expression system" means host cells which have stably integrated a recombinant transcriptional unit into chromosomal DNA or carry the recombinant transcriptional unit extra chromosomally. The cells can be prokaryotic or eukaryotic. Recombinant expression systems as defined herein will express heterologous polypeptides or proteins upon induction of the regulatory elements linked to the DNA segment or synthetic gene to be expressed.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described in Sambrook et al., *Molecular Cloning: A Laboratory Manual,* 2nd Edition, Cold Spring Harbor Laboratory Press, Cold Spring Harbor, N.Y. (1989), the disclosure of which is hereby incorporated by reference in its entirety.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly expressed gene to direct transcription of a downstream structural sequence. Such promoters can be derived from operons encoding glycolytic enzymes such as 3-phosphoglycerate kinase (PGK), alpha-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, when desirable, provide amplification within the host.

Suitable prokaryotic hosts for transformation include strains of *E. coli, B. subtilis, Salmonella typhimurium* and various species within the genera *Pseudomonas* and *Streptomyces*. Others may, also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC™ 37017). Such commercial vectors include, for example, pKK223-3 (available form Pharmacia Fine Chemicals, Uppsala, Sweden) and GEM 1 (available from Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter, where it is inducible, is derepressed or induced by appropriate means (e.g., temperature shift or chemical induction) and cells are cultured for an additional period to provide for expression of the induced gene product.

Thereafter cells are typically harvested, generally by centrifugation, disrupted to release expressed protein, generally by physical or chemical means, and the resulting crude extract is retained for further purification.

Various mammalian cell culture systems can also be employed to express recombinant protein. Examples of mammalian expression systems include the COS-7 lines of monkey kidney fibroblasts, described in Gluzman, *Cell* 23:175 (1981), and other cell lines capable of expressing a compatible vector, for example, the C127, 3T3, CHO, HeLa and BHK cell lines.

Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Recombinant polypeptides and proteins produced in bacterial culture is usually isolated by initial extraction from cell pellets, followed by one or more salting-out, aqueous ion exchange or size exclusion chromatography steps. Microbial cells employed in expression of proteins can be disrupted by any convenient method, including freeze-thaw cycling, sonication, mechanical disruption, or use of cell lysing agents. Protein refolding steps can be used, as necessary, in completing configuration of the mature protein. Finally, high performance liquid chromatography (HPLC) can be employed for final purification steps.

The present invention further includes isolated polypeptides, proteins and nucleic acid molecules which are substantially equivalent to those herein described. As used herein, substantially equivalent can refer both to nucleic acid and amino acid sequences, for example a mutant sequence, that varies from a reference sequence by one or more substitutions, deletions, or additions, the net effect of which does not result in an adverse functional dissimilarity between reference and subject sequences. For purposes of the present invention, sequences having equivalent biological activity, and equivalent expression characteristics are considered substantially equivalent. For purposes of determining equivalence, truncation of the mature sequence should be disregarded.

The invention further provides methods of obtaining homologs from other strains of *Streptococcus pneumoniae*, of the fragments of the *Streptococcus pneumoniae* genome of the present invention and homologs of the proteins encoded by the ORFs of the present invention. As used herein, a sequence or protein of *Streptococcus pneumoniae* is defined as a homolog of a fragment of the *Streptococcus pneumoniae* fragments or contigs or a protein encoded by one of the ORFs of the present invention, if it shares significant homology to one of the fragments of the *Streptococcus pneumoniae* genome of the present invention or a protein encoded by one of the ORFs of the present invention. Specifically, by using the sequence disclosed herein as a probe or as primers, and techniques such as PCR cloning and colony/plaque hybridization, one skilled in the art can obtain homologs.

As used herein, two nucleic acid molecules or proteins are said to "share significant homology" if the two contain regions which possess greater than 85% sequence (amino acid or nucleic acid) homology. Preferred homologs in this regard are those with more than 90% homology. Especially preferred are those with 93% or more homology. Among especially preferred homologs those with 95% or more homology are particularly preferred. Very particularly preferred among these are those with 97% and even more particularly preferred among those are homologs with 99% or more homology. The most preferred homologs among these are those with 99.9% homology or more. It will be understood that, among measures of homology, identity is particularly preferred in this regard.

Region specific primers or probes derived from the nucleotide sequence provided in SEQ ID NOS:1-391 or from a nucleotide sequence at least 95%, particularly at least 99%, especially at least 99.5% identical to a sequence of SEQ ID NOS:1-391 can be used to prime DNA synthesis and PCR amplification, as well as to identify colonies containing cloned DNA encoding a homolog. Methods suitable to this aspect of the present invention are well known and have been described in great detail in many publications such as, for example, Innis et al., PCR Protocols, Academic Press, San Diego, Calif. (1990)).

When using primers derived from SEQ ID NOS:1-391 or from a nucleotide sequence having an aforementioned identity to a sequence of SEQ ID NOS:1-391, one skilled in the art will recognize that by employing high stringency conditions (e.g., annealing at 50-60° C. in 6×SSC and 50% formamide, and washing at 50-65° C. in 0.5×SSC) only sequences which are greater than 75% homologous to the primer will be amplified. By employing lower stringency conditions (e.g., hybridizing at 35-37° C. in 5×SSC and 40-45% formamide, and washing at 42° C. in 0.5×SSC), sequences which are greater than 40-50% homologous to the primer will also be amplified.

When using DNA probes derived from SEQ ID NOS:1-391, or from a nucleotide sequence having an aforementioned identity to a sequence of SEQ ID NOS:1-391, for colony/plaque hybridization, one skilled in the art will recognize that by employing high stringency conditions (e.g., hybridizing at 50-65° C. in 5×SSC and 50% formamide, and washing at 50-65° C. in 0.5×SSC), sequences having regions which are greater than 90% homologous to the probe can be obtained, and that by employing lower stringency conditions (e.g., hybridizing at 35-37° C. in 5×SSC and 40-45% formamide, and washing at 42° C. in 0.5×SSC), sequences having regions which are greater than 35-45% homologous to the probe will be obtained.

Any organism can be used as the source for homologs of the present invention so long as the organism naturally expresses such a protein or contains genes encoding the same. The most preferred organism for isolating homologs are bacteria which are closely related to Streptococcus pneumoniae.

Illustrative Uses of Compositions of the Invention

Each ORF provided in Tables 1 and 2 is identified with a function by homology to a known gene or polypeptide. As a result, one skilled in the art can use the polypeptides of the present invention for commercial, therapeutic and industrial purposes consistent with the type of putative identification of the polypeptide. Such identifications permit one skilled in the art to use the Streptococcus pneumoniae ORFs in a manner similar to the known type of sequences for which the identification is made; for example, to ferment a particular sugar source or to produce a particular metabolite. A variety of reviews illustrative of this aspect of the invention are available, including the following reviews on the industrial use of enzymes, for example, BIOCHEMICAL ENGINEERING AND BIOTECHNOLOGY HANDBOOK, 2nd Ed., MacMillan Publications, Ltd. NY (1991) and BIOCATALYSTS IN ORGANIC SYNTHESES, Tramper et al., Eds., Elsevier Science Publishers, Amsterdam, The Netherlands (1985). A variety of exemplary uses that illustrate this and similar aspects of the present invention are discussed below.

1. Biosynthetic Enzymes

Open reading frames encoding proteins involved in mediating the catalytic reactions involved in intermediary and macromolecular metabolism, the biosynthesis of small molecules, cellular processes and other functions includes enzymes involved in the degradation of the intermediary products of metabolism, enzymes involved in central intermediary metabolism, enzymes involved in respiration, both aerobic and anaerobic, enzymes involved in fermentation, enzymes involved in ATP proton motor force conversion, enzymes involved in broad regulatory function, enzymes involved in amino acid synthesis, enzymes involved in nucleotide synthesis, enzymes involved in cofactor and vitamin synthesis, can be used for industrial biosynthesis.

The various metabolic pathways present in Streptococcus pneumoniae can be identified based on absolute nutritional requirements as well as by examining the various enzymes identified in Table 1-3 and SEQ ID NOS:1-391.

Of particular interest are polypeptides involved in the degradation of intermediary metabolites as well as non-macromolecular metabolism. Such enzymes include amylases, glucose oxidases, and catalase.

Proteolytic enzymes are another class of commercially important enzymes. Proteolytic enzymes find use in a number of industrial processes including the processing of flax and other vegetable fibers, in the extraction, clarification and depectinization of fruit juices, in the extraction of vegetables' oil and in the maceration of fruits and vegetables to give unicellular fruits. A detailed review of the proteolytic enzymes used in the food industry is provided in Rombouts et al., Symbiosis 21:79 (1986) and Voragen et al. in Biocatalysts In Agricultural Biotechnology, Whitaker et al., Eds., American Chemical Society Symposium Series 389:93 (1989).

The metabolism of sugars is an important aspect of the primary metabolism of Streptococcus pneumoniae. Enzymes involved in the degradation of sugars, such as, particularly, glucose, galactose, fructose and xylose, can be used in industrial fermentation. Some of the important sugar transforming enzymes, from a commercial viewpoint, include sugar isomerases such as glucose isomerase. Other metabolic enzymes have found commercial use such as glucose oxidases which produces ketogulonic acid (KGA). KGA is an intermediate in the commercial production of ascorbic acid using the Reichstein's procedure, as described in Krueger et al., Biotechnology 6(A), Rhine et al., Eds., Verlag Press, Weinheim, Germany (1984).

Glucose oxidase (GOD) is commercially available and has been used in purified form as well as in an immobilized form for the deoxygenation of beer. See, for instance, Hartmeir et al., Biotechnology Letters 1:21 (1979). The most important application of GOD is the industrial scale fermentation of gluconic acid. Market for gluconic acids which are used in the detergent, textile, leather, photographic, pharmaceutical, food, feed and concrete industry, as described, for example, in Bigelis et al., beginning on page 357 in GENE MANIPULATIONS AND FUNGI; Benett et al., Eds., Academic Press, New York (1985). In addition to industrial applications, GOD has found applications in medicine for quantitative determination of glucose in body fluids recently in biotechnology for analyzing syrups from starch and cellulose hydrosylates. This application is described in Owusu et al., Biochem. et Biophysica. Acta. 872:83 (1986), for instance.

The main sweetener used in the world today is sugar which comes from sugar beets and sugar cane. In the field of industrial enzymes, the glucose isomerase process shows the largest expansion in the market today. Initially, soluble enzymes were used and later immobilized enzymes were developed (Krueger et al., *Biotechnology, The Textbook of Industrial Microbiology*, Sinauer Associated Incorporated, Sunderland, Mass. (1990)). Today, the use of glucose-produced high fructose syrups is by far the largest industrial business using immobilized enzymes. A review of the industrial use of these enzymes is provided by Jorgensen, Starch 40:307 (1988).

Proteinases, such as alkaline serine proteinases, are used as detergent additives and thus represent one of the largest volumes of microbial enzymes used in the industrial sector. Because of their industrial importance, there is a large body of published and unpublished information regarding the use of these enzymes in industrial processes. (See Faultman et al., Acid Proteases Structure Function and Biology, Tang, J., ed., Plenum Press, New York (1977) and Godfrey et al., Industrial Enzymes, MacMillan Publishers, Surrey, UK (1983) and Hepner et al., Report Industrial Enzymes by 1990, Hel Hepner & Associates, London (1986)).

Another class of commercially usable proteins of the present invention are the microbial lipases, described by, for instance, Macrae et al., *Philosophical Transactions of the Chiral Society of London* 310:227 (1985) and Poserke, *Journal of the American Oil Chemist Society* 61:1758 (1984). A major use of lipases is in the fat and oil industry for the production of neutral glycerides using lipase catalyzed inter-esterification of readily available triglycerides. Application of lipases include the use as a detergent additive to facilitate the removal of fats from fabrics in the course of the washing procedures.

The use of enzymes, and in particular microbial enzymes, as catalyst for key steps in the synthesis of complex organic molecules is gaining popularity at a great rate. One area of great interest is the preparation of chiral intermediates. Preparation of chiral intermediates is of interest to a wide range of synthetic chemists particularly those scientists involved with the preparation of new pharmaceuticals, agrochemicals, fragrances and flavors. (See Davies et al., *Recent Advances in the Generation of Chiral Intermediates Using Enzymes*, CRC Press, Boca Raton, Fla. (1990)). The following reactions catalyzed by enzymes are of interest to organic chemists: hydrolysis of carboxylic acid esters, phosphate esters, amides and nitriles, esterification reactions, trans-esterification reactions, synthesis of amides, reduction of alkanones and oxoalkanates, oxidation of alcohols to carbonyl compounds, oxidation of sulfides to sulfoxides, and carbon bond forming reactions such as the aldol reaction.

When considering the use of an enzyme encoded by one of the ORFs of the present invention for biotransformation and organic synthesis it is sometimes necessary to consider the respective advantages and disadvantages of using a microorganism as opposed to an isolated enzyme. Pros and cons of using a whole cell system on the one hand or an isolated partially purified enzyme on the other hand, has been described in detail by Bud et al., Chemistry in Britain (1987), p. 127.

Amino transferases, enzymes involved in the biosynthesis and metabolism of amino acids, are useful in the catalytic production of amino acids. The advantages of using microbial based enzyme systems is that the amino transferase enzymes catalyze the stereo-selective synthesis of only L-amino acids and generally possess uniformly high catalytic rates. A description of the use of amino transferases for amino acid production is provided by Roselle-David, *Methods of Enzymology* 136:479 (1987).

Another category of useful proteins encoded by the ORFs of the present invention include enzymes involved in nucleic acid synthesis, repair, and recombination.

2. Generation of Antibodies

As described here, the proteins of the present invention, as well as homologs thereof, can be used in a variety of procedures and methods known in the art which are currently applied to other proteins. The proteins of the present invention can further be used to generate an antibody which selectively binds the protein. Such antibodies can be either monoclonal or polyclonal antibodies, as well fragments of these antibodies, and humanized forms.

The invention further provides antibodies which selectively bind to one of the proteins of the present invention and hybridomas which produce these antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (Campbell, A. M., *Monoclonal Antibody Technology: Laboratory Techniques In Biochemistry And Molecular Biology*, Elsevier Science Publishers, Amsterdam, The Netherlands (1984); St. Groth et al., *J. Immunol. Methods* 35: 1-21 (1980), Kohler and Milstein, *Nature* 256:495-497 (1975)), the trioma technique, the human B-cell hybridoma technique (Kozbor et al., *Immunology Today* 4:72 (1983), pgs. 77-96 of Cole et al., in *Monoclonal Antibodies And Cancer Therapy*, Alan R. Liss, Inc. (1985)). Any animal (mouse, rabbit, etc.) which is known to produce antibodies can be immunized with the pseudogene polypeptide. Methods for immunization are well known in the art. Such methods include subcutaneous or interperitoneal injection of the polypeptide. One skilled in the art will recognize that the amount of the protein encoded by the ORF of the present invention used for immunization will vary based on the animal which is immunized, the antigenicity of the peptide and the site of injection.

The protein which is used as an immunogen may be modified or administered in an adjuvant in order to increase the protein's antigenicity. Methods of increasing the antigenicity of a protein are well known in the art and include, but are not limited to coupling the antigen with a heterologous protein (such as globulin or galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109-124 (1988)).

Hybridomas secreting the desired antibodies are cloned and the class and subclass is determined using procedures known in the art (Campbell, A. A, *Monoclonal Antibody Technology: Laboratory Techniques in Biochemistry and Molecular Biology*, Elsevier Science Publishers, Amsterdam, The Netherlands (1984)).

Techniques described for the production of single chain antibodies (U.S. Pat. No. 4,946,778) can be adapted to produce single chain antibodies to proteins of the present invention.

For polyclonal antibodies, antibody containing antisera is isolated from the immunized animal and is screened for the presence of antibodies with the desired specificity using one of the above-described procedures.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example see Sternberger et al., *J. Histochem. Cytochem.* 18:315 (1970); Bayer, E. A. et al., *Meth. Enzym.* 62:308 (1979); Engval, E. et al., *Immunol.* 109:129 (1972); Goding, J. W., *J. Immunol. Meth.* 13:215 (1976)).

The labeled antibodies of the present invention can be used for in vitro, in vivo, and in situ assays to identify cells or tissues in which a fragment of the *Streptococcus pneumoniae* genome is expressed.

The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., "Handbook of Experimental Immunology" 4th Ed., Blackwell Scientific Publications, Oxford, England, Chapter 10 (1986); Jacoby, W. D. et al., Meth. Enzym. 34 Academic Press, N. Y. (1974)). The immobilized antibodies of the present invention can be used for in vitro, in vivo, and in situ assays as well as for immunoaffinity purification of the proteins of the present invention.

3. Diagnostic Assays and Kits

The present invention further provides methods to identify the expression of one of the ORFs of the present invention, or homolog thereof, in a test sample, using one of the DFs or antibodies of the present invention.

In detail, such methods comprise incubating a test sample with one or more of the antibodies or one or more of the DFs of the present invention and assaying for binding of the DFs or antibodies to components within the test sample.

Conditions for incubating a DF or antibody with a test sample vary. Incubation conditions depend on the format employed in the assay, the detection methods employed, and the type and nature of the DF or antibody used in the assay. One skilled in the art will recognize that any one of the commonly available hybridization, amplification or immunological assay formats can readily be adapted to employ the DFs or antibodies of the present invention. Examples of such assays can be found in Chard, T., *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the DFs or antibodies of the present invention; and (b) one or more other containers comprising one or more of the following: wash reagents, reagents capable of detecting presence of a bound DF or antibody.

In detail, a compartmentalized kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or DF.

Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed DFs and antibodies of the present invention can be readily incorporated into one of the established kit formats which are well known in the art.

4. Screening Assay for Binding Agents

Using the isolated proteins of the present invention, the present invention further provides methods of obtaining and identifying agents which bind to a protein encoded by one of the ORFs of the present invention or to one of the fragments and the *Streptococcus pneumoniae* fragment and contigs herein described.

In general, such methods comprise steps of:

contacting an agent with an isolated protein encoded by one of the ORFs of the present invention, or an isolated fragment of the *Streptococcus pneumoniae* genome; and determining whether the agent binds to said protein or said fragment.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention.

Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., "Application of Synthetic Peptides: Antisense Peptides," in *Synthetic Peptides, A User's Guide*, W. H. Freeman, NY (1992), pp. 289-307, and Kaspczak et al., *Biochemistry* 28:9230-8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control.

One class of DNA binding agents are agents which contain base residues which hybridize or form a triple helix by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., *Nucl. Acids Res.* 6:3073 (1979); Cooney et al., *Science* 241:456 (1988); and Dervan et al., *Science* 251:1360 (1991)) or to the mRNA itself (antisense—Okano, *J. Neurochem.* 56:560 (1991); *Oligodeoxynucleotides as Antisense Inhibitors of Gene Expression*, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention can be used to design antisense and triple helix-forming oligonucleotides, and other DNA binding agents.

5. Pharmaceutical Compositions and Vaccines

The present invention further provides pharmaceutical agents which can be used to modulate the growth or pathogenicity of *Streptococcus pneumoniae*, or another related organism, in vivo or in vitro. As used herein, a "pharmaceutical agent" is defined as a composition of matter which can be formulated using known techniques to provide a pharmaceutical compositions. As used herein, the "pharmaceutical agents of the present invention" refers the pharmaceutical agents which are derived from the proteins encoded by the ORFs of the present invention or are agents which are identified using the herein described assays.

As used herein, a pharmaceutical agent is said to "modulate the growth pathogenicity of *Streptococcus pneumoniae* or a related organism, in vivo or in vitro," when the agent reduces the rate of growth, rate of division, or viability of the organism in question. The pharmaceutical agents of the present invention can modulate the growth or pathogenicity of an organism in many fashions, although an understanding of the underlying mechanism of action is not needed to practice the use of the pharmaceutical agents of the present invention. Some agents will modulate the growth by binding to an important protein thus blocking the biological activity of the protein, while other agents may bind to a component of the outer surface of the organism blocking attachment or rendering the organism more prone to act the bodies nature immune system. Alternatively, the agent may comprise a protein encoded by one of the ORFs of the present invention and serve as a vaccine. The development and use of a vaccine based on outer membrane components are well known in the art.

As used herein, a "related organism" is a broad term which refers to any organism whose growth can be modulated by one of the pharmaceutical agents of the present invention. In general, such an organism will contain a homolog of the protein which is the target of the pharmaceutical agent or the protein used as a vaccine. As such, related organisms do not need to be bacterial but may be fungal or viral pathogens.

The pharmaceutical agents and compositions of the present invention may be administered in a convenient manner, such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 1 mg/kg body weight and in most cases they will be administered in an amount not in excess of about 1 g/kg body weight per day. In most cases, the dosage is from about 0.1 mg/kg to about 10 g/kg body weight daily, taking into account the routes of administration, symptoms, etc.

The agents of the present invention can be used in native form or can be modified to form a chemical derivative. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in, among other sources, REMINGTON'S PHARMACEUTICAL SCIENCES (1980) cited elsewhere herein.

For example, such moieties may change an immunological character of the functional derivative, such as affinity for a given antibody. Such changes in immunomodulation activity are measured by the appropriate assay, such as a competitive type immunoassay. Modifications of such protein properties as redox or thermal stability, biological half-life, hydrophobicity, susceptibility to proteolytic degradation or the tendency to aggregate with carriers or into multimers also may be effected in this way and can be assayed by methods well known to the skilled artisan.

The therapeutic effects of the agents of the present invention may be obtained by providing the agent to a patient by any suitable means (e.g., inhalation, intravenously, intramuscularly, subcutaneously, enterally, or parenterally). It is preferred to administer the agent of the present invention so as to achieve an effective concentration within the blood or tissue in which the growth of the organism is to be controlled. To achieve an effective blood concentration, the preferred method is to administer the agent by injection. The administration may be by continuous infusion, or by single or multiple injections.

In providing a patient with one of the agents of the present invention, the dosage of the administered agent will vary depending upon such factors as the patient's age, weight, height, sex, general medical condition, previous medical history, etc. In general, it is desirable to provide the recipient with a dosage of agent which is in the range of from about 1 pg/kg to 10 mg/kg (body weight of patient), although a lower or higher dosage may be administered. The therapeutically effective dose can be lowered by using combinations of the agents of the present invention or another agent.

As used herein, two or more compounds or agents are said to be administered "in combination" with each other when either (1) the physiological effects of each compound, or (2) the serum concentrations of each compound can be measured at the same time. The composition of the present invention can be administered concurrently with, prior to, or following the administration of the other agent.

The agents of the present invention are intended to be provided to recipient subjects in an amount sufficient to decrease the rate of growth (as defined above) of the target organism.

The administration of the agent(s) of the invention may be for either a "prophylactic" or "therapeutic" purpose. When provided prophylactically, the agent(s) are provided in advance of any symptoms indicative of the organisms growth. The prophylactic administration of the agent(s) serves to prevent, attenuate, or decrease the rate of onset of any subsequent infection. When provided therapeutically, the agent(s) are provided at (or shortly after) the onset of an indication of infection. The therapeutic administration of the compound(s) serves to attenuate the pathological symptoms of the infection and to increase the rate of recovery.

The agents of the present invention are administered to a subject, such as a mammal, or a patient, in a pharmaceutically acceptable form and in a therapeutically effective concentration. A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The agents of the present invention can be formulated according to known methods to prepare pharmaceutically useful compositions, whereby these materials, or their functional derivatives, are combined in a mixture with a pharmaceutically acceptable carrier vehicle. Suitable vehicles and their formulation, inclusive of other human proteins, e.g., human serum albumin, are described, for example, in REMINGTON'S PHARMACEUTICAL SCIENCES, 16$^{th}$ Ed., Osol, A., Ed., Mack Publishing, Easton Pa. (1980). In order to form a pharmaceutically acceptable composition suitable for effective administration, such compositions will contain an effective amount of one or more of the agents of the present invention, together with a suitable amount of carrier vehicle.

Additional pharmaceutical methods may be employed to control the duration of action. Control release preparations may be achieved through the use of polymers to complex or absorb one or more of the agents of the present invention. The controlled delivery may be effectuated by a variety of well known techniques, including formulation with macromolecules such as, for example, polyesters, polyamino acids, polyvinyl, pyrrolidone, ethylenevinylacetate, methylcellulose, carboxymethylcellulose, or protamine, sulfate, adjusting the concentration of the macromolecules and the agent in the formulation, and by appropriate use of methods of incorporation, which can be manipulated to effectuate a desired time course of release. Another possible method to control the duration of action by controlled release preparations is to incorporate agents of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization with, for example, hydroxymethylcellulose or gelatine-microcapsules and poly (methylmethacylate) microcapsules, respectively, or in colloidal drug delivery systems, for example, liposomes, albumin microspheres, microemulsions, nanoparticles, and nanocapsules or in macroemulsions. Such techniques are disclosed in REMINGTON'S PHARMACEUTICAL SCIENCES (1980).

The invention further provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In addition, the agents of the present invention may be employed in conjunction with other therapeutic compounds.

6. Shot-Gun Approach to Megabase DNA Sequencing

The present invention further demonstrates that a large sequence can be sequenced using a random shotgun approach. This procedure, described in detail in the examples that follow, has eliminated the up front cost of isolating and ordering overlapping or contiguous subclones prior to the start of the sequencing protocols.

Certain aspects of the present invention are described in greater detail in the examples that follow. The examples are provided by way of illustration. Other aspects and embodiments of the present invention are contemplated by the inventors, as will be clear to those of skill in the art from reading the present disclosure.

ILLUSTRATIVE EXAMPLES

Libraries and Sequencing

1. Shotgun Sequencing Probability Analysis

The overall strategy for a shotgun approach to whole genome sequencing follows from the Lander and Waterman (Landerman and Waterman, *Genomics* 2:231 (1988)) application of the equation for the Poisson distribution. According to this treatment, the probability, P, that any given base in a sequence of size L, in nucleotides, is not sequenced after a certain amount, n, in nucleotides, of random sequence has been determined can be calculated by the equation $P=e^{-m}$, where m is L/n, the fold coverage. For instance, for a genome of 2.8 Mb, m=1 when 2.8 Mb of sequence has been randomly generated (1× coverage). At that point, $P=e^{-1}=0.37$. The probability that any given base has not been sequenced is the same as the probability that any region of the whole sequence L has not been determined and, therefore, is equivalent to the fraction of the whole sequence that has yet to be determined. Thus, at one-fold coverage, approximately 37% of a polynucleotide of size L, in nucleotides has not been sequenced. When 14 Mb of sequence has been generated, coverage is 5× for a 2.8 Mb and the unsequenced fraction drops to 0.0067 or 0.67%. 5× coverage of a 2.8 Mb sequence can be attained by sequencing approximately 17,000 random clones from both insert ends with an average sequence read length of 410 bp.

Similarly, the total gap length, G, is determined by the equation $G=Le^{-m}$, and the average gap size, g, follows the equation, g=L/n. Thus, 5× coverage leaves about 240 gaps averaging about 82 bp in size in a sequence of a polynucleotide 2.8 Mb long.

The treatment above is essentially that of Lander and Waterman, *Genomics* 2: 231 (1988).

2. Random Library Construction

In order to approximate the random model described above during actual sequencing, a nearly ideal library of cloned genomic fragments is required. The following library construction procedure was developed to achieve this end.

*Streptococcus pneumoniae* DNA is prepared by phenol extraction. A mixture containing 200 µg DNA in 1.0 ml of 300 mM sodium acetate, 10 mM Tris-HCl, 1 mM Na-EDTA, 50% glycerol is processed through a nebulizer (IPI Medical Products) with a stream of nitrogen adjusted to 35 Kpa for 2 minutes. The sonicated DNA is ethanol precipitated and redissolved in 500 µl TE buffer.

To create blunt-ends, a 100 µl aliquot of the resuspended DNA is digested with 5 units of BAL31 nuclease (New England BioLabs) for 10 min at 30° C. in 200 µl BAL31 buffer. The digested DNA is phenol-extracted, ethanol-precipitated, redissolved in 100 µl TE buffer, and then size-fractionated by electrophoresis through a 1.0% low melting temperature agarose gel. The section containing DNA fragments 1.6-2.0 kb in size is excised from the gel, and the LGT agarose is melted and the resulting solution is extracted with phenol to separate the agarose from the DNA. DNA is ethanol precipitated and redissolved in 20 µl of TE buffer for ligation to vector.

A two-step ligation procedure is used to produce a plasmid library with 97% inserts, of which >99% were single inserts. The first ligation mixture (50 ul) contains 2 µg of DNA fragments, 2 µg pUC18 DNA (Pharmacia) cut with SmaI and dephosphorylated with bacterial alkaline phosphatase, and 10 units of T4 ligase (GIBCO/BRL) and is incubated at 14° C. for 4 hr. The ligation mixture then is phenol extracted and ethanol precipitated, and the precipitated DNA is dissolved in 20 µl TE buffer and electrophoresed on a 1.0% low melting agarose gel. Discrete bands in a ladder are visualized by ethidium bromide-staining and UV illumination and identified by size as insert (I), vector (v), v+1, v+2i, v+3i, etc. The portion of the gel containing v+I DNA is excised and the v+I DNA is recovered and resuspended into 20 µl TE. The v+I DNA then is blunt-ended by T4 polymerase treatment for 5 min. at 37° C. in a reaction mixture (50 ul) containing the v+I linears, 500 µM each of the 4 dNTPs, and 9 units of T4 polymerase (New England BioLabs), under recommended buffer conditions. After phenol extraction and ethanol precipitation the repaired v+I linears are dissolved in 20 µl TE. The final ligation to produce circles is carried out in a 50 µl reaction containing 5 µl of v+I linears and 5 units of T4 ligase at 14° C. overnight. After 10 min. at 70° C. the following day, the reaction mixture is stored at −20° C.

This two-stage procedure results in a molecularly random collection of single-insert plasmid recombinants with minimal contamination from double-insert chimeras (<1%) or free vector (<3%).

Since deviation from randomness can arise from propagation the DNA in the host, *E. coli* host cells deficient in all recombination and restriction functions (A. Greener, *Strategies* 3 (1):5 (1990)) are used to prevent rearrangements, deletions, and loss of clones by restriction. Furthermore, transformed cells are plated directly on antibiotic diffusion plates to avoid the usual broth recovery phase which allows multiplication and selection of the most rapidly growing cells.

Plating is carried out as follows. A 100 µl aliquot of Epicurian Coli SURE II Supercompetent Cells (Stratagene 200152) is thawed on ice and transferred to a chilled Falcon 2059 tube on ice. A 1.7 µl aliquot of 1.42 M beta-mercaptoethanol is added to the aliquot of cells to a final concentration of 25 mM. Cells are incubated on ice for 10 min. A 1 µl aliquot of the final ligation is added to the cells and incubated on ice for 30 min. The cells are heat pulsed for 30 sec. at 42° C. and placed back on ice for 2 min. The outgrowth period in liquid culture is eliminated from this protocol in order to minimize the preferential growth of any given transformed cell. Instead the transformation mixture is plated directly on a nutrient rich SOB plate containing a 5 ml bottom layer of SOB agar (5% SOB agar: 20 g tryptone, 5 g yeast extract, 0.5 g NaCl, 1.5% Difco Agar per liter of media). The 5 ml bottom layer is supplemented with 0.4 ml of 50 mg/ml ampicillin per 100 ml SOB agar. The 15 ml top layer of SOB agar is supplemented with 1 ml X-Gal (2%), 1 ml MgCl (1 M), and 1 ml MgSO/100 ml SOB agar. The 15 ml top layer is poured just prior to plating. Our titer is approximately 100 colonies/10 µl aliquot of transformation.

All colonies are picked for template preparation regardless of size. Thus, only clones lost due to "poison" DNA or deleterious gene products are deleted from the library, resulting in a slight increase in gap number over that expected.

3. Random DNA Sequencing

High quality double stranded DNA plasmid templates are prepared using a "boiling bead" method developed in collaboration with Advanced Genetic Technology Corp. (Gaithersburg, Md.) (Adams et al., *Science* 252:1651 (1991); Adams et al., *Nature* 355:632 (1992)). Plasmid preparation is performed in a 96-well format for all stages of DNA preparation from bacterial growth through final DNA purification. Template concentration is determined using Hoechst Dye and a Millipore Cytofluor. DNA concentrations are not adjusted, but low-yielding templates are identified where possible and not sequenced.

Templates are also prepared from two *Streptococcus pneumoniae* lambda genomic libraries. An amplified library is constructed in the vector Lambda GEM-12 (Promega) and an unamplified library is constructed in Lambda DASH II (Stratagene). In particular, for the unamplified lambda library, *Streptococcus pneumoniae* DNA (>100 kb) is partially digested in a reaction mixture (200 ul) containing 50 µg DNA, 1× Sau3AI buffer, 20 units Sau3AI for 6 min. at 23° C. The digested DNA was phenol-extracted and electrophoresed on a 0.5% low melting agarose gel at 2V/cm for 7 hours. Fragments from 15 to 25 kb are excised and recovered in a final volume of 6 ul. One µl of fragments is used with 1 µl of DASHII vector (Stratagene) in the recommended ligation reaction. One µl of the ligation mixture is used per packaging reaction following the recommended protocol with the Gigapack II XL Packaging Extract (Stratagene, #227711). Phage are plated directly without amplification from the packaging mixture (after dilution with 500 µl of recommended SM buffer and chloroform treatment). Yield is about $2.5 \times 10^3$ pfu/ul. The amplified library is prepared essentially as above except the lambda GEM-12 vector is used. After packaging, about $3.5 \times 10^4$ pfu are plated on the restrictive NM539 host. The lysate is harvested in 2 ml of SM buffer and stored frozen in 7% dimethylsulfoxide. The phage titer is approximately $1 \times 10^9$ pfu/ml.

Liquid lysates (100 µl) are prepared from randomly selected plaques (from the unamplified library) and template is prepared by long-range PCR using T7 and T3 vector-specific primers.

Sequencing reactions are carried out on plasmid and/or PCR templates using the AB Catalyst LabStation with Applied Biosystems PRISM Ready Reaction Dye Primer Cycle Sequencing Kits for the M13 forward (M13-21) and the M13 reverse (M13RP1) primers (Adams et al., *Nature* 368: 474 (1994)). Dye terminator sequencing reactions are carried out on the lambda templates on a Perkin-Elmer 9600 Thermocycler using the Applied Biosystems Ready Reaction Dye Terminator Cycle Sequencing kits. T7 and SP6 primers are used to sequence the ends of the inserts from the Lambda GEM-12 library and T7 and T3 primers are used to sequence the ends of the inserts from the Lambda DASH H library. Sequencing reactions are performed by eight individuals using an average of fourteen AB 373 DNA Sequencers per day. All sequencing reactions are analyzed using the Stretch modification of the AB 373, primarily using a 34 cm well-to-read distance. The overall sequencing success rate very approximately is about 85% for M13-21 and M13RP I sequences and 65% for dye-terminator reactions. The average usable read length is 485 bp for M13-21 sequences, 445 bp for MI3RP1 sequences, and 375 bp for dye-terminator reactions.

Richards et al., Chapter 28 in AUTOMATED DNA SEQUENCING AND ANALYSIS, M. D. Adams, C. Fields, J. C. Venter, Eds., Academic Press, London, (1994) described the value of using sequence from both ends of sequencing templates to facilitate ordering of contigs in shotgun assembly projects of lambda and cosmid clones. We balance the desirability of both-end sequencing (including the reduced cost of lower total number of templates) against shorter readlengths for sequencing reactions performed with the M13RP1 (reverse) primer compared to the M13-21 (forward) primer. Approximately one-half of the templates are sequenced from both ends. Random reverse sequencing reactions are done based on successful forward sequencing reactions. Some M13RP1 sequences are obtained in a semi-directed fashion: M13-21: sequences pointing outward at the ends of contigs are chosen for M13RP1 sequencing in an effort to specifically order contigs.

4. Protocol for Automated Cycle Sequencing

The sequencing is carried out using ABI Catalyst robots and AB 373 Automated DNA Sequencers. The Catalyst robot is a publicly available sophisticated pipetting and temperature control robot which has been developed specifically for DNA sequencing reactions. The Catalyst combines pre-aliquoted templates and reaction mixes consisting of deoxy- and dideoxynucleotides, the thermostable Taq DNA polymerase, fluorescently-labeled sequencing primers, and reaction buffer. Reaction mixes and templates are combined in the wells of an aluminum 96-well thermocycling plate. Thirty consecutive cycles of linear amplification (i.e., one primer synthesis) steps are performed including denaturation, annealing of primer and template, and extension; i.e., DNA synthesis. A heated lid with rubber gaskets on the thermocycling plate prevents evaporation without the need for an oil overlay.

Two sequencing protocols are used: one for dye-labeled primers and a second for dye-labeled dideoxy chain terminators. The shotgun sequencing involves use of four dye-labeled sequencing primers, one for each of the four terminator nucleotide. Each dye-primer is labeled with a different fluorescent dye, permitting the four individual reactions to be combined into one lane of the 373 DNA Sequencer for electrophoresis, detection, and base-calling. ABI currently supplies pre-mixed reaction mixes in bulk packages containing all the necessary non-template reagents for sequencing. Sequencing can be done with both plasmid and PCR-generated templates with both dye-primers and dye-terminators with approximately equal fidelity, although plasmid templates generally give longer usable sequences.

Thirty-two reactions are loaded per AB373 Sequencer each day, for a total of 960 samples. Electrophoresis is run overnight following the manufacturer's protocols, and the data is collected for twelve hours. Following electrophoresis and fluorescence detection, the ABI 373 performs automatic lane tracking and base-calling. The lane-tracking is confirmed visually. Each sequence electropherogram (or fluorescence lane trace) is inspected visually and assessed for quality. Trailing sequences of low quality are removed and the sequence itself is loaded via software to a Sybase database (archived daily to 8 mm tape). Leading vector polylinker sequence is removed automatically by a software program. Average edited lengths of sequences from the standard ABI 373 are around 400 bp and depend mostly on the quality of the template used for the sequencing reaction. ABI 373 Sequencers converted to Stretch Liners provide a longer electrophoresis path prior to fluorescence detection and increase the average number of usable bases to 500-600 bp.

Informatics

1. Data Management

A number of information management systems for a largescale sequencing lab have been developed. (For review see, for instance, Kerlavage et al., *Proceedings of the Twenty-Sixth Annual Hawaii International Conference on System Sciences*, IEEE Computer Society Press, Washington D.C., 585 (1993)) The system used to collect and assemble the sequence data was developed using the Sybase relational database management system and was designed to automate data flow wherever possible and to reduce user error. The database stores and correlates all information collected during the entire operation from template preparation to final analysis of the genome. Because the raw output of the ABI 373 Sequencers was based on a Macintosh platform and the data management system chosen was based on a Unix platform, it was necessary to design and implement a variety of multi-user, client-server applications which allow the raw data as well as analysis results to flow seamlessly into the database with a minimum of user effort.

2. Assembly

An assembly engine (TIGR Assembler) developed for the rapid and accurate assembly of thousands of sequence fragments was employed to generate contigs. The TIGR assembler simultaneously clusters and assembles fragments of the genome. In order to obtain the speed necessary to assemble more than $10^4$ fragments, the algorithm builds a hash table of 12 bp oligonucleotide subsequences to generate a list of potential sequence fragment overlaps. The number of potential overlaps for each fragment determines which fragments are likely to fall into repetitive elements. Beginning with a single seed sequence fragment, TIGR Assembler extends the current contig by attempting to add the best matching fragment based on oligonucleotide content. The contig and candidate fragment are aligned using a modified version of the Smith-Waterman algorithm which provides for optimal gapped alignments (Waterman, M. S., *Methods in Enzymology* 164:765 (1988)). The contig is extended by the fragment only if strict criteria for the quality of the match are met. The match criteria include the minimum length of overlap, the maximum length of an unmatched end, and the minimum percentage match. These criteria are automatically lowered by the algorithm in regions of minimal coverage and raised in regions with a possible repetitive element. The number of potential overlaps for each fragment determines which fragments are likely to fall into repetitive elements. Fragments representing the boundaries of repetitive elements and potentially chimeric fragments are often rejected based on partial mismatches at the ends of alignments and excluded from the current contig. TIGR Assembler is designed to take advantage of clone size information coupled with sequencing from both ends of each template. It enforces the constraint that sequence fragments from two ends of the same template point toward one another in the contig and are located within a certain range of base pairs (definable for each clone based on the known clone size range for a given library).

The process resulted in 391 contigs as represented by SEQ ID NOs:1-391.

3. Identifying Genes

The predicted coding regions of the *Streptococcus pneumoniae* genome were initially defined with the program GeneMark, which finds ORFs using a probabilistic classification technique. The predicted coding region sequences were used in searches against a database of all nucleotide sequences from GenBank (October, 1997), using the BLASTN search method to identify overlaps of 50 or more nucleotides with at least a 95% identity. Those ORFs with nucleotide sequence matches are shown in Table 1. The ORFs without such matches were translated to protein sequences and compared to a non-redundant database of known proteins generated by combining the Swiss-prot, PIR and GenPept databases. ORFs that matched a database protein with BLASTP probability less than or equal to 0.01 are shown in Table 2. The table also lists assigned functions based on the closest match in the databases. ORFs that did not match protein or nucleotide sequences in the databases at these levels are shown in Table 3.

Illustrative Applications

1. Production of an Antibody to a *Streptococcus pneumoniae* Protein

Substantially pure protein or polypeptide is isolated from the transfected or transformed cells using any one of the methods known in the art. The protein can also be produced in a recombinant prokaryotic expression system, such as *E. coli*, or can be chemically synthesized. Concentration of protein in the final preparation is adjusted, for example, by concentration on an Amicon filter device, to the level of a few micrograms/ml. Monoclonal or polyclonal antibody to the protein can then be prepared as follows.

2. Monoclonal Antibody Production by Hybridoma Fusion

Monoclonal antibody to epitopes of any of the peptides identified and isolated as described can be prepared from murine hybridomas according to the classical method of Kohler, G. and Milstein, C., *Nature* 256:495 (1975) or modifications of the methods thereof. Briefly, a mouse is repetitively inoculated with a few micrograms of the selected protein over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and modified methods thereof. Selected positive clones can be expanded and their monoclonal antibody product harvested for use. Detailed procedures for monoclonal antibody production are described in Davis, L. et al., *Basic Methods in Molecular Biology*, Elsevier, New York. Section 21-2 (1989).

3. Polyclonal Antibody Production by Immunization

Polyclonal antiserum containing antibodies to heterogeneous epitopes of a single protein can be prepared by immunizing suitable animals with the expressed protein described above, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al., *J. Clin. Endocrinol. Metab.* 33:988-991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental immunology*, Wier, D., ed, Blackwell (1973). Plateau concentration of antibody is usually in the range of 0.1 to 0.2 mg/ml of serum (about 12M). Affinity of the antisera for the antigen is determined by preparing competitive binding curves, as described, for example, by Fisher, D., Chap. 42 in: *Manual of Clinical Immunology*, second edition, Rose and Friedman, eds., Amer. Soc. For Microbiology, Washington, D.C. (1980)

Antibody preparations prepared according to either protocol are useful in quantitative immunoassays which determine concentrations of antigen-bearing substances in biological samples; they are also used semi-quantitatively or qualitatively to identify the presence of antigen in a biological sample. In addition, antibodies are useful in various animal models of pneumococcal disease as a means of evaluating the protein used to make the antibody as a potential vaccine target or as a means of evaluating the antibody as a potential immunotherapeutic or immunoprophylactic reagent.

4. Preparation of PCR Primers and Amplification of DNA

Various fragments of the *Streptococcus pneumoniae* genome, such as those of Tables 1-3 and SEQ ID NOS:1-391 can be used, in accordance with the present invention, to prepare PCR primers for a variety of uses. The PCR primers are preferably at least 15 bases, and more preferably at least 18 bases in length. When selecting a primer sequence, it is preferred that the primer pairs have approximately the same G/C ratio, so that melting temperatures are approximately the same. The PCR primers and amplified DNA of this Example find use in the Examples that follow.

5. Gene Expression from DNA Sequences Corresponding to ORFs

A fragment of the *Streptococcus pneumoniae* genome provided in Tables 1-3 is introduced into an expression vector using conventional technology. Techniques to transfer cloned sequences into expression vectors that direct protein translation in mammalian, yeast, insect or bacterial expression systems are well known in the art. Commercially available vectors and expression systems are available from a variety of suppliers including Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism, as explained by Hatfield et al., U.S. Pat. No. 5,082,767, incorporated herein by this reference.

The following is provided as one exemplary method to generate polypeptide(s) from cloned ORFs of the *Streptococcus pneumoniae* genome fragment. Bacterial ORFs generally lack a poly A addition signal. The addition signal sequence can be added to the construct by, for example, splicing out the poly A addition sequence from pSG5 (Stratagene) using BglI and SalI restriction endonuclease enzymes and incorporating it into the mammalian expression vector pXT1 (Stratagene) for use in eukaryotic expression systems. pXT1 contains the LTRs and a portion of the gag gene of Moloney Murine Leukemia Virus. The positions of the LTRs in the construct allow efficient stable transfection. The vector includes the Herpes Simplex thymidine kinase promoter and the selectable neomycin gene. The *Streptococcus pneumoniae* DNA is obtained by PCR from the bacterial vector using oligonucleotide primers complementary to the *Streptococcus pneumoniae* DNA and containing restriction endonuclease sequences for PstI incorporated into the 5' primer and BglII at the 5' end of the corresponding *Streptococcus pneumoniae* DNA 3' primer, taking care to ensure that the *Streptococcus pneumoniae* DNA is positioned such that its followed with the poly A addition sequence. The purified fragment obtained from the resulting PCR reaction is digested with PstI, blunt ended with an exonuclease, digested with BglII, purified and ligated to pXT1, now containing a poly A addition sequence and digested BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). The protein is preferably released into the supernatant. However if the protein has membrane binding domains, the protein may additionally be retained within the cell or expression may be restricted to the cell surface. Since it may be necessary to purify and locate the transfected product, synthetic 15-mer peptides synthesized from the predicted *Streptococcus pneumoniae* DNA sequence are injected into mice to generate antibody to the polypeptide encoded by the *Streptococcus pneumoniae* DNA.

Alternatively and if antibody production is not possible, the *Streptococcus pneumoniae* DNA sequence is additionally incorporated into eukaryotic expression vectors and expressed as, for example, a globin fusion. Antibody to the globin moiety then is used to purify the chimeric protein. Corresponding protease cleavage sites are engineered between the globin moiety and the polypeptide encoded by the *Streptococcus pneumoniae* DNA so that the latter may be freed from the formed by simple protease digestion. One useful expression vector for generating globin chimerics is pSG5 (Stratagene). This vector encodes a rabbit globin. Intron II of the rabbit globin gene facilitates splicing of the expressed transcript, and the polyadenylation signal incorporated into the construct increases the level of expression. These techniques are well known to those skilled in the art of molecular biology. Standard methods are published in methods texts such as Davis et al., cited elsewhere herein, and many of the methods are available from the technical assistance representatives from Stratagene, Life Technologies, Inc., or Promega. Polypeptides of the invention also may be produced using in vitro translation systems such as in vitro Express™ Translation Kit (Stratagene).

While the present invention has been described in some detail for purposes of clarity and understanding, one skilled in the art will appreciate that various changes in form and detail can be made without departing from the true scope of the invention.

All patents, patent applications and publications referred to above are hereby incorporated by reference.

TABLE 1

*S. pneumoniae* - Coding regions containing known sequences

| Contig ID | ORF ID | Start (nt) | Stop (nt) | match acession | match gene name | percent ident | HSP nt length | ORF nt length |
|---|---|---|---|---|---|---|---|---|
| 1 | 1 | 437 | 1003 | gb\|U41735\| | *Streptococcus pneumoniae* peptide methionine sulfoxide reductase (msrA) and homoserine kinase homolog (thrB) genes, complete cds | 92 | 200 | 567 |
| 2 | 5 | 6169 | 5720 | gb\|U04047\| | *Streptococcus pneumoniae* SSZ dextran glucosidase gene and insertion sequence IS1202 transposase gene, complete cds | 96 | 450 | 450 |
| 2 | 6 | 6592 | 6167 | emb\|Z83335\|SPZ8 | *S. pneumoniae* dexB, cap1[A, B, C, D, E, F, G, H, I, J, K] genes, dTDP-rhamnose biosynthesis genes and aliA gene | 98 | 426 | 426 |
| 3 | 11 | 9770 | 9147 | emb\|Z83335\|SPZ8 | *S. pneumoniae* dexB, cap1[A, B, C, D, E, F, G, H, I, J, K] genes, dTDP-rhamnose biosynthesis genes and aliA gene | 94 | 624 | 624 |
| 3 | 12 | 10489 | 9671 | emb\|Z83335\|SPZ8 | *S. pneumoniae* dexB, cap1[A, B, C, D, E, F, G, H, I, J, K] genes, dTDP-rhamnose biosynthesis genes and aliA gene | 91 | 819 | 819 |
| 3 | 13 | 11546 | 12019 | gb\|U43526\| | *Streptococcus pneumoniae* neuraminidase B (nanB) gene, complete cds, and neuraminidase (nanA) gene, partial cds | 99 | 474 | 474 |
| 3 | 14 | 12017 | 13375 | gb\|U43526\| | *Streptococcus pneumoniae* neuraminidase B (nanB) gene, complete cds, and neuraminidase (nanA) gene, partial cds | 99 | 1359 | 1359 |
| 3 | 15 | 13421 | 14338 | gb\|U43526\| | *Streptococcus pneumoniae* neuraminidase B (nanB) gene, complete cds, and neuraminidase (nanA) gene, partial cds | 99 | 918 | 918 |
| 3 | 16 | 14329 | 15171 | gb\|U43526\| | *Streptococcus pneumoniae* neuraminidase B (nanB) gene, complete cds, and neuraminidase (nanA) gene, partial cds | 99 | 843 | 843 |
| 3 | 17 | 15132 | 17282 | gb\|U43526\| | *Streptococcus pneumoniae* neuraminidase B (nanB) gene, complete cds, and neuraminidase (nanA) gene, partial cds | 99 | 2151 | 2151 |
| 3 | 18 | 17267 | 18397 | gb\|U43526\| | *Streptococcus pneumoniae* neuraminidase B (nanB) gene, complete cds, and neuraminidase (nanA) gene, partial cds | 99 | 1069 | 1131 |
| 4 | 1 | 46 | 1188 | emb\|Y11463\|SPDN | *Streptococcus pneumoniae* dnaG, rpoD, cpoA genes and ORF3 and ORF5 | 99 | 1143 | 1143 |
| 4 | 2 | 1198 | 2529 | emb\|Y11463\|SPDN | *Streptococcus pneumoniae* dnaG, rpoD, cpoA genes and ORF3 and ORF5 | 99 | 876 | 1332 |
| 5 | 7 | 11297 | 11473 | gb\|U41735\| | *Streptococcus pneumoniae* peptide methionine sulfoxide reductase (msrA) and homoserine kinase homolog (thrB) genes, complete cds | 82 | 175 | 177 |
| 6 | 7 | 7125 | 7364 | emb\|Z77726\|SPIS | *S. pneumoniae* DNA for insertion sequence IS1318 (1372 bp) | 93 | 238 | 240 |
| 6 | 8 | 7322 | 7570 | emb\|Z77725\|SPIS | *S. pneumoniae* DNA for insertion sequence IS1381 (966 bp) | 95 | 160 | 249 |
| 6 | 9 | 7533 | 7985 | emb\|Z77725\|SPIS | *S. pneumoniae* DNA for insertion sequence IS1381 (966 bp) | 99 | 453 | 453 |
| 6 | 23 | 20197 | 19733 | emb\|Z83335\|SPZ8 | *S. pneumoniae* dexB, cap1[A, B, C, D, E, F, G, H, I, J, K] genes, dTDP-rhamnose biosynthesis genes and aliA gene | 96 | 465 | 465 |
| 7 | 10 | 8305 | 7682 | emb\|Z83335\|SPZ8 | *S. pneumoniae* dexB, cap1[A, B, C, D, E, F, G, H, I, J, K] genes, dTDP-rhamnose biosynthesis genes and aliA gene | 95 | 624 | 624 |
| 7 | 11 | 9024 | 8206 | emb\|Z83335\|SPZ8 | *S. pneumoniae* dexB, cap1[A, B, C, D, E, F, G, H, I, J, K] genes, dTDP-rhamnose biosynthesis genes and aliA gene | 95 | 819 | 819 |
| 10 | 13 | 9304 | 8078 | gb\|L29323\| | *Streptococcus pneumoniae* methyl transferase (mtr) gene cluster, complete cds | 93 | 513 | 1227 |
| 11 | 2 | 548 | 919 | emb\|Z79691\|SOOR | *S. pneumoniae* yorf[A, B, C, D, E], ftsL, pbpX and regR genes | 99 | 316 | 372 |
| 11 | 3 | 892 | 1980 | emb\|Z79691\|SOOR | *S. pneumoniae* yorf[A, B, C, D, E], ftsL, pbpX and regR genes | 99 | 1089 | 1089 |
| 11 | 5 | 3040 | 3477 | emb\|Z79691\|SOOR | *S. pneumoniae* yorf[A, B, C, D, E], ftsL, pbpX and regR genes | 99 | 259 | 438 |
| 11 | 6 | 3480 | 3247 | emb\|Z79691\|SOOR | *S. pneumoniae* yorf[A, B, C, D, E], ftsL, pbpX and regR genes | 99 | 234 | 234 |
| 11 | 7 | 3601 | 4557 | emb\|Z79691\|SOOR | *S. pneumoniae* yorf[A, B, C, D, E], ftsL, pbpX and regR genes | 98 | 957 | 957 |

TABLE 1-continued

*S. pneumoniae* - Coding regions containing known sequences

| Contig ID | ORF ID | Start (nt) | Stop (nt) | match acession | match gene name | percent ident | HSP nt length | ORF nt length |
|---|---|---|---|---|---|---|---|---|
| 11 | 8 | 4506 | 4886 | emb\|Z79691\|SOOR | *S. pneumoniae* yorf[A, B, C, D, E], ftsL, pbpX and regR genes | 99 | 381 | 381 |
| 11 | 9 | 4884 | 7142 | emb\|X16367\|SPPB | *Streptococcus pneumoniae* pbpX gene for penicillin binding protein 2X | 99 | 2259 | 2259 |
| 11 | 10 | 7132 | 8124 | emb\|X16367\|SPPB | *Streptococcus pneumoniae* pbpX gene for penicillin binding protein 2X | 98 | 70 | 993 |
| 13 | 1 | 53 | 1126 | gb\|M31296\| | *S. pneumoniae* recP gene, complete cds | 99 | 437 | 1074 |
| 14 | 3 | 1837 | 2148 | emb\|Z83335\|SPZ8 | *S. pneumoniae* dexB, cap1[A, B, C, D, E, F, G, H, I, J, K] genes, dTDP-rhamnose biosynthesis genes and aliA gene | 87 | 96 | 312 |
| 14 | 4 | 2518 | 2108 | gb\|M36180\| | *Streptococcus pneumoniae* transposase, (comA and comB) and SAICAR synthetase (purC) genes, complete cds | 98 | 411 | 411 |
| 15 | 9 | 8942 | 8511 | gb\|U09239\| | *Streptococcus pneumoniae* type 19F capsular polysaccharide biosynthesis operon, (cps19fABCDEFGHIJKLMNO) genes, complete cds, and aliA gene, partial cds | 89 | 340 | 432 |
| 17 | 7 | 3910 | 3458 | emb\|Z77726\|SPIS | *S. pneumoniae* DNA for insertion sequence IS1318 (1372 bp) | 98 | 453 | 453 |
| 17 | 8 | 4304 | 3873 | emb\|Z77727\|SPIS | *S. pneumoniae* DNA for insertion sequence IS1318 (823 bp) | 96 | 382 | 432 |
| 19 | 1 | 41 | 529 | emb\|X94909\|SPIG | *S. pneumoniae* iga gene | 75 | 368 | 489 |
| 19 | 2 | 554 | 757 | gb\|L07752\| | *Streptococcus pneumoniae* attachment site (attB), DNA sequence | 99 | 167 | 204 |
| 19 | 3 | 946 | 1827 | gb\|L07752\| | *Streptococcus pneumoniae* attachment site (attB), DNA sequence | 94 | 100 | 882 |
| 20 | 1 | 937 | 182 | gb\|U33315\| | *Streptococcus pneumoniae* orfL gene, partial cds, competence stimulating peptide precursor (comC), histidine protein kinase (comD) and response regulator (comE) genes, complete cds, tRNA-Arg and tRNA-Gln genes | 99 | 756 | 756 |
| 20 | 2 | 2271 | 931 | gb\|U33315\| | *Streptococcus pneumoniae* orfL gene, partial cds, competence stimulating peptide precursor (comC), histidine protein kinase (comD) and response regulator (comE) genes, complete cds, tRNA-Arg and tRNA-Gln genes | 98 | 1341 | 1341 |
| 20 | 3 | 3175 | 2684 | gb\|U76218\| | *Streptococcus pneumoniae* competence stimulating peptide precursor ComC (comC), histidine kinase homolog ComD (comD), and response regulator homolog ComE (comE) genes, complete cds | 99 | 492 | 492 |
| 20 | 4 | 3322 | 4527 | gb\|AF000658\| | *Streptococcus pneumoniae* R801 tRNA-Arg gene, partial sequence, and putative serine protease (sphtra), SPSpoJ (spspoJ), initiator protein (spdnaa) and beta subunit of DNA polymerase III (spdnan) genes, complete cds | 99 | 1206 | 1206 |
| 20 | 5 | 4573 | 5343 | gb\|AF000658\| | *Streptococcus pneumoniae* R801 tRNA-Arg gene, partial sequence, and putative serine protease (sphtra), SPSpoJ (spspoJ), initiator protein (spdnaa) and beta subunit of DNA polymerase III (spdnan) genes, complete cds | 99 | 771 | 771 |
| 20 | 6 | 5532 | 6917 | gb\|AF000658\| | *Streptococcus pneumoniae* R801 tRNA-Arg gene, partial sequence, and putative serine protease (sphtra), SPSpoJ (spspoJ), initiator protein (spdnaa) and beta subunit of DNA polymerase III (spdnan) genes, complete cds | 99 | 1386 | 1386 |
| 20 | 7 | 6995 | 8212 | gb\|AF000658\| | *Streptococcus pneumoniae* R801 tRNA-Arg gene, partial sequence, and putative serine protease (sphtra), SPSpoJ (spspoJ), initiator protein (spdnaa) and beta subunit of DNA polymerase III (spdnan) genes, complete cds | 99 | 1218 | 1218 |
| 20 | 8 | 8214 | 8471 | gb\|AF000658\| | *Streptococcus pneumoniae* R801 tRNA-Arg gene, partial sequence, and putative serine protease (sphtra), SPSpoJ (spspoJ), initiator protein (spdnaa) and beta subunit of DNA polymerase III (spdnan) genes, complete cds | 98 | 258 | 258 |
| 20 | 9 | 8534 | 9670 | gb\|AF000658\| | *Streptococcus pneumoniae* R801 tRNA-Arg gene, partial sequence, and putative serine protease (sphtra), SPSpoJ (spspoJ), initiator protein (spdnaa) and beta subunit of DNA polymerase III (spdnan) genes, complete cds | 99 | 134 | 1137 |
| 22 | 14 | 11887 | 12267 | emb\|Z77726\|SPIS | *S. pneumoniae* DNA for insertion sequence IS1318 (1372 bp) | 99 | 226 | 381 |
| 22 | 15 | 12708 | 12256 | emb\|Z77727\|SPIS | *S. pneumoniae* DNA for insertion sequence IS1318 (823 bp) | 97 | 353 | 453 |
| 22 | 16 | 13165 | 12662 | emb\|Z77726\|SPIS | *S. pneumoniae* DNA for insertion sequence IS1318 (1372 bp) | 98 | 504 | 504 |
| 22 | 23 | 18398 | 18910 | emb\|Z86112\|SPZ8 | *S. pneumoniae* genes encoding galacturonosyl transferase and transposase and insertion sequence IS1515 | 95 | 463 | 513 |
| 22 | 24 | 18829 | 19299 | emb\|Z86112\|SPZ8 | *S. pneumoniae* genes encoding galacturonosyl transferase and transposase and insertion sequence IS1515 | 99 | 443 | 471 |
| 23 | 5 | 5624 | 4203 | emb\|X52474\|SPPL | *S. pneumoniae* ply gene for pneumolysin | 99 | 1422 | 1422 |
| 23 | 6 | 6063 | 5629 | gb\|M17717\| | *S. pneumoniae* pneumolysin gene, complete cds | 98 | 197 | 435 |
| 26 | 1 | 5500 | 2 | emb\|X94909\|SPIG | *S. pneumoniae* iga gene | 87 | 3487 | 5499 |
| 26 | 2 | 5823 | 5584 | gb\|U47687\| | *Streptococcus pneumoniae* immunoglobulin A1 protease (iga) gene, complete cds | 99 | 151 | 240 |
| 26 | 3 | 6878 | 5685 | gb\|U47687\| | *Streptococcus pneumoniae* immunoglobulin A1 protease (iga) gene, complete cds | 100 | 50 | 1194 |
| 26 | 8 | 14498 | 14854 | emb\|Z83335\|SPZ8 | *S. pneumoniae* dexB, cap1[A, B, C, D, E, F, G, H, I, J, K] genes, dTDP-rhamnose biosynthesis genes and aliA gene | 99 | 338 | 357 |
| 26 | 9 | 14763 | 14924 | emb\|Z83335\|SPZ8 | *S. pneumoniae* dexB, cap1[A, B, C, D, E, F, G, H, I, J, K] genes, dTDP-rhamnose biosynthesis genes and aliA gene | 100 | 94 | 162 |

TABLE 1-continued

S. pneumoniae - Coding regions containing known sequences

| Contig ID | ORF ID | Start (nt) | Stop (nt) | match acession | match gene name | percent ident | HSP nt length | ORF nt length |
|---|---|---|---|---|---|---|---|---|
| 26 | 10 | 14922 | 15173 | gb|U04047| | Streptococcus pneumoniae SSZ dextran glucosidase gene and insertion sequence IS1202 transposase gene, complete cds | 97 | 242 | 252 |
| 28 | 1 | 80 | 505 | emb|Z83335|SPZ8 | S. pneumoniae dexB, cap1[A, B, C, D, E, F, G, H, I, J, K] genes, dTDP-rhamnose biosynthesis genes and aliA gene | 99 | 426 | 426 |
| 28 | 2 | 503 | 952 | gb|U04047| | Streptococcus pneumoniae SSZ dextran glucosidase gene and insertion sequence IS1202 transposase gene, complete cds | 97 | 450 | 450 |
| 28 | 3 | 780 | 1298 | gb|U04047| | Streptococcus pneumoniae SSZ dextran glucosidase gene and insertion sequence IS1202 transposase gene, complete cds | 96 | 181 | 519 |
| 34 | 1 | 207 | 1523 | gb|L08611| | Streptococcus pneumoniae maltose/maltodextrin uptake (malX) and two maltodextrin permease (malC and malD) genes, complete cds | 99 | 1317 | 1317 |
| 34 | 2 | 1477 | 2367 | gb|L08611| | Streptococcus pneumoniae maltose/maltodextrin uptake (malX) and two maltodextrin permease (malC and malD) genes, complete cds | 96 | 795 | 891 |
| 34 | 3 | 2593 | 3420 | gb|L21856| | Streptococcus pneumoniae malA gene, complete cds; malR gene, complete cds | 96 | 446 | 828 |
| 34 | 4 | 2790 | 2647 | gb|L21856| | Streptococcus pneumoniae malA gene, complete cds; malR gene, complete cds | 98 | 137 | 144 |
| 34 | 5 | 3418 | 4416 | gb|L21856| | Streptococcus pneumoniae malA gene, complete cds; malR gene, complete cds | 96 | 999 | 999 |
| 34 | 9 | 7764 | 7507 | gb|U41735| | Streptococcus pneumoniae peptide methionine sulfoxide reductase (msrA) and homoserine kinase homolog (thrB) genes, complete cds | 93 | 201 | 258 |
| 34 | 16 | 10562 | 10257 | emb|X63602|SPBO | S. pneumoniae mmsA-Box | 92 | 238 | 306 |
| 35 | 4 | 1176 | 1439 | emb|Z83335|SPZ8 | S. pneumoniae dexB, cap1[A, B, C, D, E, F, G, H, I, J, K] genes, dTDP-rhamnose biosynthesis genes and aliA gene | 87 | 248 | 264 |
| 35 | 5 | 1458 | 1961 | gb|U09239| | Streptococcus pneumoniae type 19F capsular polysaccharide biosynthesis operon, (cps19fABCDEFGHIJKLMNO) genes, complete cds, and aliA gene, partial cds | 98 | 264 | 504 |
| 35 | 17 | 16172 | 15477 | emb|X85787|SPCP | S. pneumoniae dexB, cps14A, cps14B, cps14C, cps14D, cps14E, cps14F, cps14G, cps14H, cps14I, cps14J, cps14K, cps14L, tasA genes | 97 | 696 | 696 |
| 35 | 18 | 16961 | 16170 | emb|Z83335|SPZ8 | S. pneumoniae dexB, cap1[A, B, C, D, E, F, G, H, I, J, K] genes, dTDP-rhamnose biosynthesis genes and aliA gene | 86 | 792 | 792 |
| 35 | 19 | 17620 | 16871 | gb|U09239| | Streptococcus pneumoniae type 19F capsular polysaccharide biosynthesis operon, (cps19fABCDEFGHIJKLMNO) genes, complete cds, and aliA gene, partial cds | 83 | 750 | 750 |
| 35 | 20 | 19061 | 17604 | emb|X85787|SPCP | S. pneumoniae dexB, cps14A, cps14B, cps14C, cps14D, cps14E, cps14F, cps14G, cps14H, cps14I, cps14J, cps14K, cps14L, tasA genes | 94 | 1458 | 1458 |
| 36 | 19 | 18960 | 18352 | gb|U40786| | Streptococcus pneumoniae surface antigen A variant precursor (psaA) and 18 kDa protein genes, complete cds, and ORF1 gene, partial cds | 99 | 609 | 609 |
| 36 | 20 | 19934 | 18966 | gb|U53509| | Streptococcus pneumoniae surface adhesin A precursor (psaA) gene, complete cds | 99 | 969 | 969 |
| 37 | 1 | 2743 | 179 | emb|Z67739|SPPA | S. pneumoniae parC, parE and transposase genes and unknown orf | 99 | 2565 | 2565 |
| 37 | 2 | 2985 | 2824 | emb|Z67739|SPPA | S. pneumoniae parC, parE and transposase genes and unknown orf | 100 | 162 | 162 |
| 37 | 3 | 5034 | 3070 | emb|Z67739|SPPA | S. pneumoniae parC, parE and transposase genes and unknown orf | 99 | 1965 | 1965 |
| 37 | 4 | 5134 | 5790 | emb|Z67739|SPPA | S. pneumoniae parC, parE and transposase genes and unknown orf | 99 | 657 | 657 |
| 37 | 5 | 6171 | 5833 | emb|Z67739|SPPA | S. pneumoniae parC, parE and transposase genes and unknown orf | 96 | 339 | 339 |
| 38 | 19 | 12969 | 13268 | gb|M28679| | S. pneumoniae promoter region DNA | 100 | 64 | 300 |
| 39 | 2 | 1256 | 2137 | gb|U41735| | Streptococcus pneumoniae peptide methionine sulfoxide reductase (msrA) and homoserine kinase homolog (thrB) genes, complete cds | 99 | 882 | 882 |
| 39 | 3 | 2405 | 3370 | gb|U41735| | Streptococcus pneumoniae peptide methionine sulfoxide reductase (msrA) and homoserine kinase homolog (thrB) genes, complete cds | 99 | 966 | 966 |
| 40 | 9 | 5253 | 7208 | gb|M29686| | S. pneumoniae mismatch repair (hexB) gene, complete cds | 99 | 1956 | 1956 |
| 41 | 1 | 3 | 1037 | emb|Z17307|SPRE | S. pneumoniae recA gene encoding RecA | 99 | 1027 | 1035 |
| 41 | 2 | 1328 | 2713 | emb|Z34303|SPCI | Streptococcus pneumoniae cin operon encoding the cinA, recA, dinF, lytA genes, and downstream sequences | 99 | 1386 | 1386 |
| 41 | 3 | 3083 | 4045 | gb|M13812| | S. pneumoniae autolysin (lytA) gene, complete cds | 99 | 963 | 963 |
| 41 | 4 | 3272 | 3096 | gb|M13812| | S. pneumoniae autolysin (lytA) gene, complete cds | 100 | 177 | 177 |
| 41 | 5 | 3603 | 3860 | gb|M13812| | S. pneumoniae autolysin (lytA) gene, complete cds | 100 | 258 | 258 |
| 41 | 6 | 4755 | 5162 | gb|L36660| | Streptococcus pneumoniae ORF, complete cds | 98 | 408 | 408 |
| 41 | 7 | 5270 | 5716 | gb|L36660| | Streptococcus pneumoniae ORF, complete cds | 98 | 447 | 447 |
| 41 | 8 | 6112 | 6918 | gb|L36660| | Streptococcus pneumoniae ORF, complete cds | 98 | 431 | 807 |
| 41 | 9 | 6916 | 7119 | gb|L36660| | Streptococcus pneumoniae ORF, complete cds | 100 | 204 | 204 |
| 41 | 10 | 7082 | 7660 | gb|L36660| | Streptococcus pneumoniae ORF, complete cds | 97 | 552 | 579 |
| 41 | 11 | 7680 | 7979 | gb|L36660| | Streptococcus pneumoniae ORF, complete cds | 98 | 81 | 300 |
| 41 | 12 | 9169 | 8717 | emb|Z77727|SPIS | S. pneumoniae DNA for insertion sequence IS1318 (823 bp) | 97 | 353 | 453 |

TABLE 1-continued

*S. pneumoniae* - Coding regions containing known sequences

| Contig ID | ORF ID | Start (nt) | Stop (nt) | match acession | match gene name | percent ident | HSP nt length | ORF nt length |
|---|---|---|---|---|---|---|---|---|
| 41 | 13 | 9533 | 9132 | emb\|Z77725\|SPIS | *S. pneumoniae* DNA for insertion sequence IS1381 (966 bp) | 95 | 160 | 402 |
| 41 | 14 | 9669 | 9475 | emb\|Z82001\|SPZ8 | *S. pneumoniae* pcpA gene and open reading frames | 100 | 189 | 195 |
| 44 | 5 | 7190 | 7555 | emb\|Z82001\|SPZ8 | *S. pneumoniae* pcpA gene and open reading frames | 99 | 366 | 366 |
| 44 | 6 | 8059 | 7607 | emb\|Z77726\|SPIS | *S. pneumoniae* DNA for insertion sequence IS1318 (1372 bp) | 97 | 453 | 453 |
| 44 | 7 | 8423 | 8022 | emb\|Z77725\|SPIS | *S. pneumoniae* DNA for insertion sequence IS1381 (966 bp) | 95 | 160 | 402 |
| 44 | 8 | 8559 | 8365 | emb\|Z82001\|SPZ8 | *S. pneumoniae* pcpA gene and open reading frames | 100 | 189 | 195 |
| 48 | 9 | 6480 | 4687 | gb\|L39074\| | *Streptococcus pneumoniae* pyruvate oxidase (spxB) gene, complete cds | 99 | 1794 | 1764 |
| 49 | 2 | 231 | 2603 | gb\|L20561\| | *Streptococcus pneumoniae* Exp7 gene, partial cds | 100 | 216 | 2373 |
| 53 | 6 | 2407 | 2156 | gb\|U04047\| | *Streptococcus pneumoniae* SSZ dextran glucosidase gene and insertion sequence IS1202 transposase gene, complete cds | 97 | 242 | 252 |
| 53 | 7 | 2566 | 2405 | emb\|Z83335\|SPZ8 | *S. pneumoniae* dexB, cap1[A, B, C, D, E, F, G, H, I, J, K] genes, dTDP-rhamnose biosynthesis genes and aliA gene | 100 | 94 | 162 |
| 53 | 8 | 2831 | 2475 | emb\|Z83335\|SPZ8 | *S. pneumoniae* dexB, cap1[A, B, C, D, E, F, G, H, I, J, K] genes, dTDP-rhamnose biosynthesis genes and aliA gene | 99 | 338 | 357 |
| 54 | 13 | 12409 | 11105 | emb\|Z83335\|SPZ8 | *S. pneumoniae* dexB, cap1[A, B, C, D, E, F, G, H, I, J, K] genes, dTDP-rhamnose biosynthesis genes and aliA gene | 67 | 591 | 1305 |
| 55 | 22 | 20488 | 19949 | emb\|Z84379\|HSZ8 | *S. pneumoniae* dfr gene (isolate 92) | 99 | 540 | 540 |
| 61 | 11 | 11864 | 9900 | emb\|Z16082\|PNAL | *Streptococcus pneumoniae* aliB gene | 98 | 1965 | 1965 |
| 63 | 1 | 3 | 239 | gb\|M18729\| | *S. pneumoniae* mismatch repair protein (hexA) gene, complete cds | 100 | 237 | 237 |
| 63 | 2 | 233 | 2611 | gb\|M18729\| | *S. pneumoniae* mismatch repair protein (hexA) gene, complete cds | 99 | 2330 | 2379 |
| 63 | 3 | 2557 | 2823 | gb\|M18729\| | *S. pneumoniae* mismatch repair protein (hexA) gene, complete cds | 99 | 266 | 267 |
| 63 | 4 | 2958 | 4664 | gb\|M18729\| | *S. pneumoniae* mismatch repair protein (hexA) gene, complete cds | 95 | 69 | 1707 |
| 67 | 6 | 3770 | 3399 | gb\|L20670\| | *Streptococcus pneumoniae* hyaluronidase gene, complete cds | 96 | 372 | 372 |
| 67 | 7 | 7161 | 4171 | gb\|L20670\| | *Streptococcus pneumoniae* hyaluronidase gene, complete cds | 99 | 2938 | 2991 |
| 70 | 1 | 1 | 702 | gb\|M14340\| | *S. pneumoniae* DpnI gene region encoding dpnC and dpnD, complete cds | 100 | 693 | 702 |
| 70 | 2 | 678 | 1160 | gb\|M14340\| | *S. pneumoniae* DpnI gene region encoding dpnC and dpnD, complete cds | 100 | 483 | 483 |
| 70 | 3 | 2490 | 1210 | gb\|M14339\| | *S. pneumoniae* DpnII gene region encoding dpnM, dpnA, dpnB, complete cds | 98 | 462 | 1281 |
| 70 | 7 | 4230 | 4424 | gb\|J04234\| | *S. pneumoniae* exodeoxyribonuclease (exoA) gene, complete cds | 99 | 147 | 195 |
| 70 | 8 | 5197 | 4316 | gb\|J04234\| | *S. pneumoniae* exodeoxyribonuclease (exoA) gene, complete cds | 99 | 881 | 882 |
| 70 | 13 | 8108 | 9874 | gb\|L20562\| | *Streptococcus pneumoniae* Exp8 gene, partial cds | 93 | 234 | 1767 |
| 71 | 22 | 27964 | 28341 | emb\|X63602\|SPBO | *S. pneumoniae* mmsA-Box | 93 | 233 | 378 |
| 72 | 5 | 4607 | 3552 | emb\|Z26850\|SPAT | *S. pneumoniae* (M222) genes for ATPase a subunit, ATPase b subunit and ATPase c subunit | 97 | 102 | 1056 |
| 73 | 1 | 471 | 133 | emb\|X63602\|SPBO | *S. pneumoniae* mmsA-Box | 91 | 193 | 339 |
| 73 | 3 | 3658 | 977 | gb\|J04479\| | *S. pneumoniae* DNA polymerase I (polA) gene, complete cds | 99 | 2682 | 2682 |
| 73 | 8 | 4864 | 5379 | gb\|M36180\| | *Streptococcus pneumoniae* transposase, (comA and comB) and SAICAR synthetase (purC) genes, complete cds | 98 | 318 | 516 |
| 77 | 3 | 2622 | 1999 | emb\|Z83335\|SPZ8 | *S. pneumoniae* dexB, cap1[A, B, C, D, E, F, G, H, I, J, K] genes, dTDP-rhamnose biosynthesis genes and aliA gene | 95 | 624 | 624 |
| 77 | 4 | 3341 | 2523 | emb\|Z83335\|SPZ8 | *S. pneumoniae* dexB, cap1[A, B, C, D, E, F, G, H, I, J, K] genes, dTDP-rhamnose biosynthesis genes and aliA gene | 91 | 819 | 819 |
| 78 | 1 | 341 | 3 | emb\|X77249\|SPR6 | *S. pneumoniae* (R6) ciaR/ciaH genes | 99 | 339 | 339 |
| 78 | 2 | 1095 | 325 | emb\|X77249\|SPR6 | *S. pneumoniae* (R6) ciaR/ciaH genes | 99 | 771 | 771 |
| 82 | 10 | 11436 | 10816 | gb\|U90721\| | *Streptococcus pneumoniae* signal peptidase I (spi) gene, complete cds | 97 | 621 | 621 |
| 82 | 11 | 12402 | 11434 | gb\|U93576\| | *Streptococcus pneumoniae* ribonuclease HII (rnhB) gene, complete cds | 98 | 953 | 969 |
| 82 | 12 | 12381 | 12704 | gb\|U93576\| | *Streptococcus pneumoniae* ribonuclease HII (rnhB) gene, complete cds | 100 | 51 | 324 |
| 83 | 8 | 3212 | 3550 | emb\|Z77727\|SPIS | *S. pneumoniae* DNA for insertion sequence IS1318 (823 bp) | 97 | 290 | 339 |
| 83 | 10 | 4662 | 6851 | gb\|M36180\| | *Streptococcus pneumoniae* transposase, (comA and comB) and SAICAR synthetase (purC) genes, complete cds | 99 | 2190 | 2190 |
| 83 | 11 | 6849 | 8213 | gb\|M36180\| | *Streptococcus pneumoniae* transposase, (comA and comB) and SAICAR synthetase (purC) genes, complete cds | 99 | 1365 | 1365 |
| 83 | 12 | 8236 | 9090 | gb\|M36180\| | *Streptococcus pneumoniae* transposase, (comA and comB) and SAICAR synthetase (purC) genes, complete cds | 99 | 855 | 855 |
| 83 | 13 | 9283 | 13017 | gb\|L15190\| | *Streptococcus pneumoniae* SAICAR synthetase (purC) gene, complete cds | 100 | 107 | 3735 |
| 83 | 23 | 22147 | 23313 | gb\|L36923\| | *Streptococcus pneumoniae* beta-N-acetylhexosaminidase (strH) gene, complete cds | 98 | 218 | 1167 |
| 83 | 24 | 23268 | 23450 | gb\|L36923\| | *Streptococcus pneumoniae* beta-N-acetylhexosaminidase (strH) gene, complete cds | 98 | 172 | 183 |
| 83 | 25 | 27527 | 23505 | gb\|L36923\| | *Streptococcus pneumoniae* beta-N-acetylhexosaminidase (strH) gene, complete cds | 99 | 3826 | 4023 |
| 83 | 26 | 28472 | 27771 | gb\|L36923\| | *Streptococcus pneumoniae* beta-N-acetylhexosaminidase (strH) gene, complete cds | 99 | 416 | 702 |
| 84 | 4 | 4554 | 6173 | emb\|Z83335\|SPZ8 | *S. pneumoniae* dexB, cap1[A, B, C, D, E, F, G, H, I, J, K] genes, dTDP-rhamnose biosynthesis genes and aliA gene | 98 | 697 | 1620 |
| 87 | 6 | 5951 | 5316 | emb\|Z77725\|SPIS | *S. pneumoniae* DNA for insertion sequence IS1381 (966 bp) | 96 | 439 | 636 |

TABLE 1-continued

*S. pneumoniae* - Coding regions containing known sequences

| Contig ID | ORF ID | Start (nt) | Stop (nt) | match acession | match gene name | percent ident | HSP nt length | ORF nt length |
|---|---|---|---|---|---|---|---|---|
| 88 | 5 | 2957 | 3511 | gb\|M36180\| | *Streptococcus pneumoniae* transposase, (comA and comB) and SAICAR synthetase (purC) genes, complete cds | 94 | 555 | 555 |
| 88 | 6 | 3466 | 4269 | gb\|M36180\| | *Streptococcus pneumoniae* transposase, (comA and comB) and SAICAR synthetase (purC) genes, complete cds | 94 | 804 | 804 |
| 89 | 13 | 9878 | 10093 | gb\|M36180\| | *Streptococcus pneumoniae* transposase, (comA and comB) and SAICAR synthetase (purC) genes, complete cds | 97 | 211 | 216 |
| 89 | 14 | 10062 | 10412 | emb\|Z83335\|SPZ8 | *S. pneumoniae* dexB, cap1[A, B, C, D, E, F, G, H, I, J, K] genes, dTDP-rhamnose biosynthesis genes and aliA gene | 97 | 335 | 351 |
| 93 | 10 | 5303 | 4941 | emb\|X63602\|SPBO | *S. pneumoniae* mmsA-Box | 89 | 237 | 363 |
| 97 | 4 | 1708 | 1520 | gb\|U41735\| | *Streptococcus pneumoniae* peptide methionine sulfoxide reductase (msrA) and homoserine kinase homolog (thrB) genes, complete cds | 91 | 140 | 189 |
| 99 | 1 | 89 | 700 | emb\|Z83335\|SPZ8 | *S. pneumoniae* dexB, cap1[A, B, C, D, E, F, G, H, I, J, K] genes, dTDP-rhamnose biosynthesis genes and aliA gene | 93 | 592 | 612 |
| 99 | 2 | 1773 | 775 | emb\|X17337\|SPAM | *Streptococcus pneumoniae* ami locus conferring aminopterin resistance | 99 | 998 | 999 |
| 99 | 3 | 2794 | 1712 | emb\|X17337\|SPAM | *Streptococcus pneumoniae* ami locus conferring aminopterin resistance | 99 | 1083 | 1083 |
| 99 | 4 | 3732 | 2788 | emb\|X17337\|SPAM | *Streptococcus pneumoniae* ami locus conferring aminopterin resistance | 100 | 945 | 945 |
| 99 | 5 | 5249 | 3714 | emb\|X17337\|SPAM | *Streptococcus pneumoniae* ami locus conferring aminopterin resistance | 100 | 1536 | 1536 |
| 99 | 6 | 7262 | 5277 | emb\|X17337\|SPAM | *Streptococcus pneumoniae* ami locus conferring aminopterin resistance | 99 | 1986 | 1986 |
| 101 | 1 | 216 | 1538 | emb\|X54225\|SPEN | *S. pneumoniae* epuA and endA genes for 7 kDa protein and membrane endonuclease | 99 | 146 | 1323 |
| 101 | 2 | 1492 | 1719 | emb\|X54225\|SPEN | *S. pneumoniae* epuA and endA genes for 7 kDa protein and membrane endonuclease | 99 | 228 | 228 |
| 101 | 3 | 1694 | 1855 | emb\|X54225\|SPEN | *S. pneumoniae* epuA and endA genes for 7 kDa protein and membrane endonuclease | 100 | 162 | 162 |
| 101 | 4 | 1701 | 2582 | emb\|X54225\|SPEN | *S. pneumoniae* epuA and endA genes for 7 kDa protein and membrane endonuclease | 100 | 882 | 882 |
| 103 | 7 | 5556 | 5041 | emb\|Z95914\|SPZ9 | *Streptococcus pneumoniae* sodA gene | 100 | 396 | 516 |
| 104 | 2 | 1347 | 1556 | emb\|Z77727\|SPIS | *S. pneumoniae* DNA for insertion sequence IS1318 (823 bp) | 83 | 206 | 210 |
| 105 | 5 | 5381 | 5028 | emb\|Z67739\|SPPA | *S. pneumoniae* parC, parE and transposase genes and unknown orf | 98 | 353 | 354 |
| 105 | 6 | 6089 | 5379 | emb\|Z67739\|SPPA | *S. pneumoniae* parC, parE and transposase genes and unknown orf | 98 | 84 | 711 |
| 107 | 4 | 2785 | 1880 | emb\|X16022\|SPPE | *S. pneumoniae* penA gene | 98 | 72 | 906 |
| 107 | 5 | 2913 | 4988 | emb\|X16022\|SPPE | *S. pneumoniae* penA gene | 99 | 1692 | 2076 |
| 107 | 6 | 4981 | 5595 | emb\|X13136\|SPPE | *Streptococcus pneumoniae* penA gene for penicillin binding protein 2B lacking N-term. (penicillin resistant strain) | 91 | 107 | 615 |
| 108 | 9 | 9068 | 8718 | emb\|Z67739\|SPPA | *S. pneumoniae* parC, parE and transposase genes and unknown orf | 95 | 342 | 351 |
| 108 | 12 | 11308 | 10922 | emb\|Z67739\|SPPA | *S. pneumoniae* parC, parE and transposase genes and unknown orf | 99 | 199 | 387 |
| 109 | 3 | 2768 | 2241 | emb\|Z77725\|SPIS | *S. pneumoniae* DNA for insertion sequence IS1381 (966 bp) | 96 | 61 | 528 |
| 109 | 4 | 2688 | 2855 | emb\|Z77726\|SPIS | *S. pneumoniae* DNA for insertion sequence IS1318 (1372 bp) | 96 | 148 | 168 |
| 109 | 5 | 2862 | 3269 | emb\|Z77727\|SPIS | *S. pneumoniae* DNA for insertion sequence IS1318 (823 bp) | 97 | 353 | 408 |
| 109 | 6 | 5320 | 3584 | gb\|M18729\| | *S. pneumoniae* mismatch repair protein (hexA) gene, complete cds | 100 | 371 | 1737 |
| 113 | 1 | 431 | 3 | gb\|M36180\| | *Streptococcus pneumoniae* transposase, (comA and comB) and SAICAR synthetase (purC) genes, complete cds | 95 | 429 | 429 |
| 113 | 10 | 9788 | 8532 | emb\|X99400\|SPDA | *S. pneumoniae* dacA gene and ORF | 99 | 1257 | 1257 |
| 113 | 11 | 9870 | 10985 | emb\|X99400\|SPDA | *S. pneumoniae* dacA gene and ORF | 99 | 1116 | 1116 |
| 114 | 3 | 2530 | 2030 | gb\|M36180\| | *Streptococcus pneumoniae* transposase, (comA and comB) and SAICAR synthetase (purC) genes, complete cds | 95 | 481 | 501 |
| 115 | 11 | 11303 | 10932 | gb\|U04047\| | *Streptococcus pneumoniae* SSZ dextran glucosidase gene and insertion sequence IS1202 transposase gene, complete cds | 97 | 372 | 372 |
| 117 | 1 | 897 | 3302 | emb\|X72967\|SPNA | *S. pneumoniae* nanA gene | 99 | 2402 | 2406 |
| 117 | 2 | 3277 | 3831 | emb\|X72967\|SPNA | *S. pneumoniae* nanA gene | 99 | 237 | 555 |
| 117 | 3 | 4327 | 3899 | gb\|M36180\| | *Streptococcus pneumoniae* transposase, (comA and comB) and SAICAR synthetase (purC) genes, complete cds | 98 | 429 | 429 |
| 121 | 2 | 1369 | 1941 | gb\|U72720\| | *Streptococcus pneumoniae* heat shock protein 70 (dnaK) gene, complete cds and DnaJ (dnaJ) gene, partial cds | 99 | 202 | 573 |
| 121 | 3 | 2412 | 4253 | gb\|U72720\| | *Streptococcus pneumoniae* heat shock protein 70 (dnaK) gene, complete cds and DnaJ (dnaJ) gene, partial cds | 99 | 1842 | 1842 |
| 122 | 8 | 5066 | 5587 | gb\|U04047\| | *Streptococcus pneumoniae* SSZ dextran glucosidase gene and insertion sequence IS1202 transposase gene, complete cds | 64 | 451 | 522 |
| 125 | 1 | 1811 | 189 | gb\|M36180\| | *Streptococcus pneumoniae* transposase, (comA and comB) and SAICAR synthetase (purC) genes, complete cds | 92 | 99 | 1623 |
| 128 | 15 | 12496 | 11204 | emb\|Z83335\|SPZ8 | *S. pneumoniae* dexB, cap1[A, B, C, D, E, F, G, H, I, J, K] genes, dTDP-rhamnose biosynthesis genes and aliA gene | 91 | 705 | 1293 |
| 134 | 1 | 1 | 492 | emb\|Y10818\|SPY1 | *S. pneumoniae* spsA gene | 99 | 203 | 492 |
| 134 | 2 | 556 | 2652 | gb\|AF019904\| | *Streptococcus pneumoniae* choline binding protein A (cbpA) gene, partial cds | 86 | 685 | 2097 |
| 134 | 3 | 1160 | 837 | emb\|Y10818\|SPY1 | *S. pneumoniae* spsA gene | 86 | 324 | 324 |
| 134 | 4 | 3952 | 2882 | gb\|AF019904\| | *Streptococcus pneumoniae* choline binding protein A (cbpA) gene, partial cds | 98 | 215 | 1071 |

TABLE 1-continued

S. pneumoniae - Coding regions containing known sequences

| Contig ID | ORF ID | Start (nt) | Stop (nt) | match acession | match gene name | percent ident | HSP nt length | ORF nt length |
|---|---|---|---|---|---|---|---|---|
| 134 | 8 | 7992 | 9848 | gb\|U12567\| | Streptococcus pneumoniae P13 glycerol-3-phosphate dehydrogenase (glpD) gene, partial cds, and glycerol uptake facilitator (glpF) and ORF3 genes, complete cds | 99 | 285 | 1857 |
| 134 | 9 | 9846 | 10622 | gb\|U12567\| | Streptococcus pneumoniae P13 glycerol-3-phosphate dehydrogenase (glpD) gene, partial cds, and glycerol uptake facilitator (glpF) and ORF3 genes, complete cds | 99 | 570 | 777 |
| 134 | 10 | 10805 | 11122 | gb\|U12567\| | Streptococcus pneumoniae P13 glycerol-3-phosphate dehydrogenase (glpD) gene, partial cds, and glycerol uptake facilitator (glpF) and ORF3 genes, complete cds | 100 | 318 | 318 |
| 137 | 13 | 7970 | 8443 | gb\|U09239\| | Streptococcus pneumoniae type 19F capsular polysaccharide biosynthesis operon, (cps19fABCDEFGHIJKLMNO) genes, complete cds, and aliA gene, partial cds | 90 | 420 | 474 |
| 137 | 14 | 8590 | 8775 | emb\|Z83335\|SPZ8 | S. pneumoniae dexB, cap1[A, B, C, D, E, F, G, H, I, J, K] genes, dTDP-rhamnose biosynthesis genes and aliA gene | 94 | 174 | 186 |
| 137 | 15 | 8773 | 8967 | emb\|Z83335\|SPZ8 | S. pneumoniae dexB, cap1[A, B, C, D, E, F, G, H, I, J, K] genes, dTDP-rhamnose biosynthesis genes and aliA gene | 98 | 195 | 195 |
| 137 | 16 | 9223 | 9687 | emb\|Z77726\|SPIS | S. pneumoniae DNA for insertion sequence IS1318 (1372 bp) | 96 | 446 | 465 |
| 137 | 17 | 9641 | 10051 | emb\|Z77727\|SPIS | S. pneumoniae DNA for insertion sequence IS1318 (823 bp) | 96 | 293 | 411 |
| 139 | 10 | 12998 | 12702 | emb\|X63602\|SPBO | S. pneumoniae mmsA-Box | 90 | 234 | 297 |
| 141 | 8 | 7805 | 8938 | emb\|Z49988\|SPMM | Streptococcus pneumoniae mmsA gene | 99 | 338 | 1134 |
| 141 | 9 | 8936 | 10972 | emb\|Z49988\|SPMM | Streptococcus pneumoniae mmsA gene | 99 | 2037 | 2037 |
| 141 | 10 | 11472 | 12467 | emb\|Z49988\|SPMM | Streptococcus pneumoniae mmsA gene | 100 | 76 | 996 |
| 142 | 2 | 257 | 814 | gb\|M80215\| | Streptococcus pneumoniae uvs402 protein gene, complete cds | 98 | 174 | 558 |
| 142 | 3 | 787 | 957 | gb\|M80215\| | Streptococcus pneumoniae uvs402 protein gene, complete cds | 100 | 142 | 171 |
| 142 | 4 | 980 | 3022 | gb\|M80215\| | Streptococcus pneumoniae uvs402 protein gene, complete cds | 95 | 1997 | 2043 |
| 142 | 5 | 3020 | 3595 | gb\|M80215\| | Streptococcus pneumoniae uvs402 protein gene, complete cds | 100 | 153 | 576 |
| 145 | 1 | 1 | 219 | emb\|Z35135\|SPAL | S. pneumoniae aliA gene for amiA-like gene A | 97 | 185 | 219 |
| 145 | 2 | 171 | 1994 | gb\|L20556\| | Streptococcus pneumoniae plpA gene, partial cds | 99 | 1811 | 1824 |
| 145 | 3 | 2287 | 7599 | emb\|Z47210\|SPDE | S. pneumoniae dexB, cap3A, cap3B and cap3C genes and orfs | 99 | 1052 | 5313 |
| 145 | 4 | 9934 | 7766 | gb\|M90527\| | Streptococcus pneumoniae penicillin-binding protein (ponA) gene, complete cds | 99 | 2169 | 2169 |
| 145 | 5 | 10488 | 9922 | gb\|M90527\| | Streptococcus pneumoniae penicillin-binding protein (ponA) gene, complete cds | 99 | 512 | 567 |
| 146 | 1 | 159 | 4 | emb\|Z82002\|SPZ8 | S. pneumoniae pcpB and pcpC genes | 98 | 156 | 156 |
| 146 | 2 | 344 | 90 | emb\|Z82002\|SPZ8 | S. pneumoniae pcpB and pcpC genes | 98 | 255 | 255 |
| 146 | 16 | 11795 | 10794 | emb\|Z82002\|SPZ8 | S. pneumoniae pcpB and pcpC genes | 85 | 276 | 1002 |
| 147 | 11 | 10678 | 10202 | emb\|Z21702\|SPUN | S. pneumoniae ung gene and mutX genes encoding uracil-DNA glycosylase and 8- oxodGTP nucleoside triphosphatase | 98 | 477 | 477 |
| 147 | 12 | 11338 | 10676 | emb\|Z21702\|SPUN | S. pneumoniae ung gene and mutX genes encoding uracil-DNA glycosylase and 8- oxodGTP nucleoside triphosphatase | 99 | 663 | 663 |
| 148 | 12 | 9009 | 8815 | gb\|U41735\| | Streptococcus pneumoniae peptide methionine sulfoxide reductase (msrA) and homoserine kinase homolog (thrB) genes, complete cds | 90 | 180 | 195 |
| 156 | 4 | 1154 | 1402 | emb\|X63602\|SPBO | S. pneumoniae mmsA-Box | 94 | 185 | 249 |
| 159 | 13 | 9048 | 8521 | gb\|M36180\| | Streptococcus pneumoniae transposase, (comA and comB) and SAICAR synthetase (purC) genes, complete cds | 98 | 526 | 528 |
| 160 | 1 | 1 | 147 | emb\|Z26851\|SPAT | S. pneumoniae (R6) genes for ATPase a subunit, ATPase b subunit and ATPase c subunit | 100 | 142 | 147 |
| 160 | 2 | 179 | 898 | emb\|Z26851\|SPAT | S. pneumoniae (R6) genes for ATPase a subunit, ATPase b subunit and ATPase c subunit | 99 | 720 | 720 |
| 160 | 3 | 906 | 1406 | emb\|Z26850\|SPAT | S. pneumoniae (M222) genes for ATPase a subunit, ATPase b subunit and ATPase c subunit | 95 | 501 | 501 |
| 160 | 4 | 1373 | 1942 | emb\|Z26850\|SPAT | S. pneumoniae (M222) genes for ATPase a subunit, ATPase b subunit and ATPase c subunit | 87 | 306 | 570 |
| 161 | 1 | 1 | 984 | emb\|X77249\|SPR6 | S. pneumoniae (R6) ciaR/ciaH genes | 99 | 984 | 984 |
| 161 | 7 | 6910 | 7497 | emb\|X83917\|SPGY | S. pneumoniae orflgyrB and gyrB gene encoding DNA gyrase B subunit | 99 | 437 | 588 |
| 161 | 8 | 7443 | 9386 | emb\|X83917\|SPGY | S. pneumoniae orflgyrB and gyrB gene encoding DNA gyrase B subunit | 98 | 1912 | 1944 |
| 163 | 1 | 2 | 2155 | gb\|L20559\| | Streptococcus pneumoniae Exp5 gene, partial cds | 98 | 327 | 2154 |
| 165 | 1 | 32 | 1618 | gb\|J01796\| | S. pneumoniae malX and malM genes encoding membrane protein and amylomaltase, complete cds, and malP gene encoding phosphorylase | 99 | 1587 | 1587 |
| 165 | 2 | 1608 | 3902 | gb\|J01796\| | S. pneumoniae malX and malM genes encoding membrane protein and amylomaltase, complete cds, and malP gene encoding phosphorylase | 100 | 280 | 2295 |
| 166 | 1 | 378 | 4 | emb\|Y11463\|SPDN | Streptococcus pneumoniae dnaG, rpoD, cpoA genes and ORF3 and ORF5 | 100 | 375 | 375 |
| 166 | 2 | 1507 | 320 | emb\|Y11463\|SPDN | Streptococcus pneumoniae dnaG, rpoD, cpoA genes and ORF3 and ORF5 | 99 | 1188 | 1188 |
| 166 | 3 | 3240 | 1432 | emb\|Y11463\|SPDN | Streptococcus pneumoniae dnaG, rpoD, cpoA genes and ORF3 and ORF5 | 99 | 563 | 1809 |
| 167 | 1 | 1077 | 328 | emb\|Z71552\|SPAD | Streptococcus pneumoniae adcCBA operon | 94 | 155 | 750 |
| 167 | 2 | 1844 | 999 | emb\|Z71552\|SPAD | Streptococcus pneumoniae adcCBA operon | 98 | 405 | 846 |
| 167 | 3 | 2714 | 1842 | emb\|Z71552\|SPAD | Streptococcus pneumoniae adcCBA operon | 97 | 604 | 873 |

TABLE 1-continued

*S. pneumoniae* - Coding regions containing known sequences

| Contig ID | ORF ID | Start (nt) | Stop (nt) | match acession | match gene name | percent ident | HSP nt length | ORF nt length |
|---|---|---|---|---|---|---|---|---|
| 167 | 4 | 3399 | 2641 | emb\|Z71552\|SPAD | *Streptococcus pneumoniae* adcCBA operon | 99 | 703 | 759 |
| 168 | 1 | 1 | 2259 | gb\|L20558\| | *Streptococcus pneumoniae* Exp4 gene, partial cds | 99 | 282 | 2259 |
| 170 | 10 | 7338 | 7685 | emb\|Z77726\|SPIS | *S. pneumoniae* DNA for insertion sequence IS1318 (1372 bp) | 95 | 315 | 348 |
| 172 | 6 | 2462 | 4981 | gb\|U47625\| | *Streptococcus pneumoniae* formate acetyltransferase (exp72) gene, partial cds | 97 | 365 | 2520 |
| 175 | 1 | 373 | 20 | gb\|M36180\| | *Streptococcus pneumoniae* transposase, (comA and comB) and SAICAR synthetase (purC) genes, complete cds | 89 | 353 | 354 |
| 175 | 4 | 1843 | 3621 | emb\|Z47210\|SPDE | *S. pneumoniae* dexB, cap3A, cap3B and cap3C genes and orfs | 95 | 89 | 1779 |
| 176 | 5 | 3984 | 2980 | emb\|Z67739\|SPPA | *S. pneumoniae* parC, parE and transposase genes and unknown orf | 100 | 573 | 1005 |
| 178 | 1 | 3 | 425 | emb\|Z67739\|SPPA | *S. pneumoniae* parC, parE and transposase genes and unknown orf | 95 | 423 | 423 |
| 179 | 1 | 426 | 70 | emb\|Z83335\|SPZ8 | *S. pneumoniae* dexB, cap1[A, B, C, D, E, F, G, H, I, J, K] genes, dTDP-rhamnose biosynthesis genes and aliA gene | 99 | 338 | 357 |
| 180 | 3 | 3084 | 1855 | emb\|X95718\|SPGY | *S. pneumoniae* gyrA gene | 99 | 381 | 1230 |
| 186 | 1 | 714 | 4 | emb\|Z79691\|SOOR | *S. pneumoniae* yorf[A, B, C, D, E], ftsL, pbpX and regR genes | 98 | 59 | 711 |
| 186 | 2 | 2254 | 608 | emb\|Z79691\|SOOR | *S. pneumoniae* yorf[A, B, C, D, E], ftsL, pbpX and regR genes | 98 | 315 | 1647 |
| 186 | 3 | 707 | 880 | emb\|Z79691\|SOOR | *S. pneumoniae* yorf[A, B, C, D, E], ftsL, pbpX and regR genes | 98 | 174 | 174 |
| 189 | 1 | 2 | 259 | gb\|U72720\| | *Streptococcus pneumoniae* heat shock protein 70 (dnaK) gene, complete cds and DnaJ (dnaJ) gene, partial cds | 99 | 258 | 258 |
| 189 | 2 | 600 | 385 | gb\|U72720\| | *Streptococcus pneumoniae* heat shock protein 70 (dnaK) gene, complete cds and DnaJ (dnaJ) gene, partial cds | 98 | 204 | 216 |
| 189 | 3 | 1018 | 851 | gb\|U72720\| | *Streptococcus pneumoniae* heat shock protein 70 (dnaK) gene, complete cds and DnaJ (dnaJ) gene, partial cds | 99 | 168 | 168 |
| 189 | 4 | 1012 | 2154 | gb\|U72720\| | *Streptococcus pneumoniae* heat shock protein 70 (dnaK) gene, complete cds and DnaJ (dnaJ) gene, partial cds | 99 | 1062 | 1143 |
| 191 | 9 | 7829 | 7524 | emb\|X63602\|SPBO | *S. pneumoniae* mmsA-Box | 95 | 234 | 306 |
| 194 | 1 | 1 | 729 | gb\|M36180\| | *Streptococcus pneumoniae* transposase, (comA and comB) and SAICAR synthetase (purC) genes, complete cds | 91 | 728 | 729 |
| 199 | 2 | 1117 | 881 | emb\|Z83335\|SPZ8 | *S. pneumoniae* dexB, cap1[A, B, C, D, E, F, G, H, I, J, K] genes, dTDP-rhamnose biosynthesis genes and aliA gene | 96 | 211 | 237 |
| 199 | 4 | 1499 | 1762 | emb\|Z83335\|SPZ8 | *S. pneumoniae* dexB, cap1[A, B, C, D, E, F, G, H, I, J, K] genes, dTDP-rhamnose biosynthesis genes and aliA gene | 89 | 248 | 264 |
| 199 | 5 | 1781 | 2284 | emb\|Z83335\|SPZ8 | *S. pneumoniae* dexB, cap1[A, B, C, D, E, F, G, H, I, J, K] genes, dTDP-rhamnose biosynthesis genes and aliA gene | 98 | 504 | 504 |
| 203 | 1 | 1977 | 337 | gb\|L20563\| | *Streptococcus pneumoniae* Exp9 gene, partial cds | 99 | 342 | 1641 |
| 204 | 1 | 1145 | 3 | gb\|L36131\| | *Streptococcus pneumoniae* exp10 gene, complete cds, recA gene, 5' end | 99 | 1143 | 1143 |
| 208 | 1 | 59 | 2296 | gb\|U89711\| | *Streptococcus pneumoniae* pneumococcal surface protein A PspA (pspA) gene, complete cds | 90 | 471 | 2238 |
| 213 | 3 | 2455 | 2123 | emb\|Z83335\|SPZ8 | *S. pneumoniae* dexB, cap1[A, B, C, D, E, F, G, H, I, J, K] genes, dTDP-rhamnose biosynthesis genes and aliA gene | 96 | 332 | 333 |
| 216 | 1 | 368 | 12 | emb\|Z83335\|SPZ8 | *S. pneumoniae* dexB, cap1[A, B, C, D, E, F, G, H, I, J, K] genes, dTDP-rhamnose biosynthesis genes and aliA gene | 99 | 338 | 357 |
| 216 | 3 | 2650 | 2327 | gb\|M28678\| | *S. pneumoniae* promoter sequence DNA | 98 | 86 | 324 |
| 222 | 1 | 417 | 4 | emb\|Z83335\|SPZ8 | *S. pneumoniae* dexB, cap1[A, B, C, D, E, F, G, H, I, J, K] genes, dTDP-rhamnose biosynthesis genes and aliA gene | 94 | 414 | 414 |
| 227 | 3 | 5266 | 4238 | emb\|AJ000336\|SP | *Streptococcus pneumoniae* ldh | 99 | 1029 | 1029 |
| 239 | 1 | 1 | 804 | gb\|M31296\| | *S. pneumoniae* recP gene, complete cds | 95 | 484 | 804 |
| 247 | 3 | 1625 | 1807 | gb\|M36180\| | *Streptococcus pneumoniae* transposase, (comA and comB) and SAICAR synthetase (purC) genes, complete cds | 94 | 178 | 183 |
| 249 | 3 | 921 | 1364 | emb\|Z83335\|SPZ8 | *S. pneumoniae* dexB, cap1[A, B, C, D, E, F, G, H, I, J, K] genes, dTDP-rhamnose biosynthesis genes and aliA gene | 94 | 443 | 444 |
| 253 | 1 | 362 | 3 | gb\|M36180\| | *Streptococcus pneumoniae* transposase, (comA and comB) and SAICAR synthetase (purC) genes, complete cds | 99 | 360 | 360 |
| 253 | 5 | 1238 | 2050 | emb\|Z83335\|SPZ8 | *S. pneumoniae* dexB, cap1[A, B, C, D, E, F, G, H, I, J, K] genes, dTDP-rhamnose biosynthesis genes and aliA gene | 95 | 420 | 813 |
| 253 | 6 | 2069 | 2572 | emb\|Z83335\|SPZ8 | *S. pneumoniae* dexB, cap1[A, B, C, D, E, F, G, H, I, J, K] genes, dTDP-rhamnose biosynthesis genes and aliA gene | 97 | 504 | 504 |
| 255 | 1 | 3 | 800 | emb\|Z82002\|SPZ8 | *S. pneumoniae* pcpB and pcpC genes | 97 | 531 | 798 |
| 255 | 2 | 798 | 1841 | emb\|Z82002\|SPZ8 | *S. pneumoniae* pcpB and pcpC genes | 97 | 672 | 1044 |
| 255 | 3 | 2493 | 1969 | emb\|Z67739\|SPPA | *S. pneumoniae* parC, parE and transposase genes and unknown orf | 92 | 435 | 525 |
| 257 | 2 | 985 | 770 | emb\|X17337\|SPAM | *Streptococcus pneumoniae* ami locus conferring aminopterin resistance | 96 | 117 | 216 |
| 257 | 3 | 1245 | 907 | gb\|M36180\| | *Streptococcus pneumoniae* transposase, (comA and comB) and SAICAR synthetase (purC) genes, complete cds | 97 | 339 | 339 |
| 267 | 2 | 495 | 1208 | gb\|U16156\| | *Streptococcus pneumoniae* dihydropteroate synthase (sulA), dihydrofolate synthetase (sulB), guanosine triphosphate cyclohydrolase (sulC), aldolase-pyrophosphokinase (sulD) genes, complete cds | 95 | 84 | 714 |
| 267 | 3 | 1291 | 2277 | gb\|U16156\| | *Streptococcus pneumoniae* dihydropteroate synthase (sulA), dihydrofolate synthetase (sulB), guanosine triphosphate cyclohydrolase (sulC), aldolase-pyrophosphokinase (sulD) genes, complete cds | 97 | 755 | 987 |

TABLE 1-continued

*S. pneumoniae* - Coding regions containing known sequences

| Contig ID | ORF ID | Start (nt) | Stop (nt) | match acession | match gene name | percent ident | HSP nt length | ORF nt length |
|---|---|---|---|---|---|---|---|---|
| 267 | 4 | 2261 | 3601 | gb|U16156| | *Streptococcus pneumoniae* dihydropteroate synthase (sulA), dihydrofolate synthetase (sulB), guanosine triphosphate cyclohydrolase (sulC), aldolase-pyrophosphokinase (sulD) genes, complete cds | 98 | 1341 | 1341 |
| 267 | 5 | 3561 | 4136 | gb|U16156| | *Streptococcus pneumoniae* dihydropteroate synthase (sulA), dihydrofolate synthetase (sulB), guanosine triphosphate cyclohydrolase (sulC), aldolase-pyrophosphokinase (sulD) genes, complete cds | 99 | 576 | 576 |
| 267 | 6 | 4164 | 4949 | gb|U16156| | *Streptococcus pneumoniae* dihydropteroate synthase (sulA), dihydrofolate synthetase (sulB), guanosine triphosphate cyclohydrolase (sulC), aldolase-pyrophosphokinase (sulD) genes, complete cds | 99 | 748 | 786 |
| 267 | 7 | 5544 | 5140 | gb|U16156| | *Streptococcus pneumoniae* dihydropteroate synthase (sulA), dihydrofolate synthetase (sulB), guanosine triphosphate cyclohydrolase (sulC), aldolase- pyrophosphokinase (sulD) genes, complete cds | 100 | 186 | 405 |
| 268 | 4 | 1793 | 1990 | emb|X63602|SPBO | *S. pneumoniae* mmsA-Box | 89 | 194 | 198 |
| 271 | 1 | 562 | 104 | gb|M29686| | *S. pneumoniae* mismatch repair (hexB) gene, complete cds | 93 | 160 | 459 |
| 291 | 1 | 75 | 524 | gb|U04047| | *Streptococcus pneumoniae* SSZ dextran glucosidase gene and insertion sequence IS1202 transposase gene, complete cds | 96 | 450 | 450 |
| 291 | 2 | 1001 | 525 | emb|Z83335|SPZ8 | *S. pneumoniae* dexB, cap1[A, B, C, D, E, F, G, H, I, J, K] genes, dTDP-rhamnose biosynthesis genes and aliA gene | 87 | 205 | 477 |
| 291 | 3 | 807 | 559 | emb|Z83335|SPZ8 | *S. pneumoniae* dexB, cap1[A, B, C, D, E, F, G, H, I, J, K] genes, dTDP-rhamnose biosynthesis genes and aliA gene | 90 | 170 | 249 |
| 291 | 4 | 1374 | 1099 | gb|M36180| | *Streptococcus pneumoniae* transposase, (comA and comB) and SAICAR synthetase (purC) genes, complete cds | 85 | 264 | 276 |
| 293 | 1 | 3 | 1673 | emb|Z67740|SPGY | *S. pneumoniae* gyrB gene and unknown orf | 98 | 553 | 1671 |
| 296 | 1 | 1434 | 151 | emb|Z47210|SPDE | *S. pneumoniae* dexB, cap3A, cap3B and cap3C genes and orfs | 99 | 430 | 1284 |
| 317 | 1 | 157 | 510 | emb|Z67739|SPPA | *S. pneumoniae* parC, parE and transposase genes and unknown orf | 89 | 353 | 354 |
| 325 | 2 | 1237 | 485 | emb|Z83335|SPZ8 | *S. pneumoniae* dexB, cap1[A, B, C, D, E, F, G, H, I, J, K] genes, dTDP-rhamnose biosynthesis genes and aliA gene | 91 | 299 | 753 |
| 326 | 1 | 1 | 462 | emb|Z82001|SPZ8 | *S. pneumoniae* pcpA gene and open reading frames | 100 | 233 | 462 |
| 327 | 1 | 603 | 64 | emb|Z83335|SPZ8 | *S. pneumoniae* dexB, cap1[A, B, C, D, E, F, G, H, I, J, K] genes, dTDP-rhamnose biosynthesis genes and aliA gene | 94 | 89 | 540 |
| 334 | 1 | 153 | 545 | gb|U41735| | *Streptococcus pneumoniae* peptide methionine sulfoxide reductase (msrA) and homoserine kinase homolog (thrB) genes, complete cds | 87 | 91 | 393 |
| 336 | 1 | 308 | 93 | emb|Z26850|SPAT | *S. pneumoniae* (M222) genes for ATPase a subunit, ATPase b subunit and ATPase c subunit | 97 | 102 | 216 |
| 350 | 1 | 1 | 519 | emb|Z67739|SPPA | *S. pneumoniae* parC, parE and transposase genes and unknown orf | 95 | 435 | 519 |
| 360 | 4 | 1598 | 1960 | emb|Z83335|SPZ8 | *S. pneumoniae* dexB, cap1[A, B, C, D, E, F, G, H, I, J, K] genes, dTDP-rhamnose biosynthesis genes and aliA gene | 94 | 353 | 363 |
| 362 | 1 | 673 | 2 | emb|Z83335|SPZ8 | *S. pneumoniae* dexB, cap1[A, B, C, D, E, F, G, H, I, J, K] genes, dTDP-rhamnose biosynthesis genes and aliA gene | 95 | 63 | 672 |
| 362 | 3 | 1168 | 728 | gb|U04047| | *Streptococcus pneumoniae* SSZ dextran glucosidase gene and insertion sequence IS1202 transposase gene, complete cds | 96 | 441 | 441 |
| 384 | 1 | 347 | 111 | emb|X85787|SPCP | *S. pneumoniae* dexB, cps14A, cps14B, cps14C, cps14D, cps14E, cps14F, cps14G, cps14H, cps14I, cps14J, cps14K, cps14L, tasA genes | 94 | 54 | 237 |

TABLE 2

*S. pneumoniae* - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 228 | 2 | 1760 | 1942 | pir|F60663|F606 | translation elongation factor Tu - *Streptococcus oralis* | 100 | 100 | 183 |
| 319 | 1 | 2 | 205 | gi|984927 | neomycin phosphotransferase [Cloning vector pBSL99] | 100 | 100 | 204 |
| 260 | 1 | 2 | 1138 | pir|F60663|F606 | translation elongation factor Tu - *Streptococcus oralis* | 99 | 98 | 1137 |
| 25 | 2 | 486 | 1394 | gi|1574495 | hypothetical [*Haemophilus influenzae*] | 98 | 96 | 909 |
| 94 | 2 | 685 | 1002 | gi|310627 | phosphoenolpyruvate:sugar phosphotransferase system HPr [*Streptococcus mutans*] | 98 | 93 | 318 |
| 312 | 1 | 190 | 2 | gi|347999 | ATP-dependent protease proteolytic subunit [*Streptococcus salivarius*] | 98 | 95 | 189 |
| 329 | 1 | 1 | 807 | gi|924848 | inosine monophosphate dehydrogenase [*Streptococcus pyogenes*] | 98 | 94 | 807 |
| 336 | 2 | 290 | 589 | gi|987050 | lacZ gene product [unidentified cloning vector] | 98 | 98 | 300 |
| 181 | 9 | 5948 | 7366 | gi|153755 | phospho-beta-D-galactosidase (EC 3.2.1.85) [*Lactococcus lactis cremoris*] | 97 | 94 | 1419 |
| 312 | 2 | 1044 | 361 | gi|347998 | uracil phosphoribosyltransferase [*Streptococcus salivarius*] | 97 | 88 | 684 |
| 32 | 8 | 6575 | 7486 | sp|P37214|ERA_S | GTP-BINDING PROTEIN ERA HOMOLOG. | 96 | 91 | 912 |

TABLE 2-continued

*S. pneumoniae* - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 94 | 3 | 951 | 2741 | gi\|153615 | phosphoenolpyruvate:sugar phosphotransferase system enzyme I [*Streptococcus salivarius*] | 96 | 92 | 1791 |
| 127 | 1 | 1 | 168 | gi\|581299 | initiation factor IF-1 [*Lactococcus lactis*] | 96 | 89 | 168 |
| 128 | 14 | 10438 | 11154 | gi\|1276873 | DeoD [*Streptococcus thermophilus*] | 96 | 93 | 717 |
| 181 | 4 | 1362 | 1598 | gi\|46606 | lacD polypeptide (AA 1-326) [*Staphylococcus aureus*] | 96 | 80 | 237 |
| 218 | 1 | 1 | 834 | gi\|1743856 | intrageneric coaggregation-relevant adhesin [*Streptococcus gordonii*] | 96 | 93 | 834 |
| 319 | 2 | 115 | 441 | gi\|208225 | heat-shock protein 82/neomcyn phosphotransferase fusion protein (hsp82-neo) [unidentified cloning vector] | 96 | 96 | 327 |
| 54 | 12 | 8622 | 10967 | gnl\|PID\|d100972 | Pyruvate formate-lyase [*Streptococcus mutans*] | 95 | 89 | 2346 |
| 181 | 2 | 606 | 1289 | gi\|149396 | lacD [*Lactococcus lactis*] | 95 | 89 | 684 |
| 46 | 3 | 3410 | 3045 | gi\|1850606 | YlxM [*Streptococcus mutans*] | 94 | 86 | 366 |
| 89 | 10 | 7972 | 7337 | gi\|703442 | thymidine kinase [*Streptococcus gordonii*] | 94 | 86 | 636 |
| 148 | 9 | 6431 | 7354 | gi\|995767 | UDP-glucose pyrophosphorylase [*Streptococcus pyogenes*] | 94 | 85 | 924 |
| 160 | 7 | 4430 | 5848 | gi\|153573 | H+ ATPase [*Enterococcus faecalis*] | 94 | 87 | 1419 |
| 2 | 3 | 4598 | 3513 | gi\|153763 | plasmin receptor [*Streptococcus pyogenes*] | 93 | 86 | 1086 |
| 12 | 8 | 7877 | 6204 | gi\|1103865 | formyl-tetrahydrofolate synthetase [*Streptococcus mutans*] | 93 | 84 | 1674 |
| 65 | 11 | 4734 | 5120 | gi\|40150 | L14 protein (AA 1-122) [*Bacillus subtilis*] | 93 | 87 | 387 |
| 68 | 1 | 53 | 1297 | gi\|47341 | antitumor protein [*Streptococcus pyogenes*] | 93 | 87 | 1245 |
| 80 | 1 | 3 | 299 | gnl\|PID\|d101166 | ribosomal protein S7 [*Bacillus subtilis*] | 93 | 84 | 297 |
| 127 | 3 | 695 | 1093 | gi\|142462 | ribosomal protein S11 [*Bacillus subtilis*] | 93 | 86 | 399 |
| 160 | 5 | 1924 | 3462 | gi\|1773264 | ATPase, alpha subunit [*Streptococcus mutans*] | 93 | 85 | 1539 |
| 211 | 5 | 3757 | 3047 | gi\|535273 | aminopeptidase C [*Streptococcus thermophilus*] | 93 | 82 | 711 |
| 262 | 1 | 16 | 564 | gi\|149394 | lacB [*Lactococcus lactis*] | 93 | 90 | 549 |
| 366 | 1 | 197 | 3 | gi\|295259 | tryptophan synthase beta subunit [*Synechocystis* sp.] | 93 | 91 | 195 |
| 25 | 3 | 1392 | 1976 | gi\|1574496 | hypothetical [*Haemophilus influenzae*] | 92 | 80 | 585 |
| 36 | 21 | 20781 | 19927 | gi\|310632 | hydrophobic membrane protein [*Streptococcus gordonii*] | 92 | 86 | 855 |
| 181 | 3 | 1265 | 1534 | gi\|149396 | lacD [*Lactococcus lactis*] | 92 | 83 | 270 |
| 181 | 7 | 3662 | 4060 | gi\|149410 | enzyme III [*Lactococcus lactis*] | 92 | 83 | 399 |
| 32 | 4 | 5631 | 3937 | gnl\|PID\|e294090 | fibronectin-binding protein-like protein A [*Streptococcus gordonii*] | 91 | 85 | 1695 |
| 46 | 2 | 3054 | 1462 | gi\|1850607 | signal recognition particle Ffh [*Streptococcus mutans*] | 91 | 84 | 1593 |
| 65 | 10 | 4442 | 4726 | pir\|S17865\|S178 | ribosomal protein S17 - *Bacillus stearothermophilus* | 91 | 80 | 285 |
| 77 | 2 | 260 | 1900 | gi\|287871 | groEL gene product [*Lactococcus lactis*] | 91 | 82 | 1641 |
| 84 | 1 | 2 | 2056 | gi\|871784 | Clp-like ATP-dependent protease binding subunit [*Bos taurus*] | 91 | 79 | 2055 |
| 99 | 8 | 10750 | 9272 | gi\|153740 | sucrose phosphorylase [*Streptococcus mutans*] | 91 | 84 | 1479 |
| 99 | 9 | 11947 | 11072 | gi\|153739 | membrane protein [*Streptococcus mutans*] | 91 | 78 | 876 |
| 127 | 5 | 2065 | 2469 | pir\|S07223\|R5BS | ribosomal protein L17 - *Bacillus stearothermophilus* | 91 | 78 | 405 |
| 132 | 6 | 9539 | 9390 | gi\|143065 | hubst [*Bacillus stearothermophilus*] | 91 | 89 | 150 |
| 137 | 8 | 4765 | 6153 | gnl\|PID\|d100347 | Na+-ATPase beta subunit [*Enterococcus hirae*] | 91 | 79 | 1389 |
| 151 | 7 | 11119 | 9734 | gi\|1815634 | glutamine synthetase type 1 [*Streptococcus agalactiae*] | 91 | 82 | 1386 |
| 201 | 2 | 1798 | 278 | gi\|2208998 | dextran glucosidase DexS [*Streptococcus suis*] | 91 | 79 | 1521 |
| 222 | 2 | 673 | 1839 | gi\|153741 | ATP-binding protein [*Streptococcus mutans*] | 91 | 85 | 1167 |
| 293 | 5 | 4113 | 4400 | gi\|1196921 | unknown protein [Insertion sequence IS861] | 91 | 71 | 288 |
| 32 | 7 | 6166 | 6570 | pir\|A36933\|A369 | diacylglycerol kinase homolog - *Streptococcus mutans* | 90 | 77 | 405 |
| 33 | 2 | 841 | 527 | gi\|1196921 | unknown protein [Insertion sequence IS861] | 90 | 70 | 315 |
| 48 | 27 | 20908 | 19757 | gnl\|PID\|e274705 | lactate oxidase [*Streptococcus iniae*] | 90 | 80 | 1152 |
| 55 | 21 | 19777 | 18515 | gnl\|PID\|e221213 | ClpX protein [*Bacillus subtilis*] | 90 | 75 | 1263 |
| 56 | 2 | 717 | 977 | gi\|1710133 | flagellar filament cap [*Borrelia burgdorferi*] | 90 | 50 | 261 |
| 65 | 1 | 1 | 606 | gi\|1165303 | L3 [*Bacillus subtilis*] | 90 | 75 | 606 |
| 114 | 1 | 2 | 988 | gi\|153562 | aspartate beta-semialdehyde dehydrogenase (EC 1.2.1.11) [*Streptococcus mutans*] | 90 | 80 | 987 |
| 120 | 1 | 1345 | 827 | gi\|407880 | ORF1 [*Streptococcus equisimilis*] | 90 | 75 | 519 |
| 159 | 12 | 7690 | 8298 | gi\|143012 | GMP synthetase [*Bacillus subtilis*] | 90 | 84 | 609 |
| 166 | 4 | 4076 | 3282 | gi\|1661179 | high affinity branched chain amino acid transport protein [*Streptococcus mutans*] | 90 | 78 | 795 |
| 183 | 1 | 28 | 1395 | gi\|308858 | ATP:pyruvate 2-O-phosphotransferase [*Lactococcus lactis*] | 90 | 76 | 1368 |
| 191 | 3 | 2891 | 1662 | gi\|149521 | tryptophan synthase beta subunit [*Lactococcus lactis*] | 90 | 78 | 1230 |
| 198 | 2 | 1551 | 436 | gi\|2323342 | (AF014460) CcpA [*Streptococcus mutans*] | 90 | 76 | 1116 |
| 305 | 1 | 37 | 783 | gi\|1573551 | asparagine synthetase A (asnA) [*Haemophilus influenzae*] | 90 | 80 | 747 |
| 8 | 3 | 2285 | 3343 | gi\|149434 | putative [*Lactococcus lactis*] | 89 | 78 | 1059 |
| 46 | 8 | 7577 | 7362 | pir\|A45434\|A454 | ribosomal protein L19 - *Bacillus stearothermophilus* | 89 | 76 | 216 |
| 49 | 9 | 8363 | 10342 | gi\|153792 | recP peptide [*Streptococcus pneumoniae*] | 89 | 83 | 1980 |
| 51 | 14 | 18410 | 19447 | gi\|308857 | ATP:D-fructose 6-phosphate 1-phosphotransferase [*Lactococcus lactis*] | 89 | 81 | 1038 |
| 57 | 11 | 9686 | 10669 | gnl\|PID\|d100932 | H2O-forming NADH Oxidase [*Streptococcus mutans*] | 89 | 77 | 984 |
| 65 | 5 | 2418 | 2786 | gi\|1165307 | S19 [*Bacillus subtilis*] | 89 | 81 | 369 |
| 65 | 8 | 3806 | 4225 | sp\|P14577\|RL16_ | 50S RIBOSOMAL PROTEIN L16. | 89 | 82 | 420 |
| 65 | 18 | 8219 | 8719 | gi\|143417 | ribosomal protein S5 [*Bacillus stearothermophilus*] | 89 | 76 | 501 |
| 73 | 9 | 6337 | 5315 | gi\|532204 | prs [*Listeria monocytogenes*] | 89 | 70 | 1023 |
| 76 | 3 | 3360 | 1465 | gnl\|PID\|e200671 | lepA gene product [*Bacillus subtilis*] | 89 | 76 | 1896 |
| 99 | 10 | 12818 | 11919 | gi\|153738 | membrane protein [*Streptococcus mutans*] | 89 | 73 | 900 |
| 120 | 2 | 3552 | 1300 | gi\|407881 | stringent response-like protein [*Streptococcus equisimilis*] | 89 | 79 | 2253 |
| 122 | 5 | 4512 | 2791 | gnl\|PID\|e280490 | unknown [*Streptococcus pneumoniae*] | 89 | 81 | 1722 |
| 176 | 1 | 669 | 4 | gi\|47394 | 5-oxoprolyl-peptidase [*Streptococcus pyogenes*] | 89 | 78 | 666 |
| 177 | 6 | 3050 | 3934 | gi\|912423 | putative [*Lactococcus lactis*] | 89 | 71 | 885 |
| 181 | 8 | 4033 | 5751 | gi\|149411 | enzyme III [*Lactococcus lactis*] | 89 | 80 | 1719 |

TABLE 2-continued

*S. pneumoniae* - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 211 | 4 | 3149 | 2793 | gi\|535273 | aminopeptidase C [*Streptococcus thermophilus*] | 89 | 83 | 357 |
| 361 | 1 | 431 | 838 | gi\|1196922 | unknown protein [Insertion sequence IS861] | 89 | 70 | 408 |
| 34 | 17 | 11839 | 10535 | sp\|P30053\|SYH_S | HISTIDYL-TRNA SYNTHETASE (EC 6.1.1.21) (HISTIDINE-TRNA LIGASE) (HISRS). | 88 | 78 | 1305 |
| 38 | 3 | 1646 | 2623 | gi\|2058544 | putative ABC transporter subunit ComYA [*Streptococcus gordonii*] | 88 | 78 | 978 |
| 54 | 1 | 3 | 227 | gnl\|PID\|d101320 | YqgU [*Bacillus subtilis*] | 88 | 66 | 225 |
| 57 | 2 | 611 | 1468 | gnl\|PID\|e134943 | putative reductase 1 [*Saccharomyces cerevisiae*] | 88 | 75 | 858 |
| 65 | 13 | 5497 | 6069 | pir\|A29102\|R5BS | ribosomal protein L5 - *Bacillus stearothermophilus* | 88 | 75 | 573 |
| 65 | 20 | 9030 | 9500 | gi\|2078381 | ribosomal protein L15 [*Staphylococcus aureus*] | 88 | 83 | 471 |
| 78 | 3 | 3636 | 1108 | gnl\|PID\|d100781 | lysyl-aminopeptidase [*Lactococcus lactis*] | 88 | 80 | 2529 |
| 106 | 12 | 12965 | 12054 | gi\|2407215 | (AF017421) putative heat shock protein HtpX [*Streptococcus gordonii*] | 88 | 72 | 912 |
| 107 | 2 | 219 | 962 | gnl\|PID\|e339862 | putative acylneuraminate lyase [*Clostridium tertium*] | 88 | 75 | 744 |
| 111 | 8 | 14073 | 10420 | gi\|402363 | RNA polymerase beta-subunit [*Bacillus subtilis*] | 88 | 74 | 3654 |
| 126 | 9 | 13096 | 12062 | gnl\|PID\|e311468 | unknown [*Bacillus subtilis*] | 88 | 74 | 1035 |
| 140 | 17 | 19143 | 18874 | gi\|1573659 | *H. influenzae* predicted coding region HI0659 [*Haemophilus influenzae*] | 88 | 61 | 270 |
| 144 | 1 | 394 | 555 | gnl\|PID\|e274705 | lactate oxidase [*Streptococcus iniae*] | 88 | 75 | 162 |
| 148 | 4 | 2723 | 3493 | gi\|1591672 | phosphate transport system ATP-binding protein [*Methanococcus jannaschii*] | 88 | 68 | 771 |
| 160 | 8 | 5853 | 6278 | gi\|1773267 | ATPase, epsilon subunit [*Streptococcus mutans*] | 88 | 65 | 426 |
| 177 | 4 | 1770 | 2885 | gi\|149426 | putative [*Lactococcus lactis*] | 88 | 72 | 1116 |
| 211 | 6 | 4140 | 3613 | gi\|535273 | aminopeptidase C [*Streptococcus thermophilus*] | 88 | 74 | 528 |
| 231 | 4 | 580 | 957 | gi\|40186 | homologous to *E. coli* ribosomal protein L27 [*Bacillus subtilis*] | 88 | 78 | 378 |
| 260 | 5 | 2387 | 2998 | gi\|1196922 | unknown protein [Insertion sequence IS861] | 88 | 69 | 612 |
| 291 | 6 | 2017 | 3375 | gnl\|PID\|d100571 | adenylosuccinate synthetase [*Bacillus subtilis*] | 88 | 75 | 1359 |
| 319 | 4 | 658 | 317 | gi\|603578 | serine/threonine kinase [*Phytophthora capsici*] | 88 | 88 | 342 |
| 40 | 5 | 4353 | 4514 | gi\|153672 | lactose repressor [*Streptococcus mutans*] | 87 | 56 | 162 |
| 49 | 10 | 10660 | 10929 | gi\|1196921 | unknown protein [Insertion sequence IS861] | 87 | 72 | 270 |
| 65 | 7 | 3140 | 3808 | gi\|1165309 | S3 [*Bacillus subtilis*] | 87 | 73 | 669 |
| 65 | 15 | 6623 | 7039 | gi\|1044978 | ribosomal protein S8 [*Bacillus subtilis*] | 87 | 73 | 417 |
| 75 | 8 | 5411 | 6625 | gi\|1877422 | galactokinase [*Streptococcus mutans*] | 87 | 78 | 1215 |
| 80 | 2 | 703 | 2805 | gnl\|PID\|d101166 | elongation factor G [*Bacillus subtilis*] | 87 | 76 | 2103 |
| 82 | 1 | 541 | 248 | gi\|1196921 | unknown protein [Insertion sequence IS861] | 87 | 69 | 294 |
| 140 | 23 | 25033 | 23897 | gnl\|PID\|e254999 | phenylalany-tRNA synthetase beta subunit [*Bacillus subtilis*] | 87 | 74 | 1137 |
| 214 | 14 | 10441 | 8516 | gi\|2281305 | glucose inhibited division protein homolog GidA [*Lactococcus lactis cremoris*] | 87 | 75 | 1926 |
| 220 | 2 | 2742 | 874 | gnl\|PID\|e324358 | product highly similar to elongation factor EF-G [*Bacillus subtilis*] | 87 | 73 | 1869 |
| 260 | 4 | 2096 | 2389 | gi\|1196921 | unknown protein [Insertion sequence IS861] | 87 | 72 | 294 |
| 323 | 1 | 27 | 650 | gi\|897795 | 30S ribosomal protein [*Pediococcus acidilactici*] | 87 | 73 | 624 |
| 357 | 1 | 154 | 570 | gi\|1044978 | ribosomal protein S8 [*Bacillus subtilis*] | 87 | 73 | 417 |
| 49 | 11 | 10927 | 11445 | gi\|1196922 | unknown protein [Insertion sequence IS861] | 86 | 63 | 519 |
| 59 | 12 | 7461 | 9224 | gi\|951051 | relaxase [*Streptococcus pneumoniae*] | 86 | 68 | 1764 |
| 65 | 4 | 1553 | 2401 | pir\|A02759\|R5BS | ribosomal protein L2 - *Bacillus stearothermophilus* | 86 | 77 | 849 |
| 65 | 23 | 10957 | 11610 | gi\|44074 | adenylate kinase [*Lactococcus lactis*] | 86 | 76 | 654 |
| 82 | 4 | 4374 | 4856 | gi\|153745 | mannitol-specific enzyme III [*Streptococcus mutans*] | 86 | 72 | 483 |
| 102 | 4 | 4270 | 4986 | gnl\|PID\|e264705 | OMP decarboxylase [*Lactococcus lactis*] | 86 | 76 | 717 |
| 106 | 6 | 7824 | 6880 | gnl\|PID\|e137598 | aspartate transcarbamylase [*Lactobacillus leichmannii*] | 86 | 68 | 945 |
| 107 | 1 | 1 | 273 | gnl\|PID\|e339862 | putative acylneuraminate lyase [*Clostridium tertium*] | 86 | 71 | 273 |
| 111 | 7 | 10432 | 6710 | gnl\|PID\|e228283 | DNA-dependent RNA polymerase [*Streptococcus pyogenes*] | 86 | 80 | 3723 |
| 131 | 9 | 5704 | 4892 | gi\|1661193 | polipoprotein diacylglycerol transferase [*Streptococcus mutans*] | 86 | 71 | 813 |
| 134 | 7 | 6430 | 7980 | gi\|2388637 | glycerol kinase [*Enterococcus faecalis*] | 86 | 73 | 1551 |
| 146 | 11 | 7473 | 6583 | gi\|1591731 | melvalonate kinase [*Methanococcus jannaschii*] | 86 | 72 | 891 |
| 153 | 2 | 595 | 2010 | gi\|2160707 | dipeptidase [*Lactococcus lactis*] | 86 | 78 | 1416 |
| 154 | 1 | 2 | 1435 | gi\|1857246 | 6-phosphogluconate dehydrogenase [*Lactococcus lactis*] | 86 | 74 | 1434 |
| 161 | 5 | 5025 | 6284 | gi\|47529 | Unknown [*Streptococcus salivarius*] | 86 | 66 | 1260 |
| 184 | 1 | 2 | 1483 | gi\|642667 | NADP-dependent glyceraldehyde-3-phosphate dehydrogenase [*Streptococcus mutans*] | 86 | 73 | 1482 |
| 210 | 8 | 3659 | 6571 | gi\|153661 | translational initiation factor IF2 [*Enterococcus faecium*] | 86 | 76 | 2913 |
| 250 | 1 | 2 | 187 | gi\|1573551 | asparagine synthetase A (asnA) [*Haemophilus influenzae*] | 86 | 68 | 186 |
| 36 | 4 | 2644 | 3909 | gi\|2149909 | cell division protein [*Enterococcus faecalis*] | 85 | 73 | 1266 |
| 38 | 4 | 2475 | 3587 | gi\|2058545 | putative ABC transporter subunit ComYB [*Streptococcus gordonii*] | 85 | 72 | 1113 |
| 38 | 5 | 3577 | 3915 | gi\|2058546 | ComYC [*Streptococcus gordonii*] | 85 | 80 | 339 |
| 57 | 5 | 2797 | 3789 | gnl\|PID\|d101316 | YqfJ [*Bacillus subtilis*] | 85 | 72 | 993 |
| 82 | 5 | 4915 | 6054 | gi\|153746 | mannitol-phosphate dehydrogenase [*Streptococcus mutans*] | 85 | 68 | 1140 |
| 83 | 15 | 14690 | 15793 | gi\|143371 | phosphoribosyl aminoimidazole synthetase (PUR-M) [*Bacillus subtilis*] | 85 | 69 | 1104 |
| 87 | 2 | 1417 | 2388 | gi\|1184967 | ScrR [*Streptococcus mutans*] | 85 | 69 | 972 |
| 108 | 3 | 2666 | 3154 | gi\|153566 | ORF (19K protein) [*Enterococcus faecalis*] | 85 | 67 | 489 |
| 127 | 2 | 312 | 692 | gi\|1044989 | ribosomal protein S13 [*Bacillus subtilis*] | 85 | 72 | 381 |
| 128 | 3 | 1534 | 2409 | gi\|1685110 | tetrahydrofolate dehydrogenase/cyclohydrolase [*Streptococcus thermophilus*] | 85 | 71 | 876 |
| 137 | 7 | 2962 | 4767 | gnl\|PID\|d100347 | Na+-ATPase alpha subunit [*Enterococcus hirae*] | 85 | 74 | 1806 |

TABLE 2-continued

*S. pneumoniae* - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 170 | 2 | 2622 | 709 | gnl\|PID\|d102006 | (AB001488) FUNCTION UNKNOWN, SIMILAR PRODUCT IN E. COLI, H. INFLUENZAE AND NEISSERIA MENINGITIDIS. [Bacillus subtilis] | 85 | 70 | 1914 |
| 187 | 5 | 3760 | 4386 | gi\|727436 | putative 20-kDa protein [Lactococcus lactis] | 85 | 65 | 627 |
| 233 | 2 | 728 | 1873 | gi\|1163116 | ORF-5 [Streptococcus pneumoniae] | 85 | 67 | 1146 |
| 234 | 3 | 962 | 1255 | gi\|2293155 | (AF008220) YtiA [Bacillus subtilis] | 85 | 61 | 294 |
| 240 | 1 | 309 | 1931 | gi\|143597 | CTP synthetase [Bacillus subtilis] | 85 | 70 | 1623 |
| 6 | 1 | 199 | 1521 | gi\|508979 | GTP-binding protein [Bacillus subtilis] | 84 | 72 | 1323 |
| 10 | 4 | 4375 | 3443 | gnl\|PID\|e339862 | putative acylneuraminate lyase [Clostridium tertium] | 84 | 70 | 933 |
| 14 | 1 | 63 | 2093 | gi\|520753 | DNA topoisomerase I [Bacillus subtilis] | 84 | 69 | 2031 |
| 19 | 4 | 1793 | 2593 | gi\|2352484 | (AF005098) RNAseH II [Lactococcus lactis] | 84 | 68 | 801 |
| 20 | 17 | 17720 | 19687 | gnl\|PID\|d100584 | cell division protein [Bacillus subtilis] | 84 | 71 | 1968 |
| 22 | 28 | 21723 | 20884 | gi\|299163 | alanine dehydrogenase [Bacillus subtilis] | 84 | 68 | 840 |
| 30 | 10 | 7730 | 6792 | gnl\|PID\|d100296 | fructokinase [Streptococcus mutans] | 84 | 75 | 939 |
| 33 | 9 | 5650 | 5300 | gi\|147194 | phnA protein [Escherichia coli] | 84 | 71 | 351 |
| 36 | 22 | 21551 | 20772 | gi\|310631 | ATP binding protein [Streptococcus gordonii] | 84 | 72 | 780 |
| 48 | 4 | 2837 | 2505 | gi\|882609 | 6-phospho-beta-glucosidase [Escherichia coli] | 84 | 69 | 333 |
| 58 | 1 | 41 | 1516 | gi\|450849 | amylase [Streptococcus bovis] | 84 | 73 | 1476 |
| 59 | 10 | 6715 | 7116 | gi\|951053 | ORF10, putative [Streptococcus pneumoniae] | 84 | 74 | 402 |
| 62 | 1 | 21 | 644 | gi\|806487 | ORF211; putative [Lactococcus lactis] | 84 | 66 | 624 |
| 65 | 17 | 7779 | 8207 | gi\|1044980 | ribosomal protein L18 [Bacillus subtilis] | 84 | 73 | 429 |
| 65 | 21 | 9507 | 10397 | gi\|44073 | SecY protein [Lactococcus lactis] | 84 | 68 | 891 |
| 106 | 4 | 5474 | 2262 | gnl\|PID\|e199387 | carbamoyl-phosphate synthase [Lactobacillus plantarum] | 84 | 73 | 3213 |
| 159 | 1 | 147 | 4 | gi\|806487 | ORF211; putative [Lactococcus lactis] | 84 | 63 | 144 |
| 163 | 4 | 4690 | 5910 | gi\|2293164 | (AF008220) SAM synthase [Bacillus subtilis] | 84 | 69 | 1221 |
| 192 | 1 | 46 | 1308 | gi\|495046 | tripeptidase [Lactococcus lactis] | 84 | 73 | 1263 |
| 348 | 1 | 671 | 6 | gi\|1787753 | (AE000245) f346; 79 pct identical to 336 amino acids of ADH1_ZYMMO SW: P20368 but has 10 additional N-ter residues [Escherichia coli] | 84 | 71 | 666 |
| 3 | 4 | 1572 | 3575 | gi\|143766 | (thrSv) (EC 6.1.1.3) [Bacillus subtilis] | 83 | 65 | 2004 |
| 9 | 6 | 3893 | 3417 | gnl\|PID\|d100576 | single strand DNA binding protein [Bacillus subtilis] | 83 | 68 | 477 |
| 17 | 15 | 7426 | 8457 | gi\|520738 | comA protein [Streptococcus pneumoniae] | 83 | 66 | 1032 |
| 20 | 12 | 13860 | 14144 | gnl\|PID\|d100583 | unknown [Bacillus subtilis] | 83 | 61 | 285 |
| 23 | 4 | 3358 | 2606 | gi\|1788294 | (AE000290) o238; This 238 aa orf is 40 pct identical (5 gaps) to 231 residues of an approx. 248 aa protein YEBC_ECOLI SW: P24237 [Escherichia coli] | 83 | 74 | 753 |
| 28 | 6 | 3304 | 3005 | gi\|1573659 | H. influenzae predicted coding region HI0659 [Haemophilus influenzae] | 83 | 57 | 300 |
| 35 | 7 | 5108 | 3867 | gi\|311707 | hypothetical nucleotide binding protein [Acholeplasma laidlawii] | 83 | 63 | 1242 |
| 55 | 19 | 17932 | 17528 | gi\|537085 | ORF_f141 [Escherichia coli] | 83 | 59 | 405 |
| 55 | 20 | 18539 | 17919 | gi\|496558 | orfX [Bacillus subtilis] | 83 | 69 | 621 |
| 65 | 6 | 2795 | 3142 | gi\|1165308 | L22 [Bacillus subtilis] | 83 | 64 | 348 |
| 68 | 6 | 6877 | 6683 | gi\|1213494 | immunoglobulin A1 protease [Streptococcus pneumoniae] | 83 | 54 | 195 |
| 87 | 15 | 15112 | 14771 | gnl\|PID\|e323522 | putative rpoZ protein [Bacillus subtilis] | 83 | 54 | 342 |
| 96 | 12 | 8963 | 9631 | gi\|47394 | 5-oxoprolyl-peptidase [Streptococcus pyogenes] | 83 | 73 | 669 |
| 98 | 1 | 3 | 263 | gi\|1183885 | glutamine-binding subunit [Bacillus subtilis] | 83 | 55 | 261 |
| 120 | 4 | 7170 | 5233 | gi\|310630 | zinc metalloprotease [Streptococcus gordonii] | 83 | 72 | 1938 |
| 127 | 7 | 2998 | 4347 | gi\|1500567 | M. jannaschii predicted coding region MJ1665 [Methanococcus jannaschii] | 83 | 72 | 1350 |
| 137 | 1 | 3 | 440 | gi\|472918 | v-type Na-ATPase [Enterococcus hirae] | 83 | 60 | 438 |
| 160 | 6 | 3466 | 4356 | gi\|1773265 | ATPase, gamma subunit [Streptococcus mutans] | 83 | 67 | 891 |
| 214 | 4 | 2278 | 2964 | gi\|663279 | transposase [Streptococcus pneumoniae] | 83 | 72 | 687 |
| 226 | 3 | 2367 | 2020 | gi\|142154 | thioredoxin [Synechococcus PCC6301] | 83 | 58 | 348 |
| 303 | 1 | 3 | 1049 | gi\|40046 | phosphoglucose isomerase A (AA 1-449) [Bacillus stearothermophilus] | 83 | 67 | 1047 |
| 303 | 2 | 1155 | 1931 | gi\|289282 | glutamyl-tRNA synthetase [Bacillus subtilis] | 83 | 67 | 777 |
| 6 | 17 | 15370 | 14318 | gi\|633147 | ribose-phosphate pyrophosphokinase [Bacillus caldolyticus] | 82 | 64 | 1053 |
| 7 | 1 | 299 | 96 | gi\|143648 | ribosomal protein L28 [Bacillus subtilis] | 82 | 69 | 204 |
| 9 | 3 | 1479 | 1090 | gi\|385178 | unknown [Bacillus subtilis] | 82 | 46 | 390 |
| 9 | 7 | 4213 | 3899 | gnl\|PID\|d100576 | ribosomal protein S6 [Bacillus subtilis] | 82 | 60 | 315 |
| 12 | 6 | 4688 | 3942 | gnl\|PID\|d100571 | unknown [Bacillus subtilis] | 82 | 68 | 747 |
| 22 | 17 | 13422 | 14837 | gi\|520754 | putative [Bacillus subtilis] | 82 | 69 | 1416 |
| 22 | 18 | 14897 | 15658 | gnl\|PID\|d101929 | uridine monophosphate kinase [Synechocystis sp.] | 82 | 62 | 762 |
| 33 | 16 | 11471 | 10641 | gnl\|PID\|d101190 | ORF4 [Streptococcus mutans] | 82 | 68 | 831 |
| 35 | 9 | 7400 | 6255 | gi\|1881543 | UDP-N-acetylglucosamine-2-epimerase [Streptococcus pneumoniae] | 82 | 68 | 1146 |
| 40 | 10 | 8003 | 7533 | gi\|1173519 | riboflavin synthase beta subunit [Actinobacillus pleuropneumoniae] | 82 | 68 | 471 |
| 48 | 32 | 23159 | 23437 | gi\|1930092 | outer membrane protein [Campylobacter jejuni] | 82 | 61 | 279 |
| 52 | 14 | 13833 | 14765 | gi\|142521 | deoxyribodipyrimidine photolyase [Bacillus subtilis] | 82 | 61 | 933 |
| 60 | 4 | 4737 | 1849 | gnl\|PID\|d102221 | (AB001610) uvrA [Deinococcus radiodurans] | 82 | 66 | 2889 |
| 62 | 4 | 2131 | 1457 | gi\|2246749 | (AF009622) thioredoxin reductase [Listeria monocytogenes] | 82 | 63 | 675 |
| 71 | 11 | 16586 | 17518 | gnl\|PID\|e322063 | ss-1,4-galactosyltransferase [Streptococcus pneumoniae] | 82 | 60 | 933 |
| 73 | 13 | 9222 | 7837 | gnl\|PID\|d100586 | unknown [Bacillus subtilis] | 82 | 65 | 1386 |
| 74 | 1 | 1 | 3771 | gnl\|PID\|d101199 | alkaline amylopullanase [Bacillus sp.] | 82 | 68 | 3771 |
| 83 | 9 | 3696 | 3983 | gnl\|PID\|e305362 | unnamed protein product [Streptococcus thermophilus] | 82 | 52 | 288 |
| 86 | 11 | 10776 | 9394 | gi\|683583 | 5-enolpyruvylshikimate-3-phosphate synthase [Lactococcus lactis] | 82 | 67 | 1383 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 89 | 12 | 8295 | 9752 | gi\|40025 | homologous to E. coli 50K [Bacillus subtilis] | 82 | 66 | 1458 |
| 115 | 9 | 10347 | 8812 | gnl\|PID\|d102090 | (AB003927) phospho-beta-galactosidase 1 [Lactobacillus gasseri] | 82 | 74 | 1536 |
| 118 | 1 | 1 | 1332 | gnl\|PID\|d100579 | seryl-tRNA synthetase [Bacillus subtilis] | 82 | 71 | 1332 |
| 151 | 3 | 4657 | 6246 | pir\|S06097\|S060 | type I site-specific deoxyribonuclease (EC 3.1.21.3) CfrA chain S - Citrobacter freundii | 82 | 66 | 1590 |
| 173 | 6 | 4183 | 3503 | gi\|2313836 | (AE000584) conserved hypothetical protein [Helicobacter pylori] | 82 | 68 | 681 |
| 177 | 12 | 5481 | 7442 | gnl\|PID\|d101999 | (AB001341) NcrB [Escherichia coli] | 82 | 58 | 1962 |
| 193 | 2 | 178 | 576 | pir\|S08564\|R3BS | ribosomal protein S9 - Bacillus stearothermophilus | 82 | 70 | 399 |
| 245 | 2 | 258 | 845 | gi\|146402 | EcoA type I restriction-modification enzyme S subunit [Escherichia coli] | 82 | 68 | 588 |
| 9 | 5 | 3400 | 3146 | gnl\|PID\|d100576 | ribosomal protein S18 [Bacillus subtilis] | 81 | 66 | 255 |
| 16 | 7 | 7484 | 8413 | gi\|1100074 | tryptophanyl-tRNA synthetase [Clostridium longisporum] | 81 | 70 | 930 |
| 20 | 11 | 10308 | 13820 | gnl\|PID\|d100583 | transcription-repair coupling factor [Bacillus subtilis] | 81 | 63 | 3513 |
| 38 | 2 | 1232 | 1606 | gi\|2058543 | putative DNA binding protein [Streptococcus gordonii] | 81 | 63 | 375 |
| 45 | 2 | 3061 | 1751 | gi\|460259 | enolase [Bacillus subtilis] | 81 | 67 | 1311 |
| 46 | 1 | 2 | 1267 | gi\|431231 | uracil permease [Bacillus caldolyticus] | 81 | 61 | 1266 |
| 48 | 3 | 2453 | 1440 | gnl\|PID\|d100453 | Mannosephosphate Isomerase [Streptococcus mutans] | 81 | 70 | 1014 |
| 54 | 2 | 1106 | 336 | gi\|154752 | transport protein [Agrobacterium tumefaciens] | 81 | 64 | 771 |
| 65 | 22 | 10306 | 10821 | gi\|44073 | SecY protein [Lactococcus lactis] | 81 | 66 | 516 |
| 89 | 4 | 3874 | 2603 | gi\|556886 | serine hydroxymethyltransferase [Bacillus subtilis] | 81 | 69 | 1272 |
| 99 | 16 | 19126 | 18929 | gi\|2313526 | (AE000557) H. pylori predicted coding region HP0411 [Helicobacter pylori] | 81 | 75 | 198 |
| 106 | 7 | 8373 | 7822 | gnl\|PID\|e199384 | pyrR [Lactobacillus plantarum] | 81 | 61 | 552 |
| 108 | 6 | 5054 | 6877 | gi\|1469939 | group B oligopeptidase PepB [Streptococcus agalactiae] | 81 | 66 | 1824 |
| 113 | 15 | 15899 | 18283 | pir\|S09411\|S094 | spoIIIE protein - Bacillus subtilis | 81 | 65 | 2385 |
| 128 | 5 | 3359 | 3634 | gi\|1685111 | orf1091 [Streptococcus thermophilus] | 81 | 69 | 276 |
| 151 | 1 | 830 | 3211 | gi\|304896 | EcoE type I restriction-modification enzyme R subunit [Escherichia coli] | 81 | 59 | 2382 |
| 159 | 11 | 6722 | 7837 | gi\|2239288 | GMP synthetase [Bacillus subtilis] | 81 | 69 | 1116 |
| 170 | 1 | 739 | 458 | gnl\|PID\|d102006 | (AB001488) FUNCTION UNKNOWN. [Bacillus subtilis] | 81 | 55 | 282 |
| 191 | 2 | 1759 | 893 | gi\|149522 | tryptophan synthase alpha subunit [Lactococcus lactis] | 81 | 65 | 867 |
| 214 | 3 | 2290 | 1994 | gi\|157587 | reverse transcriptase endonuclease [Drosophila virilis] | 81 | 43 | 297 |
| 217 | 4 | 4415 | 4008 | gi\|466473 | cellobiose phosphotransferase enzyme II' [Bacillus stearothermophilus] | 81 | 59 | 408 |
| 262 | 2 | 569 | 868 | gi\|153675 | tagatose 6-P kinase [Streptococcus mutans] | 81 | 68 | 300 |
| 299 | 1 | 663 | 4 | gnl\|PID\|e301154 | StySKI methylase [Salmonella enterica] | 81 | 60 | 660 |
| 366 | 2 | 376 | 83 | gi\|149521 | tryptophan synthase beta subunit [Lactococcus lactis] | 81 | 65 | 294 |
| 12 | 10 | 8766 | 9242 | gi\|1216490 | DNA/pantothenate metabolism flavoprotein [Streptococcus mutans] | 80 | 64 | 477 |
| 17 | 11 | 6050 | 5748 | gnl\|PID\|e305362 | unnamed protein product [Streptococcus thermophilus] | 80 | 67 | 303 |
| 17 | 16 | 8455 | 9066 | gi\|703126 | leucocin A translocator [Leuconostoc gelidum] | 80 | 59 | 612 |
| 18 | 3 | 2440 | 1613 | gi\|1591672 | phosphate transport system ATP-binding protein [Methanococcus jannaschii] | 80 | 58 | 828 |
| 27 | 3 | 4248 | 1579 | gi\|452309 | valyl-tRNA synthetase [Bacillus subtilis] | 80 | 69 | 2670 |
| 28 | 7 | 3671 | 3288 | gi\|1573660 | H. influenzae predicted coding region HI0660 [Haemophilus influenzae] | 80 | 63 | 384 |
| 32 | 2 | 902 | 1933 | gnl\|PID\|e264499 | dihydroorotate dehydrogenase B [Lactococcus lactis] | 80 | 66 | 1032 |
| 39 | 1 | 1 | 1266 | gnl\|PID\|e234078 | hom [Lactococcus lactis] | 80 | 63 | 1266 |
| 52 | 5 | 4363 | 3593 | gi\|1183884 | ATP-binding subunit [Bacillus subtilis] | 80 | 57 | 771 |
| 54 | 5 | 4550 | 4744 | gi\|2198820 | (AF004225) Cux/CDP(1B1); Cux/CDP homeoprotein [Mus musculus] | 80 | 60 | 195 |
| 59 | 11 | 7109 | 7486 | gi\|951052 | ORF9, putative [Streptococcus pneumoniae] | 80 | 68 | 378 |
| 65 | 3 | 1230 | 1550 | pir\|A02815\|R5BS | ribosomal protein L23 - Bacillus stearothermophilus | 80 | 69 | 321 |
| 65 | 12 | 5174 | 5503 | pir\|A02819\|R5BS | ribosomal protein L24 - Bacillus stearothermophilus | 80 | 70 | 330 |
| 66 | 9 | 9884 | 10687 | gi\|2313836 | (AE000584) conserved hypothetical protein [Helicobacter pylori] | 80 | 66 | 804 |
| 82 | 2 | 648 | 2438 | gi\|622991 | mannitol transport protein [Bacillus stearothermophilus] | 80 | 65 | 1791 |
| 85 | 1 | 950 | 630 | gi\|528995 | polyketide synthase [Bacillus subtilis] | 80 | 46 | 321 |
| 89 | 8 | 6870 | 5779 | gi\|853776 | peptide chain release factor 1 [Bacillus subtilis] | 80 | 63 | 1092 |
| 93 | 12 | 8718 | 7438 | gnl\|PID\|d101959 | hypothetical protein [Synechocystis sp.] | 80 | 60 | 1281 |
| 106 | 5 | 6854 | 5751 | gnl\|PID\|e199386 | glutaminase of carbamoyl-phosphate synthase [Lactobacillus plantarum] | 80 | 65 | 1104 |
| 109 | 2 | 2160 | 1450 | gi\|40056 | phoP gene product [Bacillus subtilis] | 80 | 59 | 711 |
| 124 | 9 | 4246 | 3953 | gnl\|PID\|d102254 | 30S ribosomal protein S16 [Bacillus subtilis] | 80 | 65 | 294 |
| 128 | 8 | 5148 | 6428 | gi\|2281308 | phosphopentomutase [Lactococcus lactis cremoris] | 80 | 66 | 1281 |
| 137 | 19 | 12665 | 11376 | gi\|159109 | NADP-dependent glutamate dehydrogenase [Giardia intestinalis] | 80 | 68 | 1290 |
| 140 | 19 | 19699 | 19457 | gi\|517210 | putative transposase [Streptococcus pyogenes] | 80 | 70 | 243 |
| 158 | 2 | 2474 | 984 | gi\|1877423 | galactose-1-P-uridyl transferase [Streptococcus mutans] | 80 | 65 | 1491 |
| 171 | 10 | 7474 | 7728 | gi\|397800 | cyclophilin C-associated protein [Mus musculus] | 80 | 60 | 255 |
| 181 | 1 | 2 | 619 | gi\|149395 | lacC [Lactococcus lactis] | 80 | 66 | 618 |
| 313 | 1 | 27 | 539 | gi\|143467 | ribosomal protein S4 [Bacillus subtilis] | 80 | 70 | 513 |
| 329 | 2 | 1652 | 858 | gi\|533080 | RecF protein [Streptococcus pyogenes] | 80 | 63 | 795 |
| 371 | 2 | 2 | 958 | gi\|442360 | ClpC adenosine triphosphatase [Bacillus subtilis] | 80 | 58 | 957 |
| 8 | 7 | 4312 | 5580 | gi\|149435 | putative [Lactococcus lactis] | 79 | 64 | 1269 |
| 23 | 1 | 1175 | 135 | gi\|1542975 | AbcB [Thermoanaerobacterium thermosulfurigenes] | 79 | 61 | 1041 |
| 33 | 14 | 9244 | 8201 | gnl\|PID\|e253891 | UDP-glucose 4-epimerase [Bacillus subtilis] | 79 | 62 | 1044 |
| 36 | 3 | 1242 | 2633 | gnl\|PID\|e324218 | ftsA [Enterococcus hirae] | 79 | 58 | 1392 |
| 38 | 13 | 7155 | 8378 | gi\|405134 | acetate kinase [Bacillus subtilis] | 79 | 58 | 1224 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 55 | 7 | 9011 | 8229 | gi|1146234 | dihydrodipicolinate reductase [*Bacillus subtilis*] | 79 | 56 | 783 |
| 65 | 19 | 8661 | 8915 | gi|2078380 | ribosomal protein L30 [*Staphylococcus aureus*] | 79 | 68 | 255 |
| 69 | 4 | 3678 | 2128 | gnl|PID|e311452 | unknown [*Bacillus subtilis*] | 79 | 64 | 1551 |
| 69 | 9 | 7881 | 7279 | gi|677850 | hypothetical protein [*Staphylococcus aureus*] | 79 | 59 | 603 |
| 72 | 10 | 8491 | 9783 | gnl|PID|d101091 | hypothetical protein [*Synechocystis* sp.] | 79 | 62 | 1293 |
| 80 | 3 | 2906 | 7300 | gi|143342 | polymerase III [*Bacillus subtilis*] | 79 | 65 | 4395 |
| 82 | 14 | 13326 | 15689 | gnl|PID|e255093 | hypothetical protein [*Bacillus subtilis*] | 79 | 65 | 2364 |
| 86 | 13 | 12233 | 11118 | gi|683582 | prephenate dehydrogenase [*Lactococcus lactis*] | 79 | 58 | 1116 |
| 92 | 3 | 940 | 1734 | gi|537286 | triosephosphate isomerase [*Lactococcus lactis*] | 79 | 65 | 795 |
| 98 | 6 | 4023 | 4742 | gnl|PID|d100262 | LivG protein [*Salmonella typhimurium*] | 79 | 63 | 720 |
| 99 | 12 | 16315 | 14150 | gi|153736 | a-galactosidase [*Streptococcus mutans*] | 79 | 64 | 2166 |
| 107 | 7 | 5684 | 6406 | gi|460080 | D-alanine:D-alanine ligase-related protein [*Enterococcus faecalis*] | 79 | 58 | 723 |
| 113 | 9 | 6858 | 8303 | gi|466882 | pps1; B1496_C2_189 [*Mycobacterium leprae*] | 79 | 64 | 1446 |
| 151 | 10 | 13424 | 12213 | gi|450686 | 3-phosphoglycerate kinase [*Thermotoga maritima*] | 79 | 60 | 1212 |
| 162 | 2 | 1158 | 3017 | gi|506700 | CapD [*Staphylococcus aureus*] | 79 | 67 | 1860 |
| 177 | 5 | 2876 | 3052 | gi|912423 | putative [*Lactococcus lactis*] | 79 | 61 | 177 |
| 177 | 8 | 4198 | 4563 | gi|149429 | putative [*Lactococcus lactis*] | 79 | 61 | 366 |
| 187 | 3 | 2728 | 2907 | gnl|PID|d102002 | (AB001488) FUNCTION UNKNOWN. [*Bacillus subtilis*] | 79 | 53 | 180 |
| 189 | 7 | 3589 | 4350 | gnl|PID|e183449 | putative ATP-binding protein of ABC-type [*Bacillus subtilis*] | 79 | 61 | 762 |
| 191 | 5 | 4249 | 3449 | gi|149519 | indoleglycerol phosphate synthase [*Lactococcus lactis*] | 79 | 66 | 801 |
| 211 | 3 | 1805 | 2737 | gi|147404 | mannose permease subunit II-M-Man [*Escherichia coli*] | 79 | 57 | 933 |
| 212 | 3 | 3863 | 3621 | gnl|PID|e209004 | glutaredoxin-like protein [*Lactococcus lactis*] | 79 | 58 | 243 |
| 215 | 1 | 987 | 715 | gi|2293242 | (AF008220) arginine succinate synthase [*Bacillus subtilis*] | 79 | 64 | 273 |
| 323 | 2 | 530 | 781 | gi|897795 | 30S ribosomal protein [*Pediococcus acidilactici*] | 79 | 67 | 252 |
| 380 | 1 | 694 | 2 | gi|1184680 | polynucleotide phosphorylase [*Bacillus subtilis*] | 79 | 64 | 693 |
| 384 | 2 | 655 | 239 | gi|143328 | phoP protein (put.); putative [*Bacillus subtilis*] | 79 | 59 | 417 |
| 6 | 3 | 2820 | 4091 | gi|853767 | UDP-N-acetylglucosamine 1-carboxyvinyltransferase [*Bacillus subtilis*] | 78 | 62 | 1272 |
| 8 | 1 | 50 | 1786 | gi|149432 | putative [*Lactococcus lactis*] | 78 | 63 | 1737 |
| 9 | 1 | 351 | 124 | gi|897793 | y98 gene product [*Pediococcus acidilactici*] | 78 | 59 | 228 |
| 15 | 8 | 7364 | 8314 | gnl|PID|d100585 | cysteine synthetase A [*Bacillus subtilis*] | 78 | 63 | 951 |
| 20 | 10 | 9738 | 10310 | gnl|PID|d100583 | stage V sporulation [*Bacillus subtilis*] | 78 | 58 | 573 |
| 20 | 16 | 17165 | 17713 | gi|49105 | hypoxanthine phosphoribosyltransferase [*Lactococcus lactis*] | 78 | 59 | 549 |
| 22 | 22 | 17388 | 18416 | gnl|PID|d101315 | YqfE [*Bacillus subtilis*] | 78 | 60 | 1029 |
| 22 | 27 | 20971 | 20612 | gi|299163 | alanine dehydrogenase [*Bacillus subtilis*] | 78 | 59 | 360 |
| 34 | 8 | 7407 | 7105 | gi|41015 | aspartate-tRNA ligase [*Escherichia coli*] | 78 | 55 | 303 |
| 35 | 8 | 6257 | 5196 | gi|1657644 | Cap8E [*Staphylococcus aureus*] | 78 | 60 | 1062 |
| 40 | 11 | 9287 | 8001 | gi|1173518 | GTP cyclohydrase II/3,4-dihydroxy-2-butanone-4-phosphate synthase [*Actinobacillus pleuropneumoniae*] | 78 | 58 | 1287 |
| 48 | 31 | 22422 | 23183 | gi|2314330 | (AE000623) glutamine ABC transporter, ATP-binding protein (glnQ) [*Helicobacter pylori*] | 78 | 58 | 762 |
| 52 | 2 | 2101 | 1430 | gi|1183887 | integral membrane protein [*Bacillus subtilis*] | 78 | 54 | 672 |
| 55 | 14 | 13605 | 12712 | gnl|PID|d102026 | (AB002150) YbbP [*Bacillus subtilis*] | 78 | 58 | 894 |
| 55 | 17 | 16637 | 15612 | gnl|PID|e313027 | hypothetical protein [*Bacillus subtilis*] | 78 | 51 | 1026 |
| 71 | 14 | 19756 | 19598 | gi|179764 | calcium channel alpha-1D subunit [*Homo sapiens*] | 78 | 57 | 159 |
| 74 | 11 | 15031 | 14018 | gi|1573279 | Holliday junction DNA helicase (ruvB) [*Haemophilus influenzae*] | 78 | 57 | 1014 |
| 75 | 9 | 6623 | 7972 | gi|1877423 | galactose-1-P-uridyl transferase [*Streptococcus mutans*] | 78 | 62 | 1350 |
| 81 | 12 | 12125 | 13906 | gi|1573607 | L-fucose isomerase (fucI) [*Haemophilus influenzae*] | 78 | 66 | 1782 |
| 82 | 3 | 2423 | 4417 | gi|153744 | ORF X; putative [*Streptococcus mutans*] | 78 | 64 | 1995 |
| 83 | 18 | 16926 | 18500 | gi|143373 | phosphoribosyl aminoimidazole carboxy formyl formyltransferase/inosine monophosphate cyclohydrolase (PUR-H(J)) [*Bacillus subtilis*] | 78 | 63 | 1575 |
| 83 | 20 | 20212 | 20775 | gi|143364 | phosphoribosyl aminoimidazole carboxylase I (PUR-E) [*Bacillus subtilis*] | 78 | 64 | 564 |
| 92 | 2 | 165 | 878 | gnl|PID|d101190 | ORF2 [*Streptococcus mutans*] | 78 | 62 | 714 |
| 98 | 8 | 5863 | 6909 | gi|2331287 | (AF013188) release factor 2 [*Bacillus subtilis*] | 78 | 63 | 1047 |
| 113 | 3 | 1071 | 2741 | gi|580914 | dnaZX [*Bacillus subtilis*] | 78 | 64 | 1671 |
| 127 | 4 | 1133 | 2071 | gi|142463 | RNA polymerase alpha-core-subunit [*Bacillus subtilis*] | 78 | 59 | 939 |
| 132 | 1 | 2782 | 497 | gi|1561763 | pullulanase [*Bacteroides thetaiotaomicron*] | 78 | 58 | 2286 |
| 135 | 4 | 2698 | 3537 | gi|1788036 | (AE000269) NH3-dependent NAD synthetase [*Escherichia coli*] | 78 | 66 | 840 |
| 140 | 24 | 26853 | 25423 | gi|1100077 | phospho-beta-glucosidase [*Clostridium longisporum*] | 78 | 64 | 1431 |
| 150 | 5 | 4690 | 4514 | gi|149464 | amino peptidase [*Lactococcus lactis*] | 78 | 42 | 177 |
| 152 | 1 | 1 | 795 | gi|639915 | NADH dehydrogenase subunit [*Thunbergia alata*] | 78 | 43 | 795 |
| 162 | 4 | 4997 | 4110 | gnl|PID|e323528 | putative YhaP protein [*Bacillus subtilis*] | 78 | 64 | 888 |
| 181 | 10 | 8651 | 7947 | gi|149402 | lactose repressor (lacR; alt.) [*Lactococcus lactis*] | 78 | 48 | 705 |
| 200 | 4 | 3627 | 4958 | gnl|PID|d100172 | invertase [*Zymomonas mobilis*] | 78 | 61 | 1332 |
| 203 | 3 | 3230 | 3015 | gi|1174237 | CycK [*Pseudomonas fluorescens*] | 78 | 57 | 216 |
| 210 | 9 | 6789 | 7172 | gi|580902 | ORF6 gene product [*Bacillus subtilis*] | 78 | 42 | 384 |
| 214 | 6 | 3810 | 2797 | gnl|PID|d102049 | P. haemolytica o-sialoglycoprotein endopeptidase; P36175 (660) transmembrane [*Bacillus subtilis*] | 78 | 60 | 1014 |
| 214 | 13 | 6322 | 8163 | gi|1377831 | unknown [*Bacillus subtilis*] | 78 | 62 | 1842 |
| 217 | 1 | 9 | 2717 | gi|488430 | alcohol dehydrogenase 2 [*Entamoeba histolytica*] | 78 | 64 | 2709 |
| 222 | 3 | 2316 | 3098 | gi|1573047 | spore germination and vegetative growth protein (gerC2) [*Haemophilus influenzae*] | 78 | 65 | 783 |
| 268 | 1 | 742 | 8 | gi|517210 | putative transposase [*Streptococcus pyogenes*] | 78 | 65 | 735 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 276 | 1 | 223 | 753 | gnl\|PID\|d100306 | ribosomal protein L1 [Bacillus subtilis] | 78 | 65 | 531 |
| 312 | 3 | 1567 | 1079 | gi\|289261 | comE ORF2 [Bacillus subtilis] | 78 | 54 | 489 |
| 339 | 1 | 117 | 794 | gi\|1916729 | CadD [Staphylococcus aureus] | 78 | 53 | 678 |
| 342 | 2 | 762 | 265 | gi\|1942439 | phosphatidylglycerophosphate synthase [Bacillus subtilis] | 78 | 59 | 498 |
| 383 | 1 | 737 | 3 | gi\|1184680 | polynucleotide phosphorylase [Bacillus subtilis] | 78 | 64 | 735 |
| 7 | 15 | 11923 | 11018 | gi\|1399855 | carboxyltransferase beta subunit [Synechococcus PCC7942] | 77 | 63 | 906 |
| 8 | 2 | 1698 | 2255 | gi\|149433 | putative [Lactococcus lactis] | 77 | 59 | 558 |
| 17 | 14 | 6948 | 7550 | gi\|520738 | comA protein [Streptococcus pneumoniae] | 77 | 60 | 603 |
| 30 | 12 | 9761 | 8967 | gi\|1000451 | TreP [Bacillus subtilis] | 77 | 43 | 795 |
| 36 | 14 | 11421 | 12131 | gi\|1573766 | phosphoglyceromutase (gpmA) [Haemophilus influenzae] | 77 | 64 | 711 |
| 55 | 3 | 3836 | 4096 | gi\|1708640 | YeaB [Bacillus subtilis] | 77 | 55 | 261 |
| 61 | 8 | 8377 | 8054 | gi\|1890649 | multidrug resistance protein LmrA [Lactococcus lactis] | 77 | 51 | 324 |
| 65 | 2 | 607 | 1254 | gi\|40103 | ribosomal protein L4 [Bacillus stearothermophilus] | 77 | 63 | 648 |
| 68 | 8 | 7509 | 7240 | gi\|47551 | MRP [Streptococcus suis] | 77 | 68 | 270 |
| 69 | 1 | 1083 | 118 | gnl\|PID\|e311493 | unknown [Bacillus subtilis] | 77 | 57 | 966 |
| 77 | 5 | 4583 | 4026 | gnl\|PID\|e281578 | hypothetical 12.2 kd protein [Bacillus subtilis] | 77 | 60 | 558 |
| 83 | 14 | 13104 | 14552 | gi\|1590947 | amidophosphoribosyltransferase [Methanococcus jannaschii] | 77 | 56 | 1449 |
| 94 | 4 | 3006 | 5444 | gnl\|PID\|d329895 | (AJ000496) cyclic nucleotide-gated channel beta subunit [Rattus norvegicus] | 77 | 66 | 2439 |
| 96 | 11 | 8518 | 8880 | gi\|551879 | ORF 1 [Lactococcus lactis] | 77 | 62 | 363 |
| 99 | 11 | 14082 | 12799 | gi\|153737 | sugar-binding protein [Streptococcus mutans] | 77 | 61 | 1284 |
| 106 | 2 | 361 | 1176 | gi\|148921 | LicD protein [Haemophilus influenzae] | 77 | 51 | 816 |
| 108 | 4 | 3152 | 4030 | gi\|1574730 | tellurite resistance protein (tehB) [Haemophilus influenzae] | 77 | 58 | 879 |
| 118 | 4 | 3520 | 3131 | gi\|1573900 | D-alanine permease (dagA) [Haemophilus influenzae] | 77 | 57 | 390 |
| 124 | 4 | 1796 | 1071 | gi\|1573162 | tRNA (guanine-N1)-methyltransferase (trmD) [Haemophilus influenzae] | 77 | 58 | 726 |
| 126 | 4 | 5909 | 4614 | gnl\|PID\|d101163 | Srb [Bacillus subtilis] | 77 | 62 | 1296 |
| 128 | 2 | 630 | 1373 | gnl\|PID\|d101328 | YqiZ [Bacillus subtilis] | 77 | 58 | 744 |
| 130 | 1 | 1 | 1287 | gnl\|PID\|e325013 | hypothetical protein [Bacillus subtilis] | 77 | 61 | 1287 |
| 139 | 5 | 4388 | 3639 | gi\|2293302 | (AF008220) YtqA [Bacillus subtilis] | 77 | 59 | 750 |
| 140 | 11 | 10931 | 9582 | gi\|289284 | cysteinyl-tRNA synthetase [Bacillus subtilis] | 77 | 64 | 1350 |
| 140 | 18 | 19451 | 19263 | gi\|517210 | putative transposase [Streptococcus pyogenes] | 77 | 66 | 189 |
| 141 | 2 | 976 | 1683 | gnl\|PID\|e157887 | URF5 (aa 1-573) [Drosophila yakuba] | 77 | 50 | 708 |
| 141 | 4 | 2735 | 5293 | gi\|556258 | secA [Listeria monocytogenes] | 77 | 59 | 2559 |
| 144 | 2 | 671 | 2173 | gnl\|PID\|d100585 | lysyl-tRNA thyntheatase [Bacillus subtilis] | 77 | 61 | 1503 |
| 163 | 5 | 6412 | 7398 | gi\|511015 | dihydroorotate dehydrogenase A [Lactococcus lactis] | 77 | 62 | 987 |
| 164 | 10 | 7841 | 7074 | gnl\|PID\|d100964 | homologue of iron dicitrate transport ATP-binding protein FecE of E. coli [Bacillus subtilis] | 77 | 52 | 768 |
| 191 | 8 | 7257 | 5791 | gi\|149516 | anthranilate synthase alpha subunit [Lactococcus lactis] | 77 | 57 | 1467 |
| 198 | 8 | 5377 | 5177 | gi\|1573856 | hypothetical [Haemophilus influenzae] | 77 | 66 | 201 |
| 213 | 1 | 202 | 462 | gi\|1743860 | Brca2 [Mus musculus] | 77 | 50 | 261 |
| 250 | 2 | 231 | 509 | gnl\|PID\|e334776 | YlbH protein [Bacillus subtilis] | 77 | 60 | 279 |
| 289 | 3 | 1737 | 1276 | gnl\|PID\|d100947 | Ribosomal Protein L10 [Bacillus subtilis] | 77 | 62 | 462 |
| 292 | 2 | 1399 | 668 | gi\|143004 | transfer RNA-Gln synthetase [Bacillus stearothermophilus] | 77 | 58 | 732 |
| 7 | 3 | 2734 | 1166 | gnl\|PID\|d101824 | peptide-chain-release factor 3 [Synechocystis sp.] | 76 | 53 | 1569 |
| 7 | 23 | 18474 | 18235 | gi\|455157 | acyl carrier protein [Cryptomonas phi] | 76 | 57 | 240 |
| 9 | 8 | 5706 | 4342 | gi\|1146247 | asparaginyl-tRNA synthetase [Bacillus subtilis] | 76 | 61 | 1365 |
| 10 | 5 | 4531 | 4385 | gnl\|PID\|e314495 | hypothetical protein [Clostridium perfringens] | 76 | 53 | 147 |
| 18 | 2 | 1615 | 842 | gi\|1591672 | phosphate transport system ATP-binding protein [Methanococcus jannaschii] | 76 | 56 | 774 |
| 22 | 37 | 27796 | 28173 | gnl\|PID\|e13389 | translation initiation factor IF3 (AA 1-172) [Bacillus stearothermophilus] | 76 | 64 | 378 |
| 35 | 6 | 3869 | 2682 | gi\|1773346 | Cap5G [Staphylococcus aureus] | 76 | 61 | 1188 |
| 48 | 28 | 21113 | 21787 | gi\|2314328 | (AE000623) glutamine ABC transporter, permease protein (glnP) [Helicobacter pylori] | 76 | 52 | 675 |
| 52 | 12 | 12881 | 13786 | gi\|142521 | deoxyribodipyrimidine photolyase [Bacillus subtilis] | 76 | 58 | 906 |
| 55 | 10 | 11521 | 10571 | gnl\|PID\|e283110 | femD [Staphylococcus aureus] | 76 | 61 | 951 |
| 57 | 8 | 7824 | 6559 | gi\|290561 | o188 [Escherichia coli] | 76 | 47 | 1266 |
| 62 | 5 | 2406 | 2095 | gnl\|PID\|e313024 | hypothetical protein [Bacillus subtilis] | 76 | 59 | 312 |
| 65 | 9 | 4223 | 4441 | gi\|40148 | L29 protein (AA 1-66) [Bacillus subtilis] | 76 | 58 | 219 |
| 68 | 2 | 1328 | 2371 | gnl\|PID\|e284233 | anabolic ornithine carbamoyltransferase [Lactobacillus plantarum] | 76 | 61 | 1044 |
| 69 | 8 | 7297 | 6005 | gnl\|PID\|d101420 | Pyrimidine nucleoside phosphorylase [Bacillus stearothermophilus] | 76 | 61 | 1293 |
| 73 | 12 | 7839 | 7267 | gnl\|PID\|e243629 | unknown [Mycobacterium tuberculosis] | 76 | 53 | 573 |
| 74 | 5 | 8433 | 7039 | gnl\|PID\|d102048 | C. thermocellum beta-glucosidase; P26208 (985) [Bacillus subtilis] | 76 | 60 | 1395 |
| 80 | 5 | 7643 | 7936 | gi\|2314030 | (AE000599) conserved hypothetical protein [Helicobacter pylori] | 76 | 61 | 294 |
| 82 | 15 | 16019 | 16996 | gi\|1573900 | D-alanine permease (dagA) [Haemophilus influenzae] | 76 | 56 | 978 |
| 83 | 19 | 18616 | 19884 | gi\|143374 | phosphoribosyl glycinamide synthetase (PUR-D; gtg start codon) [Bacillus subtilis] | 76 | 60 | 1269 |
| 86 | 14 | 13409 | 12231 | gi\|143806 | AroF [Bacillus subtilis] | 76 | 58 | 1179 |
| 87 | 1 | 3 | 1442 | gi\|153804 | sucrose-6-phosphate hydrolase [Streptococcus mutans] | 76 | 59 | 1440 |
| 87 | 16 | 15754 | 15110 | gnl\|PID\|e323500 | putative Gmk protein [Bacillus subtilis] | 76 | 56 | 645 |
| 93 | 4 | 1769 | 1539 | gi\|1574820 | 1,4-alpha-glucan branching enzyme (glgB) [Haemophilus influenzae] | 76 | 46 | 231 |
| 94 | 1 | 51 | 365 | gi\|144313 | 6.0 kd ORF [Plasmid ColE1] | 76 | 73 | 315 |
| 116 | 2 | 2151 | 1678 | gi\|153841 | pneumococcal surface protein A [Streptococcus pneumoniae] | 76 | 59 | 474 |
| 123 | 6 | 3442 | 5895 | gi\|1314297 | ClpC ATPase [Listeria monocytogenes] | 76 | 59 | 2454 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 126 | 3 | 2156 | 2932 | gnl\|PID\|d101328 | YqiZ [*Bacillus subtilis*] | 76 | 61 | 777 |
| 128 | 10 | 6973 | 7797 | gi\|944944 | purine nucleoside phosphorylase [*Bacillus subtilis*] | 76 | 60 | 825 |
| 131 | 11 | 6186 | 5812 | gi\|1674310 | (AE000058) *Mycoplasma pneumoniae*, MG085 homolog, from *M. genitalium* [*Mycoplasma pneumoniae*] | 76 | 47 | 375 |
| 139 | 4 | 3641 | 3192 | gi\|2293302 | (AF008220) YtqA [*Bacillus subtilis*] | 76 | 53 | 450 |
| 140 | 14 | 14872 | 12536 | gi\|1184680 | polynucleotide phosphorylase [*Bacillus subtilis*] | 76 | 62 | 2337 |
| 143 | 2 | 2583 | 3905 | gi\|143795 | transfer RNA-Tyr synthetase [*Bacillus subtilis*] | 76 | 61 | 1323 |
| 170 | 6 | 5095 | 6114 | gnl\|PID\|d100959 | ycgQ [*Bacillus subtilis*] | 76 | 44 | 1020 |
| 180 | 2 | 1927 | 557 | gi\|40019 | ORF 821 (aa 1-821) [*Bacillus subtilis*] | 76 | 53 | 1371 |
| 191 | 7 | 5815 | 5228 | gi\|551880 | anthranilate synthase beta subunit [*Lactococcus lactis*] | 76 | 61 | 588 |
| 195 | 3 | 3829 | 2444 | gi\|2149905 | D-glutamic acid adding enzyme [*Enterococcus faecalis*] | 76 | 60 | 1386 |
| 200 | 3 | 1914 | 3629 | gi\|431272 | lysis protein [*Bacillus subtilis*] | 76 | 58 | 1716 |
| 201 | 1 | 431 | 207 | gi\|2208998 | dextran glucosidase DexS [*Streptococcus suis*] | 76 | 57 | 225 |
| 214 | 2 | 1283 | 2380 | gi\|663278 | transposase [*Streptococcus pneumoniae*] | 76 | 55 | 1098 |
| 225 | 3 | 2338 | 3411 | gi\|1552775 | ATP-binding protein [*Escherichia coli*] | 76 | 56 | 1074 |
| 233 | 1 | 2 | 724 | gi\|1163115 | neuraminidase B [*Streptococcus pneumoniae*] | 76 | 60 | 723 |
| 347 | 1 | 523 | 38 | gi\|537033 | ORF_f356 [*Escherichia coli*] | 76 | 60 | 486 |
| 356 | 2 | 842 | 165 | gi\|2149905 | D-glutamic acid adding enzyme [*Enterococcus faecalis*] | 76 | 61 | 678 |
| 366 | 3 | 734 | 348 | gi\|149520 | phosphoribosyl anthranilate isomerase [*Lactococcus lactis*] | 76 | 69 | 387 |
| 5 | 8 | 12599 | 11484 | gi\|1574293 | fimbrial transcription regulation repressor (pilB) [*Haemophilus influenzae*] | 75 | 61 | 1116 |
| 6 | 13 | 12553 | 11894 | gnl\|PID\|d102050 | ydiH [*Bacillus subtilis*] | 75 | 51 | 660 |
| 9 | 10 | 7282 | 6062 | gi\|142538 | aspartate aminotransferase [*Bacillus sp.*] | 75 | 55 | 1221 |
| 10 | 12 | 8080 | 7940 | gi\|149493 | SCRFI methylase [*Lactococcus lactis*] | 75 | 56 | 141 |
| 18 | 5 | 4266 | 3301 | gnl\|PID\|d101319 | YqgH [*Bacillus subtilis*] | 75 | 52 | 966 |
| 22 | 4 | 1838 | 2728 | gi\|1373157 | orf-X; hypothetical protein; Method: conceptual translation supplied by author [*Bacillus subtilis*] | 75 | 62 | 891 |
| 30 | 11 | 9015 | 7828 | gi\|153801 | enzyme scr-II [*Streptococcus mutans*] | 75 | 64 | 1188 |
| 31 | 5 | 2362 | 2030 | gi\|2293211 | (AF008220) putative thioredoxin [*Bacillus subtilis*] | 75 | 53 | 333 |
| 32 | 9 | 7484 | 8359 | gnl\|PID\|d100560 | formamidopyrimidine-DNA glycosylase [*Streptococcus mutans*] | 75 | 61 | 876 |
| 33 | 4 | 1735 | 1448 | gi\|413976 | ipa-52r gene product [*Bacillus subtilis*] | 75 | 53 | 288 |
| 33 | 10 | 6470 | 5769 | gi\|533105 | unknown [*Bacillus subtilis*] | 75 | 56 | 702 |
| 33 | 12 | 6878 | 7183 | pir\|A00205\|FECL | ferredoxin [4Fe-4S] - *Clostridium thermaceticum* | 75 | 56 | 306 |
| 36 | 1 | 181 | 2 | gi\|2088739 | (AF003141) strong similarity to the FABP/P2/CRBP/CRABP family of transporters [*Caenorhabditis elegans*] | 75 | 43 | 180 |
| 38 | 22 | 14510 | 15379 | gi\|1574058 | hypothetical [*Haemophilus influenzae*] | 75 | 56 | 870 |
| 48 | 33 | 23398 | 24066 | gi\|1930092 | outer membrane protein [*Campylobacter jejuni*] | 75 | 56 | 669 |
| 51 | 1 | 2 | 319 | gi\|43985 | nifS-like gene [*Lactobacillus delbrueckii*] | 75 | 55 | 318 |
| 51 | 10 | 8318 | 11683 | gi\|537192 | CG Site No. 620; alternate gene names hs, hsp, hsr, rrn; apparent frameshift in GenBank Accession Number X06545 [*Escherichia coli*] | 75 | 50 | 3366 |
| 54 | 18 | 19566 | 20759 | gi\|666069 | orf2 gene product [*Lactobacillus leichmannii*] | 75 | 58 | 1194 |
| 57 | 9 | 8448 | 7822 | gi\|290561 | o188 [*Escherichia coli*] | 75 | 50 | 627 |
| 65 | 14 | 6072 | 6356 | gi\|606241 | 30S ribosomal subunit protein S14 [*Escherichia coli*] | 75 | 64 | 285 |
| 70 | 4 | 3071 | 2472 | gi\|1256617 | adenine phosphoribosyltransferase [*Bacillus subtilis*] | 75 | 57 | 600 |
| 71 | 24 | 30399 | 29404 | gi\|1574390 | C4-dicarboxylate transport protein [*Haemophilus influenzae*] | 75 | 57 | 996 |
| 73 | 2 | 910 | 455 | gnl\|PID\|249656 | YneT [*Bacillus subtilis*] | 75 | 57 | 456 |
| 79 | 1 | 1810 | 491 | gi\|1146219 | 28.2% of identity to the *Escherichia coli* GTP-binding protein Era; putative [*Bacillus subtilis*] | 75 | 59 | 1320 |
| 82 | 6 | 6360 | 6536 | gi\|1655715 | BztD [*Rhodobacter capsulatus*] | 75 | 55 | 177 |
| 83 | 6 | 1938 | 2975 | gnl\|PID\|323529 | putative PlsX protein [*Bacillus subtilis*] | 75 | 56 | 1038 |
| 93 | 11 | 7368 | 5317 | gi\|39989 | methionyl-tRNA synthetase [*Bacillus stearothermophilus*] | 75 | 58 | 2052 |
| 93 | 13 | 9409 | 8699 | gi\|1591493 | glutamine transport ATP-binding protein Q [*Methanococcus jannaschii*] | 75 | 54 | 711 |
| 95 | 1 | 1795 | 47 | gnl\|PID\|e323510 | YloV protein [*Bacillus subtilis*] | 75 | 57 | 1749 |
| 103 | 2 | 362 | 1186 | gnl\|PID\|e266928 | unknown [*Mycobacterium tuberculosis*] | 75 | 64 | 825 |
| 104 | 1 | 691 | 915 | gi\|460026 | repressor protein [*Streptococcus pneumoniae*] | 75 | 54 | 225 |
| 113 | 5 | 2951 | 3883 | gnl\|PID\|d101119 | ABC transporter subunit [*Synechocystis sp.*] | 75 | 55 | 933 |
| 121 | 1 | 320 | 1390 | gi\|2145131 | repressor of class I heat shock gene expression HrcA [*Streptococcus mutans*] | 75 | 58 | 1071 |
| 127 | 6 | 2614 | 3000 | gi\|1500451 | *M. jannaschii* predicted coding region MJ1558 [*Methanococcus jannaschii*] | 75 | 44 | 387 |
| 137 | 18 | 10082 | 10687 | gi\|393116 | P-glycoprotein 5 [*Entamoeba histolytica*] | 75 | 52 | 606 |
| 149 | 11 | 8499 | 9338 | gnl\|PID\|d100582 | unknown [*Bacillus subtilis*] | 75 | 55 | 840 |
| 151 | 6 | 9100 | 7673 | gi\|40467 | HsdS polypeptide, part of CfrA family [*Citrobacter freundii*] | 75 | 57 | 1428 |
| 158 | 1 | 986 | 3 | gnl\|PID\|e253891 | UDP-glucose 4-epimerase [*Bacillus subtilis*] | 75 | 63 | 984 |
| 172 | 8 | 5653 | 6774 | gi\|142978 | glycerol dehydrogenase [*Bacillus stearothermophilus*] | 75 | 56 | 1122 |
| 172 | 9 | 7139 | 9730 | gnl\|PID\|e268456 | unknown [*Mycobacterium tuberculosis*] | 75 | 58 | 2592 |
| 173 | 1 | 261 | 79 | gnl\|PID\|e236469 | C10C5.6 [*Caenorhabditis elegans*] | 75 | 50 | 183 |
| 185 | 3 | 3066 | 2014 | gi\|1574806 | spermidine/putrescine transport ATP-binding protein (potA) [*Haemophilus influenzae*] | 75 | 56 | 1053 |
| 191 | 6 | 5235 | 4213 | gi\|149518 | phosphoribosyl anthranilate transferase [*Lactococcus lactis*] | 75 | 61 | 1023 |
| 226 | 2 | 1774 | 1181 | gi\|2314588 | (AE000642) conserved hypothetical protein [*Helicobacter pylori*] | 75 | 65 | 594 |
| 231 | 1 | 1 | 153 | gi\|40173 | homolog of *E. coli* ribosomal protein L21 [*Bacillus subtilis*] | 75 | 57 | 153 |
| 234 | 1 | 2 | 418 | gi\|2293259 | (AF008220) YtqI [*Bacillus subtilis*] | 75 | 59 | 417 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 279 | 1 | 552 | 151 | gi\|1119198 | unknown protein [*Bacillus subtilis*] | 75 | 50 | 402 |
| 291 | 7 | 3558 | 3827 | gi\|40011 | ORF17 (AA 1-161) [*Bacillus subtilis*] | 75 | 48 | 270 |
| 375 | 2 | 137 | 628 | gi\|410137 | ORFX13 [*Bacillus subtilis*] | 75 | 58 | 492 |
| 6 | 20 | 16721 | 17560 | gi\|2293323 | (AF008220) YtdI [*Bacillus subtilis*] | 74 | 53 | 840 |
| 7 | 6 | 4682 | 6052 | gi\|1354211 | PET112-like protein [*Bacillus subtilis*] | 74 | 60 | 1371 |
| 18 | 4 | 3341 | 2427 | gnl\|PID\|d101319 | YqgI [*Bacillus subtilis*] | 74 | 54 | 915 |
| 21 | 6 | 5885 | 4800 | gi\|1072381 | glutamyl-aminopeptidase [*Lactococcus lactis*] | 74 | 59 | 1086 |
| 24 | 2 | 739 | 548 | gi\|2314762 | (AE000655) ABC transporter, permease protein (yaeE) [*Helicobacter pylori*] | 74 | 46 | 192 |
| 25 | 1 | 2 | 367 | gnl\|PID\|d100932 | H2O-forming NADH Oxidase [*Streptococcus mutans*] | 74 | 63 | 366 |
| 38 | 18 | 11432 | 12964 | gi\|537034 | ORF_o488 [*Escherichia coli*] | 74 | 57 | 1533 |
| 48 | 10 | 8924 | 6669 | gi\|1513069 | P-type adenosine triphosphatase [*Listeria monocytogenes*] | 74 | 53 | 2256 |
| 55 | 11 | 11964 | 11401 | gnl\|PID\|e283110 | femD [*Staphylococcus aureus*] | 74 | 64 | 564 |
| 61 | 2 | 1782 | 427 | gi\|2293216 | (AF008220) putative UDP-N-acetylmuramate-alanine ligase [*Bacillus subtilis*] | 74 | 55 | 1356 |
| 76 | 10 | 9414 | 8065 | gnl\|PID\|d101325 | YqiB [*Bacillus subtilis*] | 74 | 54 | 1350 |
| 83 | 2 | 666 | 926 | pir\|C33496\|C334 | hisC homolog - Bacillus subtilis | 74 | 55 | 261 |
| 86 | 9 | 8985 | 8080 | gi\|683585 | prephenate dehydratase [*Lactococcus lactis*] | 74 | 55 | 906 |
| 102 | 5 | 5005 | 5652 | gi\|143394 | OMP-PRPP transferase [*Bacillus subtilis*] | 74 | 57 | 648 |
| 103 | 5 | 4364 | 3267 | gnl\|PID\|e323524 | YloN protein [*Bacillus subtilis*] | 74 | 62 | 1098 |
| 108 | 7 | 6864 | 7592 | gnl\|PID\|e257631 | methyltransferase [*Lactococcus lactis*] | 74 | 56 | 729 |
| 131 | 2 | 478 | 146 | gnl\|PID\|d101320 | YqgZ [*Bacillus subtilis*] | 74 | 45 | 333 |
| 133 | 2 | 1380 | 919 | gnl\|PID\|e313025 | hypothetical protein [*Bacillus subtilis*] | 74 | 60 | 462 |
| 137 | 9 | 6167 | 6787 | gnl\|PID\|d100479 | Na+-ATPase subunit D [*Enterococcus hirae*] | 74 | 53 | 621 |
| 149 | 4 | 3008 | 3883 | gnl\|PID\|d100581 | high level kasgamycin resistance [*Bacillus subtilis*] | 74 | 55 | 876 |
| 157 | 2 | 243 | 824 | gi\|1573373 | methylated-DNA-protein-cysteine methyltransferase (dat1) [*Haemophilus influenzae*] | 74 | 48 | 582 |
| 164 | 6 | 3515 | 4249 | gi\|410131 | ORFX7 [*Bacillus subtilis*] | 74 | 48 | 582 |
| 167 | 7 | 5446 | 5201 | gi\|413927 | ipa-3r gene product [*Bacillus subtilis*] | 74 | 55 | 246 |
| 171 | 1 | 1 | 1818 | gnl\|PID\|d102251 | beta-galactosidase [*Bacillus circulans*] | 74 | 62 | 1818 |
| 172 | 4 | 1064 | 2392 | gi\|466474 | cellobiose phosphotransferase enzyme II" [*Bacillus stearothermophilus*] | 74 | 50 | 1329 |
| 185 | 1 | 326 | 3 | gi\|1573646 | Mg(2+) transport ATPase protein C (mgtC) (SP: P22037) [*Haemophilus influenzae*] | 74 | 68 | 324 |
| 188 | 2 | 1089 | 2018 | gi\|1573008 | ATP dependent translocator homolog (msbA) [*Haemophilus influenzae*] | 74 | 44 | 930 |
| 189 | 11 | 6491 | 7174 | gi\|1661199 | sakacin A production response regulator [*Streptococcus mutans*] | 74 | 60 | 684 |
| 210 | 2 | 520 | 1287 | gi\|2293207 | (AF008220) YtmQ [*Bacillus subtilis*] | 74 | 60 | 768 |
| 261 | 1 | 836 | 192 | gi\|666983 | putative ATP binding subunit [*Bacillus subtilis*] | 74 | 55 | 645 |
| 263 | 3 | 1619 | 3655 | gi\|663232 | Similarity with S. cerevisiae hypothetical 137.7 kD protein in subtelomeric Y' repeat region [*Saccharomyces cerevisiae*] | 74 | 42 | 2037 |
| 265 | 2 | 844 | 1227 | gi\|49272 | Asparaginase [*Bacillus licheniformis*] | 74 | 64 | 384 |
| 368 | 1 | 1 | 942 | gi\|603998 | unknown [*Saccharomyces cerevisiae*] | 74 | 39 | 942 |
| 7 | 16 | 13357 | 11921 | gnl\|PID\|d101324 | YqhX [*Bacillus subtilis*] | 73 | 57 | 1437 |
| 17 | 10 | 5706 | 5449 | gnl\|PID\|e305362 | unnamed protein product [*Streptococcus thermophilus*] | 73 | 47 | 258 |
| 31 | 2 | 522 | 244 | gnl\|PID\|d100576 | single strand DNA binding protein [*Bacillus subtilis*] | 73 | 55 | 279 |
| 32 | 6 | 5667 | 6194 | gnl\|PID\|d101315 | YqfG [*Bacillus subtilis*] | 73 | 58 | 528 |
| 34 | 15 | 10281 | 9790 | gnl\|PID\|d102151 | (AB001684) ORF42c [*Chlorella vulgaris*] | 73 | 46 | 492 |
| 40 | 12 | 9876 | 9226 | gi\|1173517 | riboflavin synthase alpha subunit [*Actinobacillus pleuropneumoniae*] | 73 | 55 | 651 |
| 55 | 2 | 3592 | 839 | gnl\|PID\|d101887 | cation-transporting ATPase PacL [*Synechocystis sp.*] | 73 | 60 | 2754 |
| 55 | 18 | 17494 | 16586 | gnl\|PID\|e265580 | unknown [*Mycobacterium tuberculosis*] | 73 | 52 | 909 |
| 65 | 16 | 7213 | 7767 | gi\|143419 | ribosomal protein L6 [*Bacillus stearothermophilus*] | 73 | 60 | 555 |
| 66 | 3 | 3300 | 3659 | gnl\|PID\|e269883 | LacF [*Lactobacillus casei*] | 73 | 52 | 360 |
| 70 | 10 | 5557 | 5733 | gi\|857631 | envelope protein [Human immunodeficiency virus type 1] | 73 | 60 | 177 |
| 71 | 4 | 6133 | 8262 | gnl\|PID\|e322063 | ss-1,4-galactosyltransferase [*Streptococcus pneumoniae*] | 73 | 45 | 2130 |
| 72 | 1 | 3 | 851 | gi\|2293177 | (AF008220) transporter [*Bacillus subtilis*] | 73 | 50 | 849 |
| 76 | 7 | 7019 | 6195 | gnl\|PID\|d101325 | YqiF [*Bacillus subtilis*] | 73 | 66 | 825 |
| 76 | 12 | 10009 | 9533 | gi\|1573086 | uridine kinase (uridine monophosphokinase) (udk) [*Haemophilus influenzae*] | 73 | 54 | 477 |
| 80 | 7 | 8113 | 9372 | gi\|1377823 | aminopeptidase [*Bacillus subtilis*] | 73 | 60 | 1260 |
| 97 | 5 | 3389 | 1668 | gnl\|PID\|d101954 | dihydroxyacid dehydratase [*Synechocystis sp.*] | 73 | 54 | 1722 |
| 98 | 9 | 6912 | 7619 | gnl\|PID\|e314991 | FtsE [*Mycobacterium tuberculosis*] | 73 | 54 | 708 |
| 108 | 11 | 10928 | 10440 | gi\|388109 | regulatory protein [*Enterococcus faecalis*] | 73 | 54 | 489 |
| 128 | 6 | 3632 | 4222 | gi\|1685111 | orf1091 [*Streptococcus thermophilus*] | 73 | 63 | 591 |
| 138 | 2 | 1575 | 394 | gi\|147326 | transport protein [*Escherichia coli*] | 73 | 60 | 1182 |
| 140 | 13 | 12538 | 11903 | pir\|E53402\|E534 | serine O-acetyltransferase (EC 2.3.1.30) - Bacillus stearothermophilus | 73 | 55 | 636 |
| 162 | 5 | 5701 | 4991 | gnl\|PID\|e323511 | putative YhaQ protein [*Bacillus subtilis*] | 73 | 50 | 711 |
| 164 | 4 | 2323 | 2790 | gi\|1592076 | hypothetical protein (SP: P25768) [*Methanococcus jannaschii*] | 73 | 52 | 468 |
| 164 | 8 | 4815 | 5546 | gi\|410137 | ORFX13 [*Bacillus subtilis*] | 73 | 56 | 732 |
| 170 | 5 | 4394 | 5302 | gnl\|PID\|d100959 | homologue of unidentified protein of E. coli [*Bacillus subtilis*] | 73 | 46 | 909 |
| 178 | 7 | 3893 | 4855 | gi\|46242 | nodulation protein B, 5'end [*Rhizobium loti*] | 73 | 56 | 963 |
| 204 | 6 | 5096 | 4278 | gnl\|PID\|e214719 | PlcR protein [*Bacillus thuringiensis*] | 73 | 41 | 819 |
| 213 | 2 | 832 | 2037 | gi\|1565296 | ribosomal protein S1 homolog; sequence specific DNA-binding protein [*Leuconostoc lactis*] | 73 | 55 | 1206 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 231 | 2 | 84 | 287 | gi\|40173 | homolog of E. coli ribosomal protein L21 [Bacillus subtilis] | 73 | 61 | 204 |
| 237 | 1 | 2 | 505 | gi\|1773151 | adenine phosphoribosyltransferase [Escherichia coli] | 73 | 51 | 504 |
| 269 | 1 | 2 | 691 | gnl\|PID\|d101328 | Yqix [Bacillus subtilis] | 73 | 36 | 690 |
| 289 | 2 | 1272 | 832 | pir\|A02771\|R7MC | ribosomal protein L7/L12 - Micrococcus luteus | 73 | 66 | 441 |
| 343 | 1 | 14 | 484 | gi\|1788125 | (AE000276) hypothetical 30.4 kD protein in manZ-cspC intergenic region [Escherichia coli] | 73 | 47 | 471 |
| 356 | 1 | 222 | 4 | gi\|2149905 | D-glutamic acid adding enzyme [Enterococcus faecalis] | 73 | 50 | 219 |
| 7 | 5 | 3165 | 4691 | gnl\|PID\|d101833 | amidase [Synechocystis sp.] | 72 | 52 | 1527 |
| 7 | 9 | 7195 | 7647 | gi\|146976 | nusB [Escherichia coli] | 72 | 54 | 453 |
| 7 | 17 | 13743 | 13300 | gnl\|PID\|e289141 | similar to hydroxymyristoyl-(acyl carrier protein) dehydratase [Bacillus subtilis] | 72 | 59 | 444 |
| 22 | 19 | 15637 | 16224 | gnl\|PID\|d101929 | ribosome releasing factor [Synechocystis sp.] | 72 | 51 | 588 |
| 33 | 17 | 12111 | 11425 | gnl\|PID\|d101190 | ORF3 [Streptococcus mutans] | 72 | 55 | 687 |
| 34 | 7 | 7147 | 5627 | gi\|396501 | aspartyl-tRNA synthetase [Thermus thermophilus] | 72 | 52 | 1521 |
| 38 | 23 | 15372 | 16085 | pir\|H64108\|H641 | L-ribulose-phosphate 4-epimerase (araD) homolog - Haemophilus influenzae (strain Rd KW20) | 72 | 54 | 714 |
| 39 | 5 | 5094 | 6905 | gnl\|PID\|e254877 | unknown [Mycobacterium tuberculosis] | 72 | 56 | 1812 |
| 40 | 6 | 4469 | 4636 | gi\|153672 | lactose repressor [Streptococcus mutans] | 72 | 58 | 168 |
| 48 | 2 | 1459 | 1253 | gi\|310380 | inhibin beta-A-subunit [Ovis aries] | 72 | 33 | 207 |
| 48 | 29 | 21729 | 22424 | gi\|2314329 | (AE000623) glutamine ABC transporter, permease protein (glnP) [Helicobacter pylori] | 72 | 49 | 696 |
| 50 | 5 | 4529 | 3288 | gi\|1750108 | YnbA [Bacillus subtilis] | 72 | 54 | 1242 |
| 51 | 3 | 1044 | 2282 | gi\|2293230 | (AF008220) YtbJ [Bacillus subtilis] | 72 | 54 | 1239 |
| 52 | 13 | 13681 | 13938 | gi\|142521 | deoxyribodipyrimidine photolyase [Bacillus subtilis] | 72 | 45 | 258 |
| 55 | 1 | 841 | 35 | gi\|882518 | ORF_o304; GTG start [Escherichia coli] | 72 | 59 | 807 |
| 75 | 5 | 2832 | 3191 | gnl\|PID\|e209886 | mercuric resistance operon regulatory protein [Bacillus subtilis] | 72 | 44 | 360 |
| 76 | 6 | 6229 | 5771 | gi\|142450 | ahrC protein [Bacillus subtilis] | 72 | 53 | 459 |
| 79 | 5 | 5065 | 4592 | gi\|2293279 | (AF008220) YtcG [Bacillus subtilis] | 72 | 46 | 474 |
| 87 | 14 | 14726 | 12309 | gnl\|PID\|e323502 | putative PriA protein [Bacillus subtilis] | 72 | 52 | 2418 |
| 91 | 1 | 444 | 662 | gi\|500691 | MYO1 gene product [Saccharomyces cerevisiae] | 72 | 50 | 219 |
| 91 | 7 | 4516 | 4764 | gi\|829615 | skeletal muscle sodium channel alpha-subunit [Equus caballus] | 72 | 38 | 249 |
| 95 | 2 | 2004 | 1717 | gnl\|PID\|e323527 | putative Asp23 protein [Bacillus subtilis] | 72 | 40 | 288 |
| 109 | 1 | 1452 | 118 | gi\|143331 | alkaline phosphatase regulatory protein [Bacillus subtilis] | 72 | 52 | 1335 |
| 126 | 1 | 3 | 2192 | gnl\|PID\|d101831 | glutamine-binding periplasmic protein [Synechocystis sp.] | 72 | 46 | 2190 |
| 130 | 3 | 1735 | 2478 | gi\|2415396 | (AF015775) carboxypeptidase [Bacillus subtilis] | 72 | 53 | 744 |
| 137 | 6 | 2585 | 2929 | gi\|472922 | v-type Na-ATPase [Enterococcus hirae] | 72 | 46 | 345 |
| 140 | 10 | 9601 | 9203 | gi\|49224 | URF 4 [Synechococcus sp.] | 72 | 48 | 399 |
| 146 | 5 | 1906 | 1247 | gnl\|PID\|e324945 | hypothetical protein [Bacillus subtilis] | 72 | 45 | 660 |
| 147 | 2 | 2084 | 1083 | gnl\|PID\|e325016 | hypothetical protein [Bacillus subtilis] | 72 | 56 | 1002 |
| 147 | 5 | 6156 | 5146 | gi\|472327 | TPP-dependent acetoin dehydrogenase beta-subunit [Clostridium magnum] | 72 | 56 | 1011 |
| 148 | 8 | 5381 | 6433 | gi\|974332 | NAD(P)H-dependent dihydroxyacetone-phosphate reductase [Bacillus subtilis] | 72 | 54 | 1053 |
| 148 | 14 | 10256 | 9675 | gnl\|PID\|d101319 | YqgN [Bacillus subtilis] | 72 | 50 | 582 |
| 159 | 8 | 4005 | 4949 | gi\|1788770 | (AE000330) o463; 24 pct identical (44 gaps) to 338 residues from penicillin-binding protein 4*, PBPE_BACSU SW: P32959 (451 aa) [Escherichia coli] | 72 | 43 | 945 |
| 172 | 10 | 9907 | 10620 | gi\|763387 | unknown [Saccharomyces cerevisiae] | 72 | 55 | 714 |
| 220 | 3 | 2862 | 3602 | gi\|1574175 | hypothetical [Haemophilus influenzae] | 72 | 50 | 741 |
| 267 | 1 | 3 | 449 | gi\|290513 | f470 [Escherichia coli] | 72 | 48 | 447 |
| 281 | 2 | 899 | 540 | gnl\|PID\|d100964 | homologue of aspartokinase 2 alpha and beta subunits LysC of B. subtilis [Bacillus subtilis] | 72 | 45 | 360 |
| 290 | 1 | 1018 | 14 | gi\|474195 | This ORF is homologous to a 40.0 kd hypothetical protein in the htrB 3'region from E. coli, Accession Number X61000 [Mycoplasma-like organism] | 72 | 54 | 1005 |
| 300 | 1 | 63 | 587 | gi\|746399 | transcription elongation factor [Escherichia coli] | 72 | 50 | 525 |
| 316 | 1 | 1326 | 4 | gi\|158127 | protein kinase C [Drosophila melanogaster] | 72 | 40 | 1323 |
| 342 | 1 | 227 | 3 | gnl\|PID\|d101164 | unknown [Bacillus subtilis] | 72 | 54 | 225 |
| 354 | 1 | 1 | 1005 | gnl\|PID\|d102048 | C. thermocellum beta-glucosidase; P26208 (985) [Bacillus subtilis] | 72 | 52 | 1005 |
| 6 | 10 | 8134 | 10467 | gnl\|PID\|e264229 | unknown [Mycobacterium tuberculosis] | 71 | 57 | 2334 |
| 7 | 20 | 16231 | 15464 | gi\|18046 | 3-oxoacyl-[acyl-carrier protein] reductase [Cuphea lanceolata] | 71 | 52 | 768 |
| 15 | 1 | 1297 | 2 | gnl\|PID\|d100571 | replicative DNA helicase [Bacillus subtilis] | 71 | 51 | 1296 |
| 15 | 4 | 4435 | 3869 | gi\|499384 | orf189 [Bacillus subtilis] | 71 | 47 | 567 |
| 18 | 6 | 5120 | 4218 | gnl\|PID\|d101318 | YqgG [Bacillus subtilis] | 71 | 51 | 903 |
| 29 | 1 | 1 | 540 | gi\|1773142 | similar to the 20.2 kd protein in TETB-EXOA region of B. subtilis [Escherichia coli] | 71 | 56 | 540 |
| 38 | 20 | 13327 | 13830 | gi\|537036 | ORF_o158 [Escherichia coli] | 71 | 48 | 504 |
| 51 | 12 | 15015 | 12676 | gi\|149528 | dipeptidyl peptidase IV [Lactococcus lactis] | 71 | 55 | 2340 |
| 55 | 23 | 21040 | 20585 | gi\|2343285 | (AF015453) surface located protein [Lactobacillus rhamnosus] | 71 | 58 | 456 |
| 60 | 2 | 705 | 265 | gnl\|PID\|d101320 | Yqgz [Bacillus subtilis] | 71 | 44 | 441 |
| 71 | 18 | 24679 | 26226 | gi\|580920 | rodD (gtaA) polypeptide (AA 1-673) [Bacillus subtilis] | 71 | 44 | 1548 |
| 71 | 25 | 30587 | 30360 | gi\|606028 | ORF_o414; Geneplot suggests frameshift near start but none found [Escherichia coli] | 71 | 50 | 228 |
| 72 | 6 | 5239 | 6729 | gi\|580835 | lysine decarboxylase [Bacillus subtilis] | 71 | 48 | 1491 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 72 | 14 | 11991 | 12878 | gi\|624085 | similar to rat beta-alanine synthetase encoded by GenBank Accession Number S27881; contains ATP/GTP binding motif [*Paramecium bursaria* Chlorella virus 1] | 71 | 54 | 888 |
| 73 | 11 | 7269 | 7033 | gi\|1906594 | PN1 [*Rattus norvegicus*] | 71 | 42 | 237 |
| 74 | 6 | 10385 | 8517 | gi\|1573733 | prolyl-tRNA synthetase (proS) [*Haemophilus influenzae*] | 71 | 52 | 1869 |
| 81 | 9 | 5772 | 6578 | gi\|147404 | mannose permease subunit II-M-Man [*Escherichia coli*] | 71 | 45 | 807 |
| 86 | 5 | 4602 | 3604 | gnl\|PID\|e322063 | ss-1,4-galactosyltransferase [*Streptococcus pneumoniae*] | 71 | 53 | 999 |
| 105 | 4 | 3619 | 4707 | gi\|2323341 | (AF014460) PepQ [*Streptococcus mutans*] | 71 | 58 | 1089 |
| 106 | 13 | 13557 | 12955 | gi\|1519287 | LemA [*Listeria monocytogenes*] | 71 | 48 | 603 |
| 114 | 2 | 1029 | 1979 | gi\|310303 | mosA [*Rhizobium meliloti*] | 71 | 55 | 951 |
| 122 | 2 | 564 | 1205 | gi\|1649037 | glutamine transport ATP-binding protein GLNQ [*Salmonella typhimurium*] | 71 | 50 | 642 |
| 132 | 5 | 9018 | 7063 | gnl\|PID\|d102049 | *H. influenzae* hypothetical ABC transporter; P44808 (974) [*Bacillus subtilis*] | 71 | 51 | 1956 |
| 140 | 1 | 1141 | 227 | gi\|1673788 | (AE000015) *Mycoplasma pneumoniae*, fructose-bisphosphate aldolase; similar to Swiss-Prot Accession Number P13243, from *B. subtilis* [*Mycoplasma pneumoniae*] | 71 | 49 | 915 |
| 140 | 5 | 5635 | 4973 | gnl\|PID\|d100964 | homologue of hypothetical protein in a rapamycin synthesis gene cluster of *Streptomyces hygroscopicus* [*Bacillus subtilis*] | 71 | 48 | 663 |
| 141 | 7 | 7369 | 7845 | gnl\|PID\|d102005 | (AB001488) FUNCTION UNKNOWN, SIMILAR PRODUCT IN *E. COLI* AND *MYCOPLASMA PNEUMONIAE*. [*Bacillus subtilis*] | 71 | 51 | 477 |
| 193 | 1 | 1 | 165 | gi\|46912 | ribosomal protein L13 [*Staphylococcus carnosus*] | 71 | 59 | 165 |
| 194 | 3 | 2205 | 1594 | gi\|535351 | CodY [*Bacillus subtilis*] | 71 | 52 | 612 |
| 199 | 3 | 1510 | 1319 | gi\|2182574 | (AE000090) Y4pE [*Rhizobium* sp. NGR234] | 71 | 45 | 192 |
| 208 | 2 | 2616 | 3752 | gi\|1787378 | (AE000213) hypothetical protein in purB 5' region [*Escherichia coli*] | 71 | 57 | 1137 |
| 209 | 2 | 2022 | 1141 | gi\|41432 | fepC gene product [*Escherichia coli*] | 71 | 46 | 882 |
| 210 | 5 | 1911 | 3071 | gi\|49316 | ORF2 gene product [*Bacillus subtilis*] | 71 | 45 | 1161 |
| 210 | 6 | 3069 | 3386 | gi\|580900 | ORF3 gene product [*Bacillus subtilis*] | 71 | 48 | 318 |
| 212 | 2 | 3561 | 1381 | gi\|557567 | ribonucleotide reductase R1 subunit [*Mycobacterium tuberculosis*] | 71 | 53 | 2181 |
| 233 | 3 | 2003 | 2920 | gnl\|PID\|d101320 | YqgR [*Bacillus subtilis*] | 71 | 50 | 918 |
| 244 | 1 | 13 | 1053 | gnl\|PID\|d100964 | homologue of aspartokinase 2 alpha and beta subunits LysC of *B. subtilis* [*Bacillus subtilis*] | 71 | 55 | 1041 |
| 251 | 2 | 1008 | 1874 | gi\|755601 | unknown [*Bacillus subtilis*] | 71 | 46 | 867 |
| 282 | 2 | 906 | 712 | gi\|1353874 | unknown [*Rhodobacter capsulatus*] | 71 | 46 | 195 |
| 312 | 4 | 2137 | 1565 | gnl\|PID\|d102245 | (AB005554) yxbF [*Bacillus subtilis*] | 71 | 34 | 573 |
| 338 | 1 | 3 | 683 | gi\|1591045 | hypothetical protein (SP: P31466) [*Methanococcus jannaschii*] | 71 | 48 | 681 |
| 346 | 1 | 3 | 164 | gi\|1591234 | hypothetical protein (SP: P42297) [*Methanococcus jannaschii*] | 71 | 36 | 162 |
| 374 | 1 | 619 | 2 | gi\|397526 | clumping factor [*Staphylococcus aureus*] | 71 | 23 | 618 |
| 377 | 1 | 688 | 2 | gi\|397526 | clumping factor [*Staphylococcus aureus*] | 71 | 23 | 687 |
| 3 | 8 | 7419 | 6958 | gnl\|PID\|e269486 | Unknown [*Bacillus subtilis*] | 70 | 42 | 462 |
| 3 | 10 | 8395 | 9075 | gnl\|PID\|e255543 | putative iron dependant repressor [*Staphylococcus epidermidis*] | 70 | 46 | 681 |
| 7 | 14 | 11024 | 10254 | gnl\|PID\|d100290 | undefined open reading frame [*Bacillus stearothermophilus*] | 70 | 55 | 771 |
| 7 | 18 | 14213 | 13719 | gnl\|PID\|d101090 | biotin carboxyl carrier protein of acetyl-CoA carboxylase [*Synechocystis* sp.] | 70 | 56 | 495 |
| 9 | 2 | 1057 | 287 | gnl\|PID\|d100581 | unknown [*Bacillus subtilis*] | 70 | 52 | 771 |
| 12 | 4 | 2610 | 1789 | gnl\|PID\|d101195 | yycJ [*Bacillus subtilis*] | 70 | 52 | 822 |
| 21 | 2 | 2586 | 1846 | gi\|2293447 | (AF008930) ATPase [*Bacillus subtilis*] | 70 | 54 | 741 |
| 22 | 13 | 10955 | 11512 | gi\|1165295 | Ydr540cp [*Saccharomyces cerevisiae*] | 70 | 50 | 558 |
| 30 | 6 | 4315 | 3980 | gi\|39478 | ATP binding protein of transport ATPases [*Bacillus firmus*] | 70 | 51 | 336 |
| 31 | 1 | 370 | 113 | gi\|662792 | single-stranded DNA binding protein [unidentified eubacterium] | 70 | 36 | 258 |
| 33 | 15 | 10639 | 9521 | gi\|1161219 | homolgous to D-amino acid dehydrogenase enzyme [*Pseudomonas aeruginosa*] | 70 | 50 | 1119 |
| 38 | 6 | 3812 | 4312 | gi\|2058547 | ComYD [*Streptococcus gordonii*] | 70 | 48 | 501 |
| 38 | 25 | 17986 | 18477 | gi\|537033 | ORF_f356 [*Escherichia coli*] | 70 | 58 | 492 |
| 40 | 13 | 11054 | 9846 | gi\|1173516 | riboflavin-specific deaminase [*Actinobacillus pleuropneumoniae*] | 70 | 52 | 1209 |
| 42 | 2 | 722 | 1954 | gi\|1146183 | putative [*Bacillus subtilis*] | 70 | 51 | 1233 |
| 43 | 3 | 2373 | 1612 | gi\|1591493 | glutamine transport ATP-binding protein Q [*Methanococcus jannaschii*] | 70 | 48 | 762 |
| 45 | 8 | 9197 | 8049 | gnl\|PID\|d102036 | subunit of ADP-glucose pyrophosphorylase [*Bacillus stearothermophilus*] | 70 | 54 | 1149 |
| 59 | 2 | 567 | 956 | gnl\|PID\|d100302 | neopullulanase [*Bacillus* sp.] | 70 | 42 | 390 |
| 60 | 3 | 1874 | 795 | gnl\|PID\|e276466 | aminopeptidase P [*Lactococcus lactis*] | 70 | 48 | 1080 |
| 61 | 4 | 5553 | 2437 | gnl\|PID\|e275074 | SNF [*Bacillus cereus*] | 70 | 51 | 3117 |
| 61 | 7 | 7914 | 6802 | gi\|1573037 | cystathionine gamma-synthase (metB) [*Haemophilus influenzae*] | 70 | 52 | 1113 |
| 63 | 7 | 5372 | 7222 | gnl\|PID\|d100974 | unknown [*Bacillus subtilis*] | 70 | 54 | 1851 |
| 68 | 7 | 7126 | 6962 | gi\|1263014 | emm18.1 gene product [*Streptococcus pyogenes*] | 70 | 37 | 165 |
| 72 | 12 | 10081 | 10911 | gi\|2313093 | (AE000524) carboxynorspermidine decarboxylase (nspC) [*Helicobacter pylori*] | 70 | 56 | 831 |
| 75 | 10 | 7888 | 8124 | gi\|1877423 | galactose-1-P-uridyl transferase [*Streptococcus mutans*] | 70 | 59 | 237 |
| 79 | 3 | 3424 | 2525 | gi\|39881 | ORF 311 (AA 1-311) [*Bacillus subtilis*] | 70 | 47 | 900 |
| 87 | 10 | 9369 | 7324 | gnl\|PID\|e323506 | putative Pkn2 protein [*Bacillus subtilis*] | 70 | 52 | 2046 |
| 96 | 14 | 10640 | 11788 | gi\|1573209 | tRNA-guanine transglycosylase (tgt) [*Haemophilus influenzae*] | 70 | 52 | 1149 |
| 113 | 2 | 574 | 1086 | gi\|433630 | A180 [*Saccharomyces cerevisiae*] | 70 | 59 | 513 |
| 123 | 5 | 2901 | 3461 | gnl\|PID\|d100585 | unknown [*Bacillus subtilis*] | 70 | 45 | 561 |
| 125 | 5 | 4593 | 4282 | gnl\|PID\|e276474 | capacitative calcium entry channel 1 [*Bos taurus*] | 70 | 35 | 312 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 129 | 5 | 4500 | 3454 | gnl|PID|d101314 | YqeT [*Bacillus subtilis*] | 70 | 47 | 1047 |
| 133 | 3 | 2608 | 1394 | gi|2293312 | (AF008220) YtfP [*Bacillus subtilis*] | 70 | 50 | 1215 |
| 135 | 1 | 420 | 662 | gnl|PID|e265530 | yorfE [*Streptococcus pneumoniae*] | 70 | 47 | 243 |
| 137 | 3 | 438 | 932 | gi|472919 | v-type Na-ATPase [*Enterococcus hirae*] | 70 | 57 | 495 |
| 138 | 1 | 440 | 3 | gi|147336 | transmembrane protein [*Escherichia coli*] | 70 | 42 | 438 |
| 140 | 16 | 18796 | 16364 | gi|976441 | N5-methyltetrahydrofolate homocysteine methyltransferase [*Saccharomyces cerevisiae*] | 70 | 53 | 2433 |
| 167 | 10 | 8263 | 6695 | gi|149535 | D-alanine activating enzyme [*Lactobacillus casei*] | 70 | 52 | 1569 |
| 204 | 4 | 3226 | 2747 | gnl|PID|d102049 | E. coli hypothetical protein; P31805 (267) [*Bacillus subtilis*] | 70 | 51 | 480 |
| 207 | 3 | 2627 | 2869 | gnl|PID|e309213 | racGAP [*Dictyostelium discoideum*] | 70 | 45 | 243 |
| 282 | 3 | 1136 | 882 | gi|1353874 | unknown [*Rhodobacter capsulatus*] | 70 | 50 | 255 |
| 6 | 21 | 17554 | 18453 | gnl|PID|e233879 | hypothetical protein [*Bacillus subtilis*] | 69 | 44 | 900 |
| 6 | 22 | 18482 | 19471 | gi|580883 | ipa-88d gene product [*Bacillus subtilis*] | 69 | 53 | 990 |
| 22 | 6 | 4682 | 5824 | gi|2209379 | (AF006720) ProJ [*Bacillus subtilis*] | 69 | 48 | 1143 |
| 22 | 9 | 7992 | 8651 | gnl|PID|d100580 | unknown [*Bacillus subtilis*] | 69 | 51 | 660 |
| 22 | 12 | 9871 | 10767 | gnl|PID|d100581 | unknown [*Bacillus subtilis*] | 69 | 51 | 897 |
| 27 | 7 | 5857 | 5348 | gnl|PID|d102012 | (AB001488) FUNCTION UNKNOWN. [*Bacillus subtilis*] | 69 | 28 | 510 |
| 36 | 10 | 7294 | 10116 | gi|437916 | isoleucyl-tRNA synthetase [*Staphylococcus aureus*] | 69 | 53 | 2823 |
| 38 | 1 | 2 | 1090 | gi|141900 | alcohol dehydrogenase (EC 1.1.1.1) [*Alcaligenes eutrophus*] | 69 | 48 | 1089 |
| 40 | 14 | 11333 | 11944 | gi|1573280 | Holliday junction DNA helicase (ruvA) [*Haemophilus influenzae*] | 69 | 44 | 612 |
| 40 | 15 | 11942 | 12517 | gi|1573653 | DNA-3-methyladenine glycosidase I (tagI) [*Haemophilus influenzae*] | 69 | 50 | 576 |
| 45 | 6 | 6947 | 5490 | gi|580887 | starch (bacterial glycogen) synthase [*Bacillus subtilis*] | 69 | 47 | 1458 |
| 48 | 34 | 24932 | 24153 | gnl|PID|e233870 | hypothetical protein [*Bacillus subtilis*] | 69 | 36 | 780 |
| 49 | 6 | 6183 | 6521 | gi|396297 | similar to phosphotransferase system enzyme II [*Escherichia coli*] | 69 | 50 | 339 |
| 49 | 8 | 7586 | 8338 | gi|396420 | similar to Alcaligenes eutrophus pHG1 D-ribulose-5-phosphate 3 epimerase [*Escherichia coli*] | 69 | 49 | 753 |
| 55 | 6 | 8262 | 7033 | gi|1146238 | poly(A) polymerase [*Bacillus subtilis*] | 69 | 50 | 1230 |
| 59 | 3 | 954 | 2333 | gnl|PID|e313038 | hypothetical protein [*Bacillus subtilis*] | 69 | 54 | 1380 |
| 62 | 3 | 1170 | 1418 | gnl|PID|d101915 | hypothetical protein [*Synechocystis sp.*] | 69 | 49 | 249 |
| 63 | 8 | 7298 | 7762 | gi|293017 | ORF3 (put.); putative [*Lactococcus lactis*] | 69 | 42 | 465 |
| 66 | 4 | 3657 | 5081 | gi|153755 | phospho-beta-D-galactosidase (EC 3.2.1.85) [*Lactococcus lactis cremoris*] | 69 | 49 | 1425 |
| 66 | 5 | 5126 | 6829 | gi|433809 | enzyme II [*Streptococcus mutans*] | 69 | 46 | 1704 |
| 71 | 6 | 10017 | 10664 | gnl|PID|e322063 | ss-1,4-galactosyltransferase [*Streptococcus pneumoniae*] | 69 | 39 | 648 |
| 71 | 21 | 27730 | 27966 | gnl|PID|d100649 | DE-cadherin [*Drosophila melanogaster*] | 69 | 30 | 237 |
| 77 | 1 | 1 | 237 | gi|287870 | groES gene product [*Lactococcus lactis*] | 69 | 44 | 237 |
| 81 | 5 | 3622 | 4101 | gi|1573605 | fucose operon protein (fucU) [*Haemophilus influenzae*] | 69 | 52 | 480 |
| 83 | 1 | 40 | 714 | pir|C33496|C334 | hisC homolog - Bacillus subtilis | 69 | 46 | 675 |
| 83 | 16 | 15742 | 16335 | gi|143372 | phosphoribosyl glycinamide formyltransferase (PUR-N) [*Bacillus subtilis*] | 69 | 46 | 594 |
| 85 | 2 | 1212 | 916 | gi|194097 | IFN-response element binding factor 1 [*Mus musculus*] | 69 | 48 | 297 |
| 91 | 5 | 3678 | 4274 | gi|1574712 | anaerobic ribonuleoside-triphosphate reductase activating protein (nrdG) [*Haemophilus influenzae*] | 69 | 44 | 597 |
| 98 | 5 | 3247 | 4032 | gnl|PID|d100262 | LivF protein [*Salmonella typhimurium*] | 69 | 51 | 786 |
| 108 | 5 | 4085 | 5056 | gnl|PID|e257629 | transcription factor [*Lactococcus lactis*] | 69 | 49 | 972 |
| 126 | 3 | 3078 | 4568 | gnl|PID|d101329 | YqjJ [*Bacillus subtilis*] | 69 | 49 | 1491 |
| 131 | 6 | 4121 | 2889 | gnl|PID|d101314 | YqeR [*Bacillus subtilis*] | 69 | 47 | 1233 |
| 136 | 2 | 1505 | 2299 | gnl|PID|d100581 | unknown [*Bacillus subtilis*] | 69 | 47 | 795 |
| 149 | 5 | 3852 | 4763 | gnl|PID|e323525 | YloQ protein [*Bacillus subtilis*] | 69 | 50 | 912 |
| 149 | 12 | 9336 | 10655 | gi|151571 | Homology with E. coli and P. aeruginosa lysA gene; product of unknown function; putative [*Pseudomonas syringae*] | 69 | 52 | 1320 |
| 153 | 4 | 3191 | 3829 | gi|1710373 | BrnQ [*Bacillus subtilis*] | 69 | 44 | 639 |
| 169 | 3 | 849 | 2324 | gnl|PID|d100582 | temperature sensitive cell division [*Bacillus subtilis*] | 69 | 49 | 1476 |
| 180 | 1 | 566 | 3 | gi|488339 | alpha-amylase [unidentified cloning vector] | 69 | 50 | 564 |
| 212 | 1 | 1196 | 231 | gi|1395209 | ribonucleotide reductase R2-2 small subunit [*Mycobacterium tuberculosis*] | 69 | 53 | 966 |
| 226 | 1 | 2 | 661 | pir|JQ2285|JQ22 | nodulin-26 - soybean | 69 | 41 | 660 |
| 233 | 5 | 3249 | 4766 | gi|472918 | v-type Na-ATPase [*Enterococcus hirae*] | 69 | 56 | 1518 |
| 235 | 3 | 660 | 1766 | gi|148945 | methylase [*Haemophilus influenzae*] | 69 | 43 | 1107 |
| 243 | 2 | 865 | 2361 | gnl|PID|d100225 | ORF5 [*Barley yellow dwarf virus*] | 69 | 69 | 1497 |
| 251 | 3 | 2899 | 1967 | gi|2289231 | macrolide-efflux protein [*Streptococcus agalactiae*] | 69 | 51 | 933 |
| 310 | 1 | 1 | 282 | gnl|PID|e322442 | peptide deformylase [*Clostridium beijerinckii*] | 69 | 55 | 282 |
| 369 | 1 | 868 | 2 | gi|397526 | clumping factor [*Staphylococcus aureus*] | 69 | 22 | 867 |
| 370 | 1 | 749 | 3 | gi|397526 | clumping factor [*Staphylococcus aureus*] | 69 | 21 | 747 |
| 379 | 1 | 44 | 280 | gnl|PID|d100649 | DE-cadherin [*Drosophila melanogaster*] | 69 | 30 | 237 |
| 388 | 1 | 260 | 72 | gi|1787524 | (AE000225) hypothetical 32.7 kD protein in trpL-btuR intergenic region [*Escherichia coli*] | 69 | 44 | 189 |
| 1 | 2 | 2006 | 3040 | gnl|PID|d101809 | ABC transporter [*Synechocystis sp.*] | 68 | 43 | 1035 |
| 12 | 5 | 3958 | 2600 | gi|2182992 | histidine kinase [*Lactococcus lactis cremoris*] | 68 | 45 | 1359 |
| 15 | 2 | 1790 | 1311 | pir|S16974|R5BS | ribosomal protein L9 - Bacillus stearothermophilus | 68 | 56 | 480 |
| 16 | 6 | 7353 | 5701 | gi|1787041 | (AE000184) o530; This 530 aa orf is 33 pct identical (14 gaps) to 525 residues of an approx. 640 aa protein YHES_HAEIN SW: P44808 [*Escherichia coli*] | 68 | 45 | 1653 |
| 17 | 12 | 6479 | 6805 | gi|553165 | acetylcholinesterase [*Homo sapiens*] | 68 | 68 | 327 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 20 | 13 | 14128 | 14505 | gi\|142700 | P competence protein (ttg start codon) (put.); putative [*Bacillus subtilis*] | 68 | 40 | 378 |
| 22 | 32 | 24612 | 25397 | gi\|289262 | comE ORF3 [*Bacillus subtilis*] | 68 | 36 | 786 |
| 30 | 7 | 4548 | 4288 | gi\|311388 | ORF1 [*Azorhizobium caulinodans*] | 68 | 46 | 261 |
| 36 | 5 | 3911 | 4585 | gi\|1573041 | hypothetical [*Haemophilus influenzae*] | 68 | 54 | 675 |
| 46 | 6 | 5219 | 6040 | gi\|1790131 | (AE000446) hypothetical 29.7 kD protein in ibpA-gyrB intergenic region [*Escherichia coli*] | 68 | 47 | 822 |
| 54 | 10 | 6235 | 7086 | gi\|882579 | CG Site No. 29739 [*Escherichia coli*] | 68 | 55 | 852 |
| 55 | 5 | 7069 | 5165 | gnl\|PID\|d101914 | ABC transporter [*Synechocystis* sp.] | 68 | 45 | 1905 |
| 71 | 3 | 6134 | 5613 | gi\|1573353 | outer membrane integrity protein (tolA) [*Haemophilus influenzae*] | 68 | 50 | 522 |
| 71 | 10 | 15342 | 16613 | gi\|580866 | ipa-12d gene product [*Bacillus subtilis*] | 68 | 31 | 1272 |
| 71 | 12 | 17560 | 18792 | gi\|44073 | SecY protein [*Lactococcus lactis*] | 68 | 35 | 1233 |
| 71 | 17 | 22295 | 24703 | gi\|1762349 | involved in protein export [*Bacillus subtilis*] | 68 | 50 | 2409 |
| 73 | 16 | 10208 | 9729 | gi\|1353537 | dUTPase [Bacteriophage r1t] | 68 | 51 | 480 |
| 86 | 18 | 17198 | 16011 | gi\|413943 | ipa-19d gene product [*Bacillus subtilis*] | 68 | 53 | 1188 |
| 87 | 17 | 17491 | 15866 | gi\|150209 | ORF 1 [*Mycoplasma mycoides*] | 68 | 43 | 1626 |
| 89 | 6 | 5139 | 4354 | gi\|1498824 | *M. jannaschii* predicted coding region MJ0062 [*Methanococcus jannaschii*] | 68 | 40 | 786 |
| 89 | 11 | 8021 | 8242 | gi\|150974 | 4-oxalocrotonate tautomerase [*Pseudomonas putida*] | 68 | 43 | 222 |
| 97 | 8 | 6755 | 5394 | gi\|2367358 | (AE000491) hypothetical 52.9 kD protein in aidB-rpsF intergenic region [*Escherichia coli*] | 68 | 41 | 1362 |
| 98 | 3 | 1418 | 2308 | gnl\|PID\|d100261 | LivA protein [*Salmonella typhimurium*] | 68 | 40 | 891 |
| 99 | 13 | 16414 | 17280 | gi\|455363 | regulatory protein [*Streptococcus mutans*] | 68 | 50 | 867 |
| 115 | 3 | 5054 | 3693 | gi\|466474 | cellobiose phosphotransferase enzyme II'' [*Bacillus stearothermophilus*] | 68 | 44 | 1362 |
| 124 | 7 | 3394 | 3221 | gnl\|PID\|d100702 | cut14 protein [*Schizosaccharomyces pombe*] | 68 | 56 | 174 |
| 125 | 2 | 2923 | 1922 | gi\|450566 | transmembrane protein [*Bacillus subtilis*] | 68 | 50 | 1002 |
| 132 | 2 | 4858 | 2888 | gnl\|PID\|d101732 | DNA ligase [*Synechocystis* sp.] | 68 | 52 | 1971 |
| 140 | 7 | 7765 | 7580 | gi\|1209711 | unknown [*Saccharomyces cerevisiae*] | 68 | 47 | 186 |
| 150 | 1 | 539 | 3 | gi\|402490 | ADP-ribosylarginine hydrolase [*Mus musculus*] | 68 | 59 | 537 |
| 164 | 1 | 58 | 867 | gnl\|PID\|e255114 | glutamate racemase [*Bacillus subtilis*] | 68 | 49 | 810 |
| 164 | 2 | 819 | 1835 | gnl\|PID\|e255117 | hypothetical protein [*Bacillus subtilis*] | 68 | 50 | 1017 |
| 169 | 7 | 3946 | 4104 | pir\|B54545\|B545 | hypothetical protein - *Lactococcus lactis* subsp. *lactis* plasmid pSL2 | 68 | 40 | 159 |
| 170 | 4 | 4247 | 4396 | gi\|304146 | spore coat protein [*Bacillus subtilis*] | 68 | 52 | 150 |
| 171 | 8 | 6002 | 7054 | gi\|38722 | precursor (aa −20 to 381) [*Acinetobacter calcoaceticus*] | 68 | 54 | 1053 |
| 198 | 3 | 2473 | 1871 | gnl\|PID\|e313075 | hypothetical protein [*Bacillus subtilis*] | 68 | 46 | 603 |
| 211 | 2 | 969 | 1802 | gi\|1439528 | EIIC-man [*Lactobacillus curvatus*] | 68 | 45 | 834 |
| 214 | 8 | 4926 | 4231 | gnl\|PID\|d102049 | *H. influenzae* hypothetical protein; P43990 (182) [*Bacillus subtilis*] | 68 | 50 | 696 |
| 217 | 6 | 4955 | 5170 | gnl\|PID\|e326966 | similar to *B. vulgaris* CMS-associated mitochondrial . . . (reverse transcriptase) [*Arabidopsis thaliana*] | 68 | 36 | 216 |
| 218 | 7 | 3930 | 4745 | gi\|2293198 | (AF008220) YtgP [*Bacillus subtilis*] | 68 | 38 | 816 |
| 220 | 6 | 4628 | 4338 | gnl\|PID\|e325791 | (AJ000005) orf1 [*Bacillus megaterium*] | 68 | 51 | 291 |
| 236 | 1 | 746 | 108 | gi\|410137 | ORFX13 [*Bacillus subtilis*] | 68 | 46 | 639 |
| 237 | 2 | 675 | 1451 | gi\|396348 | homoserine transsuccinylase [*Escherichia coli*] | 68 | 49 | 777 |
| 250 | 4 | 771 | 1229 | gi\|310859 | ORF2 [*Synechococcus* sp.] | 68 | 50 | 459 |
| 254 | 1 | 517 | 155 | gi\|1787105 | (AE000189) o648 was o669; This 669 aa orf is 40 pct identical (1 gaps) to 217 residues of an approx. 232 aa protein YBBA_HAEIN SW: P45247 [*Escherichia coli*] | 68 | 44 | 363 |
| 337 | 1 | 1 | 774 | gnl\|PID\|e261990 | putative orf [*Bacillus subtilis*] | 68 | 47 | 774 |
| 345 | 1 | 3 | 653 | gi\|149513 | thymidylate synthase (EC 2.1.1.45) [*Lactococcus lactis*] | 68 | 61 | 651 |
| 386 | 2 | 417 | 4 | gi\|1573353 | outer membrane integrity protein (tolA) [*Haemophilus influenzae*] | 68 | 51 | 414 |
| 2 | 4 | 5722 | 4697 | gi\|1592141 | *M. jannaschii* predicted coding region MJ1507 [*Methanococcus jannaschii*] | 67 | 26 | 1026 |
| 3 | 6 | 5397 | 4591 | gi\|2293175 | (AF008220) signal transduction regulator [*Bacillus subtilis*] | 67 | 44 | 807 |
| 5 | 2 | 2301 | 574 | gi\|2313385 | (AE000547) para-aminobenzoate synthetase (pabB) [*Helicobacter pylori*] | 67 | 48 | 1728 |
| 6 | 19 | 16063 | 16758 | gi\|413931 | ipa-7d gene product [*Bacillus subtilis*] | 67 | 41 | 696 |
| 22 | 8 | 7094 | 7897 | gi\|1928962 | pyrroline-5-carboxylate reductase [*Actinidia deliciosa*] | 67 | 51 | 804 |
| 29 | 10 | 8335 | 9072 | gi\|468745 | gtcR gene product [*Bacillus brevis*] | 67 | 41 | 738 |
| 31 | 3 | 1379 | 585 | gi\|2425123 | (AF019986) PksB [*Dictyostelium discoideum*] | 67 | 49 | 795 |
| 32 | 11 | 8849 | 10150 | gi\|42029 | ORF1 gene product [*Escherichia coli*] | 67 | 47 | 1302 |
| 36 | 16 | 14830 | 15546 | gi\|1592142 | ABC transporter, probable ATP-binding subunit [*Methanococcus jannaschii*] | 67 | 43 | 717 |
| 38 | 9 | 4958 | 5392 | gnl\|PID\|e214803 | T22B3.3 [*Caenorhabditis elegans*] | 67 | 47 | 435 |
| 38 | 21 | 13775 | 14512 | gi\|537037 | ORF_o216 [*Escherichia coli*] | 67 | 52 | 738 |
| 45 | 9 | 10428 | 9181 | gi\|551710 | branching enzyme (glgB) (EC 2.4.1.18) [*Bacillus stearothermophilus*] | 67 | 51 | 1248 |
| 48 | 23 | 18344 | 17514 | gi\|413949 | ipa-25d gene product [*Bacillus subtilis*] | 67 | 50 | 831 |
| 50 | 2 | 1773 | 952 | gnl\|PID\|d101330 | YqjQ [*Bacillus subtilis*] | 67 | 55 | 822 |
| 53 | 1 | 431 | 3 | gi\|1574291 | fimbrial transcription regulation repressor (pilB) [*Haemophilus influenzae*] | 67 | 40 | 429 |
| 55 | 13 | 12740 | 11946 | gnl\|PID\|e252990 | ORF YDL037c [*Saccharomyces cerevisiae*] | 67 | 51 | 795 |
| 61 | 9 | 9210 | 8329 | gnl\|PID\|e264711 | ATP-binding cassette transporter A [*Staphylococcus aureus*] | 67 | 50 | 882 |
| 71 | 2 | 5614 | 6117 | gi\|1197667 | vitellogenin [*Anolis pulchellus*] | 67 | 36 | 504 |
| 81 | 7 | 4489 | 4983 | gi\|1142714 | phosphoenolpyruvate:mannose phosphotransferase element IIB [*Lactobacillus curvatus*] | 67 | 42 | 495 |
| 83 | 7 | 2957 | 3214 | gi\|1276746 | Acyl carrier protein [*Porphyra purpurea*] | 67 | 37 | 258 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 86 | 8 | 8140 | 6809 | gi|1147744 | PSR [Enterococcus hirae] | 67 | 45 | 1332 |
| 97 | 3 | 986 | 1366 | gnl|PID|d102235 | (AB000631) unnamed protein product [Streptococcus mutans] | 67 | 43 | 381 |
| 102 | 1 | 601 | 1413 | gi|682765 | mccB gene product [Escherichia coli] | 67 | 36 | 813 |
| 106 | 3 | 1109 | 1987 | gi|148921 | LicD protein [Haemophilus influenzae] | 67 | 43 | 879 |
| 115 | 4 | 5982 | 5656 | gi|895750 | putative cellobiose phosphotransferase enzyme III [Bacillus subtilis] | 67 | 44 | 327 |
| 115 | 7 | 8421 | 8077 | gi|466473 | cellobiose phosphotransferase enzyme II' [Bacillus stearothermophilus] | 67 | 51 | 345 |
| 127 | 13 | 8127 | 7021 | gi|147326 | transport protein [Escherichia coli] | 67 | 45 | 1107 |
| 136 | 3 | 2215 | 2859 | gnl|PID|d100581 | unknown [Bacillus subtilis] | 67 | 49 | 645 |
| 140 | 21 | 23317 | 20906 | gnl|PID|d101912 | phenylalanyl-tRNA synthetase [Synechocystis sp.] | 67 | 43 | 2412 |
| 146 | 6 | 2894 | 1893 | gi|2182994 | histidine kinase [Lactococcus lactis cremoris] | 67 | 44 | 1002 |
| 151 | 8 | 11476 | 11117 | gnl|PID|d100085 | ORF129 [Bacillus cereus] | 67 | 48 | 360 |
| 160 | 10 | 7453 | 8646 | gi|2281317 | OrfB; similar to a Streptococcus pneumoniae putative membrane protein encoded by GenBank Accession Number X99400; inactivation of the OrfB gene leads to UV-sensitivity and to decrease of homologous recombination (plasmidic test) [Lactococcus l | 67 | 46 | 1194 |
| 163 | 3 | 3099 | 4505 | gnl|PID|d101317 | YqfR [Bacillus subtilis] | 67 | 47 | 1407 |
| 167 | 8 | 6704 | 5454 | gi|1161933 | DltB [Lactobacillus casei] | 67 | 45 | 1251 |
| 169 | 4 | 2322 | 2879 | gnl|PID|d101331 | YqkG [Bacillus subtilis] | 67 | 41 | 558 |
| 171 | 11 | 7656 | 8384 | gi|153841 | pneumococcal surface protein A [Streptococcus pneumoniae] | 67 | 50 | 729 |
| 188 | 3 | 1930 | 3723 | gi|1542975 | AbcB [Thermoanaerobacterium thermosulfurigenes] | 67 | 46 | 1794 |
| 189 | 6 | 3599 | 3141 | gnl|PID|e325178 | Hypothetical protein [Bacillus subtilis] | 67 | 52 | 459 |
| 205 | 3 | 1663 | 2211 | gi|606073 | ORF_o169 [Escherichia coli] | 67 | 47 | 549 |
| 207 | 4 | 2896 | 3456 | gi|2276374 | DtxR/iron regulated lipoprotein precursor [Corynebacterium diphtheriae] | 67 | 49 | 561 |
| 217 | 3 | 4086 | 3703 | gi|895750 | putative cellobiose phosphotransferase enzyme III [Bacillus subtilis] | 67 | 42 | 384 |
| 246 | 2 | 291 | 662 | gi|1842438 | unknown [Bacillus subtilis] | 67 | 43 | 372 |
| 252 | 1 | 2 | 745 | gi|2351768 | PspA [Streptococcus pneumoniae] | 67 | 41 | 744 |
| 265 | 3 | 1134 | 1811 | gi|2313847 | (AB000585) L-asparaginase II (ansB) [Helicobacter pylori] | 67 | 42 | 678 |
| 295 | 1 | 1 | 375 | gi|2276374 | DtxR/iron regulated lipoprotein precursor [Corynebacterium diphtheriae] | 67 | 43 | 375 |
| 1 | 7 | 4898 | 5146 | gnl|PID|e255179 | unknown [Mycobacterium tuberculosis] | 66 | 56 | 249 |
| 3 | 1 | 389 | 3 | gnl|PID|e269548 | Unknown [Bacillus subtilis] | 66 | 48 | 387 |
| 3 | 20 | 19267 | 20805 | gi|39956 | IIGlc [Bacillus subtilis] | 66 | 50 | 1539 |
| 4 | 3 | 2545 | 2718 | gi|1787564 | (AE000228) phage shock protein C [Escherichia coli] | 66 | 36 | 174 |
| 5 | 9 | 13197 | 12592 | gi|1574291 | fimbrial transcription regulation repressor (pilB) [Haemophilus influenzae] | 66 | 46 | 606 |
| 9 | 4 | 2872 | 1451 | gnl|PID|e266928 | unknown [Mycobacterium tuberculosis] | 66 | 43 | 1422 |
| 12 | 2 | 1469 | 1200 | gi|520407 | orf2; GTG start codon [Bacillus thuringiensis] | 66 | 42 | 270 |
| 15 | 12 | 10979 | 9897 | gi|2314738 | (AE000653) translation elongation factor EF-Ts (tsf) [Helicobacter pylori] | 66 | 49 | 1083 |
| 16 | 2 | 1312 | 734 | gnl|PID|d102245 | (AB005554) yxbF [Bacillus subtilis] | 66 | 35 | 579 |
| 22 | 3 | 1372 | 1851 | gi|1480916 | signal peptidase type II [Lactococcus lactis] | 66 | 38 | 480 |
| 22 | 7 | 5828 | 7096 | gnl|PID|e206261 | gamma-glutamyl phosphate reductase [Streptococcus thermophilus] | 66 | 51 | 1269 |
| 22 | 20 | 16194 | 17138 | gnl|PID|e281914 | YitL [Bacillus subtilis] | 66 | 50 | 945 |
| 30 | 2 | 530 | 976 | gi|2314379 | (AE000627) ABC transporter, ATP-binding protein (yhcG) [Helicobacter pylori] | 66 | 40 | 447 |
| 32 | 1 | 199 | 984 | gi|312444 | ORF2 [Bacillus caldolyticus] | 66 | 49 | 786 |
| 33 | 13 | 8352 | 7234 | gi|1387979 | 44% identity over 302 residues with hypothetical protein from Synechocystis sp, accession D64006_CD; expression induced by environmental stress; some similarity to glycosyl transferases; two potential membrane-spanning helices [Bacillus subtil | 66 | 44 | 1119 |
| 34 | 6 | 5658 | 4708 | gnl|PID|e250724 | orf2 [Lactobacillus sake] | 66 | 39 | 951 |
| 34 | 14 | 9792 | 9574 | gi|1590997 | M. jannaschii predicted coding region MJ0272 [Methanococcus jannaschii] | 66 | 48 | 219 |
| 35 | 16 | 15163 | 14501 | gi|1773352 | Cap5M [Staphylococcus aureus] | 66 | 46 | 663 |
| 36 | 9 | 6173 | 6976 | gi|1518680 | minicell-associated protein DivIVA [Bacillus subtilis] | 66 | 35 | 804 |
| 36 | 11 | 10396 | 10824 | bbs|155344 | insulin activator factor, INSAF [human, Pancreatic insulinoma, Peptide Partial, 744 aa] [Homo sapiens] | 66 | 43 | 429 |
| 48 | 1 | 28 | 1419 | gnl|PID|e325204 | hypothetical protein [Bacillus subtilis] | 66 | 50 | 1392 |
| 48 | 7 | 3810 | 4112 | gi|2182574 | (AE000090) Y4pE [Rhizobium sp. NGR234] | 66 | 40 | 303 |
| 52 | 4 | 3595 | 2789 | gi|388565 | major cell-binding factor [Campylobacter jejuni] | 66 | 52 | 807 |
| 54 | 3 | 2662 | 1076 | gnl|PID|d101831 | glutamine-binding periplasmic protein [Synechocystis sp.] | 66 | 43 | 1587 |
| 61 | 10 | 9740 | 9183 | gnl|PID|e154144 | mdr gene product [Staphylococcus aureus] | 66 | 44 | 558 |
| 72 | 13 | 10893 | 11993 | gi|2313129 | (AE000526) H. pylori predicted coding region HP0049 [Helicobacter pylori] | 66 | 44 | 1101 |
| 74 | 9 | 13267 | 12476 | gi|1573941 | hypothetical [Haemophilus influenzae] | 66 | 43 | 792 |
| 75 | 1 | 2 | 868 | gi|1574631 | nicotinamide mononucleotide transporter (pnuC) [Haemophilus influenzae] | 66 | 48 | 867 |
| 75 | 7 | 5303 | 4275 | gi|41312 | put. EBG repressor protein [Escherichia coli] | 66 | 40 | 1029 |
| 82 | 7 | 6813 | 8123 | gnl|PID|e255128 | trigger factor [Bacillus subtilis] | 66 | 53 | 1311 |
| 83 | 3 | 905 | 1219 | pir|C33496|C334 | hisC homolog - Bacillus subtilis | 66 | 44 | 315 |
| 86 | 10 | 9407 | 8925 | gi|683584 | shikimate kinase [Lactococcus lactis] | 66 | 41 | 483 |
| 88 | 10 | 7001 | 6060 | gi|2098719 | putative fimbrial-associated protein [Actinomyces naeslundii] | 66 | 52 | 942 |
| 89 | 1 | 951 | 4 | gi|410118 | ORFX19 [Bacillus subtilis] | 66 | 41 | 948 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 93 | 7 | 3661 | 2711 | gi|1787936 | (AE000260) f298; This 298 aa orf is 51 pct identical (5 gaps) to 297 residues of an approx. 304 aa protein YCSN_BACSU SW: P42972 [Escherichia coli] | 66 | 49 | 951 |
| 104 | 3 | 1805 | 3049 | gi|1469784 | putative cell division protein ftsW [Enterococcus hirae] | 66 | 48 | 1245 |
| 106 | 14 | 13576 | 14253 | gi|40027 | homologous to E. coli gidB [Bacillus subtilis] | 66 | 52 | 678 |
| 107 | 3 | 965 | 1864 | gi|144858 | ORF A [Clostridium perfringens] | 66 | 49 | 900 |
| 112 | 7 | 5718 | 6593 | gi|609332 | DprA [Haemophilus influenzae] | 66 | 43 | 876 |
| 115 | 1 | 3 | 302 | gi|727367 | Hyrlp [Saccharomyces cerevisiae] | 66 | 56 | 300 |
| 122 | 1 | 3 | 566 | gnl|PID|d101328 | YqiY [Bacillus subtilis] | 66 | 36 | 564 |
| 126 | 8 | 11759 | 11046 | gnl|PID|d101163 | ORF3 [Bacillus subtilis] | 66 | 48 | 714 |
| 128 | 11 | 8201 | 8431 | gi|726288 | growth associated protein GAP-43 [Xenopus laevis] | 66 | 41 | 231 |
| 131 | 8 | 4894 | 4508 | gi|486661 | TMnm related protein [Saccharomyces cerevisiae] | 66 | 39 | 387 |
| 140 | 3 | 3236 | 2574 | gi|40056 | phoP gene product [Bacillus subtilis] | 66 | 36 | 663 |
| 140 | 15 | 16318 | 15434 | gi|1658189 | 5,10-methylenetetrahydrofolate reductase [Erwinia carotovora] | 66 | 48 | 885 |
| 146 | 12 | 7926 | 7636 | gi|40056 | transposase [Synechocystis sp.] | 66 | 42 | 291 |
| 147 | 6 | 7137 | 6154 | gi|472326 | TPP-dependent acetoin dehydrogenase alpha-subunit [Clostridium magnum] | 66 | 48 | 984 |
| 149 | 6 | 4435 | 5430 | gnl|PID|d101887 | pentose-5-phosphate-3-epimerase [Synechocystis sp.] | 66 | 46 | 996 |
| 149 | 13 | 10754 | 11575 | gi|42371 | pyruvate formate-lyase activating enzyme (AA 1-246) [Escherichia coli] | 66 | 42 | 822 |
| 186 | 4 | 2578 | 2270 | gnl|PID|d101199 | ORF11 [Enterococcus faecalis] | 66 | 41 | 309 |
| 207 | 2 | 2340 | 2597 | gnl|PID|e321893 | envelope glycoprotein gp160 [Human immunodeficiency virus type 1] | 66 | 46 | 258 |
| 210 | 7 | 3358 | 3678 | gi|49318 | ORF4 gene product [Bacillus subtilis] | 66 | 46 | 321 |
| 217 | 8 | 5143 | 5355 | gi|49538 | thrombin receptor [Cricetulus longicaudatus] | 66 | 38 | 213 |
| 220 | 4 | 3875 | 3642 | gi|466648 | alternate name ORFD of L23635 [Escherichia coli] | 66 | 33 | 234 |
| 223 | 1 | 1070 | 138 | gnl|PID|e247187 | zinc finger protein [Bacteriophage phigle] | 66 | 45 | 933 |
| 224 | 2 | 1864 | 2640 | gi|1176399 | putative ABC transporter subunit [Staphylococcus epidermidis] | 66 | 41 | 777 |
| 243 | 1 | 3 | 872 | dbj|AB000617_2 | (AB000617) YcdH [Bacillus subtilis] | 66 | 45 | 870 |
| 268 | 2 | 891 | 568 | gi|517210 | putative transposase [Streptococcus pyogenes] | 66 | 60 | 324 |
| 322 | 1 | 2 | 643 | gi|1499836 | Zn protease [Methanococcus jannaschii] | 66 | 40 | 642 |
| 5 | 10 | 13909 | 13178 | gi|1574292 | hypothetical [Haemophilus influenzae] | 65 | 34 | 732 |
| 6 | 11 | 10465 | 11190 | gi|142854 | homologous to E. coli radC gene product and to unidentified protein from Staphylococcus aureus [Bacillus subtilis] | 65 | 48 | 726 |
| 7 | 2 | 647 | 405 | pir|C64146|C641 | hypothetical protein HI0259 - Haemophilus influenzae (strain Rd KW20) | 65 | 42 | 243 |
| 7 | 7 | 6246 | 6821 | gnl|PID|d101323 | YqhU [Bacillus subtilis] | 65 | 50 | 576 |
| 10 | 2 | 1873 | 1397 | gi|1163111 | ORF-1 [Streptococcus pneumoniae] | 65 | 54 | 477 |
| 16 | 3 | 1428 | 2222 | gnl|PID|e325010 | hypothetical protein [Bacillus subtilis] | 65 | 45 | 795 |
| 21 | 4 | 3815 | 3357 | gnl|PID|e314910 | hypothetical protein [Staphylococcus sciuri] | 65 | 40 | 459 |
| 22 | 34 | 25776 | 26384 | gi|1123030 | CpxA [Actinobacillus pleuropneumoniae] | 65 | 42 | 609 |
| 43 | 2 | 1648 | 290 | gi|1044826 | F14E5.1 [Caenorhabditis elegans] | 65 | 38 | 1359 |
| 48 | 13 | 10062 | 10856 | gi|1573390 | hypothetical [Haemophilus influenzae] | 65 | 45 | 795 |
| 48 | 22 | 17521 | 16883 | gi|1573391 | hypothetical [Haemophilus influenzae] | 65 | 37 | 639 |
| 48 | 25 | 19027 | 18533 | gnl|PID|e264484 | YCR020c, len: 215 [Saccharomyces cerevisiae] | 65 | 38 | 495 |
| 49 | 3 | 3856 | 5334 | gi|1480429 | putative transcriptional regulator [Bacillus stearothermophilus] | 65 | 32 | 1479 |
| 50 | 6 | 5337 | 4519 | gi|171963 | tRNA isopentenyl transferase [Saccharomyces cerevisiae] | 65 | 42 | 819 |
| 52 | 15 | 14728 | 15588 | gi|1499745 | M. jannaschii predicted coding region MJ0912 [Methanococcus jannaschii] | 65 | 46 | 861 |
| 59 | 7 | 3963 | 4745 | gi|496514 | orf zeta [Streptococcus pyogenes] | 65 | 42 | 783 |
| 68 | 3 | 2500 | 3483 | gi|887824 | ORF_o310 [Escherichia coli] | 65 | 46 | 984 |
| 69 | 3 | 2171 | 1077 | gnl|PID|e311453 | unknown [Bacillus subtilis] | 65 | 42 | 1095 |
| 69 | 7 | 6029 | 5325 | gi|809660 | deoxyribose-phosphate aldolase [Bacillus subtilis] | 65 | 55 | 705 |
| 71 | 5 | 8536 | 9783 | gi|1573224 | glycosyl transferase lgtC (GP: U14554_4) [Haemophilus influenzae] | 65 | 42 | 1248 |
| 72 | 8 | 7664 | 8527 | gnl|PID|e267589 | Unknown, highly similar to several spermidine synthases [Bacillus subtilis] | 65 | 39 | 864 |
| 76 | 5 | 5773 | 4097 | gnl|PID|d101723 | DNA REPAIR PROTEIN RECN (RECOMBINATION PROTEIN N). [Escherichia coli] | 65 | 44 | 1677 |
| 76 | 9 | 8099 | 7875 | gi|1574276 | exodeoxyribonuclease, small subunit (xseB) [Haemophilus influenzae] | 65 | 38 | 225 |
| 84 | 2 | 2870 | 2352 | gi|2313188 | (AE000532) conserved hypothetical protein [Helicobacter pylori] | 65 | 41 | 519 |
| 86 | 15 | 14495 | 13407 | gnl|PID|d101880 | 3-dehydroquinate synthase [Synechocystis sp.] | 65 | 44 | 1089 |
| 87 | 3 | 3706 | 2423 | gi|151259 | HMG-CoA reductase (EC 1.1.1.88) [Pseudomonas mevalonii] | 65 | 51 | 1284 |
| 88 | 3 | 2425 | 2736 | gi|1098510 | unknown [Lactococcus lactis] | 65 | 30 | 312 |
| 89 | 2 | 1627 | 1007 | gnl|PID|d102008 | (AB001488) SIMILAR TO ORF14 OF ENTEROCOCCUS FAECALIS TRANSPOSON TN916. [Bacillus subtilis] | 65 | 41 | 621 |
| 111 | 6 | 6635 | 6186 | gnl|PID|e246063 | NM23/nucleoside diphosphate kinase [Xenopus laevis] | 65 | 50 | 450 |
| 116 | 1 | 3 | 1016 | gnl|PID|d101125 | queuosine biosynthesis protein QueA [Synechocystis sp.] | 65 | 44 | 1014 |
| 123 | 1 | 69 | 389 | gi|498839 | ORF2 [Clostridium perfringens] | 65 | 36 | 321 |
| 123 | 7 | 6522 | 7190 | gi|1575577 | DNA-binding response regulator [Thermotoga maritima] | 65 | 39 | 669 |
| 125 | 3 | 3821 | 2859 | gnl|PID|e257609 | sugar-binding transport protein [Anaerocellum thermophilum] | 65 | 47 | 963 |
| 137 | 12 | 8015 | 7818 | gi|2182574 | (AE000090) Y4pE [Rhizobium sp. NGR234] | 65 | 41 | 198 |
| 147 | 4 | 5021 | 3885 | gi|472329 | dihydrolipoamide acetyltransferase [Clostridium magnum] | 65 | 47 | 1137 |
| 148 | 2 | 1053 | 1931 | gnl|PID|d101319 | YqgH [Bacillus subtilis] | 65 | 42 | 879 |
| 151 | 2 | 3212 | 4687 | gi|304897 | EcoE type I restriction modification enzyme M subunit [Escherichia coli] | 65 | 50 | 1476 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 156 | 2 | 730 | 437 | gi\|310893 | membrane protein [*Theileria parva*] | 65 | 47 | 294 |
| 164 | 7 | 4256 | 4837 | gi\|410132 | ORFX8 [*Bacillus subtilis*] | 65 | 48 | 582 |
| 169 | 6 | 3192 | 3914 | gi\|1552737 | similar to purine nucleoside phosphorylase (deoD) [*Escherichia coli*] | 65 | 41 | 723 |
| 176 | 4 | 2951 | 2220 | gnl\|PID\|e339500 | oligopeptide binding lipoprotein [*Streptococcus pneumoniae*] | 65 | 43 | 732 |
| 195 | 4 | 4556 | 3900 | gi\|1592142 | ABC transporter, probable ATP-binding subunit [*Methanococcus jannaschii*] | 65 | 40 | 657 |
| 196 | 1 | 160 | 1572 | gnl\|PID\|d102004 | (AB001488) PROBABLE UDP-N-ACETYLMURAMOYLALANYL-D-GLUTAMYL-2,6-DIAMINOLIGASE (EC 6.3.2.15). [*Bacillus subtilis*] | 65 | 51 | 1413 |
| 204 | 2 | 2246 | 1215 | gi\|143156 | membrane bound protein [*Bacillus subtilis*] | 65 | 37 | 1032 |
| 210 | 4 | 1544 | 1891 | gi\|49315 | ORF1 gene product [*Bacillus subtilis*] | 65 | 48 | 348 |
| 242 | 2 | 1625 | 723 | gi\|1787540 | (AE000226) f249; This 249 aa orf is 32 pct identical (8 gaps) to 244 residues of an approx. 272 aa protein AGAR_ECOLI SW: P42902 [*Escherichia coli*] | 65 | 42 | 903 |
| 284 | 1 | 1 | 900 | gi\|559861 | clyM [Plasmid pAD1] | 65 | 36 | 900 |
| 304 | 1 | 2 | 574 | gnl\|PID\|e290934 | unknown [*Mycobacterium tuberculosis*] | 65 | 52 | 573 |
| 315 | 1 | 2 | 1483 | gi\|790694 | mannuronan C-5-epimerase [*Azotobacter vinelandii*] | 65 | 57 | 1482 |
| 320 | 1 | 3 | 569 | gnl\|PID\|d102048 | K. aerogenes, histidine utilization repressor; P12380 (199) DNA binding [*Bacillus subtilis*] | 65 | 46 | 567 |
| 358 | 1 | 1 | 309 | gnl\|PID\|e323508 | YloS protein [*Bacillus subtilis*] | 65 | 55 | 309 |
| 2 | 7 | 7571 | 6696 | gi\|1498753 | nicotinate-nucleotide pyrophosphorylase [*Rhodospirillum rubrum*] | 64 | 47 | 876 |
| 6 | 6 | 5924 | 6802 | gnl\|PID\|d101111 | methionine aminopeptidase [*Synechocystis* sp.] | 64 | 52 | 879 |
| 8 | 4 | 3417 | 3686 | gi\|1045935 | DNA helicase II [*Mycoplasma genitalium*] | 64 | 58 | 270 |
| 11 | 4 | 3249 | 2689 | gnl\|PID\|e265529 | OrfB [*Streptococcus pneumoniae*] | 64 | 46 | 561 |
| 15 | 7 | 6504 | 7145 | gi\|1762328 | Ycr59c/YigZ homolog [*Bacillus subtilis*] | 64 | 45 | 642 |
| 22 | 11 | 9548 | 9895 | gnl\|PID\|d100581 | unknown [*Bacillus subtilis*] | 64 | 38 | 348 |
| 22 | 30 | 22503 | 23174 | gi\|289260 | comE ORF1 [*Bacillus subtilis*] | 64 | 44 | 672 |
| 26 | 7 | 14375 | 14199 | gi\|409286 | bmrU [*Bacillus subtilis*] | 64 | 30 | 177 |
| 27 | 2 | 1510 | 1334 | gi\|40795 | DdeI methylase [*Desulfovibrio vulgaris*] | 64 | 51 | 177 |
| 29 | 2 | 614 | 297 | gi\|2326168 | type VII collagen [*Mus musculus*] | 64 | 50 | 318 |
| 35 | 2 | 368 | 721 | pir\|JC1151\|JC11 | hypothetical 20.3K protein (insertion sequence IS1131) - *Agrobacterium tumefaciens* (strain PO22) plasmid Ti | 64 | 50 | 354 |
| 40 | 1 | 3 | 449 | gi\|46970 | epiD gene product [*Staphylococcus epidermidis*] | 64 | 41 | 447 |
| 40 | 7 | 4683 | 4976 | gnl\|PID\|e325792 | (AJ000005) glucose kinase [*Bacillus megaterium*] | 64 | 45 | 294 |
| 45 | 7 | 8068 | 6920 | gnl\|PID\|d102036 | subunit of ADP-glucose pyrophosphorylase [*Bacillus stearothermophilus*] | 64 | 40 | 1149 |
| 51 | 2 | 301 | 1059 | gi\|43985 | nifS-like gene [*Lactobacillus delbrueckii*] | 64 | 54 | 759 |
| 51 | 13 | 15251 | 18397 | gi\|2293260 | (AF008220) DNA-polymerase III alpha-chain [*Bacillus subtilis*] | 64 | 46 | 3147 |
| 53 | 3 | 1157 | 555 | gi\|1574292 | hypothetical [*Haemophilus influenzae*] | 64 | 47 | 603 |
| 58 | 2 | 4236 | 1606 | gi\|1573826 | alanyl-tRNA synthetase (alaS) [*Haemophilus influenzae*] | 64 | 51 | 2631 |
| 66 | 1 | 3 | 1259 | gi\|895749 | putative cellobiose phosphotransferase enzyme II" [*Bacillus subtilis*] | 64 | 42 | 1257 |
| 68 | 5 | 5213 | 6556 | gi\|436965 | [malA] gene products [*Bacillus stearothermophilus*] | 64 | 47 | 1344 |
| 69 | 6 | 5356 | 4949 | gnl\|PID\|d101316 | Cdd [*Bacillus subtilis*] | 64 | 52 | 408 |
| 74 | 4 | 6948 | 5038 | gi\|726480 | L-glutamine-D-fructose-6-phosphate amidotransferase [*Bacillus subtilis*] | 64 | 50 | 1911 |
| 75 | 3 | 1283 | 1465 | bbs\|133379 | TLS-CHOP = fusion protein(CHOP = C/EBP transcription factor, TLS = nuclear RNA-binding protein) [human, myxoid liposarcomas cells, Peptide Mutant, 462 aa] [*Homo sapiens*] | 64 | 57 | 183 |
| 81 | 13 | 14016 | 14231 | gi\|143175 | methanol dehydrogenase alpha-10 subunit [*Bacillus* sp.] | 64 | 35 | 216 |
| 83 | 22 | 21851 | 22090 | gnl\|PID\|d101315 | YqfA [*Bacillus subtilis*] | 64 | 44 | 240 |
| 87 | 11 | 10046 | 9300 | gnl\|PID\|e323505 | putative Ptc1 protein [*Bacillus subtilis*] | 64 | 43 | 747 |
| 98 | 7 | 5032 | 5706 | gnl\|PID\|e233880 | hypothetical protein [*Bacillus subtilis*] | 64 | 38 | 675 |
| 105 | 1 | 2 | 1276 | gi\|1657503 | similar to *S. aureus* mercury(II) reductase [*Escherichia coli*] | 64 | 45 | 1275 |
| 113 | 7 | 5136 | 6410 | gnl\|PID\|d101119 | NifS [*Synechocystis* sp.] | 64 | 50 | 1275 |
| 119 | 1 | 2 | 1297 | gnl\|PID\|e320520 | hypothetical protein [*Natronobacterium pharaonis*] | 64 | 37 | 1296 |
| 123 | 3 | 1125 | 2156 | gnl\|PID\|e253284 | ORF YDL244w [*Saccharomyces cerevisiae*] | 64 | 40 | 1032 |
| 124 | 5 | 2331 | 1780 | gnl\|PID\|d101884 | hypothetical protein [*Synechocystis* sp.] | 64 | 50 | 552 |
| 129 | 4 | 3467 | 2709 | gnl\|PID\|d101314 | YqeU [*Bacillus subtilis*] | 64 | 52 | 759 |
| 131 | 1 | 152 | 3 | gi\|1377841 | unknown [*Bacillus subtilis*] | 64 | 42 | 150 |
| 137 | 11 | 7196 | 7549 | pir\|JC1151\|JC11 | hypothetical 20.3K protein (insertion sequence IS1131) *Agrobacterium tumefaciens* (strain PO22) plasmid Ti | 64 | 50 | 354 |
| 139 | 3 | 3226 | 2651 | gi\|2293301 | (AF008220) YtqB [*Bacillus subtilis*] | 64 | 44 | 576 |
| 146 | 10 | 6730 | 5648 | gi\|1322245 | mevalonate pyrophosphate decarboxylase [*Rattus norvegicus*] | 64 | 45 | 1083 |
| 147 | 1 | 2 | 1018 | gnl\|PID\|e137033 | unknown gene product [*Lactobacillus leichmannii*] | 64 | 46 | 1017 |
| 148 | 11 | 8430 | 8783 | gi\|2130630 | (AF000430) dynamin-like protein [*Homo sapiens*] | 64 | 28 | 354 |
| 156 | 7 | 4313 | 3612 | gnl\|PID\|d102050 | transmembrane [*Bacillus subtilis*] | 64 | 31 | 702 |
| 157 | 4 | 1299 | 2114 | gnl\|PID\|d100892 | homologous to Gln transport system permease proteins [*Bacillus subtilis*] | 64 | 43 | 816 |
| 162 | 6 | 5880 | 6362 | gi\|517204 | ORF1, putative 42 kDa protein [*Streptococcus pyogenes*] | 64 | 58 | 483 |
| 164 | 13 | 9707 | 8769 | gnl\|PID\|d100964 | homologue of ferric anguibactin transport system permerase protein FatD of *V. anguillarum* [*Bacillus subtilis*] | 64 | 40 | 939 |
| 175 | 5 | 3906 | 4598 | gi\|534045 | antiterminator [*Bacillus subtilis*] | 64 | 39 | 693 |

TABLE 2-continued

*S. pneumoniae* - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 189 | 10 | 6154 | 6507 | gi\|581307 | response regulator [*Lactobacillus plantarum*] | 64 | 33 | 354 |
| 191 | 4 | 3519 | 2863 | gi\|149520 | phosphoribosyl anthranilate isomerase [*Lactococcus lactis*] | 64 | 46 | 657 |
| 202 | 1 | 76 | 1140 | gnl\|PID\|e293806 | O-acetylhomoserine sulfhydrylase [*Leptospira meyeri*] | 64 | 47 | 1065 |
| 224 | 1 | 234 | 1571 | gi\|1573393 | collagenase (prtC) [*Haemophilus influenzae*] | 64 | 42 | 1338 |
| 231 | 3 | 291 | 647 | gi\|40174 | ORF X [*Bacillus subtilis*] | 64 | 43 | 357 |
| 253 | 3 | 709 | 1089 | pir\|JC1151\|JC11 | hypothetical 20.3K protein (insertion sequence IS1131) - *Agrobacterium tumefaciens* (strain PO22) plasmid Ti | 64 | 50 | 381 |
| 265 | 1 | 820 | 2 | gi\|1377832 | unknown [*Bacillus subtilis*] | 64 | 31 | 819 |
| 297 | 1 | 1 | 660 | gi\|1590871 | collagenase [*Methanococcus jannaschii*] | 64 | 48 | 660 |
| 328 | 1 | 263 | 21 | gi\|992651 | Gin4p [*Saccharomyces cerevisiae*] | 64 | 41 | 243 |
| 5 | 4 | 8730 | 8098 | gi\|556885 | Unknown [*Bacillus subtilis*] | 63 | 48 | 633 |
| 10 | 6 | 5178 | 4483 | gi\|1573101 | hypothetical [*Haemophilus influenzae*] | 63 | 40 | 696 |
| 12 | 11 | 9324 | 9902 | gi\|806536 | membrane protein [*Bacillus acidopullulyticus*] | 63 | 42 | 579 |
| 15 | 10 | 8897 | 9187 | gi\|722339 | unknown [*Acetobacter xylinum*] | 63 | 40 | 291 |
| 17 | 2 | 1031 | 309 | gnl\|PID\|e217602 | PlnU [*Lactobacillus plantarum*] | 63 | 32 | 723 |
| 18 | 8 | 7778 | 6975 | gi\|1377843 | unknown [*Bacillus subtilis*] | 63 | 45 | 804 |
| 26 | 4 | 9780 | 7078 | gi\|142440 | ATP-dependent nuclease [*Bacillus subtilis*] | 63 | 46 | 2703 |
| 29 | 5 | 3488 | 4192 | gi\|1377829 | unknown [*Bacillus subtilis*] | 63 | 35 | 705 |
| 34 | 11 | 8830 | 7988 | gnl\|PID\|d101198 | ORF8 [*Enterococcus faecalis*] | 63 | 45 | 843 |
| 35 | 3 | 1187 | 876 | gi\|722339 | unknown [*Acetobacter xylinum*] | 63 | 39 | 312 |
| 48 | 15 | 12509 | 11691 | gi\|1573389 | hypothetical [*Haemophilus influenzae*] | 63 | 41 | 819 |
| 51 | 11 | 12719 | 12189 | gi\|142450 | ahrC protein [*Bacillus subtilis*] | 63 | 35 | 531 |
| 55 | 4 | 3979 | 5022 | gi\|1708640 | YeaB [*Bacillus subtilis*] | 63 | 41 | 1044 |
| 55 | 15 | 13669 | 14670 | gnl\|PID\|e311502 | thioredoxine reductase [*Bacillus subtilis*] | 63 | 44 | 1002 |
| 68 | 10 | 9242 | 8919 | sp\|P37686\|YIAY_ | HYPOTHETICAL 40.2 KD PROTEIN IN AVTA-SELB INTERGENIC REGION (F382). | 63 | 40 | 324 |
| 86 | 7 | 6554 | 5685 | gi\|1574382 | lic-1 operon protein (licD) [*Haemophilus influenzae*] | 63 | 41 | 870 |
| 88 | 8 | 6085 | 5180 | gi\|2098719 | putative fimbrial-associated protein [*Actinomyces naeslundii*] | 63 | 43 | 906 |
| 96 | 8 | 5858 | 6484 | gi\|1052803 | orflgyrb gene product [*Streptococcus pneumoniae*] | 63 | 38 | 627 |
| 100 | 1 | 240 | 1940 | gi\|7171 | fucosidase [*Dictyostelium discoideum*] | 63 | 36 | 1701 |
| 104 | 4 | 3063 | 5765 | gi\|144985 | phosphoenolpyruvate carboxylase [*Corynebacterium glutamicum*] | 63 | 46 | 2703 |
| 106 | 8 | 9189 | 8554 | gi\|533099 | endonuclease III [*Bacillus subtilis*] | 63 | 45 | 636 |
| 122 | 6 | 4704 | 4886 | gnl\|PID\|d101139 | transposase [*Synechocystis* sp.] | 63 | 39 | 183 |
| 128 | 7 | 4517 | 5203 | gnl\|PID\|d101434 | orf2 [*Methanobacterium thermoautotrophicum*] | 63 | 50 | 687 |
| 137 | 4 | 963 | 1547 | gi\|472920 | v-type Na-ATPase [*Enterococcus hirae*] | 63 | 27 | 585 |
| 142 | 7 | 4100 | 4585 | gnl\|PID\|e313025 | hypothetical protein [*Bacillus subtilis*] | 63 | 44 | 486 |
| 159 | 5 | 1741 | 2571 | gi\|1787043 | (AE000184) f271; This 271 aa orf is 24 pct identical (16 gaps) to 265 residues of an approx. 272 aa protein YIDA_ECOLI SW: P09997 [*Escherichia coli*] | 63 | 39 | 831 |
| 171 | 12 | 8803 | 14406 | gnl\|PID\|e324918 | IgA1 protease [*Streptococcus sanguis*] | 63 | 48 | 5604 |
| 177 | 1 | 3 | 347 | gi\|1773150 | hypothetical 14.8 kd protein [*Escherichia coli*] | 63 | 34 | 345 |
| 178 | 2 | 423 | 917 | gi\|722339 | unknown [*Acetobacter xylinum*] | 63 | 41 | 495 |
| 178 | 3 | 794 | 1012 | gi\|1591582 | cobalamin biosynthesis protein N [*Methanococcus jannaschii*] | 63 | 36 | 219 |
| 195 | 1 | 1377 | 175 | gnl\|PID\|e324217 | ftsQ [*Enterococcus hirae*] | 63 | 33 | 1203 |
| 234 | 5 | 1739 | 1527 | gi\|1591582 | cobalamin biosynthesis protein N [*Methanococcus jannaschii*] | 63 | 36 | 213 |
| 249 | 1 | 81 | 257 | gi\|1000453 | TreR [*Bacillus subtilis*] | 63 | 41 | 177 |
| 283 | 1 | 127 | 1347 | gi\|396486 | ORF8 [*Bacillus subtilis*] | 63 | 44 | 1221 |
| 293 | 3 | 2804 | 3466 | gi\|722339 | unknown [*Acetobacter xylinum*] | 63 | 37 | 663 |
| 311 | 1 | 905 | 486 | gi\|1877424 | UDP-galactose 4-epimerase [*Streptococcus mutans*] | 63 | 46 | 420 |
| 324 | 1 | 2 | 556 | gi\|1477741 | histidine periplasmic binding protein P29 [*Campylobacter jejuni*] | 63 | 36 | 555 |
| 365 | 1 | 219 | 13 | gi\|2252843 | (AF013293) No definition line found [*Arabidopsis thaliana*] | 63 | 33 | 207 |
| 382 | 1 | 88 | 378 | gi\|722339 | unknown [*Acetobacter xylinum*] | 63 | 40 | 291 |
| 385 | 3 | 364 | 158 | gi\|2252843 | (AF013293) No definition line found [*Arabidopsis thaliana*] | 63 | 33 | 207 |
| 2 | 1 | 2495 | 288 | gnl\|PID\|e325007 | penicillin-binding protein [*Bacillus subtilis*] | 62 | 42 | 2208 |
| 3 | 23 | 23374 | 24231 | gnl\|PID\|e254993 | hypothetical protein [*Bacillus subtilis*] | 62 | 35 | 858 |
| 6 | 16 | 14320 | 13193 | gnl\|PID\|e349614 | nifS-like protein [*Mycobacterium leprae*] | 62 | 37 | 1128 |
| 7 | 8 | 6819 | 7232 | gnl\|PID\|d101324 | YqhY [*Bacillus subtilis*] | 62 | 32 | 414 |
| 7 | 19 | 15466 | 14207 | gnl\|PID\|d101804 | beta ketoacyl-acyl carrier protein synthase [*Synechocystis* sp.] | 62 | 43 | 1260 |
| 7 | 21 | 17155 | 16229 | gnl\|PID\|e323514 | putative FabD protein [*Bacillus subtilis*] | 62 | 46 | 927 |
| 7 | 24 | 19526 | 18519 | gi\|1276434 | beta-ketoacyl-ACP synthase III [*Cuphea wrightii*] | 62 | 37 | 1008 |
| 12 | 7 | 5904 | 4702 | gi\|1573768 | A/G-specific adenine glycosylase (mutY) [*Haemophilus influenzae*] | 62 | 43 | 1203 |
| 12 | 9 | 8032 | 8793 | gi\|1591587 | pantothenate metabolism flavoprotein [*Methanococcus jannaschii*] | 62 | 33 | 762 |
| 15 | 11 | 9678 | 9328 | pir\|JC1151\|JC11 | hypothetical 20.3K protein (insertion sequence IS1131) - *Agrobacterium tumefaciens* (strain PO22) plasmid Ti | 62 | 43 | 351 |
| 17 | 4 | 2609 | 2442 | gi\|1591081 | *M. jannaschii* predicted coding region MJ0374 [*Methanococcus jannaschii*] | 62 | 43 | 168 |
| 17 | 5 | 3053 | 2835 | gi\|149570 | role in the expression of lactacin F, part of the laf operon [*Lactobacillus* sp.] | 62 | 44 | 219 |
| 22 | 10 | 8627 | 9538 | gnl\|PID\|d100580 | similar to *B. subtilis* DnaH [*Bacillus subtilis*] | 62 | 43 | 912 |
| 30 | 3 | 865 | 2043 | gi\|2314379 | (AE000627) ABC transporter, ATP-binding protein (yhcG) [*Helicobacter pylori*] | 62 | 43 | 1179 |
| 33 | 5 | 2235 | 1636 | gi\|413976 | ipa-52r gene product [*Bacillus subtilis*] | 62 | 44 | 600 |
| 38 | 11 | 5689 | 6123 | gi\|148231 | o251 [*Escherichia coli*] | 62 | 34 | 435 |
| 40 | 17 | 14272 | 13328 | gnl\|PID\|d101904 | hypothetical protein [*Synechocystis* sp.] | 62 | 43 | 945 |
| 42 | 1 | 3 | 311 | gi\|1146182 | putative [*Bacillus subtilis*] | 62 | 41 | 309 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 44 | 2 | 1267 | 4005 | gi\|1786952 | (AE000176) o877; 100 pct identical to the first 86 residues of the 100 aa hypothetical protein fragment YBGB_ECOLI SW: P54746 [*Escherichia coli*] | 62 | 43 | 2739 |
| 48 | 12 | 9732 | 9304 | gi\|662920 | repressor protein [*Enterococcus hirae*] | 62 | 32 | 429 |
| 51 | 8 | 5664 | 7181 | gnl\|PID\|e301153 | StySKI methylase [*Salmonella enterica*] | 62 | 44 | 1518 |
| 52 | 3 | 2791 | 2099 | gi\|1183886 | integral membrane protein [*Bacillus subtilis*] | 62 | 41 | 693 |
| 55 | 16 | 15702 | 14704 | gnl\|PID\|e313028 | hypothetical protein [*Bacillus subtilis*] | 62 | 40 | 999 |
| 59 | 6 | 3418 | 3984 | gi\|2065483 | unknown [*Lactococcus lactis lactis*] | 62 | 32 | 567 |
| 63 | 5 | 4997 | 4809 | gi\|149771 | pilin gene inverting protein (PivML) [*Moraxella lacunata*] | 62 | 28 | 189 |
| 70 | 14 | 10002 | 10739 | gi\|992977 | bplG gene product [*Bordetella pertussis*] | 62 | 45 | 738 |
| 71 | 13 | 18790 | 20382 | gi\|1280135 | coded for by *C. elegans* cDNA cm21e6; coded for by *C. elegans* cDNA cm01e2; similar to melibiose carrier protein (thiomethylgalactoside permease II) [*Caenorhabditis elegans*] | 62 | 62 | 1593 |
| 71 | 28 | 32217 | 32768 | gnl\|PID\|d101312 | YqeG [*Bacillus subtilis*] | 62 | 35 | 552 |
| 74 | 7 | 11666 | 10383 | gi\|1552753 | hypothetical [*Escherichia coli*] | 62 | 38 | 1284 |
| 80 | 8 | 9370 | 9609 | gnl\|PID\|d102002 | (AB001488) FUNCTION UNKNOWN. [*Bacillus subtilis*] | 62 | 46 | 240 |
| 97 | 10 | 9068 | 7041 | gi\|882463 | protein-N(pi)-phosphohistidine-sugar phosphotransferase [*Escherichia coli*] | 62 | 42 | 2028 |
| 98 | 4 | 2306 | 3268 | gnl\|PID\|d101496 | BraE (integral membrane protein) [*Pseudomonas aeruginosa*] | 62 | 42 | 963 |
| 102 | 3 | 2823 | 3539 | gnl\|PID\|e313010 | hypothetical protein [*Bacillus subtilis*] | 62 | 24 | 717 |
| 103 | 3 | 2795 | 1242 | gnl\|PID\|d102049 | *H. influenzae* hypothetical ABC transporter; P44808 (974) [*Bacillus subtilis*] | 62 | 41 | 1554 |
| 111 | 2 | 2035 | 3462 | gi\|581297 | NisP [*Lactococcus lactis*] | 62 | 44 | 1428 |
| 112 | 4 | 3154 | 4080 | gi\|1574379 | lic-1 operon protein (licA) [*Haemophilus influenzae*] | 62 | 39 | 927 |
| 112 | 6 | 4939 | 5649 | gi\|1574381 | lic-1 operon protein (licC) [*Haemophilus influenzae*] | 62 | 39 | 711 |
| 124 | 3 | 1137 | 721 | gi\|1573024 | anaerobic ribonucleoside-triphosphate reductase (nrdD) [*Haemophilus influenzae*] | 62 | 45 | 417 |
| 124 | 6 | 3162 | 2329 | gi\|609076 | leucyl aminopeptidase [*Lactobacillus delbrueckii*] | 62 | 40 | 834 |
| 126 | 7 | 11073 | 7516 | gnl\|PID\|d101163 | ORF4 [*Bacillus subtilis*] | 62 | 38 | 3558 |
| 129 | 6 | 4983 | 4540 | pir\|S41509\|S415 | zinc finger protein EP6 - Chilo iridescent virus | 62 | 48 | 444 |
| 131 | 7 | 4510 | 4103 | gi\|1857245 | unknown [*Lactococcus lactis*] | 62 | 42 | 408 |
| 149 | 2 | 1923 | 2579 | gi\|1592142 | ABC transporter, probable ATP-binding subunit [*Methanococcus jannaschii*] | 62 | 41 | 657 |
| 149 | 7 | 5360 | 6055 | gnl\|PID\|e323508 | YloS protein [*Bacillus subtilis*] | 62 | 40 | 696 |
| 156 | 1 | 450 | 238 | gnl\|PID\|e254644 | membrane protein [*Streptococcus pneumoniae*] | 62 | 40 | 213 |
| 156 | 6 | 3606 | 2935 | gnl\|PID\|d102050 | transmembrane [*Bacillus subtilis*] | 62 | 37 | 672 |
| 171 | 2 | 1779 | 2291 | gi\|43941 | EIII-B Sor PTS [*Klebsiella pneumoniae*] | 62 | 35 | 513 |
| 172 | 2 | 385 | 723 | gi\|895750 | putative cellobiose phosphotransferase enzyme III [*Bacillus subtilis*] | 62 | 39 | 339 |
| 173 | 3 | 2599 | 893 | gi\|1591732 | cobalt transport ATP-binding protein O [*Methanococcus jannaschii*] | 62 | 42 | 1707 |
| 179 | 2 | 492 | 1754 | gi\|1574071 | *H. influenzae* predicted coding region HI1038 [*Haemophilus influenzae*] | 62 | 38 | 1263 |
| 181 | 6 | 2856 | 3707 | gi\|1777435 | LacT [*Lactobacillus casei*] | 62 | 42 | 852 |
| 185 | 2 | 2074 | 311 | gi\|2182397 | (AE000073) Y4fN [*Rhizobium* sp. NGR234] | 62 | 41 | 1764 |
| 200 | 2 | 1061 | 1984 | gi\|450566 | transmembrane protein [*Bacillus subtilis*] | 62 | 37 | 924 |
| 202 | 3 | 2583 | 3473 | gi\|42219 | P35 gene product (AA 1-314) [*Escherichia coli*] | 62 | 41 | 891 |
| 210 | 3 | 1374 | 1565 | gi\|49315 | ORF1 gene product [*Bacillus subtilis*] | 62 | 45 | 192 |
| 211 | 1 | 3 | 971 | gi\|147402 | mannose permease subunit III-Man [*Escherichia coli*] | 62 | 43 | 969 |
| 223 | 2 | 1495 | 1034 | gnl\|PID\|d101190 | ORF2 [*Streptococcus mutans*] | 62 | 41 | 462 |
| 228 | 1 | 34 | 909 | gi\|530063 | glycerol uptake facilitator [*Streptococcus pneumoniae*] | 62 | 44 | 876 |
| 234 | 2 | 90 | 917 | gi\|2293259 | (AF008220) YtqI [*Bacillus subtilis*] | 62 | 38 | 828 |
| 282 | 5 | 1765 | 1487 | gnl\|PID\|e276475 | galactokinase [*Arabidopsis thaliana*] | 62 | 33 | 279 |
| 375 | 1 | 1 | 159 | gi\|1674231 | (AE000052) *Mycoplasma pneumoniae*, hypothetical protein homolog; similar to Swiss-Prot Accession Number P35155, from *B. subtilis* [*Mycoplasma pneumoniae*] | 62 | 40 | 159 |
| 385 | 5 | 584 | 357 | gi\|1573353 | outer membrane integrity protein (tolA) [*Haemophilus influenzae*] | 62 | 47 | 228 |
| 3 | 19 | 18550 | 19269 | gi\|606162 | ORF_f229 [*Escherichia coli*] | 61 | 41 | 720 |
| 7 | 4 | 2725 | 3225 | gi\|2114425 | similar to *Synechocystis* sp. hypothetical protein, encoded by GenBank Accession Number D64006 [*Bacillus subtilis*] | 61 | 42 | 501 |
| 17 | 6 | 3326 | 3054 | gi\|149569 | lactacin F [*Lactobacillus* sp.] | 61 | 43 | 273 |
| 44 | 3 | 4061 | 4957 | gnl\|PID\|d101068 | xylose repressor [*Synechocystis* sp.] | 61 | 38 | 897 |
| 54 | 11 | 8388 | 7234 | gnl\|PID\|d101329 | YqjH [*Bacillus subtilis*] | 61 | 42 | 1155 |
| 57 | 6 | 3974 | 6037 | gnl\|PID\|d101316 | YqfK [*Bacillus subtilis*] | 61 | 42 | 2064 |
| 58 | 5 | 7356 | 6565 | sp\|P45169\|POTC_ | SPERMIDINE/PUTRESCINE TPANSPORT SYSTEM PERMEASE PROTEIN POTC. | 61 | 34 | 792 |
| 67 | 1 | 3 | 692 | gi\|537108 | ORF_f254 [*Escherichia coli*] | 61 | 46 | 690 |
| 68 | 9 | 8816 | 7890 | gi\|19501 | pPLZ12 gene product (AA 1-184) [*Lupinus polyphyllus*] | 61 | 41 | 927 |
| 70 | 15 | 10737 | 12008 | gi\|992976 | bplF gene product [*Bordetella pertussis*] | 61 | 44 | 1272 |
| 72 | 11 | 9759 | 10202 | gnl\|PID\|d101833 | carboxynorspermidine decarboxylase [*Synechocystis* sp.] | 61 | 36 | 444 |
| 76 | 8 | 7881 | 7003 | gnl\|PID\|d100305 | farnesyl diphosphate synthase [*Bacillus stearothermophilus*] | 61 | 45 | 879 |
| 87 | 4 | 4914 | 3697 | gi\|528991 | unknown [*Bacillus subtilis*] | 61 | 42 | 1218 |
| 87 | 13 | 12311 | 11361 | gi\|1789683 | (AE000407) methionyl-tRNA formyltransferase [*Escherichia coli*] | 61 | 44 | 951 |
| 91 | 2 | 731 | 2989 | gi\|537080 | ribonucleoside triphosphate reductase [*Escherichia coli*] | 61 | 45 | 2259 |
| 105 | 3 | 2711 | 3499 | gnl\|PID\|d101851 | hypothetical protein [*Synechocystis* sp.] | 61 | 44 | 789 |
| 115 | 6 | 7968 | 6478 | gi\|895747 | putative cel operon regulator [*Bacillus subtilis*] | 61 | 36 | 1491 |
| 123 | 8 | 7181 | 8518 | gi\|1209527 | protein histidine kinase [*Enterococcus faecalis*] | 61 | 40 | 1338 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 126 | 6 | 7525 | 6725 | gi\|1787043 | (AE000184) f271; This 271 aa orf is 24 pct identical (16 gaps) to 265 residues of an approx. 272 aa protein YIDA_ECOLI SW: P09997 [Escherichia coli] | 61 | 38 | 801 |
| 128 | 1 | 1 | 639 | gnl\|PID\|d101328 | YqiY [Bacillus subtilis] | 61 | 41 | 639 |
| 139 | 7 | 4794 | 5054 | gi\|1022726 | unknown [Staphylococcus haemolyticus] | 61 | 41 | 261 |
| 139 | 9 | 12632 | 5913 | gnl\|PID\|e270014 | beta-galactosidase [Thermoanaerobacter ethanolicus] | 61 | 41 | 6720 |
| 143 | 1 | 2552 | 42 | gi\|520541 | penicillin-binding proteins 1A and 1B [Bacillus subtilis] | 61 | 42 | 2511 |
| 148 | 16 | 12125 | 11424 | gi\|1552743 | tetrahydrodipicolinate N-succinyltransferase [Escherichia coli] | 61 | 42 | 702 |
| 162 | 3 | 4112 | 3456 | gnl\|PID\|d101829 | phosphoglycolate phosphatase [Synechocystis sp.] | 61 | 30 | 657 |
| 172 | 3 | 727 | 1077 | gnl\|PID\|d102048 | B. subtilis, cellobiose phosphotransferase system, celA; P46318 (220) [Bacillus subtilis] | 61 | 44 | 351 |
| 177 | 3 | 1101 | 1772 | gnl\|PID\|d100574 | unknown [Bacillus subtilis] | 61 | 43 | 672 |
| 202 | 2 | 1278 | 2585 | gi\|1045831 | hypothetical protein (GB: L18965_6) [Mycoplasma genitalium] | 61 | 36 | 1308 |
| 224 | 3 | 2782 | 3144 | gi\|1591144 | M. jannaschii predicted coding region MJ0440 [Methanococcus jannaschii] | 61 | 30 | 363 |
| 225 | 4 | 3395 | 3766 | gi\|1552774 | hypothetical [Escherichia coli] | 61 | 40 | 372 |
| 249 | 2 | 212 | 802 | gi\|1000453 | TreR [Bacillus subtilis] | 61 | 42 | 591 |
| 254 | 2 | 843 | 484 | gnl\|PID\|d100417 | ORF120 [Escherichia coli] | 61 | 36 | 360 |
| 257 | 1 | 3 | 350 | gnl\|PID\|e255315 | unknown [Mycobacterium tuberculosis] | 61 | 42 | 348 |
| 293 | 4 | 3971 | 3657 | pir\|JC1151\|JC11 | hypothetical 20.3K protein (insertion sequence IS1131) - Agrobacterium tumefaciens (strain PO22) plasmid Ti | 61 | 45 | 315 |
| 301 | 1 | 949 | 17 | gi\|2291209 | (AF016424) contains similarity to acyltransferases [Caenorhabditis elegans] | 61 | 33 | 933 |
| 373 | 1 | 1066 | 287 | gi\|393396 | Tb-292 membrane associated protein [Trypanosoma brucei subgroup] | 61 | 38 | 780 |
| 3 | 24 | 24473 | 24955 | gi\|537093 | ORF_o153b [Escherichia coli] | 60 | 27 | 483 |
| 6 | 5 | 4636 | 5739 | gi\|2293258 | (AF008220) YtoI [Bacillus subtilis] | 60 | 35 | 1104 |
| 6 | 12 | 11936 | 11187 | gi\|293017 | ORF3 (put.); putative [Lactococcus lactis] | 60 | 44 | 750 |
| 17 | 13 | 6708 | 6484 | gi\|149569 | lactacin F [Lactobacillus sp.] | 60 | 32 | 225 |
| 18 | 7 | 6977 | 5670 | gi\|1788140 | (AE000278) o481; This 481 aa orf is 35 pct identical (19 gaps) to 309 residues of an approx. 856 aa protein NOL1_HUMAN SW: P46087 [Escherichia coli] | 60 | 43 | 1308 |
| 20 | 15 | 15878 | 17167 | gnl\|PID\|d100584 | unknown [Bacillus subtilis] | 60 | 44 | 1290 |
| 22 | 1 | 1 | 243 | gnl\|PID\|d102050 | transmembrane [Bacillus subtilis] | 60 | 36 | 243 |
| 32 | 10 | 8296 | 8964 | gi\|2293275 | (AF008220) YtaG [Bacillus subtilis] | 60 | 37 | 669 |
| 38 | 15 | 8837 | 9697 | gi\|40023 | B. subtilis genes rpmH, rnpA, 50 kd, gidA and gidB [Bacillus subtilis] | 60 | 35 | 861 |
| 43 | 6 | 8610 | 5944 | gi\|171787 | protein kinase 1 [Saccharomyces cerevisiae] | 60 | 36 | 2667 |
| 44 | 1 | 1 | 1269 | gnl\|PID\|e235823 | unknown [Schizosaccharomyces pombe] | 60 | 44 | 1269 |
| 45 | 10 | 11138 | 10368 | gi\|397488 | 1,4-alpha-glucan branching enzyme [Bacillus subtilis] | 60 | 43 | 771 |
| 48 | 19 | 15766 | 14378 | gnl\|PID\|e205173 | orf1 [Lactobacillus helveticus] | 60 | 39 | 1389 |
| 48 | 21 | 16727 | 16951 | gnl\|PID\|d102041 | (AB002668) unnamed protein product [Haemophilus actinomycetemcomitans] | 60 | 32 | 225 |
| 50 | 1 | 2 | 898 | gnl\|PID\|e246537 | ORF286 protein [Pseudomonas stutzeri] | 60 | 31 | 897 |
| 62 | 2 | 638 | 1177 | gnl\|PID\|d100587 | unknown [Bacillus subtilis] | 60 | 42 | 540 |
| 68 | 4 | 3590 | 5203 | gi\|1573583 | H. influenzae predicted coding region HI0594 [Haemophilus influenzae] | 60 | 36 | 1614 |
| 70 | 11 | 5781 | 6182 | gnl\|PID\|d102014 | (AB001488) SIMILAR TO YDFR GENE PRODUCT OF THIS ENTRY (YDFR_BACSU). [Bacillus subtilis] | 60 | 33 | 402 |
| 70 | 12 | 6343 | 8133 | gnl\|PID\|e324970 | hypothetical protein [Bacillus subtilis] | 60 | 38 | 1791 |
| 71 | 8 | 11701 | 14157 | gi\|580866 | ipa-12d gene product [Bacillus subtilis] | 60 | 33 | 2457 |
| 74 | 8 | 12509 | 11664 | gnl\|PID\|d101832 | phosphatidate cytidylyltransferase [Synechocystis sp.] | 60 | 45 | 846 |
| 76 | 4 | 4116 | 3367 | gi\|2352096 | orf; similar to serine/threonine protein phosphatase [Fervidobacterium islandicum] | 60 | 39 | 750 |
| 80 | 4 | 7372 | 7665 | gi\|1786420 | (AE000131) f86; 100 pct identical to GB: ECODINJ_6 ACCESSION: D38582 [Escherichia coli] | 60 | 30 | 294 |
| 81 | 6 | 4073 | 4522 | gi\|147402 | mannose permease subunit III-Man [Escherichia coli] | 60 | 35 | 450 |
| 86 | 1 | 940 | 155 | gi\|143177 | putative [Bacillus subtilis] | 60 | 26 | 786 |
| 92 | 1 | 1 | 192 | gi\|396348 | homoserine transsuccinylase [Escherichia coli] | 60 | 45 | 192 |
| 93 | 14 | 10619 | 9384 | gi\|1788389 | (AE000297) o464; This 464 aa orf is 33 pct identical (9 gaps) to 331 residues of an approx. 416 aa protein MTRC_NEIGO SW: P43505 [Escherichia coli] | 60 | 27 | 1236 |
| 94 | 5 | 5548 | 8121 | gnl\|PID\|e329895 | (AJ000496) cyclic nucleotide-gated channel beta subunit [Rattus norvegicus] | 60 | 50 | 2574 |
| 97 | 7 | 5396 | 4533 | gi\|1591396 | transketolase' [Methanococcus jannaschii] | 60 | 43 | 864 |
| 102 | 2 | 2081 | 2833 | gnl\|PID\|e320929 | hypothetical protein [Mycobacterium tuberculosis] | 60 | 43 | 753 |
| 106 | 9 | 9773 | 9183 | gnl\|PID\|e334782 | YlbN protein [Bacillus subtilis] | 60 | 31 | 591 |
| 113 | 8 | 6361 | 6837 | gi\|466875 | nifU; B1496_C1_157 [Mycobacterium leprae] | 60 | 43 | 477 |
| 115 | 2 | 2755 | 524 | gnl\|PID\|e328143 | (AJ000332) Glucosidase II [Homo sapiens] | 60 | 32 | 2232 |
| 122 | 7 | 4763 | 5068 | gnl\|PID\|d101876 | transposase [Synechocystis sp.] | 60 | 39 | 306 |
| 127 | 8 | 4510 | 5283 | gi\|1777938 | Pgm [Treponema pallidum] | 60 | 38 | 774 |
| 138 | 4 | 3082 | 2672 | gnl\|PID\|e325196 | hypothetical protein [Bacillus subtilis] | 60 | 36 | 411 |
| 139 | 1 | 177 | 4 | gnl\|PID\|d100680 | ORF [Thermus thermophilus] | 60 | 39 | 174 |
| 139 | 11 | 14520 | 13009 | gi\|537145 | ORF_f437 [Escherichia coli] | 60 | 30 | 1512 |
| 140 | 2 | 2592 | 1249 | gi\|1209527 | protein histidine kinase [Enterococcus faecalis] | 60 | 37 | 1344 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 141 | 1 | 210 | 1049 | gi|463181 | E5 ORF from bp 3842 to 4081; putative [*Human papillomavirus* type 33] | 60 | 34 | 840 |
| 141 | 5 | 5368 | 6405 | gi|145362 | tyrosine-sensitive DAHP synthase (aroF) [*Escherichia coli*] | 60 | 41 | 1038 |
| 142 | 6 | 3558 | 4049 | gi|600711 | putative [*Bacillus subtilis*] | 60 | 37 | 492 |
| 148 | 10 | 7742 | 8713 | gnl|PID|e313022 | hypothetical protein [*Bacillus subtilis*] | 60 | 27 | 972 |
| 153 | 5 | 3667 | 4278 | gi|2293322 | (AF008220) branch-chain amino acid transporter [*Bacillus subtilis*] | 60 | 42 | 612 |
| 155 | 1 | 1413 | 748 | gi|2104504 | putative UDP-glucose dehydrogenase [*Escherichia coli*] | 60 | 40 | 666 |
| 158 | 3 | 3116 | 2472 | gnl|PID|d100872 | a negative regulator of pho regulon [*Pseudomonas aeruginosa*] | 60 | 37 | 645 |
| 159 | 3 | 778 | 1386 | gnl|PID|e308090 | product highly similar to *Bacillus anthracis* CapA protein [*Bacillus subtilis*] | 60 | 48 | 609 |
| 163 | 7 | 8049 | 8468 | gnl|PID|d101313 | YqeN [*Bacillus subtilis*] | 60 | 38 | 420 |
| 170 | 3 | 4130 | 2688 | gi|1574179 | *H. influenzae* predicted coding region HI1244 [*Haemophilus influenzae*] | 60 | 39 | 1443 |
| 171 | 7 | 4717 | 5901 | gi|606076 | ORF_o384 [*Escherichia coli*] | 60 | 44 | 1185 |
| 183 | 3 | 2440 | 2135 | gi|1877427 | repressor [*Streptococcus pyogenes* phage T12] | 60 | 38 | 306 |
| 191 | 10 | 9444 | 8428 | gi|415664 | catabolite control protein [*Bacillus megaterium*] | 60 | 42 | 1017 |
| 200 | 1 | 139 | 1083 | gi|438462 | transmembrane protein [*Bacillus subtilis*] | 60 | 37 | 945 |
| 201 | 3 | 3895 | 1928 | gi|475112 | enzyme IIabc [*Pediococcus pentosaceus*] | 60 | 39 | 1968 |
| 214 | 15 | 10930 | 10439 | gi|1573407 | hypothetical [*Haemophilus influenzae*] | 60 | 39 | 492 |
| 218 | 4 | 2145 | 2363 | gi|608520 | myosin heavy chain kinase A [*Dictyostelium discoideum*] | 60 | 31 | 219 |
| 226 | 4 | 2518 | 2351 | gi|437705 | hyaluronidase [*Streptococcus pneumoniae*] | 60 | 53 | 168 |
| 242 | 1 | 725 | 3 | gi|43938 | Sor regulator [*Klebsiella pneumoniae*] | 60 | 41 | 723 |
| 245 | 1 | 1 | 288 | gi|304897 | EcoE type I restriction modification enzyme M subunit [*Escherichia coli*] | 60 | 56 | 288 |
| 251 | 1 | 905 | 45 | gi|671632 | unknown [*Staphylococcus aureus*] | 60 | 36 | 861 |
| 259 | 1 | 969 | 82 | gi|153794 | rgg [*Streptococcus gordonii*] | 60 | 32 | 888 |
| 260 | 2 | 1492 | 1662 | pir|S31840|S318 | probable transposase - *Bacillus stearothermophilus* | 60 | 26 | 171 |
| 274 | 1 | 836 | 96 | gi|1592173 | N-ethylammeline chlorohydrolase [*Methanococcus jannaschii*] | 60 | 40 | 741 |
| 308 | 1 | 463 | 2 | gi|1787397 | (AE000214) o157 [*Escherichia coli*] | 60 | 43 | 462 |
| 318 | 1 | 3 | 308 | gnl|PID|e137594 | xerC recombinase [*Lactobacillus leichmannii*] | 60 | 42 | 306 |
| 344 | 1 | 73 | 522 | gi|509672 | repressor protein [Bacteriophage Tuc2009] | 60 | 32 | 450 |
| 5 | 1 | 576 | 4 | gi|2293147 | (AF008220) YtxM [*Bacillus subtilis*] | 59 | 31 | 573 |
| 7 | 22 | 18140 | 17142 | gnl|PID|e280724 | unknown [*Mycobacterium tuberculosis*] | 59 | 39 | 999 |
| 10 | 1 | 1413 | 4 | gi|1353880 | sialidase L [*Macrobdella decora*] | 59 | 41 | 1410 |
| 15 | 6 | 6463 | 5156 | gi|580841 | F1 [*Bacillus subtilis*] | 59 | 35 | 1308 |
| 22 | 2 | 479 | 1393 | gi|142469 | als operom regulatory protein [*Bacillus subtilis*] | 59 | 34 | 915 |
| 22 | 5 | 2698 | 4614 | gnl|PID|e280623 | PCPA [*Streptococcus pneumoniae*] | 59 | 44 | 1917 |
| 30 | 1 | 208 | 558 | gnl|PID|e233868 | hypothetical protein [*Bacillus subtilis*] | 59 | 37 | 351 |
| 30 | 4 | 3678 | 2455 | gnl|PID|e202290 | unknown [*Lactobacillus sake*] | 59 | 33 | 1224 |
| 35 | 13 | 12201 | 11071 | gnl|PID|e238664 | hypothetical protein [*Bacillus subtilis*] | 59 | 35 | 1131 |
| 35 | 14 | 13288 | 12182 | gi|1657647 | Cap8H [*Staphylococcus aureus*] | 59 | 39 | 1107 |
| 36 | 18 | 18076 | 17897 | gi|1500535 | M. jannaschii predicted coding region MJ1635 [*Methanococcus jannaschii*] | 59 | 33 | 180 |
| 38 | 12 | 6172 | 7137 | gi|2293239 | (AF008220) YtxK [*Bacillus subtilis*] | 59 | 34 | 966 |
| 42 | 3 | 1952 | 3361 | gi|1684845 | pinin [*Canis familiaris*] | 59 | 40 | 1410 |
| 50 | 3 | 2678 | 1728 | gnl|PID|d101329 | YqjK [*Bacillus subtilis*] | 59 | 41 | 951 |
| 56 | 5 | 1870 | 2388 | gnl|PID|e137594 | xerC recombinase [*Lactobacillus leichmannii*] | 59 | 41 | 519 |
| 61 | 6 | 6812 | 5628 | gnl|PID|e311516 | aminotransferase [*Bacillus subtilis*] | 59 | 40 | 1185 |
| 67 | 5 | 2382 | 3023 | gi|1146190 | 2-keto-3-deoxy-6-phosphogluconate aldolase [*Bacillus subtilis*] | 59 | 36 | 642 |
| 69 | 10 | 8567 | 8899 | gi|1573628 | antothenate kinase (coaA) [*Haemophilus influenzae*] | 59 | 38 | 333 |
| 87 | 12 | 11383 | 10055 | gnl|PID|e323504 | putative Fmu protein [*Bacillus subtilis*] | 59 | 44 | 1329 |
| 113 | 14 | 13927 | 15894 | gi|1673731 | (AE000010) *Mycoplasma pneumoniae*, fructose-permease IIBC component; similar to Swiss-Prot Accession Number P20966, from *E. coli* [*Mycoplasma pneumoniae*] | 59 | 43 | 1968 |
| 115 | 8 | 8766 | 8521 | gi|1590886 | M. jannaschii predicted coding region MJ0110 [*Methanococcus jannaschii*] | 59 | 38 | 246 |
| 119 | 2 | 1966 | 1526 | gnl|PID|e209005 | homologous to ORF2 in nrdEF operons of *E. coli* and *S. typhimurium* [*Lactococcus lactis*] | 59 | 43 | 441 |
| 128 | 17 | 13438 | 13178 | gnl|PID|e279632 | unknown [*Mycobacterium tuberculosis*] | 59 | 38 | 261 |
| 140 | 22 | 23903 | 23388 | gi|482922 | protein with homology to pai1 repressor of *B. subtilis* [*Lactobacillus delbrueckii*] | 59 | 40 | 516 |
| 148 | 13 | 9697 | 9014 | gnl|PID|d102005 | (AB001488) FUNCTION UNKNOWN, SIMILAR PRODUCT IN *H. INFLUENZAE* AND SYNECHOCYSTIS. [*Bacillus subtilis*] | 59 | 32 | 684 |
| 149 | 10 | 7213 | 8244 | gi|710422 | cmp-binding-factor 1 [*Staphylococcus aureus*] | 59 | 40 | 1032 |
| 164 | 9 | 6993 | 6013 | gnl|PID|d100965 | ferric anguibactin-binding protein precursor FatB of *V. anguillarum* [*Bacillus subtilis*] | 59 | 41 | 981 |
| 164 | 12 | 8836 | 7823 | gnl|PID|d100964 | homologue of ferric anguibactin transport system permerase protein FatC of *V. anguillarum* [*Bacillus subtilis*] | 59 | 35 | 1014 |
| 177 | 2 | 401 | 1072 | gi|289759 | coded for by *C. elegans* cDNA CE2G3 (GenBank: Z14728); putative [*Caenorhabditis elegans*] | 59 | 40 | 672 |
| 177 | 7 | 3841 | 4200 | gi|2313445 | (AE000551) *H. pylori* predicted coding region HP0342 [*Helicobacter pylori*] | 59 | 38 | 360 |
| 183 | 4 | 2768 | 2508 | gi|509672 | repressor protein [Bacteriophage Tuc2009] | 59 | 50 | 261 |
| 186 | 6 | 3398 | 2820 | gi|606080 | ORF_o290; Geneplot suggests frameshift linking to o267, not found [*Escherichia coli*] | 59 | 38 | 579 |

TABLE 2-continued

*S. pneumoniae* - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 190 | 3 | 3120 | 1711 | gi\|1613768 | histidine protein kinase [*Streptococcus pneumoniae*] | 59 | 32 | 1410 |
| 194 | 2 | 1621 | 1019 | gnl\|PID\|d100579 | unknown [*Bacillus subtilis*] | 59 | 40 | 603 |
| 198 | 7 | 5205 | 4306 | gnl\|PID\|e313073 | hypothetical protein [*Bacillus subtilis*] | 59 | 38 | 900 |
| 220 | 5 | 4362 | 3958 | gnl\|PID\|d101322 | YqhL [*Bacillus subtilis*] | 59 | 46 | 405 |
| 242 | 3 | 1573 | 2367 | gi\|1787045 | (AE000184) f308; This 308 aa orf is 35 pct identical (35 gaps) to 305 residues of an approx. 296 aa protein PFLC_ECOLI SW: P32675 [*Escherichia coli*] | 59 | 42 | 795 |
| 247 | 2 | 1154 | 1480 | gi\|40073 | ORF107 [*Bacillus subtilis*] | 59 | 39 | 327 |
| 256 | 1 | 868 | 2 | gnl\|PID\|d101924 | hemolysin [*Synechocystis* sp.] | 59 | 39 | 867 |
| 258 | 1 | 65 | 820 | gi\|2246532 | ORF 73, contains large complex repeat CR 73 [Kaposi's sarcoma-associated herpesvirus] | 59 | 20 | 756 |
| 270 | 1 | 386 | 1126 | gnl\|PID\|d102092 | YfnB [*Bacillus subtilis*] | 59 | 40 | 741 |
| 281 | 1 | 552 | 166 | gi\|666062 | putative [*Lactococcus lactis*] | 59 | 31 | 387 |
| 309 | 1 | 3 | 479 | gi\|405879 | yeiH [*Escherichia coli*] | 59 | 38 | 477 |
| 363 | 1 | 2 | 1894 | gi\|915208 | gastric mucin [*Sus scrofa*] | 59 | 31 | 1893 |
| 387 | 2 | 425 | 84 | gi\|160671 | S antigen precursor [*Plasmodium falciparum*] | 59 | 44 | 342 |
| 5 | 6 | 11323 | 10465 | gnl\|PID\|d101812 | LumQ [*Synechocystis* sp.] | 58 | 29 | 759 |
| 29 | 4 | 2098 | 3513 | gnl\|PID\|d100479 | Na+-ATPase subunit J [*Enterococcus hirae*] | 58 | 39 | 1416 |
| 30 | 5 | 4058 | 3651 | gi\|39478 | ATP binding protein of transport ATPases [*Bacillus firmus*] | 58 | 34 | 408 |
| 33 | 6 | 2983 | 2210 | gnl\|PID\|d101164 | unknown [*Bacillus subtilis*] | 58 | 45 | 774 |
| 36 | 8 | 5316 | 6179 | gi\|1518679 | orf [*Bacillus subtilis*] | 58 | 32 | 864 |
| 43 | 5 | 5926 | 3971 | gi\|1788150 | (AE000278) protease II [*Escherichia coli*] | 58 | 37 | 1956 |
| 46 | 5 | 3704 | 5221 | gnl\|PID\|e267329 | Unknown [*Bacillus subtilis*] | 58 | 42 | 1518 |
| 48 | 14 | 11722 | 11066 | gnl\|PID\|d101771 | thiamin biosynthetic bifunctional enzyme [*Synechocystis* sp.] | 58 | 34 | 657 |
| 52 | 1 | 1229 | 3 | gnl\|PID\|d101291 | reductase [*Pseudomonas aeruginosa*] | 58 | 35 | 1227 |
| 53 | 2 | 702 | 412 | gi\|2313357 | (AE000545) cytochrome c biogenesis protein (ccdA) [*Helicobacter pylori*] | 58 | 25 | 291 |
| 58 | 4 | 6586 | 5498 | gi\|147329 | transport protein [*Escherichia coli*] | 58 | 41 | 1089 |
| 69 | 5 | 4934 | 3807 | gnl\|PID\|e311492 | unknown [*Bacillus subtilis*] | 58 | 41 | 1128 |
| 71 | 27 | 31357 | 32277 | gi\|2408014 | hypothetical protein [*Schizosaccharomyces pombe*] | 58 | 33 | 921 |
| 72 | 4 | 3586 | 2882 | gi\|18694 | nodulin-21 (AA 1-201) [*Glycine max*] | 58 | 34 | 705 |
| 74 | 3 | 4937 | 4230 | gi\|2293252 | (AF008220) YtmO [*Bacillus subtilis*] | 58 | 33 | 708 |
| 79 | 4 | 4594 | 3422 | gi\|1217989 | ORF3 [*Streptococcus pneumoniae*] | 58 | 44 | 1173 |
| 82 | 8 | 10585 | 8171 | gi\|882711 | exonuclease V alpha-subunit [*Escherichia coli*] | 58 | 38 | 2415 |
| 86 | 17 | 16017 | 15337 | gi\|47642 | 5-dehydroquinate hydrolyase (3-dehydroquinase) [*Salmonella typhi*] | 58 | 32 | 681 |
| 97 | 2 | 931 | 560 | gi\|153794 | rgg [*Streptococcus gordonii*] | 58 | 32 | 372 |
| 108 | 2 | 358 | 2724 | gi\|537020 | vacB gene product [*Escherichia coli*] | 58 | 37 | 2367 |
| 111 | 5 | 4593 | 5240 | gi\|1592142 | ABC transporter, probable ATP-binding subunit [*Methanococcus jannaschii*] | 58 | 36 | 648 |
| 120 | 3 | 4421 | 5110 | gnl\|PID\|d101320 | YqgX [*Bacillus subtilis*] | 58 | 47 | 690 |
| 128 | 16 | 13131 | 12673 | gi\|662919 | ORF U [*Enterococcus hirae*] | 58 | 42 | 459 |
| 132 | 3 | 6174 | 4939 | gi\|1800301 | macrolide-efflux determinant [*Streptococcus pneumoniae*] | 58 | 35 | 1236 |
| 133 | 1 | 111 | 890 | gnl\|PID\|e269488 | Unknown [*Bacillus subtilis*] | 58 | 36 | 780 |
| 160 | 11 | 8615 | 9865 | gi\|473901 | ORF1 [*Lactococcus lactis*] | 58 | 39 | 1251 |
| 161 | 6 | 6268 | 6849 | gnl\|PID\|d101024 | DJ-1 protein [*Homo sapiens*] | 58 | 32 | 582 |
| 169 | 1 | 214 | 2 | gnl\|PID\|d100447 | translation elongation factor-3 [*Chlorella virus*] | 58 | 31 | 213 |
| 187 | 1 | 487 | 2 | gi\|475114 | regulatory protein [*Pediococcus pentosaceus*] | 58 | 38 | 486 |
| 187 | 6 | 4384 | 4620 | gi\|167475 | dessication-related protein [*Craterostigma plantagineum*] | 58 | 55 | 237 |
| 190 | 2 | 1464 | 1640 | gnl\|PID\|d246727 | competence pheromone [*Streptococcus gordonii*] | 58 | 38 | 177 |
| 192 | 2 | 2012 | 1344 | gnl\|PID\|d100556 | rat GCP360 [*Rattus rattus*] | 58 | 44 | 669 |
| 206 | 1 | 1292 | 696 | gnl\|PID\|e202579 | product similar to WrbA [*Lactobacillus sake*] | 58 | 35 | 597 |
| 216 | 2 | 2333 | 555 | gnl\|PID\|e325036 | hypothetical protein [*Bacillus subtilis*] | 58 | 33 | 1779 |
| 217 | 5 | 5250 | 4321 | gi\|466474 | cellobiose phosphotransferase enzyme II" [*Bacillus stearothermophilus*] | 58 | 38 | 930 |
| 217 | 7 | 5636 | 5106 | gnl\|PID\|d102048 | *B. subtilis* cellobiose phosphotransferase system celB; P46317 (998) transmembrane [*Bacillus subtilis*] | 58 | 44 | 531 |
| 232 | 1 | 2 | 811 | gi\|1573777 | cell division ATP-binding protein (ftsE) [*Haemophilus influenzae*] | 58 | 39 | 810 |
| 264 | 1 | 2 | 715 | gi\|973330 | NatA [*Bacillus subtilis*] | 58 | 32 | 714 |
| 280 | 1 | 33 | 767 | gi\|1786187 | (AE000111) hypothetical 29.6 kD protein in thrC-talB intergenic region [*Escherichia coli*] | 58 | 31 | 735 |
| 306 | 1 | 845 | 3 | gnl\|PID\|e334780 | YlbL protein [*Bacillus subtilis*] | 58 | 47 | 843 |
| 360 | 3 | 1556 | 1092 | sp\|P46351\|YZGD_ | HYPOTHETICAL 45.4 KD PROTEIN IN THIAMINASE I 5'REGION. | 58 | 32 | 465 |
| 363 | 5 | 2160 | 1867 | gi\|160671 | S antigen precursor [*Plasmodium falciparum*] | 58 | 51 | 294 |
| 372 | 1 | 806 | 3 | gi\|393394 | Tb-291 membrane associated protein [*Trypanosoma brucei* subgroup] | 58 | 37 | 804 |
| 382 | 2 | 749 | 519 | pir\|JC1151\|JC11 | hypothetical 20.3K protein (insertion sequence IS1131) - *Agrobacterium tumefaciens* (strain PO22) plasmid Ti | 58 | 41 | 231 |
| 3 | 9 | 8409 | 7471 | gi\|1499745 | *M. jannaschii* predicted coding region MJ0912 [*Methanococcus jannaschii*] | 57 | 38 | 939 |
| 10 | 10 | 7674 | 7507 | gi\|1737169 | homologue to SKP1 [*Arabidopsis thaliana*] | 57 | 30 | 168 |
| 11 | 1 | 2 | 412 | gnl\|PID\|d100139 | ORF [*Acetobacter pasteurianus*] | 57 | 42 | 411 |
| 31 | 4 | 2032 | 1388 | gi\|2293213 | (AF008220) YtpR [*Bacillus subtilis*] | 57 | 37 | 645 |
| 33 | 11 | 6931 | 6449 | gnl\|PID\|e324949 | hypothetical protein [*Bacillus subtilis*] | 57 | 36 | 483 |
| 45 | 5 | 5446 | 5060 | gi\|1592204 | phosphoserine phosphatase [*Methanococcus jannaschii*] | 57 | 44 | 387 |
| 49 | 7 | 6523 | 7632 | gi\|155369 | PTS enzyme-II fructose [*Xanthomonas campestris*] | 57 | 35 | 1110 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 52 | 6 | 4520 | 6850 | gi\|1574144 | single-stranded-DNA-specific exonuclease (recJ) [*Haemophilus influenzae*] | 57 | 35 | 2331 |
| 53 | 5 | 2079 | 1795 | gi\|1843580 | replicase-associated polyprotein [oat blue dwarf virus] | 57 | 46 | 285 |
| 63 | 6 | 5312 | 4995 | gi\|2182608 | (AE000094) Y4rJ [*Rhizobium* sp. NGR234] | 57 | 39 | 318 |
| 72 | 15 | 13883 | 13059 | gnl\|PID\|d100892 | homologous to SwissProt: YIDA_ECOLI hypothetical protein [*Bacillus subtilis*] | 57 | 40 | 825 |
| 79 | 2 | 2561 | 1815 | gnl\|PID\|d100965 | homologue of NADPH-flavin oxidoreductase Frp of *V. harveyi* [*Bacillus subtilis*] | 57 | 44 | 747 |
| 82 | 9 | 9596 | 9763 | gi\|1206045 | short region of similarity to glycerophosphoryl diester phosphodiesterases [*Caenorhabditis elegans*] | 57 | 35 | 168 |
| 86 | 16 | 15371 | 14493 | gi\|1787983 | (AE000264) o288; 92 pct identical (1 gaps) to 222 residues of fragment YDIB_ECOLI SW: P28244 (223 aa)[*Escherichia coli*] | 57 | 34 | 879 |
| 93 | 3 | 1695 | 1177 | gi\|1500003 | mutator mutT protein [*Methanococcus jannaschii*] | 57 | 33 | 519 |
| 96 | 6 | 3026 | 4519 | gi\|559882 | threonine synthase [*Arabidopsis thaliana*] | 57 | 43 | 1494 |
| 99 | 14 | 17211 | 18212 | gi\|773349 | BirA protein [*Bacillus subtilis*] | 57 | 44 | 1002 |
| 112 | 8 | 7448 | 7903 | gi\|1591393 | *M. jannaschii* predicted coding region MJ0678 [*Methanococcus jannaschii*] | 57 | 30 | 456 |
| 113 | 16 | 18627 | 18328 | pir\|A45605\|A456 | mature-parasite-infected erythrocyte surface antigen MESA - *Plasmodium falciparum* | 57 | 22 | 300 |
| 123 | 2 | 343 | 1110 | pir\|F64149\|F641 | hypothetical protein HI0355 - *Haemophilus influenzae* (strain Rd KW20) | 57 | 38 | 768 |
| 123 | 4 | 2108 | 2884 | gnl\|PID\|d102148 | (AB001684) sulfate transport system permease protein [*Chlorella vulgaris*] | 57 | 39 | 777 |
| 127 | 10 | 6477 | 5587 | gi\|1573082 | nitrogenase C (nifC) [*Haemophilus influenzae*] | 57 | 35 | 891 |
| 128 | 13 | 9251 | 9790 | gi\|153692 | pneumolysin [*Streptococcus pneumoniae*] | 57 | 38 | 540 |
| 131 | 4 | 2139 | 1363 | gi\|42081 | nagD gene product (AA 1-250) [*Escherichia coli*] | 57 | 36 | 777 |
| 136 | 1 | 214 | 1221 | bbs\|148453 | SpaA = endocarditis immunodominant antigen [*Streptococcus sobrinus*, MUCOB 263, Peptide, 1566 aa] [*Streptococcus sobrinus*] | 57 | 44 | 1008 |
| 140 | 25 | 28701 | 26851 | gi\|505576 | beta-glucoside permease [*Bacillus subtilis*] | 57 | 38 | 1851 |
| 141 | 6 | 6395 | 7438 | gi\|995560 | unknown [*Schizosaccharomyces pombe*] | 57 | 41 | 1044 |
| 144 | 3 | 3231 | 2785 | gnl\|PID\|d100139 | ORF [*Acetobacter pasteurianus*] | 57 | 42 | 447 |
| 155 | 4 | 5454 | 4564 | gi\|600431 | glycosyl transerase [*Erwinia amylovora*] | 57 | 34 | 891 |
| 159 | 9 | 4877 | 5854 | gi\|290509 | o307 [*Escherichia coli*] | 57 | 35 | 978 |
| 167 | 11 | 9710 | 9249 | gnl\|PID\|d100139 | ORF [*Acetobacter pasteurianus*] | 57 | 42 | 462 |
| 171 | 6 | 4023 | 4436 | gi\|147402 | mannose permease subunit III-Man [*Escherichia coli*] | 57 | 29 | 414 |
| 178 | 4 | 2170 | 1076 | gnl\|PID\|d102004 | (AB001488) ATP-DEPENDENT RNA HELICASE DEAD HOMOLOG. [*Bacillus subtilis*] | 57 | 39 | 1095 |
| 190 | 1 | 145 | 1455 | gi\|149420 | export/processing protein [*Lactococcus lactis*] | 57 | 30 | 1311 |
| 198 | 1 | 298 | 95 | gi\|522268 | unidentified ORF22 [*Bacteriophage bIL67*] | 57 | 36 | 204 |
| 203 | 2 | 3195 | 2110 | gnl\|PID\|e283915 | orf c01003 [*Sulfolobus solfataricus*] | 57 | 41 | 1086 |
| 205 | 1 | 40 | 507 | gi\|1439527 | EIIA-man [*Lactobacillus curvatus*] | 57 | 28 | 468 |
| 214 | 7 | 4243 | 3797 | gnl\|PID\|d102049 | *H. influenzae*, ribosomal protein alanine acetyltransferase; P44305 (189) [*Bacillus subtilis*] | 57 | 48 | 447 |
| 268 | 3 | 1767 | 1276 | gi\|43979 | *L. curvatus* small cryptic plasmid gene for rep protein [*Lactobacillus curvatus*] | 57 | 36 | 492 |
| 351 | 1 | 324 | 34 | gnl\|PID\|e275871 | T03F6.b [*Caenorhabditis elegans*] | 57 | 31 | 291 |
| 386 | 1 | 226 | 2 | gi\|160671 | S antigen precursor [*Plasmodium falciparum*] | 57 | 45 | 225 |
| 5 | 5 | 10486 | 8777 | gi\|405857 | yehU [*Escherichia coli*] | 56 | 33 | 1710 |
| 8 | 5 | 3674 | 3910 | gi\|467199 | pksC; L518_F1_2 [*Mycobacterium leprae*] | 56 | 39 | 237 |
| 10 | 3 | 3442 | 1874 | gnl\|PID\|d101907 | sodium-coupled permease [*Synechocystis* sp.] | 56 | 36 | 1569 |
| 21 | 1 | 1880 | 333 | gi\|2313949 | (AE000593) osmoprotection protein (proWX) [*Helicobacter pylori*] | 56 | 33 | 1548 |
| 22 | 29 | 21968 | 22456 | gnl\|PID\|d102001 | (AB001488) PROBABLE ACETYLTRANSFERASE. [*Bacillus subtilis*] | 56 | 37 | 489 |
| 27 | 1 | 1361 | 3 | gi\|215132 | ea59 (525) [*Bacteriophage lambda*] | 56 | 30 | 1359 |
| 28 | 9 | 4667 | 4278 | gi\|1592090 | DNA repair protein RAD2 [*Methanococcus jannaschii*] | 56 | 29 | 390 |
| 33 | 1 | 3 | 386 | gnl\|PID\|d100139 | ORF [*Acetobacter pasteurianus*] | 56 | 41 | 384 |
| 36 | 7 | 5122 | 5397 | pir\|PQ0053\|PQ00 | hypothetical protein (proC 3' region) - *pseudomonas aeruginosa* (strain PAO) (fragment) | 56 | 28 | 276 |
| 40 | 4 | 3137 | 4318 | gi\|1800301 | macrolide-efflux determinant [*Streptococcus pneumoniae*] | 56 | 27 | 1182 |
| 40 | 16 | 12511 | 13191 | gnl\|PID\|e217602 | PlnU [*Lactobacillus plantarum*] | 56 | 38 | 681 |
| 48 | 17 | 13775 | 13023 | gi\|143729 | transcription activator [*Bacillus subtilis*] | 56 | 35 | 753 |
| 75 | 4 | 1674 | 2594 | gnl\|PID\|d102036 | membrane protein [*Bacillus stearothermophilus*] | 56 | 25 | 921 |
| 85 | 3 | 1842 | 1459 | gnl\|PID\|d100139 | ORF [*Acetobacter pasteurianus*] | 56 | 41 | 384 |
| 89 | 7 | 5815 | 4940 | gi\|853777 | product similar to *E. coli* PRFA2 protein [*Bacillus subtilis*] | 56 | 42 | 876 |
| 105 | 2 | 1360 | 2718 | gnl\|PID\|d101913 | hypothetical protein [*Synechocystis* sp.] | 56 | 37 | 1359 |
| 112 | 3 | 2151 | 3194 | gi\|537201 | ORF_o345 [*Escherichia coli*] | 56 | 31 | 1044 |
| 113 | 4 | 2754 | 2963 | gnl\|PID\|d100340 | ORF [Plum pox virus] | 56 | 28 | 210 |
| 122 | 3 | 1203 | 2054 | gi\|1649035 | high-affinity periplasmic glutamine binding protein [*Salmonella typhimurium*] | 56 | 30 | 852 |
| 124 | 8 | 3939 | 3694 | gnl\|PID\|e248893 | unknown [*Mycobacterium tuberculosis*] | 56 | 27 | 246 |
| 125 | 4 | 4403 | 4107 | gnl\|PID\|d100247 | human non-muscle myosin heavy chain [*Homo sapiens*] | 56 | 32 | 297 |
| 127 | 11 | 6608 | 6405 | gi\|2182397 | (AE000073) Y4fN [*Rhizobium* sp. NGR234] | 56 | 35 | 204 |
| 134 | 5 | 4769 | 3849 | gnl\|PID\|d101870 | hypothetical protein [*Synechocystis* sp.] | 56 | 39 | 921 |
| 137 | 10 | 6814 | 7245 | gi\|1592011 | sulfate permease (cysA) [*Methanococcus jannaschii*] | 56 | 34 | 432 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 142 | 8 | 5019 | 4582 | pir\|A47071\|A470 | orf1 immediately 5' of nifS - *Bacillus subtilis* | 56 | 29 | 438 |
| 146 | 8 | 4676 | 3660 | gnl\|PID\|d101911 | hypothetical protein [*Synechocystis* sp.] | 56 | 32 | 1017 |
| 148 | 3 | 1906 | 2739 | gnl\|PID\|d101099 | phosphate transport system permease protein PstA [*Synechocystis* sp.] | 56 | 36 | 834 |
| 150 | 4 | 4449 | 2743 | gnl\|PID\|e304628 | probably site-specific recombinase of the resolvase family of enzymes [*Bacteriophage* TP21] | 56 | 27 | 1707 |
| 172 | 1 | 2 | 208 | gi\|1787791 | (AE000249) f317; This 317 aa orf is 27 pct identical (16 gaps) to 301 residues of an approx. 320 aa protein YXXC_BACSU SW: P39140 [*Escherichia coli*] | 56 | 34 | 207 |
| 172 | 7 | 4979 | 5668 | gi\|396293 | similar to Bacillus subtilis hypoth. 20 kDa protein, in tsr 3' region [*Escherichia coli*] | 56 | 40 | 690 |
| 186 | 7 | 3732 | 3367 | gi\|1732200 | PTS permease for mannose subunit IIPMan [*Vibrio furnissii*] | 56 | 36 | 366 |
| 187 | 2 | 2402 | 819 | pir\|S57904\|S579 | virR49 protein - *Streptococcus pyogenes* (strain CS101, serotype M49) | 56 | 35 | 1584 |
| 204 | 3 | 2772 | 2239 | gi\|606376 | ORF_o162 [*Escherichia coli*] | 56 | 35 | 534 |
| 206 | 3 | 3342 | 1633 | gi\|559861 | clyM [Plasmid pAD1] | 56 | 38 | 1710 |
| 219 | 3 | 1689 | 1096 | gi\|1146197 | putative [*Bacillus subtilis*] | 56 | 27 | 594 |
| 230 | 2 | 409 | 1485 | pir\|C60328\|C603 | hypothetical protein 2 (sr 5' region) - *Streptococcus mutans* (strain OMZ175, serotype f) | 56 | 40 | 1077 |
| 233 | 4 | 2930 | 3268 | gi\|1041785 | rhoptry protein [*plasmodium yoelii*] | 56 | 24 | 339 |
| 273 | 2 | 1543 | 2724 | gi\|143089 | iep protein [*Bacillus subtilis*] | 56 | 32 | 1182 |
| 353 | 1 | 1 | 516 | gnl\|PID\|e325000 | hypothetical protein [*Bacillus subtilis*] | 56 | 41 | 516 |
| 359 | 1 | 87 | 641 | gi\|1786952 | (AE000176) o877; 100 pct identical to the first 86 residues of the 100 aa hypothetical protein fragment YBGB_ECOLI SW: P54746 [*Escherichia coli*] | 56 | 46 | 555 |
| 363 | 7 | 4482 | 4198 | gi\|1573353 | outer membrane integrity protein (tolA) [*Haemophilus influenzae*] | 56 | 38 | 285 |
| 376 | 1 | 2 | 508 | gnl\|PID\|e325031 | hypothetical protein [*Bacillus subtilis*] | 56 | 33 | 507 |
| 18 | 1 | 836 | 177 | gnl\|PID\|d100872 | a negative regulator of pho regulon [*Pseudomonas aeruginosa*] | 55 | 31 | 660 |
| 28 | 4 | 1824 | 1618 | gnl\|PID\|e316518 | STAT protein [*Dictyostelium discoideum*] | 55 | 40 | 207 |
| 29 | 6 | 4496 | 5041 | gi\|1088261 | unknown protein [*Anabaena* sp.] | 55 | 31 | 546 |
| 38 | 16 | 9695 | 10702 | gi\|580905 | B. subtilis genes rpmH, rnpA, 50 kd, gidA and gidB [*Bacillus subtilis*] | 55 | 31 | 1008 |
| 49 | 5 | 5727 | 6182 | gi\|1786951 | (AE000176) heat-responsive regulatory protein [*Escherichia coli*] | 55 | 29 | 456 |
| 51 | 4 | 2381 | 3241 | gnl\|PID\|d101293 | YbbA [*Bacillus subtilis*] | 55 | 42 | 861 |
| 52 | 9 | 9640 | 10866 | gi\|153016 | ORF 419 protein [*Staphylococcus aureus*] | 55 | 23 | 1227 |
| 53 | 4 | 1813 | 1349 | gi\|896042 | OspF [*Borrelia burgdorferi*] | 55 | 30 | 465 |
| 60 | 5 | 4794 | 5756 | gi\|1499876 | magnesium and cobalt transport protein [*Methanococcus jannaschii*] | 55 | 38 | 963 |
| 71 | 9 | 14176 | 15408 | gi\|1857120 | glycosyl transferase [*Neisseria meningitidis*] | 55 | 41 | 1233 |
| 75 | 6 | 3189 | 4229 | gnl\|PID\|e209890 | NAD alcohol dehydrogenase [*Bacillus subtilis*] | 55 | 44 | 1041 |
| 108 | 10 | 10488 | 9820 | gnl\|PID\|e324997 | hypothetical protein [*Bacillus subtilis*] | 55 | 36 | 669 |
| 113 | 12 | 12273 | 13037 | gnl\|PID\|e311496 | unknown [*Bacillus subtilis*] | 55 | 34 | 765 |
| 113 | 13 | 13007 | 13945 | gi\|1573423 | 1-phosphofructokinase (fruK) [*Haemophilus influenzae*] | 55 | 39 | 939 |
| 126 | 5 | 6764 | 5907 | gi\|1790131 | (AE000446) hypothetical 29.7 kD protein in ibpA-gyrB intergenic region [*Escherichia coli*] | 55 | 37 | 858 |
| 129 | 3 | 2719 | 902 | gnl\|PID\|d101425 | Pz-peptidase [*Bacillus licheniformis*] | 55 | 35 | 1818 |
| 138 | 3 | 2593 | 1610 | gi\|142833 | ORF2 [*Bacillus subtilis*] | 55 | 37 | 984 |
| 140 | 6 | 6916 | 5633 | gnl\|PID\|d100964 | homologue of hypothetical protein in a rapamycin synthesis gene cluster of *Streptomyces hygroscopicus* [*Bacillus subtilis*] | 55 | 26 | 1284 |
| 147 | 3 | 3854 | 2136 | gi\|472330 | dihydrolipoamide dehydrogenase [*Clostridium magnum*] | 55 | 39 | 1719 |
| 147 | 10 | 10204 | 8921 | gnl\|PID\|e73078 | dihydroorotase [*Lactobacillus leichmannii*] | 55 | 38 | 1284 |
| 148 | 5 | 3430 | 4119 | gi\|290572 | peripheral membrane protein U [*Escherichia coli*] | 55 | 29 | 690 |
| 148 | 6 | 4171 | 4650 | gi\|695769 | transposase [*Xanthobacter autotrophicus*] | 55 | 37 | 480 |
| 149 | 14 | 12564 | 11650 | gnl\|PID\|d101329 | YqjG [*Bacillus subtilis*] | 55 | 32 | 915 |
| 156 | 3 | 1113 | 550 | gi\|2314496 | (AE000634) conserved hypothetical integral membrane protein [*Helicobacter pylori*] | 55 | 34 | 564 |
| 159 | 10 | 6625 | 5897 | gi\|290533 | similar to E. coli ORF adjacent to suc operon; similar to gntR class of regulatory proteins [*Escherichia coli*] | 55 | 29 | 729 |
| 164 | 3 | 1784 | 2332 | gnl\|PID\|e255118 | hypothetical protein [*Bacillus subtilis*] | 55 | 37 | 549 |
| 164 | 5 | 2772 | 3521 | gi\|40348 | put. resolvase Tnp I (AA 1-284) [*Bacillus thuringiensis*] | 55 | 35 | 750 |
| 164 | 11 | 7428 | 7216 | gnl\|PID\|e249407 | unknown [*Mycobacterium tuberculosis*] | 55 | 38 | 213 |
| 167 | 5 | 3860 | 3345 | gi\|535052 | involved in protein secretion [*Bacillus subtilis*] | 55 | 28 | 516 |
| 186 | 5 | 2880 | 2563 | gi\|606080 | ORF_o290; Geneplot suggests frameshift linking to o267, not found [*Escherichia coli*] | 55 | 35 | 318 |
| 189 | 8 | 4311 | 5396 | gnl\|PID\|e183450 | hypothetical EcsB protein [*Bacillus subtilis*] | 55 | 32 | 1086 |
| 192 | 5 | 3270 | 3079 | gi\|1196504 | vitellogenin convertase [*Aedes aegypti*] | 55 | 38 | 192 |
| 195 | 2 | 2454 | 1384 | gi\|1574693 | transferase, peptidoglycan synthesis (murG) [*Haemophilus influenzae*] | 55 | 33 | 1071 |
| 198 | 4 | 3013 | 2471 | gnl\|PID\|e313074 | hypothetical protein [*Bacillus subtilis*] | 55 | 29 | 543 |
| 214 | 1 | 373 | 744 | gnl\|PID\|d101741 | transposase [*Synechocystis* sp.] | 55 | 33 | 372 |
| 219 | 2 | 1115 | 456 | gi\|288301 | ORF2 gene product [*Bacillus megaterium*] | 55 | 30 | 660 |
| 263 | 7 | 3742 | 3443 | gi\|18137 | cgcr-4 product [*Chlamydomonas reinhardtii*] | 55 | 48 | 300 |
| 285 | 1 | 2 | 829 | gnl\|PID\|d100974 | unknown [*Bacillus subtilis*] | 55 | 40 | 828 |
| 286 | 1 | 650 | 249 | gi\|396844 | ORF (18 kDa) [*Vibrio cholerae*] | 55 | 31 | 402 |
| 297 | 2 | 1229 | 1696 | gi\|150848 | prtC [*Porphyromonas gingivalis*] | 55 | 39 | 468 |
| 309 | 2 | 218 | 982 | gi\|1574491 | hypothetical [*Haemophilus influenzae*] | 55 | 35 | 765 |
| 328 | 2 | 646 | 224 | gi\|571500 | prohibitin [*Saccharomyces cerevisiae*] | 55 | 27 | 423 |
| 330 | 1 | 1340 | 474 | gi\|396397 | soxS [*Escherichia coli*] | 55 | 29 | 867 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 364 | 3 | 2538 | 1546 | gi\|393394 | Tb-291 membrane associated protein [*Trypanosoma brucei* subgroup] | 55 | 36 | 993 |
| 368 | 3 | 941 | 105 | gi\|160671 | S antigen precursor [*Plasmodium falciparum*] | 55 | 40 | 837 |
| 3 | 5 | 4604 | 3624 | gi\|2293176 | (AF008220) signal transduction protein kinase [*Bacillus subtilis*] | 54 | 26 | 981 |
| 9 | 11 | 7746 | 7246 | gi\|1146245 | putative [*Bacillus subtilis*] | 54 | 38 | 501 |
| 38 | 24 | 16213 | 17937 | gi\|1480429 | putative transcriptional regulator [*Bacillus stearothermophilus*] | 54 | 27 | 1725 |
| 40 | 8 | 5076 | 4882 | gi\|39989 | methionyl-tRNA synthetase [*Bacillus stearothermophilus*] | 54 | 35 | 195 |
| 43 | 4 | 3980 | 2367 | gnl\|PID\|e148611 | ABC transporter [*Lactobacillus helveticus*] | 54 | 25 | 1614 |
| 52 | 10 | 10844 | 12103 | gi\|1762962 | FemA [*Staphylococcus simulans*] | 54 | 29 | 1260 |
| 57 | 1 | 3 | 512 | gi\|558177 | endo-1,4-beta-xylanase [*Cellulomonas fimi*] | 54 | 36 | 510 |
| 58 | 3 | 4749 | 4246 | gnl\|PID\|d101237 | hypothetical [*Bacillus subtilis*] | 54 | 29 | 504 |
| 71 | 7 | 10684 | 11703 | gi\|510255 | orf3 [*Escherichia coli*] | 54 | 31 | 1020 |
| 71 | 20 | 27546 | 27737 | gi\|202543 | serotonin receptor [*Rattus norvegicus*] | 54 | 31 | 192 |
| 72 | 2 | 844 | 1098 | gi\|148613 | srnB gene product [Plasmid F] | 54 | 37 | 255 |
| 72 | 7 | 7438 | 6695 | gi\|1196496 | recombinase [*Moraxella bovis*] | 54 | 38 | 744 |
| 74 | 10 | 14043 | 13465 | gi\|1200342 | ORF 3 gene product [*Bradyrhizobium japonicum*] | 54 | 32 | 579 |
| 74 | 12 | 16483 | 15995 | gi\|2317798 | maturase-related protein [*Pseudomonas alcaligenes*] | 54 | 30 | 489 |
| 86 | 3 | 2877 | 2155 | gi\|46988 | orf9.6 possibly encodes the O unit polymerase [*Salmonella enterica*] | 54 | 34 | 723 |
| 89 | 5 | 4433 | 3921 | gi\|147211 | phnO protein [*Escherichia coli*] | 54 | 41 | 513 |
| 90 | 1 | 3 | 464 | gi\|2317798 | maturase-related protein [*Pseudomonas alcaligenes*] | 54 | 30 | 462 |
| 96 | 10 | 8058 | 8510 | gnl\|PID\|d102015 | (AB001488) SIMILAR TO SALMONELLA TYPHIMURIUM SLYY GENE REQUIRED FOR SURVIVAL IN MACROPHAGE. [*Bacillus subtilis*] | 54 | 32 | 453 |
| 97 | 6 | 4662 | 3604 | gi\|1591394 | transketolase" [*Methanococcus jannaschii*] | 54 | 30 | 1059 |
| 106 | 11 | 10406 | 12010 | gi\|606286 | ORF_o637 [*Escherichia coli*] | 54 | 32 | 1605 |
| 147 | 8 | 8663 | 7404 | gnl\|PID\|d101615 | ORF_ID: o319#7; similar to [SwissProt Accession Number P37340] [*Escherichia coli*] | 54 | 35 | 1260 |
| 171 | 4 | 2477 | 3223 | gi\|1439528 | EIIC-man [*Lactobacillus curvatus*] | 54 | 36 | 747 |
| 174 | 2 | 2068 | 1787 | gnl\|PID\|d100518 | motor protein [*Homo sapiens*] | 54 | 35 | 282 |
| 188 | 1 | 526 | 1188 | gnl\|PID\|e250352 | unknown [*Mycobacterium tuberculosis*] | 54 | 31 | 663 |
| 198 | 5 | 3582 | 2884 | gnl\|PID\|e313074 | hypothetical protein [*Bacillus subtilis*] | 54 | 33 | 699 |
| 207 | 1 | 1 | 1641 | gnl\|PID\|d101813 | hypothetical protein [*Synechocystis* sp.] | 54 | 24 | 1641 |
| 210 | 1 | 2 | 655 | gi\|2293206 | (AF008220) YtmP [*Bacillus subtilis*] | 54 | 29 | 654 |
| 225 | 2 | 966 | 2357 | gnl\|PID\|e330194 | R11H6.1 [*Caenorhabditis elegans*] | 54 | 39 | 1392 |
| 241 | 1 | 1681 | 347 | gnl\|PID\|d101813 | hypothetical protein [*Synechocystis* sp.] | 54 | 26 | 1335 |
| 263 | 2 | 907 | 1395 | gnl\|PID\|d101886 | transposase [*Synechocystis* sp.] | 54 | 30 | 489 |
| 263 | 6 | 3450 | 2977 | gi\|160671 | S antigen precursor [*Plasmodium falciparum*] | 54 | 47 | 474 |
| 277 | 3 | 2517 | 1363 | gi\|1196926 | unknown protein [*Streptococcus mutans*] | 54 | 30 | 1155 |
| 307 | 1 | 828 | 4 | gi\|2293198 | (AF008220) YtgP [*Bacillus subtilis*] | 54 | 28 | 825 |
| 325 | 1 | 19 | 768 | gi\|2182507 | (AE000083) Y4lH [*Rhizobium sp. NGR234*] | 54 | 37 | 750 |
| 332 | 2 | 898 | 590 | gi\|1591815 | ADP-ribosylglycohydrolase (draG) [*Methanococcus jannaschii*] | 54 | 32 | 309 |
| 385 | 4 | 240 | 479 | gi\|530878 | amino acid feature: N-glycosylation sites, aa 41 . . . 43, 46 . . . 48, 51 . . . 53, 72 . . . 74, 107 . . . 109, 128 . . . 130, 132 . . . 134, 158 . . . 160, 163 . . . 165; amino acid feature: Rod protein domain, aa 169 . . . 340; amino acid feature: globular protein domai | 54 | 49 | 240 |
| 7 | 25 | 19702 | 19493 | gnl\|PID\|e255111 | hypothetical protein [*Bacillus subtilis*] | 53 | 32 | 210 |
| 23 | 3 | 2497 | 2033 | gnl\|PID\|d102015 | (AB001488) SIMILAR TO *SALMONELLA TYPHIMURIUM* SLYY GENE REQUIRED FOR SURVIVAL IN MACROPHAGE. [*Bacillus subtilis*] | 53 | 25 | 465 |
| 29 | 11 | 9042 | 10121 | gi\|143331 | alkaline phosphatase regulatory protein [*Bacillus subtilis*] | 53 | 31 | 1080 |
| 33 | 3 | 1479 | 1009 | pir\|S10655\|S106 | hypothetical protein X - *Pyrococcus woesei* (fragment) | 53 | 33 | 471 |
| 36 | 6 | 4583 | 5134 | gnl\|PID\|e316029 | unknown [*Mycobacterium tuberculosis*] | 53 | 30 | 552 |
| 38 | 14 | 8521 | 8898 | gi\|580904 | homologous to E. coli rnpA [*Bacillus subtilis*] | 53 | 30 | 378 |
| 52 | 7 | 7007 | 8686 | gi\|1377831 | unknown [*Bacillus subtilis*] | 53 | 29 | 1680 |
| 54 | 17 | 17555 | 19564 | gi\|666069 | orf2 gene product [*Lactobacillus leichmannii*] | 53 | 36 | 2010 |
| 56 | 1 | 1 | 681 | gi\|1592266 | restriction modification system S subunit [*Methanococcus jannaschii*] | 53 | 32 | 681 |
| 57 | 10 | 9431 | 8487 | gi\|1788543 | (AE000310) f351; Residues 1-121 are 100 pct identical to YOJL_ECOLI SW: P33944 (122 aa) and aa 152-351 are 100 pct identical to YOJK_ECOLI SW: P33943 [*Escherichia coli*] | 53 | 31 | 945 |
| 61 | 1 | 429 | 4 | gnl\|PID\|e236467 | B0024.12 [*Caenorhabditis elegans*] | 53 | 33 | 426 |
| 71 | 1 | 5772 | 4 | gi\|393394 | Tb-291 membrane associated protein [*Trypanosoma brucei* subgroup] | 53 | 33 | 5769 |
| 72 | 3 | 894 | 2840 | gi\|2293178 | (AF008220) YtsD [*Bacillus subtilis*] | 53 | 27 | 1947 |
| 73 | 14 | 9793 | 9212 | gi\|1778556 | putative cobalamin synthesis protein [*Escherichia coli*] | 53 | 32 | 582 |
| 88 | 7 | 5217 | 4342 | gi\|2098719 | putative fimbrial-associated protein [*Actinomyces naeslundii*] | 53 | 38 | 876 |
| 93 | 5 | 2395 | 1688 | gi\|563366 | gluconate oxidoreductase [*Gluconobacter oxydans*] | 53 | 33 | 708 |
| 96 | 9 | 6632 | 7762 | gi\|517204 | ORF1, putative 42 kDa protein [*Streptococcus pyogenes*] | 53 | 42 | 1131 |
| 108 | 8 | 7629 | 8600 | gi\|149581 | maturation protein [*Lactobacillus paracasei*] | 53 | 32 | 972 |
| 128 | 9 | 6412 | 6972 | gnl\|PID\|e317237 | unknown [*Mycobacterium tuberculosis*] | 53 | 36 | 561 |
| 128 | 12 | 8429 | 9253 | gi\|311070 | pentraxin fusion protein [*Xenopus laevis*] | 53 | 31 | 825 |
| 148 | 1 | 3 | 950 | pir\|A61607\|A616 | probable hemolysin precursor - *Streptococcus agalactiae* (strain 74-360) | 53 | 36 | 948 |
| 163 | 2 | 2162 | 3022 | gi\|1755150 | nocturnin [*Xenopus laevis*] | 53 | 30 | 861 |
| 171 | 3 | 2304 | 2624 | gi\|1732200 | PTS permease for mannose subunit IIPMan [*Vibrio furnissii*] | 53 | 32 | 321 |
| 182 | 5 | 3785 | 3051 | gnl\|PID\|d100572 | unknown [*Bacillus subtilis*] | 53 | 35 | 735 |
| 209 | 3 | 2948 | 1935 | gi\|1778505 | ferric enterobactin transport protein [*Escherichia coli*] | 53 | 28 | 1014 |
| 218 | 5 | 3884 | 2406 | gi\|40162 | murE gene product [*Bacillus subtilis*] | 53 | 34 | 1479 |

TABLE 2-continued

_S. pneumoniae_ - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 250 | 3 | 473 | 790 | gnl\|PID\|e334776 | YlbH protein [Bacillus subtilis] | 53 | 30 | 318 |
| 275 | 1 | 1 | 1611 | gnl\|PID\|d101314 | YqeW [Bacillus subtilis] | 53 | 35 | 1611 |
| 332 | 1 | 544 | 2 | gi\|409286 | bmrU [Bacillus subtilis] | 53 | 31 | 543 |
| 2 | 2 | 2543 | 3445 | gnl\|PID\|e233879 | hypothetical protein [Bacillus subtilis] | 52 | 39 | 903 |
| 3 | 22 | 22402 | 23376 | gi\|38969 | lacF gene product [Agrobacterium radiobacter] | 52 | 36 | 975 |
| 5 | 3 | 8094 | 2356 | gnl\|PID\|e324915 | IgA1 protease [Streptococcus sanguis] | 52 | 32 | 5739 |
| 22 | 26 | 19961 | 20212 | gi\|152901 | ORF 3 [Spirochaeta aurantia] | 52 | 35 | 252 |
| 22 | 31 | 23140 | 24666 | gi\|289262 | comE ORF3 [Bacillus subtilis] | 52 | 32 | 1527 |
| 27 | 6 | 5397 | 4801 | gi\|39573 | P20 (AA 1-178) [Bacillus licheniformis] | 52 | 35 | 597 |
| 35 | 10 | 8604 | 7357 | gi\|508241 | putative O-antigen transporter [Escherichia coli] | 52 | 27 | 1248 |
| 45 | 4 | 4801 | 3662 | gnl\|PID\|d102243 | (AB005554) homologs are found in E. coli and H. influenzae; see SWISS_PROT ACC#: P42100 [Bacillus subtilis] | 52 | 36 | 1140 |
| 48 | 18 | 14385 | 13726 | gnl\|PID\|205174 | orf2 [Lactobacillus helveticus] | 52 | 25 | 660 |
| 49 | 4 | 5321 | 5755 | gi\|2317740 | (AF013987) nitrogen regulatory IIA protein [Vibrio cholerae] | 52 | 19 | 435 |
| 54 | 4 | 2773 | 4668 | gi\|1500472 | M. jannaschii predicted coding region MJ1577 [Methanococcus jannaschii] | 52 | 36 | 1896 |
| 54 | 6 | 5250 | 4969 | gi\|2182453 | (AE000079) Y4iO [Rhizobium sp. NGR234] | 52 | 40 | 282 |
| 66 | 6 | 8400 | 6955 | gi\|43140 | TrkG protein [Escherichia coli] | 52 | 30 | 1446 |
| 71 | 26 | 30659 | 31312 | gnl\|PID\|e314993 | unknown [Mycobacterium tuberculosis] | 52 | 23 | 654 |
| 75 | 2 | 1673 | 1035 | gnl\|PID\|d102271 | (AB001683) FarA [Streptomyces sp.] | 52 | 27 | 639 |
| 81 | 3 | 1439 | 2893 | gnl\|PID\|e311458 | rhamnulose kinase [Bacillus subtilis] | 52 | 32 | 1455 |
| 81 | 8 | 4987 | 5781 | gi\|147403 | mannose permease subunit II-P-Man [Escherichia coli] | 52 | 37 | 795 |
| 83 | 21 | 20687 | 21853 | gi\|143365 | phosphoribosyl aminoimidazole carboxylase II (PUR-K; ttg start codon) [Bacillus subtilis] | 52 | 37 | 1167 |
| 86 | 6 | 5785 | 4592 | gi\|1276879 | EpsF [Streptococcus thermophilus] | 52 | 26 | 1194 |
| 86 | 20 | 19390 | 17861 | gi\|454844 | ORF 3 [Schistosoma mansoni] | 52 | 26 | 1530 |
| 96 | 13 | 10540 | 9659 | gi\|288299 | ORF1 gene product [Bacillus megaterium] | 52 | 33 | 882 |
| 111 | 1 | 2 | 2026 | gi\|148309 | cytolysin B transport protein [Enterococcus faecalis] | 52 | 27 | 2025 |
| 112 | 2 | 1457 | 2167 | gi\|471234 | orf1 [Haemophilus influenzae] | 52 | 33 | 711 |
| 118 | 3 | 2931 | 2365 | bbs\|151233 | Mip = 24 kda macrophage infectivity potentiator protein [Legionella pneumophila, Philadelphia-1, Peptide, 184 aa] [Legionella pneumophila] | 52 | 33 | 567 |
| 122 | 9 | 5646 | 5951 | gi\|8214 | myosin heavy chain [Drosophila melanogaster] | 52 | 36 | 306 |
| 122 | 11 | 6159 | 6374 | gi\|434025 | dihydrolipoamide acetyltransferase [Pelobacter carbinolicus] | 52 | 52 | 216 |
| 134 | 6 | 4880 | 6313 | gi\|153733 | M protein trans-acting positive regulator [Streptococcus pyogenes] | 52 | 43 | 1434 |
| 135 | 3 | 1238 | 2716 | gnl\|PID\|e245024 | unknown [Mycobacterium tuberculosis] | 52 | 35 | 1479 |
| 141 | 3 | 1681 | 2319 | gnl\|PID\|d100573 | unknown [Bacillus subtilis] | 52 | 32 | 639 |
| 161 | 4 | 2562 | 5024 | gi\|1146243 | 22.4% identity with Escherichia coli DNA-damage inducible protein . . . ; putative [Bacillus subtilis] | 52 | 36 | 2463 |
| 173 | 2 | 968 | 183 | gi\|1215693 | putative orf; GT9_orf434 [Mycoplasma pneumoniae] | 52 | 30 | 786 |
| 198 | 6 | 4400 | 3567 | gnl\|PID\|e313010 | hypothetical protein [Bacillus subtilis] | 52 | 26 | 834 |
| 210 | 12 | 8844 | 9107 | gi\|497647 | DNA gyrase subunit B [Mycoplasma genitalium] | 52 | 38 | 264 |
| 214 | 10 | 5264 | 5431 | gi\|550697 | envelope protein [Human immunodeficiency virus type 1] | 52 | 36 | 168 |
| 225 | 1 | 15 | 884 | gi\|1552773 | hypothetical [Escherichia coli] | 52 | 34 | 870 |
| 230 | 1 | 39 | 362 | gnl\|PID\|d100582 | unknown [Bacillus subtilis] | 52 | 28 | 324 |
| 287 | 1 | 871 | 2 | gnl\|PID\|e335028 | protease/peptidase [Mycobacterium leprae] | 52 | 29 | 870 |
| 363 | 2 | 1305 | 4 | gi\|393394 | Tb-291 membrane associated protein [Trypanosoma brucei subgroup] | 52 | 32 | 1302 |
| 23 | 2 | 2048 | 1173 | gnl\|PID\|e254943 | unknown [Mycobacterium tuberculosis] | 51 | 30 | 876 |
| 29 | 3 | 742 | 1521 | gi\|929900 | 5'-methylthioadenosine phosphorylase [Sulfolobus solfataricus] | 51 | 31 | 780 |
| 45 | 1 | 410 | 1597 | gi\|1877429 | integrase [Streptococcus pyogenes phage T12] | 51 | 32 | 1188 |
| 48 | 26 | 19227 | 18946 | gi\|2314455 | (AE000633) transcriptional regulator (tenA) [Helicobacter pylori] | 51 | 33 | 282 |
| 73 | 5 | 4276 | 4016 | gi\|474177 | alpha-D-1,4-glucosidase [Staphylococcus xylosus] | 51 | 31 | 261 |
| 81 | 11 | 8935 | 12057 | gi\|311070 | pentraxin fusion protein [Xenopus laevis] | 51 | 31 | 3123 |
| 83 | 5 | 1195 | 1986 | gnl\|PID\|d101316 | YqfI [Bacillus subtilis] | 51 | 33 | 792 |
| 98 | 10 | 7531 | 8538 | gi\|41500 | ORF 3 (AA 1-352); 38 kD (put. ftsX) [Escherichia coli] | 51 | 28 | 1008 |
| 113 | 6 | 3908 | 5173 | gi\|466882 | pps1; B1496_C2_189 [Mycobacterium leprae] | 51 | 27 | 1266 |
| 124 | 1 | 326 | 57 | gi\|2191168 | (AF007270) contains similarity to myosin heavy chain [Arabidopsis thaliana] | 51 | 32 | 270 |
| 129 | 10 | 7286 | 6816 | gi\|1046241 | orf14 [Bacteriophage HP1] | 51 | 30 | 471 |
| 143 | 3 | 4963 | 3983 | gi\|1354935 | probable copper-transporting atpase [Escherichia coli] | 51 | 26 | 981 |
| 148 | 15 | 11359 | 10226 | gi\|2293256 | (AF008220) putative hippurate hydrolase [Bacillus subtilis] | 51 | 36 | 1134 |
| 149 | 8 | 6003 | 7313 | gi\|1633572 | Herpesvirus saimiri ORF73 homolog [Kaposi's sarcoma-associated herpes-like virus] | 51 | 21 | 1311 |
| 151 | 9 | 12092 | 11550 | gnl\|PID\|e281580 | hypothetical 40.7 kd protein [Bacillus subtilis] | 51 | 34 | 543 |
| 159 | 6 | 2555 | 3208 | gi\|146944 | CMP-N-acetylneuraminic acid synthetase [Escherichia coli] | 51 | 36 | 654 |
| 174 | 1 | 1797 | 4 | gi\|1773166 | probable copper-transporting atpase [Escherichia coli] | 51 | 28 | 1794 |
| 265 | 4 | 2231 | 1773 | gnl\|PID\|e256400 | anti-P. falciparum antigenic polypeptide [Saimiri sciureus] | 51 | 18 | 459 |
| 277 | 2 | 643 | 1311 | pir\|S32915\|S329 | pilD protein - Neisseria gonorrhoeae | 51 | 33 | 669 |
| 350 | 1 | 890 | 3 | gi\|290509 | o307 [Escherichia coli] | 51 | 30 | 888 |
| 363 | 4 | 1228 | 4485 | gi\|1707247 | partial CDS [Caenorhabditis elegans] | 51 | 23 | 3258 |
| 367 | 1 | 1701 | 4 | gi\|393394 | Tb-291 membrane associated protein [Trypanosoma brucei subgroup] | 51 | 32 | 1698 |
| 15 | 5 | 5174 | 4497 | gnl\|PID\|e58151 | F3 [Bacillus subtilis] | 50 | 38 | 678 |
| 16 | 4 | 2220 | 2582 | gnl\|PID\|e325010 | hypothetical protein [Bacillus subtilis] | 50 | 29 | 363 |
| 19 | 5 | 2591 | 4159 | gi\|1552733 | similar to voltage-gated chloride channel protein [Escherichia coli] | 50 | 30 | 1569 |
| 25 | 4 | 2701 | 1997 | gi\|887849 | ORF_f219 [Escherichia coli] | 50 | 27 | 705 |

TABLE 2-continued

_S. pneumoniae_ - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 35 | 1 | 211 | 417 | gnl\|PID\|e236697 | unknown [_Saccharomyces cerevisiae_] | 50 | 33 | 207 |
| 39 | 4 | 3416 | 5152 | gnl\|PID\|d100974 | unknown [_Bacillus subtilis_] | 50 | 27 | 1737 |
| 51 | 7 | 4000 | 5181 | gi\|1592027 | carbamoyl-phosphate synthase, pyrimidine-specific, large subunit [_Methanococcus jannaschii_] | 50 | 27 | 1182 |
| 51 | 9 | 7179 | 8303 | gi\|1591847 | type I restriction-modification enzyme, S subunit [_Methanococcus jannaschii_] | 50 | 28 | 1125 |
| 52 | 8 | 8740 | 9534 | gi\|144297 | acetyl esterase (XynC) [_Caldocellum saccharolyticum_] | 50 | 34 | 795 |
| 52 | 16 | 16591 | 15770 | gi\|2108229 | basic surface protein [_Lactobacillus fermentum_] | 50 | 34 | 822 |
| 57 | 7 | 6031 | 6336 | gi\|2275264 | 60S ribosomal protein L7B [_Schizosaccharomyces pombe_] | 50 | 40 | 306 |
| 71 | 23 | 29348 | 28383 | gnl\|PID\|d101328 | YqjA [_Bacillus subtilis_] | 50 | 30 | 966 |
| 86 | 12 | 11155 | 10769 | gnl\|PID\|e324964 | hypothetical protein [_Bacillus subtilis_] | 50 | 24 | 387 |
| 93 | 2 | 1205 | 330 | gi\|1066016 | similar to Escherichia coli pyruvate, water dikinase, Swiss-Prot Accession Number P23538 [_Pyrococcus furiosus_] | 50 | 24 | 876 |
| 96 | 5 | 1673 | 2959 | gnl\|PID\|e322433 | gamma-glutamylcysteine synthetase [_Brassica juncea_] | 50 | 29 | 1287 |
| 98 | 2 | 218 | 1171 | gi\|151110 | leucine-, isoleucine-, and valine-binding protein [_Pseudomonas aeruginosa_] | 50 | 30 | 954 |
| 103 | 4 | 3303 | 2785 | gi\|154330 | O-antigen ligase [_Salmonella typhimurium_] | 50 | 31 | 519 |
| 115 | 5 | 6480 | 5980 | gi\|895747 | putative cel operon regulator [_Bacillus subtilis_] | 50 | 26 | 501 |
| 129 | 11 | 7559 | 7305 | gi\|1216475 | skeletal muscle ryanodine receptor [_Homo sapiens_] | 50 | 32 | 255 |
| 129 | 13 | 8192 | 7965 | gi\|152271 | 319-kDA protein [_Rhizobium meliloti_] | 50 | 30 | 228 |
| 151 | 5 | 7634 | 6819 | gi\|40348 | put. resolvase Tnp I (AA 1-284) [_Bacillus thuringiensis_] | 50 | 35 | 816 |
| 153 | 1 | 1 | 597 | gnl\|PID\|d102015 | (AB001488) SIMILAR TO NITROREDUCTASE. [_Bacillus subtilis_] | 50 | 29 | 597 |
| 155 | 5 | 5986 | 5432 | gi\|1276880 | EpsG [_Streptococcus thermophilus_] | 50 | 28 | 555 |
| 160 | 9 | 7390 | 6323 | gi\|1786983 | (AE000179) o331; 92 pct identical to the 333 aa hypothetical protein YBHE_ECOLI SW: P52697; 26 pct identical to 167 residues of the 373 aa protein MLE_TRICU SW: P46057; SW: P52697 [_Escherichia coli_] | 50 | 30 | 1068 |
| 163 | 6 | 7396 | 8091 | gnl\|PID\|d101313 | YqeN [_Bacillus subtilis_] | 50 | 22 | 696 |
| 167 | 6 | 5232 | 3940 | gi\|413926 | ipa-2r gene product [_Bacillus subtilis_] | 50 | 27 | 1293 |
| 169 | 2 | 807 | 130 | gnl\|PID\|e304540 | endolysin [_Bacteriophage Bastille_] | 50 | 35 | 678 |
| 171 | 5 | 3168 | 4025 | gi\|606080 | ORF_o290; Geneplot suggests frameshift linking to o267, not found [_Escherichia coli_] | 50 | 27 | 858 |
| 210 | 11 | 8151 | 8414 | gi\|330038 | HRV 2 polyprotein [Human rhinovirus] | 50 | 25 | 264 |
| 364 | 1 | 1538 | 135 | gi\|393396 | Tb-292 membrane associated protein [_Trypanosoma brucei_ subgroup] | 50 | 31 | 1404 |
| 10 | 7 | 5911 | 5090 | gi\|144859 | ORF B [_Clostridium perfringens_] | 49 | 24 | 822 |
| 26 | 5 | 10754 | 9768 | gi\|142440 | ATP-dependent nuclease [_Bacillus subtilis_] | 49 | 31 | 987 |
| 66 | 7 | 9777 | 8398 | gi\|414170 | trkA gene product [_Methanosarcina mazei_] | 49 | 26 | 1380 |
| 77 | 6 | 5364 | 4648 | gnl\|PID\|e285322 | RecX protein [_Mycobacterium smegmatis_] | 49 | 28 | 717 |
| 82 | 13 | 12689 | 13249 | gnl\|PID\|e255091 | hypothetical protein [_Bacillus subtilis_] | 49 | 20 | 561 |
| 93 | 9 | 4866 | 4531 | gi\|40067 | X gene product [_Bacillus sphaericus_] | 49 | 26 | 336 |
| 112 | 5 | 4019 | 4948 | gi\|1574380 | lic-1 operon protein (licB) [_Haemophilus influenzae_] | 49 | 27 | 930 |
| 129 | 7 | 6058 | 4949 | gnl\|PID\|e267587 | Unknown [_Bacillus subtilis_] | 49 | 35 | 1110 |
| 135 | 5 | 3875 | 4438 | gi\|39573 | P20 (AA 1-178) [_Bacillus licheniformis_] | 49 | 25 | 564 |
| 154 | 2 | 1423 | 1953 | gnl\|PID\|d101102 | regulatory components of sensory transduction system [_Synechocystis_ sp.] | 49 | 29 | 531 |
| 156 | 5 | 2878 | 1637 | gnl\|PID\|d101732 | hypothetical protein [_Synechocystis_ sp.] | 49 | 25 | 1242 |
| 173 | 5 | 3500 | 2940 | gi\|490324 | LORF X gene product [unidentified] | 49 | 30 | 561 |
| 182 | 1 | 1057 | 2 | gi\|331002 | first methionine codon in the ECLF1 ORF [Saimiriine herpesvirus 2] | 49 | 25 | 1056 |
| 192 | 6 | 5352 | 3667 | gi\|2394472 | (AF024499) contains similarity to homeobox domains [_Caenorhabditis elegans_] | 49 | 23 | 1686 |
| 253 | 4 | 1129 | 1350 | gi\|531116 | SIR4 protein [_Saccharomyces cerevisiae_] | 49 | 23 | 222 |
| 277 | 1 | 600 | 136 | gi\|396844 | ORF (18 kDa) [_Vibrio cholerae_] | 49 | 32 | 465 |
| 327 | 3 | 1435 | 887 | gi\|733524 | phosphatidylinositol-4,5-diphosphate 3-kinase [_Dictyostelium discoideum_] | 49 | 24 | 549 |
| 365 | 3 | 1436 | 132 | gi\|393394 | Tb-291 membrane associated protein [_Trypanosoma brucei_ subgroup] | 49 | 31 | 1305 |
| 33 | 7 | 4461 | 3277 | gi\|145644 | codes for a protein of unknown function [_Escherichia coli_] | 48 | 26 | 1185 |
| 40 | 2 | 652 | 1776 | gnl\|PID\|e290649 | ornithine decarboxylase [_Nicotiana tabacum_] | 48 | 29 | 1125 |
| 67 | 4 | 1377 | 2384 | gi\|1772652 | 2-keto-3-deoxygluconate kinase [_Haloferax alicantei_] | 48 | 30 | 1008 |
| 74 | 2 | 4269 | 3871 | gi\|2182678 | (AE000101) Y4vJ [_Rhizobium_ sp. NGR234] | 48 | 27 | 399 |
| 81 | 2 | 1326 | 541 | gi\|153672 | lactose repressor [_Streptococcus mutans_] | 48 | 33 | 786 |
| 81 | 4 | 2981 | 3646 | gi\|146042 | fuculose-1-phosphate aldolase (fucA) [_Escherichia coli_] | 48 | 30 | 666 |
| 97 | 1 | 602 | 51 | gi\|153794 | rgg [_Streptococcus gordonii_] | 48 | 29 | 552 |
| 110 | 1 | 1 | 3132 | gi\|1381114 | prtB gene product [_Lactobacillus delbrueckii_] | 48 | 23 | 3132 |
| 131 | 5 | 2914 | 2147 | gnl\|PID\|e183811 | Acyl-ACP thioesterase [_Brassica napus_] | 48 | 27 | 768 |
| 133 | 4 | 3494 | 2628 | gnl\|PID\|e261988 | putative ORF [_Bacillus subtilis_] | 48 | 27 | 867 |
| 139 | 6 | 4231 | 4599 | gi\|1049388 | ZK470.1 gene product [_Caenorhabditis elegans_] | 48 | 23 | 369 |
| 139 | 8 | 5036 | 5665 | gi\|1022725 | unknown [_Staphylococcus haemolyticus_] | 48 | 29 | 630 |
| 140 | 12 | 11936 | 11007 | gnl\|PID\|d102049 | H. influenzae, ribosomal protein alanine acetyltransferase; P44305 (189) [_Bacillus subtilis_] | 48 | 27 | 930 |
| 146 | 9 | 5670 | 4654 | gi\|1591731 | melvalonate kinase [_Methanococcus jannaschii_] | 48 | 24 | 1017 |
| 161 | 3 | 1280 | 2374 | gnl\|PID\|d101578 | Collagenase precursor (EC 3.4.—.—). [_Escherichia coli_] | 48 | 24 | 1095 |
| 172 | 11 | 10581 | 11048 | gnl\|PID\|d101132 | hypothetical protein [_Synechocystis_ sp.] | 48 | 27 | 468 |

TABLE 2-continued

*S. pneumoniae* - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 182 | 4 | 2930 | 2586 | gi\|40067 | X gene product [*Bacillus sphaericus*] | 48 | 37 | 345 |
| 210 | 15 | 10786 | 11196 | sp\|P13940\|LE29_ | LATE EMBRYOGENESIS ABUNDANT PROTEIN D-29 (LEA D-29). | 48 | 30 | 411 |
| 214 | 12 | 6231 | 6482 | gi\|40389 | non-toxic components [*Clostridium botulinum*] | 48 | 26 | 252 |
| 221 | 1 | 704 | 3 | gi\|1573364 | H. influenzae predicted coding region HI0392 [*Haemophilus influenzae*] | 48 | 27 | 702 |
| 227 | 2 | 647 | 3928 | gi\|1673693 | (AE000005) *Mycoplasma pneumoniae*, C09_orf718 Protein [*Mycoplasma pneumoniae*] | 48 | 30 | 3282 |
| 253 | 2 | 480 | 758 | gnl\|PID\|e236697 | unknown [*Saccharomyces cerevisiae*] | 48 | 31 | 279 |
| 363 | 3 | 1874 | 1122 | gi\|18137 | cgcr-4 product [*Chlamydomonas reinhardtii*] | 48 | 40 | 753 |
| 389 | 1 | 505 | 2 | gi\|18137 | cgcr-4 product [*Chlamydomonas reinhardtii*] | 48 | 38 | 504 |
| 3 | 21 | 20879 | 22258 | gnl\|PID\|e264778 | putative maltose-binding pootein [*Streptomyces coelicolor*] | 47 | 33 | 1380 |
| 6 | 4 | 4089 | 4658 | gi\|39573 | P20 (AA 1-178) [*Bacillus licheniformis*] | 47 | 23 | 570 |
| 15 | 3 | 3736 | 1760 | gnl\|PID\|d100572 | unknown [*Bacillus subtilis*] | 47 | 25 | 1977 |
| 35 | 15 | 14516 | 13263 | gi\|1773351 | Cap5L [*Staphylococcus aureus*] | 47 | 20 | 1254 |
| 51 | 6 | 3547 | 4002 | pir\|A37024\|A370 | 32K antigen precursor - *Mycobacterium tuberculosis* | 47 | 38 | 456 |
| 55 | 8 | 10154 | 9273 | gi\|39848 | U3 [*Bacillus subtilis*] | 47 | 26 | 882 |
| 92 | 4 | 1753 | 3276 | gnl\|PID\|e280611 | PCPC [*Streptococcus pneumoniae*] | 47 | 35 | 1524 |
| 127 | 9 | 5589 | 5386 | gi\|1786458 | (AE000134) f120; This 120 aa orf is 76 pct identical (0 gaps) to 42 residues of an approx. 48 aa protein Y127_HAEIN SW: P43949 [*Escherichia coli*] | 47 | 32 | 204 |
| 130 | 3 | 1232 | 1759 | gnl\|PID\|e266555 | unknown [*Mycobacterium tuberculosis*] | 47 | 23 | 528 |
| 140 | 4 | 4951 | 3542 | gnl\|PID\|d100964 | homologue of hypothetical protein in a rapamycin synthesis gene cluster of Streptomyces hygroscopicus [*Bacillus subtilis*] | 47 | 24 | 1410 |
| 151 | 4 | 6814 | 6200 | gi\|1522674 | M. jannaschii predicted coding region MJECL41 [*Methanococcus jannaschii*] | 47 | 27 | 615 |
| 157 | 3 | 803 | 1174 | gnl\|PID\|d101320 | YqgZ [*Bacillus subtilis*] | 47 | 25 | 372 |
| 178 | 5 | 3267 | 2155 | gi\|2367190 | (AE000390) o334; sequence change joins ORFs ygjR & ygjS from earlier version (YGJR_ECOLI SW: P42599 and YGJS_ECOLI SW: P42600) [*Escherichia coli*] | 47 | 30 | 1113 |
| 273 | 1 | 2 | 1549 | gnl\|PID\|e254973 | autolysin sensor kinase [*Bacillus subtilis*] | 47 | 32 | 1548 |
| 300 | 2 | 880 | 644 | gi\|1835755 | zinc finger protein Png-1 [*Mus musculus*] | 47 | 22 | 237 |
| 54 | 14 | 14182 | 12638 | pir\|S43609\|S436 | rofA protein - *Streptococcus pyogenes* | 46 | 24 | 1545 |
| 88 | 1 | 2 | 1018 | gnl\|PID\|e223891 | xylose repressor [*Anaerocellum thermophilum*] | 46 | 27 | 1017 |
| 96 | 7 | 4553 | 5860 | gnl\|PID\|d101652 | ORF_ID: o347#5; similar to [SwissProt Accession Number P45272] [*Escherichia coli*] | 46 | 23 | 1308 |
| 112 | 1 | 1127 | 3 | gi\|2209215 | (AF004325) putative oligosaccharide repeat unit transporter [I *Streptococcus pneumoniae*] | 46 | 24 | 1125 |
| 122 | 13 | 7308 | 7982 | gi\|1054776 | hr44 gene product [*Homo sapiens*] | 46 | 34 | 675 |
| 127 | 14 | 9198 | 8125 | gi\|1469286 | afuA gene product [*Actinobacillus pleuropneumoniae*] | 46 | 28 | 1074 |
| 132 | 4 | 7093 | 6197 | gi\|153794 | rgg [*Streptococcus gordonii*] | 46 | 26 | 897 |
| 140 | 8 | 8220 | 7723 | gi\|1235795 | pullulanase [*Thermoanaerobacterium thermosulfurigenes*] | 46 | 21 | 498 |
| 140 | 9 | 9205 | 8315 | gi\|407878 | leucine rich protein [*Streptococcus equisimilis*] | 46 | 27 | 891 |
| 162 | 1 | 1 | 1125 | gi\|1143209 | ORF7; Method: conceptual translation supplied by author [*Shigella sonnei*] | 46 | 25 | 1125 |
| 199 | 1 | 1 | 585 | gi\|1947171 | (AF000299) No definition line found [*Caenorhabditis elegans*] | 46 | 28 | 585 |
| 223 | 3 | 1971 | 1477 | sp\|P02562\|MYSS_ | MYOSIN HEAVY CHAIN, SKELETAL MUSCLE (FRAGMENTS). | 46 | 27 | 495 |
| 232 | 2 | 760 | 1608 | gi\|1016112 | ycf38 gene product [*Cyanophora paradoxa*] | 46 | 28 | 849 |
| 292 | 1 | 687 | 220 | gi\|1673744 | (AE000011) *Mycoplasma pneumoniae*, cytidine deaminase; similar to GenBank Accession Number C53312, from *M. pirum* [*Mycoplasma pneumoniae*] | 46 | 29 | 468 |
| 30 | 8 | 5843 | 6472 | gi\|1788049 | (AE000270) o235; This 235 aa orf is 29 pct identical (10 gaps) to 198 residues of an approx. 216 aa protein YTXB_BACSU SW: P06568 [*Escherichia coli*] | 45 | 24 | 630 |
| 48 | 6 | 3461 | 3868 | gi\|722339 | unknown [*Acetobacter xylinum*] | 45 | 29 | 408 |
| 60 | 1 | 307 | 2 | gi\|1699079 | coded for by C. elegans cDNA yk41h4.3; coded for by C. elegans cDNA yk148g10.5; coded for by C. elegans cDNA yk152g5.5; coded for by C. elegans cDNA yk59a10.5; coded for by C. elegans cDNA yk41h4.5; coded for by C. elegans cDNA cm20g10; coded | 45 | 36 | 306 |
| 72 | 16 | 14371 | 14874 | gi\|1321900 | NADH dehydrogenase (ubiquinone) [*Artemia franciscana*] | 45 | 25 | 504 |
| 99 | 7 | 9158 | 7941 | gi\|152192 | mutation causes a succinoglucan-minus phenotype; ExoQ is atransmembrane protein; third gene of the exoYFQ operon;; putative [*Rhizobium meliloti*] | 45 | 28 | 1218 |
| 127 | 12 | 7046 | 6606 | bbs\|153689 | HitB = iron utilization protein [*Haemophilus influenzae*, type b, DL42, NTHI TN106, Peptide, 506 aa] [*Haemophilus influenzae*] | 45 | 24 | 441 |
| 137 | 5 | 1561 | 2619 | gi\|472921 | v-type Na-ATPase [*Enterococcus hirae*] | 45 | 33 | 1059 |
| 209 | 1 | 774 | 364 | gi\|304141 | restriction endonuclease beta subunit [*Bacillus coagulans*] | 45 | 28 | 411 |
| 314 | 1 | 604 | 2 | gi\|1480457 | latex allergen [*Hevea brasiliensis*] | 45 | 31 | 603 |
| 20 | 18 | 19782 | 20288 | gi\|433942 | ORF [*Lactococcus lactis*] | 44 | 26 | 507 |
| 87 | 8 | 7030 | 6452 | gi\|537207 | ORF_f277 [*Escherichia coli*] | 44 | 26 | 579 |
| 166 | 5 | 4909 | 4037 | gnl\|PID\|e308082 | membrane transport protein [*Bacillus subtilis*] | 44 | 25 | 873 |
| 247 | 1 | 818 | 75 | gnl\|PID\|d100718 | ORF1 [*Bacillus sp.*] | 44 | 20 | 744 |

TABLE 2-continued

S. pneumoniae - Putative coding regions of novel proteins similar to known proteins

| Contig ID | ORF ID | Start (nt) | Stop (nt) | match acession | match gene name | % sim | % ident | length (nt) |
|---|---|---|---|---|---|---|---|---|
| 32 | 3 | 1885 | 3876 | gi|2351768 | PspA [*Streptococcus pneumoniae*] | 43 | 24 | 1992 |
| 36 | 17 | 15467 | 18256 | gi|1045739 | *M. genitalium* predicted coding region MG064 [*Mycoplasma genitalium*] | 43 | 26 | 2790 |
| 54 | 15 | 14656 | 17343 | gi|520541 | penicillin-binding proteins 1A and 1B [*Bacillus subtilis*] | 43 | 27 | 2688 |
| 67 | 2 | 696 | 1352 | gi|536934 | yjcA gene product [*Escherichia coli*] | 43 | 29 | 657 |
| 139 | 2 | 2416 | 338 | gi|396400 | similar to eukaryotic Na+/H+ exchangers [*Escherichia coli*] | 43 | 24 | 2079 |
| 298 | 1 | 3 | 809 | gi|413972 | ipa-48r gene product [*Bacillus subtilis*] | 43 | 24 | 807 |
| 387 | 1 | 47 | 427 | gi|2315652 | (AF016669) No definition line found [*Caenorhabditis elegans*] | 43 | 30 | 381 |
| 185 | 4 | 4221 | 3127 | gi|2182399 | (AE000073) Y4fP [*Rhizobium* sp. NGR234] | 41 | 25 | 1095 |
| 340 | 1 | 582 | 70 | gnl|PID|e218681 | CDP-diacylglycerol synthetase [*Arabidopsis thaliana*] | 41 | 20 | 513 |
| 363 | 6 | 4205 | 1914 | gi|1256742 | R27-2 protein [*Trypanosoma cruzi*] | 41 | 27 | 2292 |
| 368 | 2 | 2 | 943 | gi|21783 | LMW glutenin (AA 1-356) [*Triticum aestivum*] | 41 | 34 | 942 |
| 155 | 3 | 4489 | 2861 | gi|42023 | member of ATP-dependent transport family, very similar to mdr proteins and hemolysin B, export protein [*Escherichia coli*] | 40 | 18 | 1629 |
| 365 | 2 | 95 | 1438 | gi|1633572 | Herpesvirus saimiri ORF73 homolog [Kaposi's sarcoma-associated herpes-like virus] | 40 | 21 | 1344 |
| 1 | 3 | 2979 | 3860 | gnl|PID|d101908 | hypothetical protein [*Synechocystis* sp.] | 39 | 26 | 882 |
| 1 | 5 | 3814 | 4647 | gnl|PID|d101961 | hypothetical protein [*Synechocystis* sp.] | 39 | 19 | 834 |
| 26 | 6 | 14035 | 10724 | gi|142439 | ATP-dependent nuclease [*Bacillus subtilis*] | 38 | 20 | 3312 |
| 47 | 1 | 3 | 4916 | gi|632549 | NF-180 [*Petromyzon marinus*] | 36 | 23 | 4914 |

TABLE 3

S. pneumoniae
Putative coding regions of novel proteins not similar to known proteins

| Contig ID | ORF ID | Start (nt) | Stop (nt) |
|---|---|---|---|
| 1 | 4 | 3428 | 3009 |
| 1 | 6 | 4611 | 4964 |
| 3 | 2 | 818 | 994 |
| 3 | 3 | 1182 | 1574 |
| 3 | 7 | 5382 | 6497 |
| 3 | 25 | 25046 | 25396 |
| 3 | 26 | 25625 | 26317 |
| 6 | 2 | 1519 | 1689 |
| 6 | 14 | 12875 | 12618 |
| 6 | 15 | 13215 | 12841 |
| 6 | 18 | 15977 | 15390 |
| 7 | 12 | 9955 | 9419 |
| 7 | 13 | 10161 | 9910 |
| 8 | 6 | 3915 | 4280 |
| 9 | 9 | 6024 | 5704 |
| 10 | 8 | 6909 | 6298 |
| 10 | 9 | 7136 | 6888 |
| 10 | 11 | 7968 | 7672 |
| 12 | 1 | 1140 | 4 |
| 12 | 3 | 1779 | 1456 |
| 14 | 2 | 1913 | 1434 |
| 16 | 1 | 1 | 243 |
| 16 | 5 | 5675 | 3087 |
| 17 | 1 | 324 | 34 |
| 17 | 3 | 1451 | 1050 |
| 17 | 9 | 4890 | 4465 |
| 20 | 14 | 14544 | 15893 |
| 21 | 3 | 3359 | 2589 |
| 21 | 5 | 4802 | 4482 |
| 22 | 21 | 17099 | 17362 |
| 22 | 25 | 19467 | 19982 |
| 22 | 33 | 25540 | 25764 |
| 22 | 35 | 26388 | 26218 |
| 22 | 36 | 26382 | 27572 |
| 23 | 7 | 6655 | 6032 |
| 23 | 8 | 7132 | 6653 |
| 24 | 1 | 36 | 518 |
| 25 | 5 | 3009 | 2641 |
| 27 | 4 | 4819 | 4223 |
| 27 | 5 | 4789 | 4956 |
| 28 | 5 | 3017 | 1797 |
| 28 | 8 | 4272 | 3850 |
| 28 | 10 | 5028 | 4597 |
| 28 | 11 | 5746 | 5072 |
| 29 | 7 | 5596 | 4919 |
| 29 | 8 | 5039 | 5518 |
| 29 | 9 | 5595 | 8207 |
| 30 | 9 | 6511 | 6263 |
| 31 | 6 | 2664 | 2344 |
| 32 | 5 | 5203 | 5538 |
| 33 | 8 | 5327 | 4668 |
| 34 | 10 | 8024 | 7740 |
| 34 | 12 | 9360 | 8641 |
| 34 | 13 | 9667 | 9377 |
| 34 | 18 | 13104 | 11902 |
| 35 | 11 | 9688 | 8588 |
| 35 | 12 | 11073 | 9670 |
| 36 | 2 | 334 | 1041 |
| 36 | 12 | 11120 | 10893 |
| 36 | 13 | 10993 | 11388 |
| 36 | 15 | 12172 | 14595 |
| 38 | 7 | 4269 | 4577 |
| 38 | 8 | 4480 | 5001 |
| 38 | 10 | 5517 | 5711 |
| 38 | 17 | 10732 | 11376 |
| 40 | 3 | 1728 | 3143 |
| 43 | 1 | 172 | 5 |
| 43 | 7 | 8884 | 8732 |
| 43 | 8 | 9568 | 9071 |
| 44 | 4 | 4831 | 6831 |
| 45 | 3 | 3204 | 3665 |
| 46 | 4 | 3875 | 3468 |
| 46 | 7 | 6074 | 7081 |
| 48 | 5 | 3196 | 3582 |
| 48 | 8 | 4579 | 4229 |
| 48 | 11 | 9323 | 8922 |
| 48 | 16 | 13042 | 12494 |
| 48 | 20 | 16342 | 15764 |
| 48 | 24 | 17971 | 18351 |
| 48 | 30 | 21979 | 21776 |

TABLE 3-continued

S. pneumoniae
Putative coding regions of novel proteins not similar to known proteins

| Contig ID | ORF ID | Start (nt) | Stop (nt) |
|---|---|---|---|
| 49 | 1 | 209 | 3 |
| 50 | 4 | 3307 | 2672 |
| 51 | 5 | 3239 | 3598 |
| 52 | 11 | 12146 | 12883 |
| 54 | 7 | 5588 | 5187 |
| 54 | 8 | 6013 | 5459 |
| 54 | 9 | 6004 | 6210 |
| 54 | 16 | 17685 | 17506 |
| 55 | 9 | 10515 | 10123 |
| 55 | 12 | 11947 | 12141 |
| 56 | 3 | 935 | 1387 |
| 56 | 4 | 1496 | 1939 |
| 57 | 3 | 1624 | 2130 |
| 57 | 4 | 2100 | 2501 |
| 58 | 6 | 7541 | 7335 |
| 59 | 1 | 2 | 430 |
| 59 | 4 | 2416 | 2736 |
| 59 | 5 | 2734 | 3063 |
| 59 | 8 | 4743 | 5549 |
| 59 | 9 | 5459 | 5929 |
| 60 | 6 | 5741 | 6451 |
| 61 | 3 | 2395 | 1772 |
| 61 | 5 | 3316 | 3176 |
| 64 | 1 | 2722 | 2 |
| 66 | 2 | 1180 | 3147 |
| 66 | 8 | 9082 | 9495 |
| 67 | 3 | 1343 | 1182 |
| 69 | 2 | 1165 | 980 |
| 70 | 5 | 4059 | 3922 |
| 70 | 6 | 4215 | 4057 |
| 70 | 9 | 5268 | 5504 |
| 71 | 15 | 20351 | 21901 |
| 71 | 16 | 21859 | 22338 |
| 71 | 19 | 26204 | 27556 |
| 72 | 9 | 8458 | 8081 |
| 73 | 4 | 3815 | 4216 |
| 73 | 6 | 4214 | 4582 |
| 73 | 7 | 4369 | 4773 |
| 73 | 10 | 7183 | 6428 |
| 73 | 15 | 9462 | 9668 |
| 76 | 1 | 524 | 195 |
| 76 | 2 | 867 | 535 |
| 76 | 11 | 8602 | 9210 |
| 80 | 6 | 7924 | 8109 |
| 81 | 1 | 244 | 2 |
| 81 | 10 | 6631 | 8931 |
| 83 | 4 | 1872 | 1150 |
| 83 | 17 | 16810 | 16460 |
| 84 | 3 | 4464 | 2929 |
| 86 | 2 | 2147 | 1092 |
| 86 | 4 | 3606 | 2875 |
| 86 | 19 | 16767 | 17114 |
| 87 | 5 | 5326 | 5000 |
| 87 | 7 | 6459 | 6001 |
| 87 | 9 | 7224 | 7006 |
| 87 | 18 | 17930 | 17670 |
| 87 | 19 | 18275 | 17928 |
| 88 | 2 | 1619 | 1840 |
| 88 | 4 | 2711 | 2878 |
| 88 | 9 | 6252 | 6016 |
| 89 | 3 | 2634 | 1621 |
| 89 | 9 | 7371 | 6868 |
| 90 | 2 | 899 | 2395 |
| 90 | 3 | 1143 | 952 |
| 91 | 3 | 2959 | 3141 |
| 91 | 4 | 3170 | 3691 |
| 91 | 6 | 4253 | 4573 |
| 93 | 1 | 391 | 2 |
| 93 | 6 | 2648 | 2379 |
| 93 | 8 | 4533 | 3712 |
| 96 | 1 | 3 | 182 |
| 96 | 2 | 904 | 632 |
| 96 | 3 | 1407 | 1147 |
| 96 | 4 | 1250 | 1420 |
| 97 | 9 | 7043 | 6753 |
| 99 | 15 | 18522 | 18692 |
| 99 | 17 | 19717 | 19541 |
| 100 | 2 | 4094 | 1980 |
| 103 | 1 | 48 | 299 |
| 103 | 6 | 4924 | 4373 |
| 104 | 5 | 6142 | 6735 |
| 105 | 7 | 6098 | 6517 |
| 106 | 1 | 1 | 363 |
| 106 | 10 | 9832 | 10212 |
| 108 | 1 | 2 | 268 |
| 111 | 3 | 3417 | 3788 |
| 111 | 4 | 3809 | 4606 |
| 115 | 10 | 10854 | 10438 |
| 116 | 3 | 2873 | 2121 |
| 118 | 2 | 2274 | 1357 |
| 122 | 4 | 2698 | 2333 |
| 122 | 10 | 5858 | 6199 |
| 122 | 12 | 6301 | 7416 |
| 124 | 2 | 346 | 690 |
| 128 | 4 | 2544 | 3368 |
| 129 | 1 | 689 | 102 |
| 129 | 2 | 1011 | 724 |
| 129 | 8 | 6454 | 6056 |
| 129 | 9 | 6540 | 6277 |
| 129 | 12 | 7809 | 7621 |
| 131 | 3 | 1433 | 756 |
| 131 | 10 | 5972 | 5673 |
| 134 | 11 | 11838 | 11209 |
| 135 | 2 | 625 | 1140 |
| 136 | 4 | 2913 | 3830 |
| 137 | 2 | 325 | 134 |
| 139 | 12 | 14027 | 14521 |
| 139 | 13 | 14840 | 14532 |
| 139 | 14 | 15363 | 14875 |
| 140 | 20 | 19822 | 20838 |
| 142 | 1 | 1 | 285 |
| 146 | 3 | 760 | 479 |
| 146 | 4 | 1149 | 778 |
| 146 | 7 | 3604 | 2885 |
| 146 | 13 | 8223 | 9401 |
| 146 | 14 | 9399 | 10676 |
| 146 | 15 | 10052 | 9750 |
| 147 | 7 | 7488 | 7276 |
| 147 | 9 | 8913 | 8647 |
| 148 | 7 | 5298 | 4765 |
| 149 | 1 | 2 | 1936 |
| 149 | 3 | 2557 | 2880 |
| 149 | 9 | 6258 | 6070 |
| 150 | 2 | 1355 | 579 |
| 150 | 3 | 2556 | 1909 |
| 153 | 3 | 2061 | 2642 |
| 154 | 3 | 1953 | 1741 |
| 155 | 2 | 2181 | 1411 |
| 156 | 8 | 4550 | 4311 |
| 157 | 1 | 37 | 294 |
| 159 | 2 | 631 | 780 |
| 159 | 4 | 1384 | 1722 |
| 159 | 7 | 3271 | 4017 |
| 161 | 2 | 1332 | 1018 |
| 165 | 3 | 5535 | 4945 |
| 166 | 6 | 5406 | 4972 |
| 167 | 9 | 6075 | 6395 |
| 169 | 5 | 2828 | 3205 |
| 170 | 7 | 6485 | 6243 |
| 170 | 8 | 6964 | 6362 |
| 170 | 9 | 7303 | 6962 |
| 170 | 11 | 8790 | 7906 |

TABLE 3-continued

S. pneumoniae
Putative coding regions of novel proteins not similar to known proteins

| Contig ID | ORF ID | Start (nt) | Stop (nt) |
|---|---|---|---|
| 171 | 9 | 7150 | 7476 |
| 172 | 5 | 2298 | 1948 |
| 173 | 4 | 2913 | 2677 |
| 175 | 2 | 659 | 835 |
| 175 | 3 | 893 | 1789 |
| 176 | 2 | 1487 | 546 |
| 176 | 3 | 2200 | 1466 |
| 177 | 9 | 4686 | 4925 |
| 177 | 10 | 4923 | 5177 |
| 177 | 11 | 5111 | 5347 |
| 177 | 13 | 7396 | 8703 |
| 178 | 6 | 3452 | 3724 |
| 181 | 5 | 1853 | 2473 |
| 182 | 2 | 2112 | 1102 |
| 182 | 3 | 2617 | 2006 |
| 183 | 2 | 2126 | 2320 |
| 185 | 5 | 4683 | 4219 |
| 185 | 6 | 4846 | 4634 |
| 187 | 4 | 2940 | 3557 |
| 188 | 4 | 3686 | 4363 |
| 188 | 5 | 4183 | 4821 |
| 188 | 6 | 5882 | 6493 |
| 189 | 5 | 3143 | 2844 |
| 189 | 9 | 5956 | 5564 |
| 191 | 1 | 618 | 4 |
| 191 | 11 | 10357 | 10001 |
| 192 | 3 | 2861 | 2268 |
| 192 | 4 | 3081 | 2878 |
| 192 | 7 | 6800 | 5331 |
| 193 | 3 | 997 | 839 |
| 194 | 4 | 2315 | 2127 |
| 195 | 5 | 6249 | 4543 |
| 195 | 6 | 6620 | 6231 |
| 196 | 2 | 1553 | 1849 |
| 197 | 1 | 1 | 861 |
| 198 | 9 | 6844 | 6644 |
| 200 | 5 | 5329 | 5769 |
| 200 | 6 | 5993 | 6595 |
| 204 | 5 | 3914 | 3276 |
| 205 | 2 | 447 | 1709 |
| 209 | 4 | 2038 | 2460 |
| 209 | 5 | 2458 | 2682 |
| 210 | 10 | 7370 | 8230 |
| 210 | 13 | 9029 | 10441 |
| 210 | 14 | 10439 | 10705 |
| 214 | 5 | 2581 | 2330 |
| 214 | 9 | 5065 | 5277 |
| 214 | 11 | 5996 | 5754 |
| 217 | 2 | 541 | 194 |
| 218 | 2 | 914 | 1432 |
| 218 | 3 | 1430 | 1972 |
| 218 | 6 | 3639 | 3821 |
| 219 | 1 | 458 | 39 |
| 220 | 1 | 869 | 600 |
| 223 | 4 | 2617 | 1964 |
| 227 | 1 | 1 | 510 |
| 234 | 4 | 1539 | 1312 |
| 234 | 6 | 2116 | 1838 |
| 235 | 1 | 52 | 312 |
| 235 | 2 | 310 | 687 |
| 238 | 1 | 660 | 64 |
| 246 | 1 | 1 | 270 |
| 248 | 1 | 3 | 362 |
| 248 | 2 | 443 | 1222 |
| 254 | 3 | 2789 | 792 |
| 258 | 2 | 1179 | 1616 |
| 260 | 3 | 1770 | 2123 |
| 263 | 1 | 653 | 177 |
| 263 | 4 | 2244 | 1900 |
| 263 | 5 | 3569 | 2973 |
| 266 | 1 | 1 | 342 |
| 266 | 2 | 177 | 1022 |
| 270 | 2 | 1124 | 1681 |
| 272 | 1 | 857 | 186 |
| 275 | 2 | 1684 | 2295 |
| 278 | 1 | 2 | 406 |
| 282 | 1 | 714 | 391 |
| 282 | 4 | 1463 | 1134 |
| 287 | 2 | 1119 | 826 |
| 288 | 1 | 540 | 4 |
| 289 | 1 | 684 | 4 |
| 291 | 5 | 1589 | 1858 |
| 293 | 2 | 2539 | 2925 |
| 294 | 1 | 21 | 608 |
| 296 | 2 | 494 | 700 |
| 296 | 3 | 670 | 843 |
| 302 | 1 | 261 | 530 |
| 309 | 3 | 559 | 350 |
| 310 | 2 | 249 | 1889 |
| 316 | 2 | 2087 | 1818 |
| 317 | 2 | 1048 | 584 |
| 318 | 2 | 313 | 777 |
| 319 | 3 | 477 | 133 |
| 327 | 2 | 912 | 607 |
| 331 | 1 | 1 | 549 |
| 333 | 1 | 2 | 535 |
| 333 | 2 | 465 | 82 |
| 333 | 3 | 127 | 342 |
| 341 | 1 | 1 | 705 |
| 345 | 2 | 895 | 701 |
| 346 | 2 | 750 | 199 |
| 349 | 1 | 1 | 198 |
| 350 | 2 | 81 | 413 |
| 355 | 1 | 44 | 973 |
| 358 | 2 | 636 | 448 |
| 360 | 2 | 948 | 628 |
| 364 | 2 | 1639 | 1265 |
| 378 | 1 | 345 | 1004 |
| 379 | 2 | 683 | 510 |
| 381 | 1 | 109 | 693 |
| 385 | 1 | 150 | 4 |
| 385 | 2 | 269 | 30 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08168205B2). An electronic copy of the "Sequence Listing" will also be available from the USPTO upon request and payment of the fee set forth in 37 CFR 1.19(b)(3).

What is claimed is:

1. An isolated protein comprising a polypeptide encoded by nucleotides 5602 to 8118 of SEQ ID NO:94.

2. The isolated protein of claim 1, wherein said protein consists of a polypeptide encoded by nucleotides 5602 to 8118 of SEQ ID NO:94.

3. A composition comprising the protein of claim 1.

4. The composition of claim 3 further comprising an carrier.

5. A composition comprising the protein of claim 2.

6. The composition of claim 5 further comprising an carrier.

* * * * *